(12) United States Patent
Donohoue et al.

(10) Patent No.: US 10,100,333 B2
(45) Date of Patent: *Oct. 16, 2018

(54) ENGINEERED NUCLEIC ACID-TARGETING NUCLEIC ACIDS

(71) Applicant: Caribou Biosciences, Inc., Berkeley, CA (US)

(72) Inventors: Paul Daniel Donohoue, Berkeley, CA (US); Andrew Paul May, San Francisco, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,863

(22) Filed: May 4, 2018

(65) Prior Publication Data

US 2018/0251788 A1  Sep. 6, 2018

Related U.S. Application Data

(63) Continuation of application No. 15/703,992, filed on Sep. 14, 2017, now Pat. No. 9,970,029, which is a continuation of application No. 15/368,570, filed on Dec. 2, 2016, now Pat. No. 9,771,600.

(60) Provisional application No. 62/263,232, filed on Dec. 4, 2015.

(51) Int. Cl.
| | | |
|---|---|---|
| *C12N 15/90* | (2006.01) | |
| *C12N 15/113* | (2010.01) | |
| *C12N 9/22* | (2006.01) | |

(52) U.S. Cl.
CPC ............ *C12N 15/902* (2013.01); *C12N 9/22* (2013.01); *C12N 15/113* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang et al. |
| 8,771,945 B1 | 7/2014 | Zhang et al. |
| 8,795,965 B2 | 8/2014 | Zhang et al. |
| 8,865,406 B2 | 10/2014 | Zhang et al. |
| 8,871,445 B2 | 10/2014 | Zhang et al. |
| 8,889,356 B2 | 11/2014 | Zhang et al. |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Zhang et al. |
| 8,945,839 B2 | 2/2015 | Zhang et al. |
| 8,993,233 B2 | 3/2015 | Zhang et al. |
| 8,999,641 B2 | 4/2015 | Zhang et al. |
| 9,115,348 B2 | 8/2015 | Haurwitz et al. |
| 9,260,752 B1 | 2/2016 | May et al. |
| 9,771,600 B2 | 9/2017 | Donohoue et al. |
| 2011/0223638 A1 | 9/2011 | Wiedenheft et al. |
| 2014/0068797 A1 | 3/2014 | Doudna et al. |
| 2014/0302563 A1 | 10/2014 | Doudna et al. |
| 2014/0315985 A1 | 10/2014 | May et al. |
| 2015/0284727 A1 | 4/2015 | Kim et al. |
| 2015/0152398 A1 | 6/2015 | Doudna et al. |
| 2015/0376586 A1 | 12/2015 | May et al. |
| 2016/0046961 A1 | 2/2016 | Jinek et al. |

FOREIGN PATENT DOCUMENTS

| | | |
|---|---|---|
| WO | WO 2013/142578 | 9/2013 |
| WO | WO 2013/176772 | 11/2013 |
| WO | WO 2014/065596 | 5/2014 |
| WO | WO 2014/093712 | 6/2014 |
| WO | WO 2014/150624 | 9/2014 |
| WO | WO 2015/071474 | 5/2015 |

OTHER PUBLICATIONS

Afonin, Kirill A. et al. "Triggering of RNA Interference with RNA-RNA, RNA-DNA, and DNA-RNA Nanoparticles." ACS Nano 9.1 (2015): 251-259. doi: 10.1021/nn504508s.
Afonin, Kirill A. et al. "In Vitro Assembly of Cubic RNA-Based Scaffolds Designed in Silico." Nature Nanotechnology 5.9 (2010): 676-682.
Andersen, Felicie F. et al. "Assembly and Structural Analysis of a Covalently Closed Nano-Scale DNA Cage." *Nucleic Acids Research* 36.4 (2008): 1113-1119 (including Supplementary Data).
Chylinski, Krzysztof, Anaïs Le Rhun, and Emmanuelle Charpentier. "The tracrRNA and Cas9 Families of Type II CRISPR-Cas Immunity Systems." RNA Biology 10.5 (2013): 726-737.
Deshpande, Pranali P, Swati Biswas, and Vladimir P Torchilin. "Current Trends in the Use of Liposomes for Tumor Targeting." Nanomedicine (London, England) 8.9 (2013): 10.2217/nnm.13.118. doi:10.2217/nnm.13.118.
Fonfara, Ines et al. "Phylogeny of Cas9 Determines Functional Exchangeability of Dual-RNA and Cas9 among Orthologous Type II CRISPR-Cas Systems." Nucleic Acids Research 42.4 (2014): 2577-2590.
Haurwitz, Rachel E. et al. "Sequence- and Structure-Specific RNA Processing by a CRISPR Endonuclease." Science (New York, N.Y.) 329.5997 (2010): 1355-1358. PMC.
Jayanna, P.K., V.P. Torchilin, and V.A. Petrenko. "Liposomes Targeted by Fusion Phage Proteins." Nanomedicine nanotechnology, biology, and medicine 5.1 (2009): 83. doi:10.1016/j.nano.2008.07.006.

(Continued)

*Primary Examiner* — James S Ketter
(74) *Attorney, Agent, or Firm* — Gary R. Fabian; Barbara G. McClung

(57) ABSTRACT

The present disclosure provides engineered polynucleotide sequences that form scaffolds and nucleoprotein complexes comprising such engineered polynucleotide sequences that form scaffolds and nucleic acid binding proteins. Nucleic acid sequences encoding the engineered polynucleotide sequences that form scaffolds, as well as expression cassettes, vectors and cells comprising such polynucleotide sequences, are described. A variety of methods for making and using the engineered polynucleotide sequences that form scaffolds are also disclosed.

20 Claims, 66 Drawing Sheets

Specification includes a Sequence Listing.

(56) References Cited

OTHER PUBLICATIONS

Lapinaite, A. et al. "The structure of the box C/D enzyme reveals regulation of RNA methylation." Nature. 502, 519-523. Oct. 24, 2013. (Published online Oct. 13, 2013.) doi:10.1038/nature12581.

Sawant, Rupa R. and Torchilin, Vladimir P. "Challenges in Development of Targeted Liposomal Therapeutics." The AAPS Journal 14.2 (2012): 303-315. doi: 10.1208/s12248-012-9330-0.

Steichen, Stephanie D., Caldorera-Moore, Mary, and Peppas, Nicholas A. "A Review of Current Nanoparticle and Targeting Moieties for the Delivery of Cancer Therapeutics." European Journal of Pharmaceutical Sciences: Official Journal of the European Federation for Pharmaceutical Sciences 48.3 (2013): 416-427. doi:10.1016/j.ejps.2012.12.006.

Sternberg, Samuel H., Rachel E. Haurwitz, and Jennifer A. Doudna. "Mechanism of Substrate Selection by a Highly Specific CRISPR Endoribonuclease." RNA 18.4 (2012): 661-672.

Tinoco, Jr., I. "Appendix 1: Structures of Base Pairs Involving at Least Two Hydrogen Bonds" and Pleij, C. "Appendix 2: RNA Pseudoknots." The RNA World (Cold Spring Harbor Monograph Series), R. F. Gesteland, et al., Cold Spring Harbor Laboratory Press, ISBN 978-0879694562 (1993).

Briner, A., et al., "Guide RNA Functional Modules Direct Cas9 Activity and Orthogonality," Molecular Cell 56:333-339 (2014).

Cong, L., et al. "Multiplex Genome Engineering Using CRISPR/Cas Systems," Science, 339:819-823, and supplementary materials (2013).

Haurwitz, R., "The CRISPR endoribonuclease Csy4 utilizes unusual sequence- and structure-specific mechanisms to recognize and process crRNAs," UC Berkeley: Molecular & Cell Biology (2012). Retrieved from: http://escholarship.org/uc/item/0rh5940p.

Jiang, W., et al., "RNA-guided editing of bacterial genomes using CRISPR-Cas systems," Nature Biotechnology 31(3):233-239 (2013). doi:10.1038/nbt.2508.

Jinek, M., et al., "A programmable dual-RNA-guided DNA endonuclease in adaptive bacterial immunity," Science 337(6096):816-21, and supplementary materials (2012).

Makarova, K.S., et al., "An updated evolutionary classification of CRISPR-Cas systems," Nature Reviews Microbiology 13(11):722-36 (2015). doi: 10.1038/nrmicro3569.

Shmakov, S., et al., "Diversity and evolution of class 2 CRISPR-Cas systems," Nature Reviews Microbiology 15(3):169-182 (2017). doi: 10.1038/nrmicro.2016.184.

SEQUENCE LISTING

<160> NUMBER OF SEQ ID NOS: 109

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 1
agtaataata cgactcacta tag         23

<210> SEQ ID NO 2
<211> LENGTH: 26
<212> TYPE: DNA
<213> ORGANISM: Artificial Sequence -continued

```
<220> FEATURE:
<223> OTHER INFORMATION: Oligonucleotide Primer

<400> SEQUENCE: 2
aagcaccgac tcggtgccac tttttc                                            26

<210> SEQ ID NO 3
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 3
taatacgact cactataggg gccactaggg acaggatgtc tcagagctat gcagt           55

<210> SEQ ID NO 4
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 4
taatacgact cactatagta ggctatagtg tagatctgtc tcagagctat gcagt           55

<210> SEQ ID NO 5
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 5
taatacgact cactatagga aaaagtggaa gcggcgagtc tcagagctat gcagt           55

<210> SEQ ID NO 6
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 6
taatacgact cactataggc gataagtcgt gtcttacgtc tcagagctat gcagt           55

<210> SEQ ID NO 7
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 7
taatacgact cactataggg gccactaggg acaggatgca catgaggatt ctcat           55

<210> SEQ ID NO 8
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 8
taatacgact cactatagta ggctatagtg tagatctgca catgaggatt ctcat           55
```

<210> SEQ ID NO 9
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 9
taatacgact cactatagga aaaagtggaa gcggcgagca catgaggatt ctcat    55

<210> SEQ ID NO 10
<211> LENGTH: 55
<212> TYPE: DNA
<213> ORGANISM: Artificial Sequence
<220> FEATURE:
<223> OTHER INFORMATION: Oligonucleotide Primer

<400> SEQUENCE: 10
taatacgact cactataggc gataagtcgt gtcttacgca catgaggatt ctcat    55

<210> SEQ ID NO 11
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 11
gtctcagagc tatgcagtcc tggacaactg ccgaacagga ctgcatagca agttgagata    60

<210> SEQ ID NO 12
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 12
gactcggtgc cacttttca agttgataac ggactagcct tatctcaact tgctatgcag    60

<210> SEQ ID NO 13
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 13
gcacatgagg attctcatga gggacggcag aagaacctca tgagaatcca agtatgtgta    60

<210> SEQ ID NO 14
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 14
gactcggtgc cacttttca agttgataac ggactagcct tacacatact tggattctca    60

<210> SEQ ID NO 15
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 15
gtctcagagc tatgcagtcc tggacaactg ccgaacctca tgagaatcca agtatgtgta    60

<210> SEQ ID NO 16
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 16
gactcggtgc cacttttca agttgataac ggactagcct tacacatact tggattctca    60

<210> SEQ ID NO 17
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 17
gcacatgagg attctcatga gggacggcag aagaacagga ctgcatagca agttgagata    60

<210> SEQ ID NO 18
<211> LENGTH: 60
<212> TYPE: DNA
<213> ORGANISM: Artificial Sequence
<220> FEATURE:
<223> OTHER INFORMATION: Oligonucleotide Primer

<400> SEQUENCE: 18
gactcggtgc cactttttca agttgataac ggactagcct tatctcaact tgctatgcag    60

<210> SEQ ID NO 19
<211> LENGTH: 237
<212> TYPE: DNA
<213> ORGANISM: Artificial Sequence
<220> FEATURE:
<223> OTHER INFORMATION: cloning oligonucleotides
<220> FEATURE:
<221> NAME/KEY: misc_feature
<222> LOCATION: (125)..(125)
<223> OTHER INFORMATION: n is a, c, g, or t

<400> SEQUENCE: 19
tacacgtact tagtcgctga agctcttcta tgcaagcaga agacggcata cgagatcgag    60
taatgtgact ggagttcaga cgtgtgctct tccgatctgc tactgggcc actagggaca    120 ggatnggtgc tagctcagat cggaagagcg tcgtgtaggg aaagagtgta ggctatagtg    180
tagatctcgg tggtcgccgt atcattggta gaagagccgt caatcgagtt cgtacct    237

<210> SEQ ID NO 20
<211> LENGTH: 4175
<212> TYPE: DNA
<213> ORGANISM: Artificial Sequence
<220> FEATURE:
<223> OTHER INFORMATION: AAVS-1 target sequence

<400> SEQUENCE: 20
ctcatgacca aaatccctta acgtgagtta cgcgcgcgtc gttccactga gcgtcagacc    60
ccgtagaaaa gatcaaagga tcttcttgag atcctttttt tctgcgcgta atctgctgct    120
tgcaaacaaa aaaaccaccg ctaccagcgg tggtttgttt gccggatcaa gagctaccaa    180

```
ctcttttcc    gaaggtaact    ggcttcagca    gagcgcagat    accaaatact    gttcttctag        240
tgtagccgta    gttagcccac    cacttcaaga    actctgtagc    accgcctaca    tacctcgctc        300
tgctaatcct    gttaccagtg    gctgctgcca    gtggcgataa    gtcgtgtctt    accgggttgg        360
actcaagacg    atagttaccg    ataaggcgc    agcggtcggg    ctgaacgggg    ggttcgtgca        420
cacagcccag    cttggagcga    acgacctaca    ccgaactgag    atacctacag    cgtgagctat        480
gagaaagcgc    cacgcttccc    gaagggagaa    aggcggacag    gtatccggta    agcggcaggg        540
tcggaacagg    agagcgcacg    agggagcttc    caggggaaa    cgcctggtat    ctttatagtc        600
ctgtcgggtt    tcgccacctc    tgacttgagc    gtcgattttt    gtgatgctcg    tcagggggc        660 ggagcctatg    gaaaaacgcc    agcaacgcgg    cctttttacg    gttcctggcc    ttttgctggc        720
cttttgctca    catgttcttt    cctgcgttat    cccctgattc    tgtggataac    cgtattaccg        780
cctttgagtg    agctgatacc    gctcgccgca    gccgaacgac    cgagcgcagc    gagtcagtga        840
gcgaggaagc    ggaaggcgag    agtagggaac    tgccaggcat    caaactaagc    agaaggcccc        900
tgacggatgg    ccttttgcg    tttctacaaa    ctctttctgt    gttgtaaaac    gacggccagt        960
cttaagctcg    ggccccctgg    gcggttctga    taacgagtaa    tcgttaatcc    gcaaataacg       1020 taaaaaccg    cttcggcggg    tttttttatg    ggggagttt    agggaaagag    catttgtcag       1080
aatatttaag    ggcgcctgtc    actttgcttg    atatatgaga    attatttaac    cttataaatg       1140 agaaaaagc    aacgcacttt    aaataagata    cgttgctttt    tcgattgatg    aacacctata       1200
attaaactat    tcatctatta    tttatgattt    tttgtatata    caatatttct    agtttgttaa       1260
agagaattaa    gaaaataaat    ctcgaaaata    ataagggaa    aatcagtttt    tgatatcaaa       1320
attatacatg    tcaacgataa    tacaaaatat    aatacaaact    ataagatgtt    atcagtattt       1380
attatgcatt    tagaataaat    tttgtgtcgc    ccttaattgt    gagcggataa    caattacgag       1440
cttcatgcac    agtgaaatca    tgaaaaattt    atttgctttg    tgagcggata    acaattataa       1500
tatgtggaat    tgtgagcgct    cacaattcca    caacggtttc    cctctagaaa    taattttgtt       1560
taacttttaa    ggaggtaaaa    aatgtacacg    tacttagtcg    ctgaagctct    tctatgcaag       1620
cagaagacgg    catacgagat    cgagtaatgt    gactggagtt    cagacgtgtg    ctcttccgat       1680
ctgctactgg    ggccactagg    gacaggattg    gtgctagctc    agatcggaag    agcgtcgtgt       1740
agggaaagag    tgtaggctat    agtgtagatc    tcggtggtcg    ccgtatcatt    ggtagaagag       1800
ccgtcaatcg    agttcgtacc    tggttgaccc    caagggcgac    accccctaat    tagcccgggc       1860
gaaaggccca    gtctttcgac    tgagcctttc    gttttatttg    atgcctggca    gttccctact       1920
ctcgcatggg    gagtccccac    actaccatcg    cgctacggc    gtttcacttc    tgagttcggc       1980
atggggtcag    gtgggaccac    cgcgctactg    ccgccaggca    acaaggggt    gttatgagcc       2040 atattcaggt    ataatgggc    tcgcgataat    gttcagaatt    ggttaattgg    ttgtaacact       2100
gacccctatt    tgtttatttt    tctaaataca    ttcaaatatg    tatccgctca    tgagacaata       2160
accctgataa    atgcttcaat    aatattgaaa    aaggaagaat    atgagccata    ttcaacggga       2220
aacgtcgagg    ccgcgattaa    attccaacat    ggatgctgat    ttatatgggt    ataaatgggc       2280
tcgcgataat    gtcgggcaat    caggtgcgac    aatctatcgc    ttgtatggga    agcccgatgc       2340
gccagagttg    tttctgaaac    atggcaaagg    tagcgttgcc    aatgatgtta    cagatgagat       2400
ggtcagacta    aactggctga    cggaatttat    gccacttccg    accatcaagc    attttatccg       2460
tactcctgat    gatgcatggt    tactcaccac    tgcgatcccc    ggaaaaacag    cgttccaggt       2520
attagaagaa    tatcctgatt    caggtgaaaa    tattgttgat    gcgctggcag    tgttcctgcg       2580
```

```
ccggttgcac tcgattcctg tttgtaattg tccttttaac agcgatcgcg tatttcgcct    2640
cgctcaggcg caatcacgaa tgaataacgg tttggttgat gcgagtgatt ttgatgacga    2700
gcgtaatggc tggcctgttg aacaagtctg gaaagaaatg cataaacttt tgccattctc    2760
accggattca gtcgtcactc atggtgattt ctcacttgat aaccttattt ttgacgaggg    2820
gaaattaata ggttgtattg atgttggacg agtcggaatc gcagaccgat accaggatct    2880
tgccatccta tggaactgcc tcggtgagtt ttctccttca ttacagaaac ggttttttca    2940
aaaatatggt attgataatc ctgatatgaa taaattgcag tttcatttga tgctcgatga    3000
gtttttctaa gcggcgcgcc atcgaatggc gcaaaacctt tcgcggtatg gcatgatagc    3060
gcccggaaga gagtcaattc agggtggtga atatgaaacc agtaacgtta tacgatgtcg    3120
cagagtatgc cggtgtctct tatcagaccg tttcccgcgt ggtgaaccag gccagccacg    3180
tttctgcgaa aacgcgggaa aaagtggaag cggcgatggc ggagctgaat tacattccca    3240
accgcgtggc acaacaactg gcgggcaaac agtcgttgct gattggcgtt gccacctcca    3300
gtctggccct gcacgcgccg tcgcaaattg tcgcggcgat taaatctcgc gccgatcaac    3360
tgggtgccag cgtggtggtg tcgatggtag aacgaagcgg cgtcgaagcc tgtaaagcgg    3420
cggtgcacaa tcttctcgcg caacgcgtca gtgggctgat cattaactat ccgctggatg    3480
accaggatgc cattgctgtg gaagctgcct gcactaatgt tccggcgtta tttcttgatg    3540
tctctgacca gacacccatc aacagtatta ttttctccca tgaggacggt acgcgactgg    3600
gcgtggagca tctggtcgca ttgggtcacc agcaaatcgc gctgttagcg ggcccattaa    3660
gttctgtctc ggcgcgtctg cgtctggctg gctggcataa atatctcact cgcaatcaaa    3720
ttcagccgat agcggaacgg gaaggcgact ggagtgccat gtccggtttt caacaaacca    3780
tgcaaatgct gaatgagggc atcgttccca ctgcgatgct ggttgccaac gatcagatgg    3840
cgctgggcgc aatgcgcgcc attaccgagt ccgggctgcg cgttggtgcg gatatctcgg    3900
tagtgggata cgacgatacc gaagatagct catgttatat cccgccgtta accaccatca    3960
aacaggattt tcgcctgctg ggcaaaccag cgtggaccg cttgctgcaa ctctctcagg    4020
gccaggcggt gaagggcaat cagctgttgc cagtctcact ggtgaaaaga aaaaccaccc    4080
tggcgcccaa tacgcaaacc gcctctcccc gcgcgttggc cgattcatta atgcagctgg    4140
cacgacaggt ttcccgactg gaaagcgggc agtga    4175

<210> SEQ ID NO 21
<211> LENGTH: 56
<212> TYPE: DNA
<213> ORGANISM: Artificial Sequence
<220> FEATURE:
<223> OTHER INFORMATION: cloning oligonucleotides

<400> SEQUENCE: 21
tacacgtact tagtcgctga agctcttcta tgcaagcaga agacggcata cgagat    56

<210> SEQ ID NO 22
<211> LENGTH: 56
<212> TYPE: DNA
<213> ORGANISM: Artificial Sequence
<220> FEATURE:
<223> OTHER INFORMATION: cloning oligonucleotides

<400> SEQUENCE: 22
aggtacgaac tcgattgacg gctcttctac caatgatacg gcgaccaccg agatct    56
```

```
<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ccccgttctc ctgtggattc                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
atcctctctg gctccatcgt                                              20

<210> SEQ ID NO 25
<211> LENGTH: 127
<212> TYPE: RNA
<213> ORGANISM: Artificial Sequence
<220> FEATURE:
<223> OTHER INFORMATION: sgRNA-1-AAVST1

<400> SEQUENCE: 25 gggggccacua gggacaggau gucucagagc uaugcagucc uggacaacug ccgaacagga  60
cugcauagca aguugagaua aggcuagucc guuaucaacu ugaaaaagug gcaccgaguc  120
ggugcuu                                                            127

<210> SEQ ID NO 26
<211> LENGTH: 127
<212> TYPE: RNA
<213> ORGANISM: Artificial Sequence
<220> FEATURE:
<223> OTHER INFORMATION: sgRNA-1-VT2

<400> SEQUENCE: 26
guaggcuaua guguagaucu gucucagagc uaugcagucc uggacaacug ccgaacagga  60
cugcauagca aguugagaua aggcuagucc guuaucaacu ugaaaaagug gcaccgaguc  120
ggugcuu                                                            127

<210> SEQ ID NO 27
<211> LENGTH: 127
<212> TYPE: RNA
<213> ORGANISM: Artificial Sequence
<220> FEATURE:
<223> OTHER INFORMATION: sgRNA-1-VT3

<400> SEQUENCE: 27
ggaaaaagug gaagcggcga gucucagagc uaugcagucc uggacaacug ccgaacagga  60
cugcauagca aguugagaua aggcuagucc guuaucaacu ugaaaaagug gcaccgaguc  120
ggugcuu                                                            127

<210> SEQ ID NO 28
<211> LENGTH: 127
<212> TYPE: RNA
<213> ORGANISM: Artificial Sequence
<220> FEATURE:
<223> OTHER INFORMATION: sgRNA-1-VT4
```

```
<400> SEQUENCE: 28
ggcgauaagu cgugucuuac gucucagagc uaugcagucc uggacaacug ccgaacagga    60
cugcauagca aguugagaua aggcuagucc guuaucaacu ugaaaagug gcaccgaguc    120 ggugcuu                                                             127

<210> SEQ ID NO 29
<211> LENGTH: 127
<212> TYPE: RNA
<213> ORGANISM: Artificial Sequence
<220> FEATURE:
<223> OTHER INFORMATION: sgRNA-2-AAVST1

<400> SEQUENCE: 29
ggggccacua gggacaggau gcacaugagg auucucauga gggacggcag aagaaccuca    60
ugagaaucca aguaugugua aggcuagucc guuaucaacu ugaaaagug gcaccgaguc    120 ggugcuu                                                             127

<210> SEQ ID NO 30
<211> LENGTH: 127
<212> TYPE: RNA
<213> ORGANISM: Artificial Sequence
<220> FEATURE:
<223> OTHER INFORMATION: sgRNA-2-VT2

<400> SEQUENCE: 30
guaggcuaua guguagaucu gcacaugagg auucucauga gggacggcag aagaaccuca    60
ugagaaucca aguaugugua aggcuagucc guuaucaacu ugaaaagug gcaccgaguc    120 ggugcuu                                                             127

<210> SEQ ID NO 31
<211> LENGTH: 127
<212> TYPE: RNA
<213> ORGANISM: Artificial Sequence
<220> FEATURE:
<223> OTHER INFORMATION: sgRNA-2-VT3

<400> SEQUENCE: 31
ggaaaaagug gaagcggcga gcacaugagg auucucauga gggacggcag aagaaccuca    60
ugagaaucca aguaugugua aggcuagucc guuaucaacu ugaaaagug gcaccgaguc    120 ggugcuu                                                             127

<210> SEQ ID NO 32
<211> LENGTH: 127
<212> TYPE: RNA
<213> ORGANISM: Artificial Sequence
<220> FEATURE:
<223> OTHER INFORMATION: sgRNA-2-VT4

<400> SEQUENCE: 32
ggcgauaagu cgugucuuac gcacaugagg auucucauga gggacggcag aagaaccuca    60
ugagaaucca aguaugugua aggcuagucc guuaucaacu ugaaaagug gcaccgaguc    120 ggugcuu                                                             127

<210> SEQ ID NO 33
<211> LENGTH: 127
<212> TYPE: RNA
<213> ORGANISM: Artificial Sequence
<220> FEATURE:
```

<223> OTHER INFORMATION: NASC-PC1-AAVST1

<400> SEQUENCE: 33

```
gggccacua gggacaggau gucucagagc uaugcagucc uggacaacug ccgaaccuca    60
ugagaaucca aguaugugua aggcuagucc guuaucaacu ugaaaaagug gcaccgaguc   120
ggugcuu                                                             127
```

<210> SEQ ID NO 34
<211> LENGTH: 127
<212> TYPE: RNA
<213> ORGANISM: Artificial Sequence
<220> FEATURE:
<223> OTHER INFORMATION: NASC-PC1-VT2

<400> SEQUENCE: 34

```
guaggcuaua guguagaucu gucucagagc uaugcagucc uggacaacug ccgaaccuca    60
ugagaaucca aguaugugua aggcuagucc guuaucaacu ugaaaaagug gcaccgaguc   120
ggugcuu                                                             127
```

<210> SEQ ID NO 35
<211> LENGTH: 127
<212> TYPE: RNA
<213> ORGANISM: Artificial Sequence
<220> FEATURE:
<223> OTHER INFORMATION: NASC-PC1-VT3

<400> SEQUENCE: 35

```
ggaaaaagug gaagcggcga gucucagagc uaugcagucc uggacaacug ccgaaccuca    60
ugagaaucca aguaugugua aggcuagucc guuaucaacu ugaaaaagug gcaccgaguc   120
ggugcuu                                                             127
```

<210> SEQ ID NO 36
<211> LENGTH: 127
<212> TYPE: RNA
<213> ORGANISM: Artificial Sequence
<220> FEATURE:
<223> OTHER INFORMATION: NASC-PC1-VT4

<400> SEQUENCE: 36

```
ggcgauaagu cgugucuuac gucucagagc uaugcagucc uggacaacug ccgaaccuca    60
ugagaaucca aguaugugua aggcuagucc guuaucaacu ugaaaaagug gcaccgaguc   120
ggugcuu                                                             127
```

<210> SEQ ID NO 37
<211> LENGTH: 127
<212> TYPE: RNA
<213> ORGANISM: Artificial Sequence
<220> FEATURE:
<223> OTHER INFORMATION: NASC-PC2- AAVST1

<400> SEQUENCE: 37

```
gggccacua gggacaggau gcacaugagg auucucauga gggacggcag aagaacagga    60
cugcauagca aguugagaua aggcuagucc guuaucaacu ugaaaaagug gcaccgaguc   120
ggugcuu                                                             127
```

<210> SEQ ID NO 38
<211> LENGTH: 127
<212> TYPE: RNA
<213> ORGANISM: Artificial Sequence
```

```
<220> FEATURE:
<223> OTHER INFORMATION: NASC-PC2-VT2

<400> SEQUENCE: 38
guaggcuaua guguagaucu gcacaugagg auucucauga gggacggcag aagaacagga        60
cugcauagca aguugagaua aggcuagucc guuaucaacu ugaaaaagug gcaccgaguc       120
ggugcuu                                                                 127

<210> SEQ ID NO 39
<211> LENGTH: 127
<212> TYPE: RNA
<213> ORGANISM: Artificial Sequence
<220> FEATURE:
<223> OTHER INFORMATION: NASC-PC2-VT3

<400> SEQUENCE: 39
ggaaaaagug gaagcggcga gcacaugagg auucucauga gggacggcag aagaacagga        60
cugcauagca aguugagaua aggcuagucc guuaucaacu ugaaaaagug gcaccgaguc       120
ggugcuu                                                                 127

<210> SEQ ID NO 40
<211> LENGTH: 127
<212> TYPE: RNA
<213> ORGANISM: Artificial Sequence
<220> FEATURE:
<223> OTHER INFORMATION: NASC-PC2-VT4

<400> SEQUENCE: 40
ggcgauaagu cgugucuuac gcacaugagg auucucauga gggacggcag aagaacagga        60
cugcauagca aguugagaua aggcuagucc guuaucaacu ugaaaaagug gcaccgaguc       120
ggugcuu                                                                 127

<210> SEQ ID NO 41
<211> LENGTH: 20
<212> TYPE: DNA
<213> ORGANISM: Homo sapiens

<400> SEQUENCE: 41
ggtggacaag cggcagatag                                                    20

<210> SEQ ID NO 42
<211> LENGTH: 20
<212> TYPE: DNA
<213> ORGANISM: Homo sapiens

<400> SEQUENCE: 42
gcaccatgtt gccggtcctc                                                    20

<210> SEQ ID NO 43
<211> LENGTH: 118
<212> TYPE: RNA
<213> ORGANISM: Artificial Sequence
<220> FEATURE:
<223> OTHER INFORMATION: sgRNA- XRCC5-T1

<400> SEQUENCE: 43
gguggacaag cggcagauag guuuuagagc uaugcuguuu uggaaacaaa acagcauagc        60
aaguuaaaau aaggcuaguc cguuaucaac uugaaaaagu ggcaccgagu cggugcuu        118

<210> SEQ ID NO 44
```

```
<211> LENGTH: 118
<212> TYPE: RNA
<213> ORGANISM: Artificial Sequence
<220> FEATURE:
<223> OTHER INFORMATION: sgRNA- XRCC5-T3

<400> SEQUENCE: 44
gcaccauguu gccgguccuc guuuuagagc uaugcuguuu uggaaacaaa acagcauagc      60
aaguuaaaau aaggcuaguc cguuaucaac uugaaaaagu ggcaccgagu cggugcuu      118

<210> SEQ ID NO 45
<211> LENGTH: 118
<212> TYPE: RNA
<213> ORGANISM: Artificial Sequence
<220> FEATURE:
<223> OTHER INFORMATION: NASCA-PC1- XRCC5-T1

<400> SEQUENCE: 45
gguggacaag cggcagauag guuuuagagc uaugcuguuu uggaaacuuu ucagcacgau      60
aaguuauuau aaggcuaguc cguuaucaac uugaaaaagu ggcaccgagu cggugcuu      118

<210> SEQ ID NO 46
<211> LENGTH: 118
<212> TYPE: RNA
<213> ORGANISM: Artificial Sequence
<220> FEATURE:
<223> OTHER INFORMATION: NASCA-PC2- XRCC5-T3

<400> SEQUENCE: 46
gcaccauguu gccgguccuc guaauagaau cgugcugaaa aggaaacaaa acagcauagc      60
aaguuaaaau aaggcuaguc cguuaucaac uugaaaaagu ggcaccgagu cggugcuu      118

<210> SEQ ID NO 47
<211> LENGTH: 50
<212> TYPE: DNA
<213> ORGANISM: Artificial Sequence
<220> FEATURE:
<223> OTHER INFORMATION: XRCC5 target region 1

<400> SEQUENCE: 47
cactctttcc ctacacgacg ctcttccgat cttgcgcatg ctcagagttc      50

<210> SEQ ID NO 48
<211> LENGTH: 48
<212> TYPE: DNA
<213> ORGANISM: Artificial Sequence
<220> FEATURE:
<223> OTHER INFORMATION: XRCC5 target region 1

<400> SEQUENCE: 48
ggagttcaga cgtgtgctct tccgatctcc aagtccatgg ctttcttt      48

<210> SEQ ID NO 49
<211> LENGTH: 52
<212> TYPE: DNA
<213> ORGANISM: Artificial Sequence
<220> FEATURE:
<223> OTHER INFORMATION: XRCC5 target region 1

<400> SEQUENCE: 49
cactctttcc ctacacgacg ctcttccgat cttttcaggc ctagcaggaa ac      52

<210> SEQ ID NO 50
<211> LENGTH: 48
```

-continued

<210> SEQ ID NO 50
<211> LENGTH: 48
<212> TYPE: DNA
<213> ORGANISM: Artificial Sequence
<220> FEATURE:
<223> OTHER INFORMATION: XRCC5 target region 1

<400> SEQUENCE: 50
ggagttcaga cgtgtgctct tccgatctcc cattctttgt cttgaccg            48

<210> SEQ ID NO 51
<211> LENGTH: 57
<212> TYPE: DNA
<213> ORGANISM: Artificial Sequence
<220> FEATURE:
<223> OTHER INFORMATION: Primer

<400> SEQUENCE: 51
caagcagaag acggcatacg agattacgtg atgtgactgg agttcagacg tgtgctc    57

<210> SEQ ID NO 52
<211> LENGTH: 58
<212> TYPE: DNA
<213> ORGANISM: Artificial Sequence
<220> FEATURE:
<223> OTHER INFORMATION: Primer

<400> SEQUENCE: 52
aatgatacgg cgaccaccga gatctacacc gtctaataca ctctttccct acacgacg    58

<210> SEQ ID NO 53
<211> LENGTH: 58
<212> TYPE: DNA
<213> ORGANISM: Artificial Sequence
<220> FEATURE:
<223> OTHER INFORMATION: Primer

<400> SEQUENCE: 53
aatgatacgg cgaccaccga gatctacact ctctccgaca ctctttccct acacgacg    58

<210> SEQ ID NO 54
<211> LENGTH: 58
<212> TYPE: DNA
<213> ORGANISM: Artificial Sequence
<220> FEATURE:
<223> OTHER INFORMATION: Primer

<400> SEQUENCE: 54
aatgatacgg cgaccaccga gatctacact cgactagaca ctctttccct acacgacg    58

<210> SEQ ID NO 55
<211> LENGTH: 58
<212> TYPE: DNA
<213> ORGANISM: Artificial Sequence
<220> FEATURE:
<223> OTHER INFORMATION: Primer

<400> SEQUENCE: 55
aatgatacgg cgaccaccga gatctacact tctagctaca ctctttccct acacgacg    58

<210> SEQ ID NO 56
<211> LENGTH: 984
<212> TYPE: PRT
<213> ORGANISM: Campylobacter jejuni

<400> SEQUENCE: 56

Met Ala Arg Ile Leu Ala Phe Ala Ile Gly Ile Ser Ser Ile Gly Trp
1               5                   10                  15

```
Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
            35                  40                  45

Arg Leu Ala Arg Ser Ala Arg Lys Arg Leu Ala Arg Arg Lys Ala Arg
50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
            115                 120                 125

Arg Gly Tyr Asp Asp Ile Lys Asn Ser Asp Asp Lys Glu Lys Gly Ala
        130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Phe Glu Glu
            210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
        370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430
```

```
Asp Phe Leu Pro Ala Phe Asn Glu Thr Tyr Tyr Lys Asp Glu Val Thr
            435                 440                 445

Asn Pro Val Val Leu Arg Ala Ile Lys Glu Tyr Arg Lys Val Leu Asn
    450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Asp Ala Glu Leu Glu Cys
                500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp Ala Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
    595                 600                 605

Lys Asn Leu Pro Thr Lys Lys Gln Lys Arg Ile Leu Asp Lys Asn Tyr
            610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
                660                 665                 670

Lys Gly Ser Lys Val His Val Glu Ala Lys Ser Gly Met Leu Thr Ser
            675                 680                 685

Ala Leu Arg His Thr Trp Gly Phe Ser Ala Lys Asp Arg Asn Asn His
    690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
    755                 760                 765

Lys Ile Asp Glu Ile Phe Val Ser Lys Pro Glu Arg Lys Lys Pro Ser
770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
    835                 840                 845

Ile Tyr Thr Met Asp Phe Ala Leu Lys Val Leu Pro Asn Lys Ala Val
```

```
                850             855             860
Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
        915                 920                 925

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980

<210> SEQ ID NO 57
<211> LENGTH: 146
<212> TYPE: RNA
<213> ORGANISM: Artificial Sequence
<220> FEATURE:
<223> OTHER INFORMATION: NASC-PC1-triplex1

<400> SEQUENCE: 57
aucuuguuga cacgaggaau guuuuagucc cuaauuaaau uucuugaaau ugguauauaa    60
ggagggacua caacaaagag uuugcgggac ucugcggggu uacaaucccc uaaaaccgcu   120
uuuaaaauuc aaauaaauuu ugcuuu                                       146

<210> SEQ ID NO 58
<211> LENGTH: 146
<212> TYPE: RNA
<213> ORGANISM: Artificial Sequence
<220> FEATURE:
<223> OTHER INFORMATION: NASC-PC2-triplex1

<400> SEQUENCE: 58
aucuuguuga cacgaggaau guuguagucc cuccuuauau accaagaaaa agaaauuuaa    60
aacugaacuc caacaaagag uuugcgggac ucugcggggu uacaaucccc uaaaaccgcu   120
uuuaaaauuc aaauaaauuu ugcuuu                                       146

<210> SEQ ID NO 59
<211> LENGTH: 146
<212> TYPE: RNA
<213> ORGANISM: Artificial Sequence
<220> FEATURE:
<223> OTHER INFORMATION: NASC-PC3-triplex1

<400> SEQUENCE: 59
aucuuguuga cacgaggaau guuggaguuc aguuuuaaau uucuugaaaa agaaauuuaa    60
uuagggacua aaacaaagag uuugcgggac ucugcggggu uacaaucccc uaaaaccgcu   120
uuuaaaauuc aaauaaauuu ugcuuu                                       146

<210> SEQ ID NO 60
<211> LENGTH: 146
<212> TYPE: RNA
<213> ORGANISM: Artificial Sequence
```

```
<220> FEATURE:
<223> OTHER INFORMATION: NASC-PC1-triplex2

<400> SEQUENCE: 60
cgauauaaua cagcaaggug guuuuagacc ccucuuccau uucgcgaaag cguuuugaga      60
gagugaacua caacaaagag uuugcgggac ucugcggggu acaauccccc uaaaaccgcu    120
uuuaaaauuc aaauaaauuu ugcuuu                                         146

<210> SEQ ID NO 61
<211> LENGTH: 146
<212> TYPE: RNA
<213> ORGANISM: Artificial Sequence
<220> FEATURE:
<223> OTHER INFORMATION: NASC-PC2-triplex2

<400> SEQUENCE: 61
cgauauaaua cagcaaggug guuguaguuc acucucucaa aacgcgaaaa agaaauuuaa     60
uaaggaacua caacaaagag uuugcgggac ucugcggggu acaauccccc uaaaaccgcu   120
uuuaaaauuc aaauaaauuu ugcuuu                                        146

<210> SEQ ID NO 62
<211> LENGTH: 146
<212> TYPE: RNA
<213> ORGANISM: Artificial Sequence
<220> FEATURE:
<223> OTHER INFORMATION: NASC-PC3-triplex2

<400> SEQUENCE: 62
cgauauaaua cagcaaggug guuguaguuc cuuauuaaau uucuugaaag cgaaauggaa     60
gaggggucua aaacaaagag uuugcgggac ucugcggggu acaauccccc uaaaaccgcu   120
uuuaaaauuc aaauaaauuu ugcuuu                                        146

<210> SEQ ID NO 63
<211> LENGTH: 144
<212> TYPE: DNA
<213> ORGANISM: Artificial Sequence
<220> FEATURE:
<223> OTHER INFORMATION: oligonucleotide sequence

<400> SEQUENCE: 63
cgtcgctatg atttgcctat atcttgttga cacgaggaat gtaaacaacg agttccgcta    60
ttgggatgga gtttaactgt cgcaactctc atcgcaatgt cagtcacctt gctgtattat   120
atcgcgcatg ataaagtacg ccat                                          144

<210> SEQ ID NO 64
<211> LENGTH: 65
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (46)..(65)
<223> OTHER INFORMATION: n is a, c, g, or u

<400> SEQUENCE: 64
cuccggcgau gucacaccga acugauaauu ucuacucuug uagaunnnnn nnnnnnnnnn    60 nnnnn                                                                65

<210> SEQ ID NO 65
```

```
<211> LENGTH: 65
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (46)..(65)
<223> OTHER INFORMATION: n is a, c, g, or u

<400> SEQUENCE: 65
ucggugugac aucgccggag uugauaaauu ucuacucuug uagaunnnnn nnnnnnnnnn      60 nnnnn                                                                 65

<210> SEQ ID NO 66
<211> LENGTH: 35
<212> TYPE: RNA
<213> ORGANISM: Artificial Sequence
<220> FEATURE:
<223> OTHER INFORMATION: NASCA polynucleotide component

<400> SEQUENCE: 66
cuccggcgau gucacaccga acugauaauu ucuac                                35

<210> SEQ ID NO 67
<211> LENGTH: 26
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (7)..(26)
<223> OTHER INFORMATION: n is a, c, g, or u

<400> SEQUENCE: 67
guagaunnnn nnnnnnnnnn nnnnnn                                          26

<210> SEQ ID NO 68
<211> LENGTH: 35
<212> TYPE: RNA
<213> ORGANISM: Artificial Sequence
<220> FEATURE:
<223> OTHER INFORMATION: NASCA polynucleotide component

<400> SEQUENCE: 68
ucggugugac aucgccggag uugauaaauu uguag                                35

<210> SEQ ID NO 69
<211> LENGTH: 26
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (7)..(26)
<223> OTHER INFORMATION: n is a, c, g, or u

<400> SEQUENCE: 69
cuacaunnnn nnnnnnnnnn nnnnnn                                          26

<210> SEQ ID NO 70
<211> LENGTH: 65
<212> TYPE: RNA
<213> ORGANISM: Artificial Sequence
<220> FEATURE:
<223> OTHER INFORMATION: NASCA polynucleotide component
```

```
<220> FEATURE:
<221> NAME/KEY: misc_feature
<222> LOCATION: (20)..(39)
<223> OTHER INFORMATION: n is a, c, g, or u

<400> SEQUENCE: 70
aauuucuacu cuuguagaun nnnnnnnnnn nnnnnnnnna cugaucuccg gcgaugucac    60
accga                                                                65

<210> SEQ ID NO 71
<211> LENGTH: 65
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (20)..(39)
<223> OTHER INFORMATION: n is a, c, g, or u

<400> SEQUENCE: 71
aauuucuacu cuuguagaun nnnnnnnnnn nnnnnnnnnu ugauaucggu gugacaucgc    60
cggag                                                                65

<210> SEQ ID NO 72
<211> LENGTH: 91
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (46)..(65)
<223> OTHER INFORMATION: n is a, c, g, or u

<400> SEQUENCE: 72
cuccggcgau gucacaccga acugauaauu ucuacucuug uagaunnnnn nnnnnnnnnn    60
nnnnnuugau agcuaaggc agcuaggguc u                                   91

<210> SEQ ID NO 73
<211> LENGTH: 65
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (46)..(65)
<223> OTHER INFORMATION: n is a, c, g, or u

<400> SEQUENCE: 73
ucggugugac aucgccggag uugauaaauu ucuacucuug uagaunnnnn nnnnnnnnnn    60 nnnnn                                                                65

<210> SEQ ID NO 74
<211> LENGTH: 65
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (20)..(39)
<223> OTHER INFORMATION: n is a, c, g, or u

<400> SEQUENCE: 74
```

```
aauuucuacu cuuguagaun nnnnnnnnnn nnnnnnnnnu accaaagacc cuagcugccu    60
uagac                                                               65
```

<210> SEQ ID NO 75
<211> LENGTH: 91
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (72)..(91)
<223> OTHER INFORMATION: n is a, c, g, or u

<400> SEQUENCE: 75

```
cuccggcgau gucacaccga acugaugucu aaggcagcua gggucuuuga uaaauuucua    60
cucuuguaga unnnnnnnnn nnnnnnnnnn n                                  91
```

<210> SEQ ID NO 76
<211> LENGTH: 91
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (72)..(91)
<223> OTHER INFORMATION: n is a, c, g, or u

<400> SEQUENCE: 76

```
ugcgaaccac ugugagccag uaccaaucgg ugugacaucg ccggaguuga uaaauuucua    60
cucuuguaga unnnnnnnnn nnnnnnnnnn n                                  91
```

<210> SEQ ID NO 77
<211> LENGTH: 61
<212> TYPE: RNA
<213> ORGANISM: Artificial Sequence
<220> FEATURE:
<223> OTHER INFORMATION: NASCA polynucleotide component

<400> SEQUENCE: 77

```
cuccggcgau gucacaccga acugaugucu aaggcagcua gggucuuuga uaaauuucua    60
c                                                                   61
```

<210> SEQ ID NO 78
<211> LENGTH: 26
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (7)..(26)
<223> OTHER INFORMATION: n is a, c, g, or u

<400> SEQUENCE: 78

```
guagaunnnn nnnnnnnnnn nnnnnn                                        26
```

<210> SEQ ID NO 79
<211> LENGTH: 61
<212> TYPE: RNA
<213> ORGANISM: Artificial Sequence
<220> FEATURE:
<223> OTHER INFORMATION: NASCA polynucleotide component

<400> SEQUENCE: 79

```
ugcgaaccac ugugagccag uaccaaucgg ugugacaucg ccggaguuga uaaauuugua    60
g                                                                    61
```

<210> SEQ ID NO 80
<211> LENGTH: 26
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (7)..(26)
<223> OTHER INFORMATION: n is a, c, g, or u

<400> SEQUENCE: 80

```
cuacaunnnn nnnnnnnnnn nnnnnn                                         26
```

<210> SEQ ID NO 81
<211> LENGTH: 146
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 81

```
nnnnnnnnnn nnnnnnnnnn guuuuagucc cuaauuaaau uucuugaaau ugguauauaa    60
ggagggacua caacaaagag uuugcgggac ucugcggggu uacaaucccc uaaaaccgcu   120
uuuaaaauuc aaauaaauuu ugcuuu                                        146
```

<210> SEQ ID NO 82
<211> LENGTH: 146
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 82

```
nnnnnnnnnn nnnnnnnnnn guuguagucc cuccuuauau accaagaaaa agaaauuuaa    60
uuagggacua aaacaaagag uuugcgggac ucugcggggu uacaaucccc uaaaaccgcu   120
uuuaaaauuc aaauaaauuu ugcuuu                                        146
```

<210> SEQ ID NO 83
<211> LENGTH: 127
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 83

```
nnnnnnnnnn nnnnnnnnnn gucucagagc uaugcagucc uggacaacug ccgaaccuca    60
ugagaaucca aguaugugua aggcuagucc guuaucaacu ugaaaagug gcaccgaguc   120
```

```
<210> SEQ ID NO 84
<211> LENGTH: 127
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 84
nnnnnnnnnn nnnnnnnnnn gcacaugagg auucucauga gggacggcag aagaacagga      60
cugcauagca aguugagaua aggcuagucc guuaucaacu ugaaaaagug gcaccgaguc     120
ggugcuu                                                              127

<210> SEQ ID NO 85
<211> LENGTH: 118
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 85
nnnnnnnnnn nnnnnnnnnn guuuuagagc uaugcuguuu uggaaagguc auguccuuca      60
aaguuguaau aaggcuaguc cguuaucaac uugaaaaagu ggcaccgagu cggugcuu      118

<210> SEQ ID NO 86
<211> LENGTH: 118
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 86
nnnnnnnnnn nnnnnnnnnn guaauagaau cgugcugaaa aggaaacaaa acagcauagc      60
aaguuaaaau aaggcuaguc cguuaucaac uugaaaaagu ggcaccgagu cggugcuu      118

<210> SEQ ID NO 87
<211> LENGTH: 118
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 87
nnnnnnnnnn nnnnnnnnnn guuacagaug aaggacauga ccgaaacuuu ucagcacgau      60
aaguuauuau aaggcuaguc cguuaucaac uugaaaaagu ggcaccgagu cggugcuu      118

<210> SEQ ID NO 88
<211> LENGTH: 45
```

```
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 88
nnnnnnnnnn nnnnnnnnnn guuuuagucc cuaauuaaau uucuu            45

<210> SEQ ID NO 89
<211> LENGTH: 45
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 89
nnnnnnnnnn nnnnnnnnnn guuguagucc cuccuuauau accaa            45

<210> SEQ ID NO 90
<211> LENGTH: 205
<212> TYPE: RNA
<213> ORGANISM: Artificial Sequence
<220> FEATURE:
<223> OTHER INFORMATION: NASCA polynucleotide component

<400> SEQUENCE: 90
aagaaauuua auuagggacu aaaacaaaga guuugcggga cucugcgggg uuacaauccc    60
cuaaaaccgc uuuuaaaauu caaauaaauu uugcuuuagu ugauaaauuu gguauauaag   120
gagggacuac aacaaagagu uugcgggacu cugcgggguu acaaucccu aaaaccgcuu    180 uuaaaauuca aauaaauuuu gcuuu                                        205

<210> SEQ ID NO 91
<211> LENGTH: 75
<212> TYPE: DNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, t or u

<400> SEQUENCE: 91
nnnnnnnnnn nnnnnnnnnn guuuuagagc tatgctgtga aaacagcata gcaaguuaaa    60
auaaggcuac ugccg                                                    75

<210> SEQ ID NO 92
<211> LENGTH: 75
<212> TYPE: DNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, t or u

<400> SEQUENCE: 92
```

```
nnnnnnnnnn nnnnnnnnnn guuuuagagc tatgctgtga aaacagcata gcaaguuaaa      60
auaaggcuag ucacg                                                       75

<210> SEQ ID NO 93
<211> LENGTH: 105
<212> TYPE: RNA
<213> ORGANISM: Artificial Sequence
<220> FEATURE:
<223> OTHER INFORMATION: NASCA polynucleotide component

<400> SEQUENCE: 93
cggcaguccg uuaucaacuu gaaaaagugg caccgagucg gugcuuaguu gauaaaucgu      60
gacguccguu aucaacuuga aaaguggca ccgagucggu gcuuu                      105

<210> SEQ ID NO 94
<211> LENGTH: 155
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (136)..(155)
<223> OTHER INFORMATION: n is a, c, g, or u

<400> SEQUENCE: 94
nnnnnnnnnn nnnnnnnnnn guuuuagagc uaugcuguga aaacagcaua gcaaguuaaa      60
auaaggcuag uccguuauca acuugaaaaa guggcaccga gucggugcuu acugauaauu     120
ucuacucuug uagaunnnnn nnnnnnnnnn nnnn                                 155

<210> SEQ ID NO 95
<211> LENGTH: 114
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 95
nnnnnnnnnn nnnnnnnnnn guuuuguac ucucaagauu caaauaacag cauagcaagu       60 uaaauaagg cuuccguua ucaacuugaa aaguggcac cgagucggug cuuu              114

<210> SEQ ID NO 96
<211> LENGTH: 116
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u

<400> SEQUENCE: 96
nnnnnnnnnn nnnnnnnnnn guuuuagagc uaugcuguua cguaaaucuu gcagaagcua      60
caaagauaag gcuucaugcc gaaaucaaca cccgucauu uuauggcagg guguuu          116
```

-continued

```
<210> SEQ ID NO 97
<211> LENGTH: 76
<212> TYPE: RNA
<213> ORGANISM: Artificial Sequence
<220> FEATURE:
<223> OTHER INFORMATION: NASCA polynucleotide component
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (57)..(76)
<223> OTHER INFORMATION: n is a, c, g, or u

<400> SEQUENCE: 97
nnnnnnnnnn nnnnnnnnnn guuuuagagc uaugcuguua ccaauugaua guagaunnnn    60
nnnnnnnnnn nnnnnn                                                    76

<210> SEQ ID NO 98
<211> LENGTH: 83
<212> TYPE: RNA
<213> ORGANISM: Artificial Sequence
<220> FEATURE:
<223> OTHER INFORMATION: NASCA polynucleotide component

<400> SEQUENCE: 98
aauuucuacu ugauaacagc auagcaaguu aaaauaaggc uauccguuau caacuugaaa    60
aaguggcacc gagucggugc uuu                                            83

<210> SEQ ID NO 99
<211> LENGTH: 1053
<212> TYPE: PRT
<213> ORGANISM: Staphylococcus aureus

<400> SEQUENCE: 99

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
                100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190
```

```
Leu Asp Gln Ser Phe Ile Asp Thr Tyr Ile Asp Leu Glu Thr Arg
        195                 200                 205
Arg Thr Tyr Tyr Glu Gly Pro Gly Gly Ser Pro Phe Gly Trp Lys
210                 215                 220
Asp Ile Lys Glu Trp Tyr Glu Met Leu Met Gly His Cys Thr Tyr Phe
225                 230                 235                 240
Pro Glu Glu Leu Arg Ser Val Lys Tyr Ala Tyr Asn Ala Asp Leu Tyr
                245                 250                 255
Asn Ala Leu Asn Asp Leu Asn Asn Leu Val Ile Thr Arg Asp Glu Asn
                260                 265                 270
Glu Lys Leu Glu Tyr Tyr Glu Lys Phe Gln Ile Ile Glu Asn Val Phe
            275                 280                 285
Lys Gln Lys Lys Lys Pro Thr Leu Lys Gln Ile Ala Lys Glu Ile Leu
290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                325                 330                 335
Ala Arg Lys Glu Ile Ile Glu Asn Ala Glu Leu Leu Asp Gln Ile Ala
                340                 345                 350
Lys Ile Leu Thr Ile Tyr Gln Ser Ser Glu Asp Ile Gln Glu Glu Leu
            355                 360                 365
Thr Asn Leu Asn Ser Glu Leu Thr Gln Glu Glu Ile Glu Gln Ile Ser
        370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
                420                 425                 430
Gln Lys Glu Ile Pro Thr Thr Leu Val Asp Asp Phe Ile Leu Ser Pro
            435                 440                 445
Val Val Lys Arg Ser Phe Ile Gln Ser Ile Lys Val Ile Asn Ala Ile
        450                 455                 460
Ile Lys Lys Tyr Gly Leu Pro Asn Asp Ile Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
                500                 505                 510
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Asn Ser Lys Lys Gly Asn Arg Thr Pro Phe Gln Tyr Leu
                580                 585                 590
Ser Ser Ser Asp Ser Lys Ile Ser Tyr Glu Thr Phe Lys Lys His Ile
            595                 600                 605
Leu Asn Leu Ala Lys Gly Lys Gly Arg Ile Ser Lys Thr Lys Lys Glu
```

-continued

```
            610                 615                 620
Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
            690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Glu Glu Thr Gly Asn Tyr
            850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
930                 935                 940

Lys Ala Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
            995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035
```

-continued

```
Tyr Glu Val Lys Ser Lys Lys His Pro Gln Ile Ile Lys Lys Gly
     1040                1045                1050

<210> SEQ ID NO 100
<211> LENGTH: 1368
<212> TYPE: PRT
<213> ORGANISM: Streptococcus pyogenes

<400> SEQUENCE: 100

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Ser Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
```

```
            355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
770                 775                 780
```

-continued

```
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185
```

```
Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 101
<211> LENGTH: 1368
<212> TYPE: PRT
<213> ORGANISM: Streptococcus pyogenes

<400> SEQUENCE: 101

Met Asp Lys Lys Tyr Ser Ile Gly Leu Ala Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

```
Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Ser Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605
```

```
Asn Glu Glu Asn Glu Asp Ile Leu Glu Asp Ile Val Leu Thr Leu Thr
    610             615                 620
Leu Phe Glu Asp Arg Glu Met Ile Glu Arg Leu Lys Thr Tyr Ala
625                 630                 635                 640
His Leu Phe Asp Asp Lys Val Met Lys Gln Leu Lys Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
        835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
```

```
                    1025                1030                1035

Tyr  Ser  Asn  Ile  Met  Asn  Phe  Phe  Lys  Thr  Glu  Ile  Thr  Leu  Ala
          1040                1045                1050

Asn  Gly  Glu  Ile  Arg  Lys  Arg  Pro  Leu  Ile  Glu  Thr  Asn  Gly  Glu
          1055                1060                1065

Thr  Gly  Glu  Ile  Val  Trp  Asp  Lys  Gly  Arg  Asp  Phe  Ala  Thr  Val
          1070                1075                1080

Arg  Lys  Val  Leu  Ser  Met  Pro  Gln  Val  Asn  Ile  Val  Lys  Lys  Thr
          1085                1090                1095

Glu  Val  Gln  Thr  Gly  Gly  Phe  Ser  Lys  Glu  Ser  Ile  Leu  Pro  Lys
          1100                1105                1110

Arg  Asn  Ser  Asp  Lys  Leu  Ile  Ala  Arg  Lys  Lys  Asp  Trp  Asp  Pro
          1115                1120                1125

Lys  Lys  Tyr  Gly  Gly  Phe  Asp  Ser  Pro  Thr  Val  Ala  Tyr  Ser  Val
          1130                1135                1140

Leu  Val  Val  Ala  Lys  Val  Glu  Lys  Gly  Lys  Ser  Lys  Lys  Leu  Lys
          1145                1150                1155

Ser  Val  Lys  Glu  Leu  Leu  Gly  Ile  Thr  Ile  Met  Glu  Arg  Ser  Ser
          1160                1165                1170

Phe  Glu  Lys  Asn  Pro  Ile  Asp  Phe  Leu  Glu  Ala  Lys  Gly  Tyr  Lys
          1175                1180                1185

Glu  Val  Lys  Lys  Asp  Leu  Ile  Ile  Lys  Leu  Pro  Lys  Tyr  Ser  Leu
          1190                1195                1200

Phe  Glu  Leu  Glu  Asn  Gly  Arg  Lys  Arg  Met  Leu  Ala  Ser  Ala  Gly
          1205                1210                1215

Glu  Leu  Gln  Lys  Gly  Asn  Glu  Leu  Ala  Leu  Pro  Ser  Lys  Tyr  Val
          1220                1225                1230

Asn  Phe  Leu  Tyr  Leu  Ala  Ser  His  Tyr  Glu  Lys  Leu  Lys  Gly  Ser
          1235                1240                1245

Pro  Glu  Asp  Asn  Glu  Gln  Lys  Gln  Leu  Phe  Val  Glu  Gln  His  Lys
          1250                1255                1260

His  Tyr  Leu  Asp  Glu  Ile  Ile  Glu  Gln  Ile  Ser  Glu  Phe  Ser  Lys
          1265                1270                1275

Arg  Val  Ile  Leu  Ala  Asp  Ala  Asn  Leu  Asp  Lys  Val  Leu  Ser  Ala
          1280                1285                1290

Tyr  Asn  Lys  His  Arg  Asp  Lys  Pro  Ile  Arg  Glu  Gln  Ala  Glu  Asn
          1295                1300                1305

Ile  Ile  His  Leu  Phe  Thr  Leu  Thr  Asn  Leu  Gly  Ala  Pro  Ala  Ala
          1310                1315                1320

Phe  Lys  Tyr  Phe  Asp  Thr  Thr  Ile  Asp  Arg  Lys  Arg  Tyr  Thr  Ser
          1325                1330                1335

Thr  Lys  Glu  Val  Leu  Asp  Ala  Thr  Leu  Ile  His  Gln  Ser  Ile  Thr
          1340                1345                1350

Gly  Leu  Tyr  Glu  Thr  Arg  Ile  Asp  Leu  Ser  Gln  Leu  Gly  Gly  Asp
          1355                1360                1365

<210> SEQ ID NO 102
<211> LENGTH: 1053
<212> TYPE: PRT
<213> ORGANISM: Staphylococcus aureus

<400> SEQUENCE: 102

Met  Lys  Arg  Asn  Tyr  Ile  Leu  Gly  Leu  Ala  Ile  Gly  Ile  Thr  Ser  Val
1               5                   10                  15
```

```
Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
```

```
                    435                 440                 445
Val Val Lys Arg Ser Phe Ile Gln Ser Ile Lys Val Ile Asn Ala Ile
        450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                    485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
        530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Ala Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860
```

Leu Thr Lys Tyr Ser Lys Lys Asp Asn Gly Pro Val Ile Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
        930                 935                 940

Lys Ala Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Lys Lys Gly
    1040                1045                1050

<210> SEQ ID NO 103
<211> LENGTH: 984
<212> TYPE: PRT
<213> ORGANISM: Campylobacter jejuni

<400> SEQUENCE: 103

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
        35                  40                  45

Arg Leu Ala Arg Ser Ala Arg Lys Arg Leu Ala Arg Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu

```
            180                 185                 190
Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
    370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
    435                 440                 445

Asn Pro Val Leu Arg Ala Ile Lys Glu Tyr Arg Lys Val Leu Asn
450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
        515                 520                 525

Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605
```

```
Lys Asn Leu Pro Thr Lys Lys Gln Lys Arg Ile Leu Asp Lys Asn Tyr
610                 615                 620
Lys Asp Lys Glu Gln Lys Asn Phe Lys Asp Arg Asn Leu Asn Asp Thr
625                 630                 635                 640
Arg Tyr Ile Ala Arg Leu Val Leu Asn Tyr Thr Lys Asp Tyr Leu Asp
                645                 650                 655
Phe Leu Pro Leu Ser Asp Asp Glu Asn Thr Lys Leu Asn Asp Thr Gln
            660                 665                 670
Lys Gly Ser Lys Val His Val Glu Ala Lys Ser Gly Met Leu Thr Ser
        675                 680                 685
Ala Leu Arg His Thr Trp Gly Phe Ser Ala Lys Asp Arg Asn Asn His
690                 695                 700
Leu His His Ala Ile Asp Ala Val Ile Ile Ala Tyr Ala Asn Asn Ser
705                 710                 715                 720
Ile Val Lys Ala Phe Ser Asp Phe Lys Lys Glu Gln Glu Ser Asn Ser
                725                 730                 735
Ala Glu Leu Tyr Ala Lys Lys Ile Ser Glu Leu Asp Tyr Lys Asn Lys
            740                 745                 750
Arg Lys Phe Phe Glu Pro Phe Ser Gly Phe Arg Gln Lys Val Leu Asp
        755                 760                 765
Lys Ile Asp Glu Ile Phe Val Ser Lys Pro Glu Arg Lys Lys Pro Ser
770                 775                 780
Gly Ala Leu His Glu Glu Thr Phe Arg Lys Glu Glu Glu Phe Tyr Gln
785                 790                 795                 800
Ser Tyr Gly Gly Lys Glu Gly Val Leu Lys Ala Leu Glu Leu Gly Lys
                805                 810                 815
Ile Arg Lys Val Asn Gly Lys Ile Val Lys Asn Gly Asp Met Phe Arg
            820                 825                 830
Val Asp Ile Phe Lys His Lys Lys Thr Asn Lys Phe Tyr Ala Val Pro
        835                 840                 845
Ile Tyr Thr Met Asp Phe Ala Leu Lys Val Leu Pro Asn Lys Ala Val
850                 855                 860
Ala Arg Ser Lys Lys Gly Glu Ile Lys Asp Trp Ile Leu Met Asp Glu
865                 870                 875                 880
Asn Tyr Glu Phe Cys Phe Ser Leu Tyr Lys Asp Ser Leu Ile Leu Ile
                885                 890                 895
Gln Thr Lys Asp Met Gln Glu Pro Glu Phe Val Tyr Tyr Asn Ala Phe
            900                 905                 910
Thr Ser Ser Thr Val Ser Leu Ile Val Ser Lys His Asp Asn Lys Phe
        915                 920                 925
Glu Thr Leu Ser Lys Asn Gln Lys Ile Leu Phe Lys Asn Ala Asn Glu
930                 935                 940
Lys Glu Val Ile Ala Lys Ser Ile Gly Ile Gln Asn Leu Lys Val Phe
945                 950                 955                 960
Glu Lys Tyr Ile Val Ser Ala Leu Gly Glu Val Thr Lys Ala Glu Phe
                965                 970                 975
Arg Gln Arg Glu Asp Phe Lys Lys
            980

<210> SEQ ID NO 104
<211> LENGTH: 1307
<212> TYPE: PRT
<213> ORGANISM: Acidaminococcus sp.
```

<400> SEQUENCE: 104

```
Met Thr Gln Phe Glu Gly Phe Thr Asn Leu Tyr Gln Val Ser Lys Thr
1               5                   10                  15
Leu Arg Phe Glu Leu Ile Pro Gln Gly Lys Thr Leu Lys His Ile Gln
            20                  25                  30
Glu Gln Gly Phe Ile Glu Asp Lys Ala Arg Asn Asp His Tyr Lys
        35                  40                  45
Glu Leu Lys Pro Ile Ile Asp Arg Ile Tyr Lys Thr Tyr Ala Asp Gln
50                  55                  60
Cys Leu Gln Leu Val Gln Leu Asp Trp Glu Asn Leu Ser Ala Ala Ile
65                  70                  75                  80
Asp Ser Tyr Arg Lys Glu Lys Thr Glu Glu Thr Arg Asn Ala Leu Ile
                85                  90                  95
Glu Glu Gln Ala Thr Tyr Arg Asn Ala Ile His Asp Tyr Phe Ile Gly
            100                 105                 110
Arg Thr Asp Asn Leu Thr Asp Ala Ile Asn Lys Arg His Ala Glu Ile
        115                 120                 125
Tyr Lys Gly Leu Phe Lys Ala Glu Leu Phe Asn Gly Lys Val Leu Lys
130                 135                 140
Gln Leu Gly Thr Val Thr Thr Thr Glu His Glu Asn Ala Leu Leu Arg
145                 150                 155                 160
Ser Phe Asp Lys Phe Thr Thr Tyr Phe Ser Gly Phe Tyr Glu Asn Arg
                165                 170                 175
Lys Asn Val Phe Ser Ala Glu Asp Ile Ser Thr Ala Ile Pro His Arg
            180                 185                 190
Ile Val Gln Asp Asn Phe Pro Lys Phe Lys Glu Asn Cys His Ile Phe
        195                 200                 205
Thr Arg Leu Ile Thr Ala Val Pro Ser Leu Arg Glu His Phe Glu Asn
210                 215                 220
Val Lys Lys Ala Ile Gly Ile Phe Val Ser Thr Ser Ile Glu Glu Val
225                 230                 235                 240
Phe Ser Phe Pro Phe Tyr Asn Gln Leu Leu Thr Gln Thr Gln Ile Asp
                245                 250                 255
Leu Tyr Asn Gln Leu Leu Gly Gly Ile Ser Arg Glu Ala Gly Thr Glu
            260                 265                 270
Lys Ile Lys Gly Leu Asn Glu Val Leu Asn Leu Ala Ile Gln Lys Asn
        275                 280                 285
Asp Glu Thr Ala His Ile Ile Ala Ser Leu Pro His Arg Phe Ile Pro
290                 295                 300
Leu Phe Lys Gln Ile Leu Ser Asp Arg Asn Thr Leu Ser Phe Ile Leu
305                 310                 315                 320
Glu Glu Phe Lys Ser Asp Glu Glu Val Ile Gln Ser Phe Cys Lys Tyr
                325                 330                 335
Lys Thr Leu Leu Arg Asn Glu Asn Val Leu Glu Thr Ala Glu Ala Leu
            340                 345                 350
Phe Asn Glu Leu Asn Ser Ile Asp Leu Thr His Ile Phe Ile Ser His
        355                 360                 365
Lys Lys Leu Glu Thr Ile Ser Ser Ala Leu Cys Asp His Trp Asp Thr
370                 375                 380
Leu Arg Asn Ala Leu Tyr Glu Arg Arg Ile Ser Glu Leu Thr Gly Lys
385                 390                 395                 400
Ile Thr Lys Ser Ala Lys Glu Lys Val Gln Arg Ser Leu Lys His Glu
                405                 410                 415
```

```
Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830
```

```
Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
       1010                1015                1020

Asn Cys Leu Val Leu Lys Asp Tyr Pro Ala Glu Lys Val Gly Gly
       1025                1030                1035

Val Leu Asn Pro Tyr Gln Leu Thr Asp Gln Phe Thr Ser Phe Ala
       1040                1045                1050

Lys Met Gly Thr Gln Ser Gly Phe Leu Phe Tyr Val Pro Ala Pro
       1055                1060                1065

Tyr Thr Ser Lys Ile Asp Pro Leu Thr Gly Phe Val Asp Pro Phe
       1070                1075                1080

Val Trp Lys Thr Ile Lys Asn His Glu Ser Arg Lys His Phe Leu
       1085                1090                1095

Glu Gly Phe Asp Phe Leu His Tyr Asp Val Lys Thr Gly Asp Phe
       1100                1105                1110

Ile Leu His Phe Lys Met Asn Arg Asn Leu Ser Phe Gln Arg Gly
       1115                1120                1125

Leu Pro Gly Phe Met Pro Ala Trp Asp Ile Val Phe Glu Lys Asn
       1130                1135                1140

Glu Thr Gln Phe Asp Ala Lys Gly Thr Pro Phe Ile Ala Gly Lys
       1145                1150                1155

Arg Ile Val Pro Val Ile Glu Asn His Arg Phe Thr Gly Arg Tyr
       1160                1165                1170

Arg Asp Leu Tyr Pro Ala Asn Glu Leu Ile Ala Leu Leu Glu Glu
       1175                1180                1185

Lys Gly Ile Val Phe Arg Asp Gly Ser Asn Ile Leu Pro Lys Leu
       1190                1195                1200

Leu Glu Asn Asp Asp Ser His Ala Ile Asp Thr Met Val Ala Leu
       1205                1210                1215

Ile Arg Ser Val Leu Gln Met Arg Asn Ser Asn Ala Ala Thr Gly
       1220                1225                1230

Glu Asp Tyr Ile Asn Ser Pro Val Arg Asp Leu Asn Gly Val Cys
```

Phe Asp Ser Arg Phe Gln Asn Pro Glu Trp Pro Met Asp Ala Asp
             1250                1255                1260

Ala Asn Gly Ala Tyr His Ile Ala Leu Lys Gly Gln Leu Leu Leu
             1265                1270                1275

Asn His Leu Lys Glu Ser Lys Asp Leu Lys Leu Gln Asn Gly Ile
             1280                1285                1290

Ser Asn Gln Asp Trp Leu Ala Tyr Ile Gln Glu Leu Arg Asn
             1295                1300                1305

<210> SEQ ID NO 105
<211> LENGTH: 1307
<212> TYPE: PRT
<213> ORGANISM: Acidaminococcus sp.

<400> SEQUENCE: 105

Met Thr Gln Phe Glu Gly Phe Thr Asn Leu Tyr Gln Val Ser Lys Thr
1                 5                  10                 15

Leu Arg Phe Glu Leu Ile Pro Gln Gly Lys Thr Leu Lys His Ile Gln
                  20                 25                 30

Glu Gln Gly Phe Ile Glu Glu Asp Lys Ala Arg Asn Asp His Tyr Lys
             35                 40                 45

Glu Leu Lys Pro Ile Ile Asp Arg Ile Tyr Lys Thr Tyr Ala Asp Gln
         50                 55                 60

Cys Leu Gln Leu Val Gln Leu Asp Trp Glu Asn Leu Ser Ala Ala Ile
65                 70                 75                 80

Asp Ser Tyr Arg Lys Glu Lys Thr Glu Glu Thr Arg Asn Ala Leu Ile
                 85                 90                 95

Glu Glu Gln Ala Thr Tyr Arg Asn Ala Ile His Asp Tyr Phe Ile Gly
            100                105                110

Arg Thr Asp Asn Leu Thr Asp Ala Ile Asn Lys Arg His Ala Glu Ile
        115                120                125

Tyr Lys Gly Leu Phe Lys Ala Glu Leu Phe Asn Gly Lys Val Leu Lys
130                135                140

Gln Leu Gly Thr Val Thr Thr Thr Glu His Glu Asn Ala Leu Leu Arg
145                150                155                160

Ser Phe Asp Lys Phe Thr Thr Tyr Phe Ser Gly Phe Tyr Glu Asn Arg
                165                170                175

Lys Asn Val Phe Ser Ala Glu Asp Ile Ser Thr Ala Ile Pro His Arg
            180                185                190

Ile Val Gln Asp Asn Phe Pro Lys Phe Lys Glu Asn Cys His Ile Phe
        195                200                205

Thr Arg Leu Ile Thr Ala Val Pro Ser Leu Arg Glu His Phe Glu Asn
    210                215                220

Val Lys Lys Ala Ile Gly Ile Phe Val Ser Thr Ser Ile Glu Glu Val
225                230                235                240

Phe Ser Phe Pro Phe Tyr Asn Gln Leu Leu Thr Gln Thr Gln Ile Asp
                245                250                255

Leu Tyr Asn Gln Leu Leu Gly Gly Ile Ser Arg Glu Ala Gly Thr Glu
            260                265                270

Lys Ile Lys Gly Leu Asn Glu Val Leu Asn Leu Ala Ile Gln Lys Asn
        275                280                285

Asp Glu Thr Ala His Ile Ile Ala Ser Leu Pro His Arg Phe Ile Pro
    290                295                300

```
Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
            370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
                610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
                675                 680                 685

Lys Thr Thr Ser Ile Asp Leu Ser Ser Leu Arg Pro Ser Ser Gln Tyr
                690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
```

```
                725                 730                 735
Thr Gly Lys Leu Tyr Leu Phe Gln Ile Tyr Asn Lys Asp Phe Ala Lys
                    740                 745                 750
Gly His His Gly Lys Pro Asn Leu His Thr Leu Tyr Trp Thr Gly Leu
                    755                 760                 765
Phe Ser Pro Glu Asn Leu Ala Lys Thr Ser Ile Lys Leu Asn Gly Gln
                    770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Leu Lys Asp Gln Lys Thr
                    805                 810                 815
Pro Ile Pro Asp Thr Leu Tyr Gln Glu Leu Tyr Asp Tyr Val Asn His
                    820                 825                 830
Arg Leu Ser His Asp Leu Ser Asp Glu Ala Arg Ala Leu Leu Pro Asn
                    835                 840                 845
Val Ile Thr Lys Glu Val Ser His Glu Ile Ile Lys Asp Arg Arg Phe
850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                    885                 890                 895
Lys Glu His Pro Glu Thr Pro Ile Ile Gly Ile Ala Arg Gly Glu Arg
                    900                 905                 910
Asn Leu Ile Tyr Ile Thr Val Ile Asp Ser Thr Gly Lys Ile Leu Glu
                    915                 920                 925
Gln Arg Ser Leu Asn Thr Ile Gln Gln Phe Asp Tyr Gln Lys Lys Leu
                    930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                    965                 970                 975
His Glu Ile Val Asp Leu Met Ile His Tyr Gln Ala Val Val Val Leu
                    980                 985                 990
Ala Asn Leu Asn Phe Gly Phe Lys Ser Lys Arg Thr Gly Ile Ala Glu
                    995                 1000                1005
Lys Ala Val Tyr Gln Gln Phe Glu Lys Met Leu Ile Asp Lys Leu
                1010                1015                1020
Asn Cys Leu Val Leu Lys Asp Tyr Pro Ala Glu Lys Val Gly Gly
                1025                1030                1035
Val Leu Asn Pro Tyr Gln Leu Thr Asp Gln Phe Thr Ser Phe Ala
                1040                1045                1050
Lys Met Gly Thr Gln Ser Gly Phe Leu Phe Tyr Val Pro Ala Pro
                1055                1060                1065
Tyr Thr Ser Lys Ile Asp Pro Leu Thr Gly Phe Val Asp Pro Phe
                1070                1075                1080
Val Trp Lys Thr Ile Lys Asn His Glu Ser Arg Lys His Phe Leu
                1085                1090                1095
Glu Gly Phe Asp Phe Leu His Tyr Asp Val Lys Thr Gly Asp Phe
                1100                1105                1110
Ile Leu His Phe Lys Met Asn Arg Asn Leu Ser Phe Gln Arg Gly
                1115                1120                1125
Leu Pro Gly Phe Met Pro Ala Trp Asp Ile Val Phe Glu Lys Asn
                1130                1135                1140
```

-continued

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Ala Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 106
<211> LENGTH: 1245
<212> TYPE: PRT
<213> ORGANISM: Lachnospiraceae bacterium

<400> SEQUENCE: 106

Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
                20                  25                  30

Lys Thr Leu Arg Phe Lys Ala Ile Pro Val Gly Lys Thr Gln Glu Asn
            35                  40                  45

Ile Asp Asn Lys Arg Leu Leu Val Glu Asp Glu Lys Arg Ala Glu Asp
        50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe

-continued

|     |     | 195 |     |     |     | 200 |     |     |     | 205 |     |
| --- | --- | --- | --- | --- | --- | --- | --- | --- | --- | --- | --- |

Glu Lys Val Asp Ala Ile Phe Asp Lys His Glu Val Gln Glu Ile Lys
210                     215                     220

Glu Lys Ile Leu Asn Ser Asp Tyr Asp Val Glu Asp Phe Phe Glu Gly
225                     230                     235                     240

Glu Phe Phe Asn Phe Val Leu Thr Gln Glu Gly Ile Asp Val Tyr Asn
                        245                     250                     255

Ala Ile Ile Gly Gly Phe Val Thr Glu Ser Gly Glu Lys Ile Lys Gly
                260                     265                     270

Leu Asn Glu Tyr Ile Asn Leu Tyr Asn Gln Lys Thr Lys Gln Lys Leu
        275                     280                     285

Pro Lys Phe Lys Pro Leu Tyr Lys Gln Val Leu Ser Asp Arg Glu Ser
290                     295                     300

Leu Ser Phe Tyr Gly Glu Gly Tyr Thr Ser Asp Glu Glu Val Leu Glu
305                     310                     315                     320

Val Phe Arg Asn Thr Leu Asn Lys Asn Ser Glu Ile Phe Ser Ser Ile
                        325                     330                     335

Lys Lys Leu Glu Lys Leu Phe Lys Asn Phe Asp Glu Tyr Ser Ser Ala
                340                     345                     350

Gly Ile Phe Val Lys Asn Gly Pro Ala Ile Ser Thr Ile Ser Lys Asp
        355                     360                     365

Ile Phe Gly Glu Trp Asn Val Ile Arg Asp Lys Trp Asn Ala Glu Tyr
370                     375                     380

Asp Asp Ile His Leu Lys Lys Lys Ala Val Thr Glu Lys Tyr Glu
385                     390                     395                     400

Asp Asp Arg Arg Lys Ser Phe Lys Lys Ile Gly Ser Phe Ser Leu Glu
                        405                     410                     415

Gln Leu Gln Glu Tyr Ala Asp Ala Asp Leu Ser Val Val Glu Lys Leu
                420                     425                     430

Lys Glu Ile Ile Ile Gln Lys Val Asp Glu Ile Tyr Lys Val Tyr Gly
        435                     440                     445

Ser Ser Glu Lys Leu Phe Asp Ala Asp Phe Val Leu Glu Lys Ser Leu
450                     455                     460

Lys Lys Asn Asp Ala Val Val Ala Ile Met Lys Asp Leu Leu Asp Ser
465                     470                     475                     480

Val Lys Ser Phe Glu Asn Tyr Ile Lys Ala Phe Phe Gly Glu Gly Lys
                        485                     490                     495

Glu Thr Asn Arg Asp Glu Ser Phe Tyr Gly Asp Phe Val Leu Ala Tyr
                500                     505                     510

Asp Ile Leu Leu Lys Val Asp His Ile Tyr Asp Ala Ile Arg Asn Tyr
        515                     520                     525

Val Thr Gln Lys Pro Tyr Ser Lys Asp Lys Phe Lys Leu Tyr Phe Gln
530                     535                     540

Asn Pro Gln Phe Met Gly Gly Trp Asp Lys Asp Lys Glu Thr Asp Tyr
545                     550                     555                     560

Arg Ala Thr Ile Leu Arg Tyr Gly Ser Lys Tyr Tyr Leu Ala Ile Met
                        565                     570                     575

Asp Lys Lys Tyr Ala Lys Cys Leu Gln Lys Ile Asp Lys Asp Asp Val
                580                     585                     590

Asn Gly Asn Tyr Glu Lys Ile Asn Tyr Lys Leu Leu Pro Gly Pro Asn
        595                     600                     605

Lys Met Leu Pro Lys Val Phe Phe Ser Lys Lys Trp Met Ala Tyr Tyr
610                     615                     620

```
Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
            645                 650                 655

Phe Lys Asp Ser Ile Ser Arg Tyr Pro Lys Trp Ser Asn Ala Tyr Asp
        660                 665                 670

Phe Asn Phe Ser Glu Thr Glu Lys Tyr Lys Asp Ile Ala Gly Phe Tyr
            675                 680                 685

Arg Glu Val Glu Glu Gln Gly Tyr Lys Val Ser Phe Glu Ser Ala Ser
690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
                740                 745                 750

Gln Ile Arg Leu Ser Gly Gly Ala Glu Leu Phe Met Arg Arg Ala Ser
            755                 760                 765

Leu Lys Lys Glu Glu Leu Val Val His Pro Ala Asn Ser Pro Ile Ala
770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
                820                 825                 830

Glu Val Arg Val Leu Leu Lys His Asp Asp Asn Pro Tyr Val Ile Gly
                835                 840                 845

Ile Asp Arg Gly Glu Arg Asn Leu Leu Tyr Ile Val Val Val Asp Gly
850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
                900                 905                 910

Asn Ile Lys Glu Leu Lys Ala Gly Tyr Ile Ser Gln Val Val His Lys
                915                 920                 925

Ile Cys Glu Leu Val Glu Lys Tyr Asp Ala Val Ile Ala Leu Glu Asp
            930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
                980                 985                 990

Gln Ile Thr Asn Lys Phe Glu Ser Phe Lys Ser Met Ser Thr Gln Asn
            995                 1000                1005

Gly Phe Ile Phe Tyr Ile Pro Ala Trp Leu Thr Ser Lys Ile Asp
        1010                1015                1020

Pro Ser Thr Gly Phe Val Asn Leu Leu Lys Thr Lys Tyr Thr Ser
        1025                1030                1035
```

-continued

```
Ile Ala Asp Ser Lys Lys Phe Ile Ser Ser Phe Asp Arg Ile Met
    1040                1045                1050
Tyr Val Pro Glu Glu Asp Leu Phe Glu Phe Ala Leu Asp Tyr Lys
    1055                1060                1065
Asn Phe Ser Arg Thr Asp Ala Asp Tyr Ile Lys Lys Trp Lys Leu
    1070                1075                1080
Tyr Ser Tyr Gly Asn Arg Ile Arg Ile Phe Arg Asn Pro Lys Lys
    1085                1090                1095
Asn Asn Val Phe Asp Trp Glu Glu Val Cys Leu Thr Ser Ala Tyr
    1100                1105                1110
Lys Glu Leu Phe Asn Lys Tyr Gly Ile Asn Tyr Gln Gln Gly Asp
    1115                1120                1125
Ile Arg Ala Leu Leu Cys Glu Gln Ser Asp Lys Ala Phe Tyr Ser
    1130                1135                1140
Ser Phe Met Ala Leu Met Ser Leu Met Leu Gln Met Arg Asn Ser
    1145                1150                1155
Ile Thr Gly Arg Thr Asp Val Asp Phe Leu Ile Ser Pro Val Lys
    1160                1165                1170
Asn Ser Asp Gly Ile Phe Tyr Asp Ser Arg Asn Tyr Glu Ala Gln
    1175                1180                1185
Glu Asn Ala Ile Leu Pro Lys Asn Ala Asp Ala Asn Gly Ala Tyr
    1190                1195                1200
Asn Ile Ala Arg Lys Val Leu Trp Ala Ile Gly Gln Phe Lys Lys
    1205                1210                1215
Ala Glu Asp Glu Lys Leu Asp Lys Val Lys Ile Ala Ile Ser Asn
    1220                1225                1230
Lys Glu Trp Leu Glu Tyr Ala Gln Thr Ser Val Lys
    1235                1240                1245

<210> SEQ ID NO 107
<211> LENGTH: 1246
<212> TYPE: PRT
<213> ORGANISM: Lachnospiraceae bacterium

<400> SEQUENCE: 107

Met Leu Lys Asn Val Gly Ile Asp Arg Leu Asp Val Glu Lys Gly Arg
1               5                   10                  15
Lys Asn Met Ser Lys Leu Glu Phe Thr Asn Cys Tyr Ser Leu Ser
            20                  25                  30
Lys Thr Leu Arg Phe Lys Ala Ile Pro Val Gly Lys Thr Gln Glu Asn
            35                  40                  45
Ile Asp Asn Lys Arg Leu Leu Val Glu Asp Glu Lys Arg Ala Glu Asp
    50                  55                  60
Tyr Lys Gly Val Lys Lys Leu Leu Asp Arg Tyr Tyr Leu Ser Phe Ile
65                  70                  75                  80
Asn Asp Val Leu His Ser Ile Lys Leu Lys Asn Leu Asn Asn Tyr Ile
                85                  90                  95
Ser Leu Phe Arg Lys Lys Thr Arg Thr Glu Lys Glu Asn Lys Glu Leu
                100                 105                 110
Glu Asn Leu Glu Ile Asn Leu Arg Lys Glu Ile Ala Lys Ala Phe Lys
            115                 120                 125
Gly Asn Glu Gly Tyr Lys Ser Leu Phe Lys Lys Asp Ile Ile Glu Thr
        130                 135                 140
Ile Leu Pro Glu Phe Leu Asp Asp Lys Asp Glu Ile Ala Leu Val Asn
145                 150                 155                 160
```

```
Ser Phe Asn Gly Phe Thr Thr Ala Phe Thr Gly Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
            195                 200                 205

Glu Lys Val Asp Ala Ile Phe Asp Lys His Glu Val Gln Glu Ile Lys
        210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
            275                 280                 285

Pro Lys Phe Lys Pro Leu Tyr Lys Gln Val Leu Ser Asp Arg Glu Ser
        290                 295                 300

Leu Ser Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
            325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
            355                 360                 365

Ile Phe Gly Glu Trp Asn Val Ile Arg Asp Lys Trp Asn Ala Glu Tyr
        370                 375                 380

Asp Asp Ile His Leu Lys Lys Ala Val Thr Glu Lys Tyr Glu
385                 390                 395             400

Asp Asp Arg Arg Lys Ser Phe Lys Lys Ile Gly Ser Phe Ser Leu Glu
            405                 410                 415

Gln Leu Gln Glu Tyr Ala Asp Ala Asp Leu Ser Val Val Glu Lys Leu
            420                 425                 430

Lys Glu Ile Ile Gln Lys Val Asp Glu Ile Tyr Lys Val Tyr Gly
            435                 440                 445

Ser Ser Glu Lys Leu Phe Asp Ala Asp Phe Val Leu Glu Lys Ser Leu
    450                 455                 460

Lys Lys Asn Asp Ala Val Ala Ile Met Lys Asp Leu Leu Asp Ser
465                 470                 475                 480

Val Lys Ser Phe Glu Asn Tyr Ile Lys Ala Phe Phe Gly Glu Gly Lys
            485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
        515                 520                 525

Val Thr Gln Lys Pro Tyr Ser Lys Asp Lys Phe Lys Leu Tyr Phe Gln
        530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
            565                 570                 575
```

```
Asp Lys Lys Tyr Ala Lys Cys Leu Gln Lys Ile Asp Lys Asp Val
            580                 585                 590

Asn Gly Asn Tyr Glu Lys Ile Asn Tyr Lys Leu Leu Pro Gly Pro Asn
        595                 600                 605

Lys Met Leu Pro Lys Val Phe Phe Ser Lys Lys Trp Met Ala Tyr Tyr
    610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
            660                 665                 670

Phe Asn Phe Ser Glu Thr Glu Lys Tyr Lys Asp Ile Ala Gly Phe Tyr
        675                 680                 685

Arg Glu Val Glu Glu Gln Gly Tyr Lys Val Ser Phe Glu Ser Ala Ser
    690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
    770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
            820                 825                 830

Glu Val Arg Val Leu Leu Lys His Asp Asp Asn Pro Tyr Val Ile Gly
        835                 840                 845

Ile Ala Arg Gly Glu Arg Asn Leu Leu Tyr Ile Val Val Val Asp Gly
    850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
        915                 920                 925

Ile Cys Glu Leu Val Glu Lys Tyr Asp Ala Val Ile Ala Leu Ala Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser  Phe Lys Ser Met Ser  Thr Gln Asn
```

```
                995                 1000                1005
Gly Phe Ile Phe Tyr Ile Pro Ala Trp Leu Thr Ser Lys Ile Asp
    1010                1015                1020

Pro Ser Thr Gly Phe Val Asn Leu Leu Lys Thr Lys Tyr Thr Ser
    1025                1030                1035

Ile Ala Asp Ser Lys Lys Phe Ile Ser Ser Phe Asp Arg Ile Met
    1040                1045                1050

Tyr Val Pro Glu Glu Asp Leu Phe Glu Phe Ala Leu Asp Tyr Lys
    1055                1060                1065

Asn Phe Ser Arg Thr Asp Ala Asp Tyr Ile Lys Lys Trp Lys Leu
    1070                1075                1080

Tyr Ser Tyr Gly Asn Arg Ile Arg Ile Phe Arg Asn Pro Lys Lys
    1085                1090                1095

Asn Asn Val Phe Asp Trp Glu Glu Val Cys Leu Thr Ser Ala Tyr
    1100                1105                1110

Lys Glu Leu Phe Asn Lys Tyr Gly Ile Asn Tyr Gln Gln Gly Asp
    1115                1120                1125

Ile Arg Ala Leu Leu Cys Glu Gln Ser Asp Lys Ala Phe Tyr Ser
    1130                1135                1140

Ser Phe Met Ala Leu Met Ser Leu Met Leu Gln Met Ala Asn Ser
    1145                1150                1155

Ile Thr Gly Arg Thr Asp Val Asp Phe Leu Ile Ser Pro Val Lys
    1160                1165                1170

Asn Ser Asp Gly Ile Phe Tyr Asp Ser Arg Asn Tyr Glu Ala Gln
    1175                1180                1185

Glu Asn Ala Ile Leu Pro Lys Asn Ala Asp Ala Asn Gly Ala Tyr
    1190                1195                1200

Asn Ile Ala Arg Lys Val Leu Trp Ala Ile Gly Gln Phe Lys Lys
    1205                1210                1215

Ala Glu Asp Glu Lys Leu Asp Lys Val Lys Ile Ala Ile Ser Asn
    1220                1225                1230

Lys Glu Trp Leu Glu Tyr Ala Gln Thr Ser Val Lys His
    1235                1240                1245

<210> SEQ ID NO 108
<211> LENGTH: 1121
<212> TYPE: PRT
<213> ORGANISM: Streptococcus thermophilus

<400> SEQUENCE: 108

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
                20                  25                  30

Arg Ile Phe Pro Ala Ala Gln Ala Glu Asn Asn Leu Val Arg Arg Thr
            35                  40                  45

Asn Arg Gln Gly Arg Arg Leu Thr Arg Arg Lys Lys His Arg Arg Val
        50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110
```

```
Val Lys His Arg Gly Ile Ser Tyr Leu Asp Asp Ala Ser Asp Asp Gly
            115                 120                 125

Asn Ser Ser Ile Gly Asp Tyr Ala Gln Ile Val Lys Glu Asn Ser Lys
130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
        515                 520                 525

Ala Asn Lys Asp Glu Lys Asp Ala Ala Met Leu Lys Ala Ala Asn Gln
```

```
           530                 535                 540
Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Ser
                580                 585                 590

Asn Gln Phe Glu Val Asp His Ile Leu Pro Leu Ser Ile Thr Phe Asp
                595                 600                 605

Asp Ser Leu Ala Asn Lys Val Leu Val Tyr Ala Thr Ala Asn Gln Glu
            610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
                660                 665                 670

Phe Asp Val Arg Lys Lys Phe Ile Glu Arg Asn Leu Val Asp Thr Arg
                675                 680                 685

Tyr Ala Ser Arg Val Val Leu Asn Ala Leu Gln Glu His Phe Arg Ala
            690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
            740                 745                 750

Leu Trp Lys Lys Gln Lys Asn Thr Leu Val Ser Tyr Ser Glu Asp Gln
        755                 760                 765

Leu Leu Asp Ile Glu Thr Gly Glu Leu Ile Ser Asp Asp Glu Tyr Lys
        770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
                820                 825                 830

Ala Lys Val Gly Lys Asp Lys Ala Asp Glu Thr Tyr Val Leu Gly Lys
            835                 840                 845

Ile Lys Asp Ile Tyr Thr Gln Asp Gly Tyr Asp Ala Phe Met Lys Ile
850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
            900                 905                 910

Tyr Lys Glu Glu His Gly Tyr Ile Arg Lys Tyr Ser Lys Gly Asn
            915                 920                 925

Gly Pro Glu Ile Lys Ser Leu Lys Tyr Tyr Asp Ser Lys Leu Gly Asn
        930                 935                 940

His Ile Asp Ile Thr Pro Lys Asp Ser Asn Asn Lys Val Val Leu Gln
945                 950                 955                 960
```

-continued

```
Ser Val Ser Pro Trp Arg Ala Asp Val Tyr Phe Asn Lys Thr Thr Gly
            965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser  Gln Glu Lys Tyr Asn  Asp Ile Lys
            995                 1000                1005

Lys Lys  Glu Gly Val Asp Ser  Asp Ser Glu Phe Lys  Phe Thr Leu
        1010                1015                1020

Tyr Lys  Asn Asp Leu Leu Leu  Val Lys Asp Thr Glu  Thr Lys Glu
        1025                1030                1035

Gln Gln  Leu Phe Arg Phe Leu  Ser Arg Thr Met Pro  Lys Gln Lys
        1040                1045                1050

His Tyr  Val Glu Leu Lys Pro  Tyr Asp Lys Gln Lys  Phe Glu Gly
        1055                1060                1065

Gly Glu  Ala Leu Ile Lys Val  Leu Gly Asn Val Ala  Asn Ser Gly
        1070                1075                1080

Gln Cys  Lys Lys Gly Leu Gly  Lys Ser Asn Ile Ser  Ile Tyr Lys
        1085                1090                1095

Val Arg  Thr Asp Val Leu Gly  Asn Gln His Ile Ile  Lys Asn Glu
        1100                1105                1110

Gly Asp  Lys Pro Lys Leu Asp  Phe
        1115                1120

<210> SEQ ID NO 109
<211> LENGTH: 1121
<212> TYPE: PRT
<213> ORGANISM: Streptococcus thermophilus

<400> SEQUENCE: 109

Met Ser Asp Leu Val Leu Gly Leu Ala Ile Gly Ile Gly Ser Val Gly
1               5                  10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Thr Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Ile Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
```

-continued

```
            195                 200                 205
Asp Glu Phe Ile Asn Arg Tyr Leu Glu Ile Leu Thr Gly Lys Arg Lys
210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
            275                 280                 285

Val Pro Thr Glu Thr Lys Lys Leu Ser Lys Glu Gln Lys Asn Gln Ile
        290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
            355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
            435                 440                 445

Ile Leu Thr Arg Leu Gly Lys Gln Lys Thr Thr Ser Ser Ser Asn Lys
        450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
            515                 520                 525

Ala Asn Lys Asp Glu Lys Asp Ala Ala Met Leu Lys Ala Ala Asn Gln
        530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Ser
            580                 585                 590

Asn Gln Phe Glu Val Asp Ala Ile Leu Pro Leu Ser Ile Thr Phe Asp
        595                 600                 605

Asp Ser Leu Ala Asn Lys Val Leu Val Tyr Ala Thr Ala Asn Gln Glu
610                 615                 620
```

-continued

```
Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
        675                 680                 685

Tyr Ala Ser Arg Val Val Leu Asn Ala Leu Gln Glu His Phe Arg Ala
    690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
            740                 745                 750

Leu Trp Lys Lys Gln Lys Asn Thr Leu Val Ser Tyr Ser Glu Asp Gln
        755                 760                 765

Leu Leu Asp Ile Glu Thr Gly Glu Leu Ile Ser Asp Asp Glu Tyr Lys
    770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
            820                 825                 830

Ala Lys Val Gly Lys Asp Lys Ala Asp Glu Thr Tyr Val Leu Gly Lys
        835                 840                 845

Ile Lys Asp Ile Tyr Thr Gln Asp Gly Tyr Asp Ala Phe Met Lys Ile
    850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
            900                 905                 910

Tyr Lys Glu Glu His Gly Tyr Ile Arg Lys Tyr Ser Lys Lys Gly Asn
        915                 920                 925

Gly Pro Glu Ile Lys Ser Leu Lys Tyr Tyr Asp Ser Lys Leu Gly Asn
    930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser  Gln Glu Lys Tyr Asn  Asp Ile Lys
        995                 1000                 1005

Lys Lys  Glu Gly Val Asp Ser  Asp Ser Glu Phe Lys  Phe Thr Leu
     1010                 1015                 1020

Tyr Lys  Asn Asp Leu Leu Leu  Val Lys Asp Thr Glu  Thr Lys Glu
     1025                 1030                 1035
```

```
Gln Gln Leu Phe Arg Phe Leu Ser Arg Thr Met Pro Lys Gln Lys
    1040            1045            1050

His Tyr Val Glu Leu Lys Pro Tyr Asp Lys Gln Lys Phe Glu Gly
    1055            1060            1065

Gly Glu Ala Leu Ile Lys Val Leu Gly Asn Val Ala Asn Ser Gly
    1070            1075            1080

Gln Cys Lys Lys Gly Leu Gly Lys Ser Asn Ile Ser Ile Tyr Lys
    1085            1090            1095

Val Arg Thr Asp Val Leu Gly Asn Gln His Ile Ile Lys Asn Glu
    1100            1105            1110

Gly Asp Lys Pro Lys Leu Asp Phe
    1115            1120
```

ENGINEERED NUCLEIC ACID-TARGETING NUCLEIC ACIDS

CROSS-REFERENCE TO RELATED APPLICATIONS

This application is a continuation of U.S. patent application Ser. No. 15/703,992, filed 14 Sep. 2017, now allowed, which is a continuation of U.S. patent application Ser. No. 15/368,570, filed 2 Dec. 2016, now U.S. Pat. No. 9,771,600, issued 26 Sep. 2017, which claims the benefit of U.S. Provisional Patent Application Ser. No. 62/263,232, filed 4 Dec. 2015, which applications are herein incorporated by reference in their entirety.

STATEMENT REGARDING FEDERALLY SPONSORED RESEARCH OR DEVELOPMENT

Not applicable.

SEQUENCE LISTING

The present application contains a Sequence Listing that has been submitted electronically in ASCII format and is hereby incorporated by reference in its entirety. The ASCII copy, created on 19 Apr. 2018, is named CBI020-12_ST25.txt and is 156 KB in size.

TECHNICAL FIELD

The present disclosure relates generally to engineered polynucleotide sequences that form scaffolds and nucleoprotein complexes comprising such scaffolds and nucleic acid binding proteins. Nucleic acid sequences encoding the scaffold polynucleotide components, as well as expression cassettes, vectors, and cells comprising the polynucleotide components are described. The disclosure also relates to methods for making and using the engineered nucleic acid sequences that form scaffolds and the nucleoprotein complexes of the present invention.

BACKGROUND

Clustered regularly interspaced short palindromic repeats (CRISPR) and CRISPR-associated proteins (Cas) constitute the CRISPR-Cas system. The CRISPR-Cas system provides adaptive immunity against foreign DNA in bacteria (see, e.g., Barrangou, R., et al., Science 315:1709-1712 (2007); Makarova, K. S., et al., Nature Reviews Microbiology 9:467-477 (2011); Garneau, J. E., et al., Nature 468:67-71 (2010); Sapranauskas, R., et al., Nucleic Acids Research 39:9275-9282 (2011)).

CRISPR-Cas systems have recently been reclassified into two classes, comprising five types and sixteen subtypes (see Makarova, K., et al., Nature Reviews Microbiology 13:1-15 (2015)). This classification is based upon identifying all Cas genes in a CRISPR-Cas locus and determining the signature genes in each CRISPR-Cas locus, ultimately placing the CRISPR-Cas systems in either Class 1 or Class 2 based upon the genes encoding the effector module, i.e., the proteins involved in the interference stage. Recently a sixth CRISPR-Cas system (Type VI) has been identified (see Abudayyeh O., et al., Science 353(6299):aaf5573 (2016)). Certain bacteria possess more than one type of CRISPR-Cas system.

Class 1 systems have a multi-subunit crRNA-effector complex, whereas Class 2 systems have a single protein, such as Cas9, Cpf1, C2c1, C2c2, C2c3, or a crRNA-effector complex. Class 1 systems comprise Type I, Type III, and Type IV systems. Class 2 systems comprise Type II, Type V, and Type VI systems.

Type II systems have cas1, cas2, and cas9 genes. The cas9 gene encodes a multi-domain protein that combines the functions of the crRNA-effector complex with DNA target sequence cleavage. Type II systems are further divided into three subtypes, subtypes II-A, II-B, and II-C. Subtype II-A contains an additional gene, csn2. Examples of organisms with a subtype II-A systems include, but are not limited to, *Streptococcus pyogenes, Streptococcus thermophilus*, and *Staphylococcus aureus*. Subtype II-B lacks the csn2 protein, but has the cas4 protein. An example of an organism with a subtype II-B system is *Legionella pneumophila*. Subtype II-C is the most common Type II system found in bacteria and has only three proteins, Cas1, Cas2, and Cas9. An example of an organism with a subtype II-C system is *Neisseria lactamica*.

Type V systems have a cpf1 gene and cas1 and cas2 genes (see Zetsche, B., et al., Cell 163:1-13 (2015)). The cpf1 gene encodes a protein, Cpf1, that has a RuvC-like nuclease domain that is homologous to the respective domain of Cas9, but lacks the HNH nuclease domain that is present in Cas9 proteins. Type V systems have been identified in several bacteria including, but not limited to, *Parcubacteria bacterium, Lachnospiraceae bacterium, Butyrivibrio proteoclasticus, Peregrinibacteria bacterium, Acidaminococcus* spp., *Porphyromonas macacae, Porphyromonas crevioricanis, Prevotella disiens, Moraxella bovoculi, Smithella* spp., *Leptospira inadai, Franciscella tularensis, Franciscella novicida, Candidatus methanoplasma termitum*, and *Eubacterium eligens*. Recently it has been demonstrated that Cpf1 also has RNase activity and is responsible for pre-crRNA processing (see Fonfara, I., et al., Nature 532(7600):517-521 (2016)).

In Class 2 systems, the crRNA is associated with a single protein and achieves interference by combining nuclease activity with RNA-binding domains and base-pair formation between the crRNA and a nucleic acid target sequence.

In Type II systems, nucleic acid target sequence binding involves Cas9 and the crRNA, as does nucleic acid target sequence cleavage. In Type II systems, the RuvC-like nuclease (RNase H fold) domain and the HNH (McrA-like) nuclease domain of Cas9 each cleave one of the strands of the double-stranded nucleic acid target sequence. The Cas9 cleavage activity of Type II systems also requires hybridization of crRNA to a tracrRNA to form a duplex that facilitates the crRNA and nucleic acid target sequence binding by the Cas9 protein.

In Type V systems, nucleic acid target sequence binding involves Cpf1 and the crRNA, as does nucleic acid target sequence cleavage. In Type V systems, the RuvC-like nuclease domain of Cpf1 cleaves one strand of the double-stranded nucleic acid target sequence, and a putative nuclease domain cleaves the other strand of the double-stranded nucleic acid target sequence in a staggered configuration, producing 5' overhangs, which is in contrast to the blunt ends generated by Cas9 cleavage.

The Cpf1 cleavage activity of Type V systems does not require hybridization of crRNA to tracrRNA to form a duplex, rather the crRNA of Type V systems uses a single crRNA that has a stem-loop structure forming an internal duplex. Cpf1 binds the crRNA in a sequence and structure specific manner that recognizes the stem loop and sequences adjacent to the stem loop, most notably the nucleotides 5' of the spacer sequences that hybridizes to the nucleic acid target sequence. This stem-loop structure is typically in the range of 15 to 19 nucleotides in length. Substitutions that disrupt this stem-loop duplex abolish cleavage activity, whereas other substitutions that do not disrupt the stem-loop duplex do not abolish cleavage activity. Nucleotides 5' of the stem loop adopt a pseudo-knot structure further stabilizing the stem-loop structure with non-canonical Watson-Crick base pairing, triplex interaction, and reverse Hoogsteen base pairing (see Yamano, T., et al., Cell 165(4):949-962 (2016)). In Type V systems, the crRNA forms a stem-loop structure at the 5' end, and the sequence at the 3' end is complementary to a sequence in a nucleic acid target sequence.

Other proteins associated with Type V crRNA and nucleic acid target sequence binding and cleavage include Class 2 candidate 1 (C2c1) and Class 2 candidate 3 (C2c3). C2c1 and C2c3 proteins are similar in length to Cas9 and Cpf1 proteins, ranging from approximately 1,100 amino acids to approximately 1,500 amino acids. C2c1 and C2c3 proteins also contain RuvC-like nuclease domains and have an architecture similar to Cpf1. C2c1 proteins are similar to Cas9 proteins in requiring a crRNA and a tracrRNA for nucleic acid target sequence binding and cleavage but have an optimal cleavage temperature of 50° C. C2c1 proteins target an AT-rich protospacer adjacent motif (PAM), similar to the PAM of Cpf1, which is 5' of the nucleic acid target sequence (see, e.g., Shmakov, S., et al., Molecular Cell 60(3):385-397 (2015)).

Class 2 candidate 2 (C2c2) does not share sequence similarity with other CRISPR effector proteins and was recently identified as a Type VI system (see Abudayyeh, O., et al., Science 353(6299):aaf5573 (2016)). C2c2 proteins have two HEPN domains and demonstrate single-stranded RNA cleavage activity. C2c2 proteins are similar to Cpf1 proteins in requiring a crRNA for nucleic acid target sequence binding and cleavage, although not requiring tracrRNA. Also, similar to Cpf1, the crRNA for C2c2 proteins forms a stable hairpin, or stem-loop structure, that aids in association with the C2c2 protein. Type VI systems have a single polypeptide RNA endonuclease that utilizes a single crRNA to direct site-specific cleavage. Additionally, after hybridizing to the target RNA complementary to the spacer, C2c2 becomes a promiscuous RNA endonuclease exhibiting non-specific endonuclease activity toward any single-stranded RNA in a sequence independent manner (see East-Seletsky, A., et al., Nature 538(7624):270-273 (2016)).

Regarding Class 2 Type II CRISPR-Cas systems, a large number of Cas9 orthologs are known in the art as well as their associated polynucleotide components (tracrRNA and crRNA) (see, e.g., Fonfara, I., et al., Nucleic Acids Research 42(4):2577-2590 (2014), including all Supplemental Data; Chylinski K., et al., Nucleic Acids Research 42(10):6091-6105 (2014), including all Supplemental Data). In addition, Cas9-like synthetic proteins are known in the art (see U.S. Published Patent Application No. 2014-0315985, published 23 Oct. 2014).

Cas9 is an exemplary Type II CRISPR Cas protein. Cas9 is an endonuclease that can be programmed by the tracrRNA/crRNA to cleave, in a site-specific manner, a DNA target sequence using two distinct endonuclease domains (HNH and RuvC/RNase H-like domains) (see U.S. Published Patent Application No. 2014-0068797, published 6 Mar. 2014; see also Jinek, M., et al., Science 337:816-821 (2012)).

Typically, each wild-type CRISPR-Cas9 system includes a crRNA and a tracrRNA. The crRNA has a region of complementarity to a potential DNA target sequence and a second region that forms base-pair hydrogen bonds with the tracrRNA to form a secondary structure, typically to form at least one stem structure. The region of complementarity to the DNA target sequence is the spacer. The tracrRNA and a crRNA interact through a number of base-pair hydrogen bonds to form secondary RNA structures. Complex formation between tracrRNA/crRNA and Cas9 protein results in conformational change of the Cas9 protein that facilitates binding to DNA, endonuclease activities of the Cas9 protein, and crRNA-guided site-specific DNA cleavage by the endonuclease Cas9. For a Cas9 protein/tracrRNA/crRNA complex to cleave a double-stranded DNA target sequence, the DNA target sequence is adjacent to a cognate PAM. By engineering a crRNA to have an appropriate spacer sequence, the complex can be targeted to cleave at a locus of interest, e.g., a locus at which sequence modification is desired.

A variety of Type II CRISPR-Cas system crRNA and tracrRNA sequences, as well as predicted secondary structures are known in the art (see, e.g., Ran, F. A., et al., Nature 520(7546):186-191 (2015), including all Supplemental Data, in particular Extended Data FIG. 1; Fonfara, I., et al., Nucleic Acids Research 42(4):2577-2590 (2014), including all Supplemental Data, in particular Supplemental Figure S 11). Predicted tracrRNA secondary structures were based on the Constraint Generation RNA folding model (Zuker, M., Nucleic Acids Research 31:3406-3415 (2003). RNA duplex secondary structures were predicted using RNAcofold of the Vienna RNA package (Bernhart, S. H., et al., Algorithms for Molecular Biology 1(1):3 (2006); Hofacker, I. L., et al., Journal of Molecular Biology 319:1059-1066 (2002)) and RNAhybrid (bibiserv.techfak.uni-bielefeld.de/rnahybrid/). The structure predictions were visualized using VARNA (Darty, K., et al., Bioinformatics 25:1974-1975 (2009)). Fonfara, I., et al., show that the crRNA/tracrRNA complex for *Campylobacter jejuni* does not have the bulge region; however, the complex retains a stem structure located 3' of the spacer that is followed in the 3' direction with another stem structure.

The spacer of Class 2 CRISPR-Cas systems can hybridize to a nucleic acid target sequence that is located 5' or 3' of a PAM, depending upon the Cas protein to be used. A PAM can vary depending upon the Cas polypeptide to be used. For example, if Cas9 from *S. pyogenes* is used, the PAM can be a sequence in the nucleic acid target sequence that comprises the sequence 5'-NRR-3', wherein R can be either A or G, N is any nucleotide, and N is immediately 3' of the nucleic acid target sequence targeted by the nucleic acid target binding sequence. A Cas protein may be modified such that a PAM may be different compared with a PAM for an unmodified Cas protein. If, for example, Cas9 from *S. pyogenes* is used, the Cas9 protein may be modified such that the PAM no longer comprises the sequence 5'-NRR-3', but instead comprises the sequence 5'-NNR-3', wherein R can be either A or G, N is any nucleotide, and N is immediately 3' of the nucleic acid target sequence targeted by the nucleic acid target sequence.

Other Cas proteins recognize other PAMs, and one of skill in the art is able to determine the PAM for any particular Cas protein. For example, Cpf1 has a thymine-rich PAM site that targets, for example, a TTTN sequence (see Fagerlund, R., et al., Genome Biology 16:251 (2015)).

The RNA-guided Cas9 endonuclease has been widely used for programmable genome editing in a variety of organisms and model systems (see, e.g., Jinek M., et al., Science 337:816-821 (2012); Jinek M., et al., eLife 2:e00471. doi: 10.7554/eLife.00471 (2013); U.S. Published Patent Application No. 2014-0068797, published 6 Mar. 2014).

Genome engineering includes altering the genome by deleting, inserting, mutating, or substituting specific nucleic acid sequences. The alteration can be gene- or location-specific. Genome engineering can use site-directed nucleases, such as Cas proteins and their cognate polynucleotides, to cut DNA, thereby generating a site for alteration. In certain cases, the cleavage can introduce a double-strand break (DSB) in the DNA target sequence. DSBs can be repaired, e.g., by non-homologous end joining (NHEJ), microhomology-mediated end joining (MMEJ), or homology-directed repair (HDR). HDR relies on the presence of a template for repair. In some examples of genome engineering, a donor polynucleotide or portion thereof can be inserted into the break.

SUMMARY OF THE INVENTION

The present invention relates generally to a nucleic acid polynucleotide composition comprising a polynucleotide complex forming a scaffold that is capable of binding a nucleic acid binding protein. Typically, a NASC polynucleotide composition is a complex of two or more engineered nucleic acid sequences forming a scaffold comprising: a repeat element 1, a repeat element 2 a nucleic acid binding protein binding element 1, a nucleic acid binding protein binding element 2, a spacer element 1 (e.g., comprising a nucleic acid target binding sequence, and a spacer element 2 (e.g., comprising a nucleic acid target binding sequence 2). The NASC polynucleotide composition is capable of associating with a nucleic acid binding protein.

In an aspect, the present invention relates to a composition of two or more engineered nucleic acid sequences forming a scaffold ("NASC") comprising a first engineered nucleic acid "NASC-PC1" and a second engineered nucleic acid component ("NASC-PC2"). The NASC-P1 comprises, in a 5' to 3' direction, a spacer element 1 comprising a nucleic acid target binding sequence 1, a repeat element 1 comprising a repeat nucleic acid sequence 1, and a nucleic acid binding protein binding element 1, wherein the spacer element 1 is covalently connected with the repeat element 1, and the repeat element 1 is covalently connected with the nucleic acid binding protein binding element 1 comprising a nucleic acid binding protein binding sequence 1. The second engineered nucleic acid component ("NASC-PC2") comprises, in a 5' to 3' direction, a spacer element 2 comprising a nucleic acid target binding sequence 2, a repeat element 2 comprising a repeat nucleic acid sequence 2, and a nucleic acid binding protein binding element 2 comprising a nucleic acid binding protein binding sequence 2, wherein the spacer element 2 is covalently connected with the repeat element 2, and the repeat element 2 is covalently connected with the nucleic acid binding protein binding element 2. In some embodiments of the present invention, the nucleic acid binding protein binding sequence 1 comprises a double-stranded nucleic acid binding protein binding sequence 1, and the nucleic acid binding protein binding sequence 2 comprises a double-stranded nucleic acid binding protein binding sequence 2. The repeat nucleic acid sequence 1 and the repeat nucleic acid sequence 2 are connected through hydrogen-bonded base pairs and the connection forms the NASC composition. The NASC composition is capable of binding a first nucleic acid binding protein (e.g., a first double-stranded nucleic acid binding protein) and a second nucleic acid binding protein (e.g., a second double-stranded nucleic acid binding protein).

Embodiments of the NASC composition include, but are not limited to, the first double-stranded nucleic acid binding protein being a Class 2 CRISPR protein and the second double-stranded nucleic acid binding protein being a Class 2 CRISPR protein. In preferred embodiments, a first double-stranded nucleic acid binding protein is a Class 2 Type II CRISPR-Cas9 protein, and a second double-stranded nucleic acid binding protein is a Class 2 Type II CRISPR-Cas9 protein. Other embodiments include wherein the first double-stranded nucleic acid binding protein is a Class 2 Type V CRISPR-Cpf1 protein, and wherein the second double-stranded nucleic acid binding protein is a Class 2 Type V CRISPR-Cpf1 protein. In further embodiments, a first double-stranded nucleic acid binding protein is a Class 2 Type II CRISPR-Cas9 protein, and a second double-stranded nucleic acid binding protein is a Class 2 Type V CRISPR-Cpf1 protein.

In some embodiments, the spacer element 1 and spacer element 2 comprise additional nucleic acid sequences. For example, the spacer element 1 can further comprise a linker element nucleic acid sequence 3' of the nucleic acid target binding sequence 1 and 5' of the repeat element 1. The spacer element 2 can further comprise a linker element nucleic acid sequence 3' of the nucleic acid target binding sequence 1 and 5' of the repeat element 1.

In further embodiments, the repeat element 1 and the repeat element 2 comprise additional sequences as follows. The repeat element 1 further comprises, in a 5' to 3' direction, a repeat nucleic acid sequence 1b, a linker element nucleic acid sequence 1, and a repeat nucleic acid sequence 1a. The repeat element 2 further comprises, in a 5' to 3' direction, a repeat nucleic acid sequence 1aC, a linker element nucleic acid sequence 2, and a repeat nucleic acid sequence 1bC. The repeat nucleic acid sequence 1b and the repeat nucleic acid sequence 1bC are connected through hydrogen-bonded base pairs, and the repeat nucleic acid sequence 1a and the repeat nucleic acid sequence 1aC are connected through hydrogen-bonded base pairs.

In additional embodiments, the repeat nucleic acid sequence 1b and the repeat sequence 1a comprise additional components as follows. The repeat nucleic acid sequence 1b can further comprise, in a 5' to 3' direction, a repeat nucleic acid sequence 1b2, a bulge nucleic acid sequence 1b1, and a repeat nucleic acid sequence 1b1. The repeat nucleic acid sequence 1a can further comprise, in a 5' to 3' direction, a repeat nucleic acid sequence 1a2, a bulge nucleic acid sequence 1a1, and a repeat nucleic acid sequence 1a1. The repeat nucleic acid sequence 1aC can further comprise, in a 5' to 3' direction, a repeat nucleic acid sequence 1a1C, a bulge nucleic acid sequence 2a2, and a repeat nucleic acid sequence 1a2C. The repeat nucleic acid sequence 1bC can further comprise, in a 5' to 3' direction, a repeat nucleic acid sequence 1b1C, a bulge nucleic acid sequence 2b2, and a repeat nucleic acid sequence 1b2C. The repeat nucleic acid sequence 1a1 and the repeat nucleic acid sequence 1a1C are connected through hydrogen-bonded base pairs, the repeat nucleic acid sequence 1a2 and the repeat nucleic acid sequence 1a2C are connected through hydrogen-bonded base pairs, the repeat nucleic acid sequence 1b1 and the repeat nucleic acid sequence 1b1C are connected through hydrogen-bonded base pairs, and the repeat nucleic acid sequence 1b2 and the repeat nucleic acid sequence 1b2C are connected through hydrogen-bonded base pairs.

In additional embodiments, the linker element nucleic acid sequence 1-2 and the linker element nucleotide sequence 2-2 comprise added nucleic acid sequences. The linker element 1-1 can comprise further comprise, in a 5' to 3' direction, a linker element nucleic acid sequence 1-2-2, a repeat nucleic acid sequence 1-2a, and a linker element nucleic acid sequence 1-2-1. The linker element nucleic acid sequence 2-2 can further comprise, in a 5' to 3' direction, a linker element nucleic acid sequence 2-2-1, a repeat nucleic acid sequence 1-2aC, and a linker element nucleic acid sequence 2-2-2. The repeat nucleic acid sequence 1-2a and the repeat nucleic acid sequence 1-2aC are connected through hydrogen-bonded base pairs and form a double-stranded nucleic acid region 1-2. In some embodiments, the double-stranded nucleic acid region 1-2 further comprises an effector protein binding site 1. The repeat nucleic acid sequence 1-2a further comprises an effector protein binding site nucleic acid sequence 1-2a. The repeat nucleic acid sequence 2 further comprises an effector protein binding site nucleic acid sequence 1-2aC. The effector binding site is formed by hydrogen base pair bonding between the effector protein binding site nucleic acid sequence 1-2a and the effector protein binding site nucleic acid sequence 1-2aC. The Csy4 protein binding site is an example of an effector protein binding site. A Csy4 protein or an enzymatically inactive Csy4 protein are capable of binding the effector binding site.

In further embodiments, the repeat nucleic acid sequence 1 further comprises an affinity tag 1 and the repeat nucleic acid sequence 2 further comprises an affinity tag 2, and the affinity tag 1 is connected with affinity tag 2.

The NASC compositions can comprise, for example, RNA, DNA, or RNA and DNA. In some embodiments, NASC-PC1, NASC-PC2, or NASC-PC1 and NASC-PC2 comprises RNA, DNA, or RNA and DNA.

In another aspect, the present invention includes a nucleic acid/protein composition comprising a NASC composition and one or more nucleic acid binding proteins. In one embodiment, the nucleic acid proteins can be a first Cas9 protein and a second Cas9 protein. For example, the first Cas9 protein is the same as the second Cas9 protein, and the first Cas9 protein and the second Cas9 protein are selected from the group consisting of a S. pyogenes Cas9 protein, a S. thermophilus Cas9 protein, a S. aureus Cas9 protein, and a C. jejuni Cas9 protein. In other embodiments, the first Cas9 protein is different from the second Cas9 protein, and the first Cas9 protein and the second Cas9 protein are selected from the group consisting of a S. pyogenes Cas9 protein, a S. thermophilus Cas9 protein, a S. aureus Cas9 protein, and a C. jejuni Cas9 protein. Additionally, the first Cas9 protein and the second Cas9 protein can be selected from the group consisting of Cas9 protein/Cas9 protein, Cas9 protein/dCas9 protein, dCas9 protein/Cas9 protein, and dCas9 protein/dCas9 protein, respectively.

In a further aspect, the present invention relates to kits comprising one or more components of a NASC composition. In some embodiments, the NASC composition comprises a NASC-PC1 and a NASC-PC2, or one or more nucleic acid sequences encoding the NASC-PC1 and the NASC-PC2, and a buffer. Kits can further comprise one or more Cas9 proteins or one or more nucleic acid sequences encoding the one or more Cas9 proteins. In further embodiments, a kit can comprise nucleoprotein complexes comprising a NASC composition and one or more Cas9 proteins.

In an additional aspect, the present invention relates to an expression vector comprising one or more nucleic acid sequences encoding one or more components of a NASC composition.

In yet another aspect, the present invention relates to a recombinant cell comprising one or more nucleic acid sequences encoding one or more components of a NASC composition.

Further aspects of the present invention include methods of using NASC composition, as described herein. One method is a method of binding DNA. The method comprises contacting a first DNA target sequence in a DNA polynucleotide and a second DNA target sequence in the DNA polynucleotide with a nucleic acid/protein composition comprising NASC composition and a nucleic acid binding protein (e.g., a Cas9 protein, and/or a Cpf1 protein), thereby facilitating binding of the nucleic acid/protein composition to the first DNA target sequence in the DNA and the second DNA target sequence in the DNA. A NASC-PC1 spacer element of the NASC composition can be complementary to the first DNA target sequence, and the NASC-PC2 spacer of the NASC composition can be complementary to the second DNA target sequence.

Another method of the present invention is a method of cutting DNA. The method comprises contacting a first DNA target sequence in the DNA polynucleotide and a second DNA target sequence in the DNA polynucleotide with a nucleic acid/protein composition comprising a NASC composition and a nucleic acid binding protein (e.g., a Cas9 protein, and/or a Cpf1 protein), thereby facilitating binding of the nucleic acid/protein composition to the first DNA target sequence and the second DNA target sequence. Binding results in cutting of the first DNA target sequence and the second DNA target sequence. A NASC-PC1 spacer element of the NASC composition can be complementary to the first DNA target sequence, and the NASC-PC2 spacer of the NASC composition can be complementary to the second DNA target sequence.

These aspects and other embodiments of the present invention using the NASC compositions and nucleoprotein particles comprising the NASC compositions of the present invention will be readily apparent to those of ordinary skill in the art in view of the disclosure herein.

BRIEF DESCRIPTION OF THE FIGURES

The figures are not proportionally rendered, nor are the figures to scale. The locations of indicators are approximate.

INCORPORATION BY REFERENCE

Figure 1A:
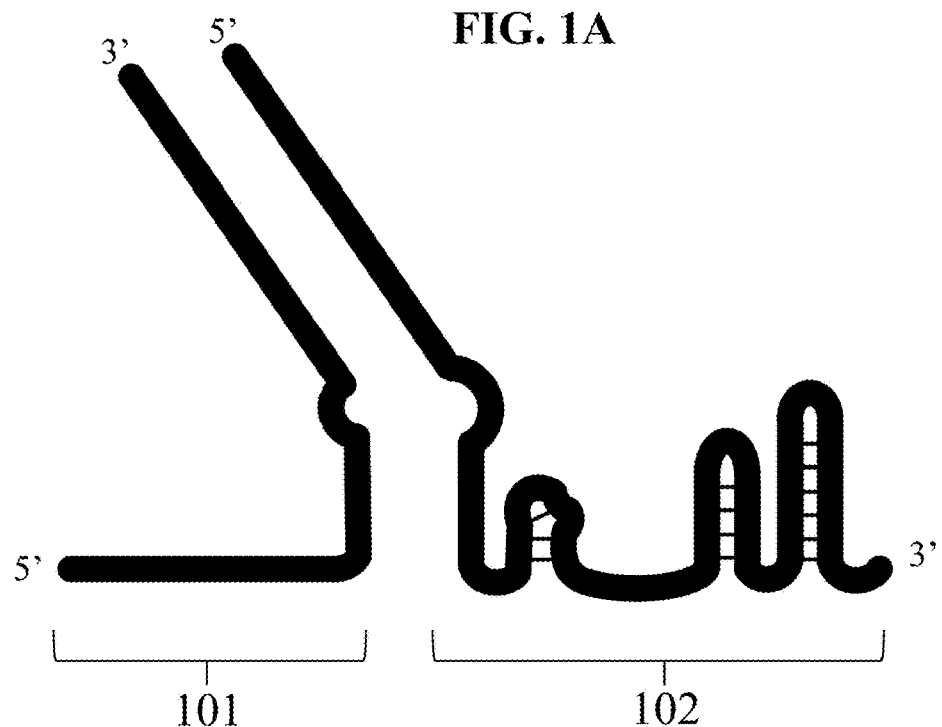
FIG. 1A, FIG. 1B, FIG. 1C, and FIG. 1D present examples of dual-guide Class 2 Type II CRISPR-associated guide RNAs.

All patents, publications, and patent applications cited in this specification are herein incorporated by reference as if each individual patent, publication, or patent application was specifically and individually indicated to be incorporated by reference in its entirety for all purposes.

DETAILED DESCRIPTION OF THE INVENTION

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a polynucleotide" includes one or more polynucleotides, and reference to "a vector" includes one or more vectors.

Unless defined otherwise, all technical and scientific terms used herein have the same meaning as commonly understood by one of ordinary skill in the art to which the invention pertains. Although other methods and materials similar, or equivalent, to those described herein can be useful in the present invention, preferred materials and methods are described herein.

In view of the teachings of the present specification, one of ordinary skill in the art can employ conventional techniques of immunology, biochemistry, chemistry, molecular biology, microbiology, cell biology, genomics, and recombinant polynucleotides, as taught, for example, by the following standard texts: Antibodies: A Laboratory Manual, Second edition, E. A. Greenfield, Cold Spring Harbor Laboratory Press, ISBN 978-1-936113-81-1 (2014); Culture of Animal Cells: A Manual of Basic Technique and Specialized Applications, 6th Edition, R. I. Freshney, Wiley-Blackwell, ISBN 978-0-470-52812-9 (2010); Transgenic Animal Technology, Third Edition: A Laboratory Handbook, C. A. Pinkert, Elsevier, ISBN 978-0124104907 (2014); The Laboratory Mouse, Second Edition, H. Hedrich, Academic Press, ISBN 978-0123820082 (2012); Manipulating the Mouse Embryo: A Laboratory Manual, R. Behringer, et al., Cold Spring Harbor Laboratory Press, ISBN 978-1936113019 (2013); PCR 2: A Practical Approach, M. J. McPherson, et al., IRL Press, ISBN 978-0199634248 (1995); Methods in Molecular Biology (Series), J. M. Walker, ISSN 1064-3745, Humana Press; RNA: A Laboratory Manual, D. C. Rio, et al., Cold Spring Harbor Laboratory Press, ISBN 978-0879698911 (2010); Methods in Enzymology (Series), Academic Press; Molecular Cloning: A Laboratory Manual (Fourth Edition), M. R. Green, et al., Cold Spring Harbor Laboratory Press, ISBN 978-1605500560 (2012); Bioconjugate Techniques, Third Edition, G. T. Hermanson, Academic Press, ISBN 978-0123822390 (2013); Methods in Plant Biochemistry and Molecular Biology, W. V. Dashek, CRC Press, ISBN 978-0849394805 (1997); Plant Cell Culture Protocols (Methods in Molecular Biology), V. M. Loyola-Vargas, et al., Humana Press, ISBN 978-1617798177 (2012); Plant Transformation Technologies, C. N. Stewart, et al., Wiley-Blackwell, ISBN 978-0813821955 (2011); Recombinant Proteins from Plants (Methods in Biotechnology), C. Cunningham, et al., Humana Press, ISBN 978-1617370212 (2010); Plant Genomics: Methods and Protocols (Methods in Molecular Biology), D. J. Somers, et al., Humana Press, ISBN 978-1588299970 (2009); Plant Biotechnology: Methods in Tissue Culture and Gene Transfer, R. Keshavachandran, et al., Orient Blackswan, ISBN 978-8173716164 (2008).

Clustered regularly interspaced short palindromic repeats (CRISPR) and related CRISPR-associated proteins (Cas proteins) constitute CRISPR-Cas systems (see, e.g., Barrangou, R., et al., Science 315:1709-1712 (2007)).

As used herein, "Cas protein" and "CRISPR-Cas protein" refer to Cas proteins including, but not limited to, Class 1 Type I Cas proteins, Class 1 Type III Cas proteins, Class 1 Type IV Cas proteins, Class 2 Type II Cas proteins, Class 2 Type V Cas proteins, and Class 2 Type VI Cas proteins. Class 2 Cas proteins include Cas9 proteins, Cas9-like proteins encoded by Cas9 orthologs, Cas9-like synthetic proteins, Cpf1 proteins, proteins encoded by Cpf1 orthologs, Cpf1-like synthetic proteins, C2c1 proteins, C2c2 proteins, C2c3 proteins, and variants and modifications thereof. In some embodiments, Cas proteins are Class 2 Cas proteins, for example one or more Class 2 Type II Cas proteins, such as Cas9, one or more Class 2 Type V Cas proteins, such as Cpf1, or one or more Class 2 Type VI Cas proteins, such as C2c2. In preferred embodiments, Cas proteins are one or more Class 2 Type II Cas proteins, such as Cas9, and one or more Class 2 Type V Cas proteins, such as Cpf1. Typically, for use in aspects of the present invention, a Cas protein is capable of interacting with one or more cognate polynucleotides (most typically, RNA) to form a nucleoprotein complex (most typically, a ribonucleoprotein complex).

"Cas9 protein," as used herein, refers to a Cas9 wild-type protein derived from Class 2 Type II CRISPR-Cas9 systems, modifications of Cas9 proteins, variants of Cas9 proteins, Cas9 orthologs, and combinations thereof. Cas9 proteins include, but not limited to, Cas9 from *Streptococcus pyogenes* (UniProtKB—Q99ZW2 (CAS9_STRP1)), *Streptococcus thermophilus* (UniProtKB—G3ECR1 (CAS9_STRTR)), and *Staphylococcus aureus* (UniProtKB—J7RUA5 (CAS9_STAAU)). Cas9 homologs can be identified using sequence similarity search methods known to one skilled in the art. "dCas9," as used herein, refers to variants of Cas9 protein that are nuclease-deactivated Cas9 proteins, also termed "catalytically inactive Cas9 protein," "enzymatically inactive Cas9," "catalytically dead Cas9" or "dead Cas9." Such molecules lack all or a portion of endonuclease activity and can therefore be used to regulate genes in an RNA-guided manner (see Jinek M., et al., Science 337:816-821 (2012)). This is accomplished by introducing mutations to catalytic residues, such as D10A in the RuvC-1 domain and H840A in the HNH domain (numbered relative to *S. pyogenes* Cas9 protein), that inactivate Cas9 nuclease function. It is understood that mutation of other catalytic residues to reduce activity of either or both of the nuclease domains can also be carried out by one skilled in the art. The resultant dCas9 is unable to cleave double-stranded DNA but retains the ability to complex with a guide nucleic acid and bind a DNA target sequence. The Cas9 double mutant with changes at amino acid positions D10A and H840A inactivates both the nuclease and nickase activities. Targeting specificity is determined by Cas9 protein binding to the PAM sequence, and by complementary base pairing of guide RNA (typically, a single-guide RNA) to the genomic locus. Cas9 is the signature protein characteristic for Class 2 Type II CRISPR systems.

"Cpf1 protein," as used herein, refers to a Cpf1 wild-type protein derived from Class 2 Type V CRISPR-Cpf1 systems, modifications of Cpf1 proteins, variants of Cpf1 proteins, Cpf1 orthologs, and combinations thereof. "dCpf1," as used herein, refers to variants of Cpf1 protein that are nuclease-deactivated Cpf1 proteins, also termed "catalytically inactive Cpf1 protein," or "enzymatically inactive Cpf1." Cpf1 proteins include, but not limited to, *Francisella novicida* (UniProtKB—A0Q7Q2 (CPF1_FRATN)), *Lachnospiraceae bacterium* (UniProtKB—A0A182DWE3 (A0A182DWE3_9FIRM)), and *Acidaminococcus* sp. (UniProtKB—U2UMQ6 (CPF1_ACISB)). Cpf1 is the signature protein characteristic for Class 2 Type V CRISPR systems. Cpf1 homologs can be identified using sequence similarity search methods known to one skilled in the art.

"Nucleic acid-targeting nucleic acid" (NATNA), as used herein, refers to one or more polynucleotides that guide a protein, such as a Cas protein (e.g., a Cas9 protein or a Cpf1 protein), to preferentially bind a nucleic acid target sequence in a polynucleotide (relative to a polynucleotide that does not comprise the nucleic acid target sequence). NATNAs can comprise ribonucleotide bases (e.g., RNA), deoxyribonucleotide bases (e.g., DNA), combinations of ribonucleotide bases and deoxyribonucleotide bases (e.g., RNA/DNA), nucleotides, nucleotide analogs, modified nucleotides, and the like, as well as synthetic, naturally occurring, and non-naturally occurring modified backbone residues or linkages, for example, as described herein. Examples of nucleic acid-targeting nucleic acids include, but are not limited to, Cas9-crRNA/tracrRNA molecules (see, e.g., FIG. 1A, FIG. 1B, FIG. 1C, and FIG. 1D), Cas9-sgRNA (see, e.g., FIG. 2A and FIG. 2B), and Cpf1-crRNA (see, e.g., FIG. 3A and FIG. 3B).

Figure 1B:
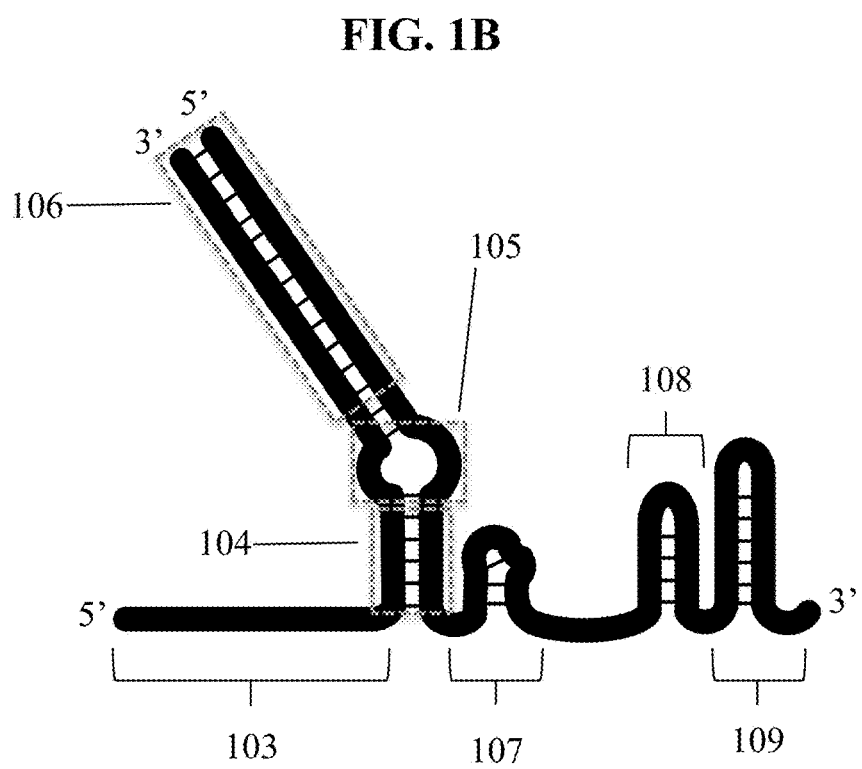
Figure 1C:
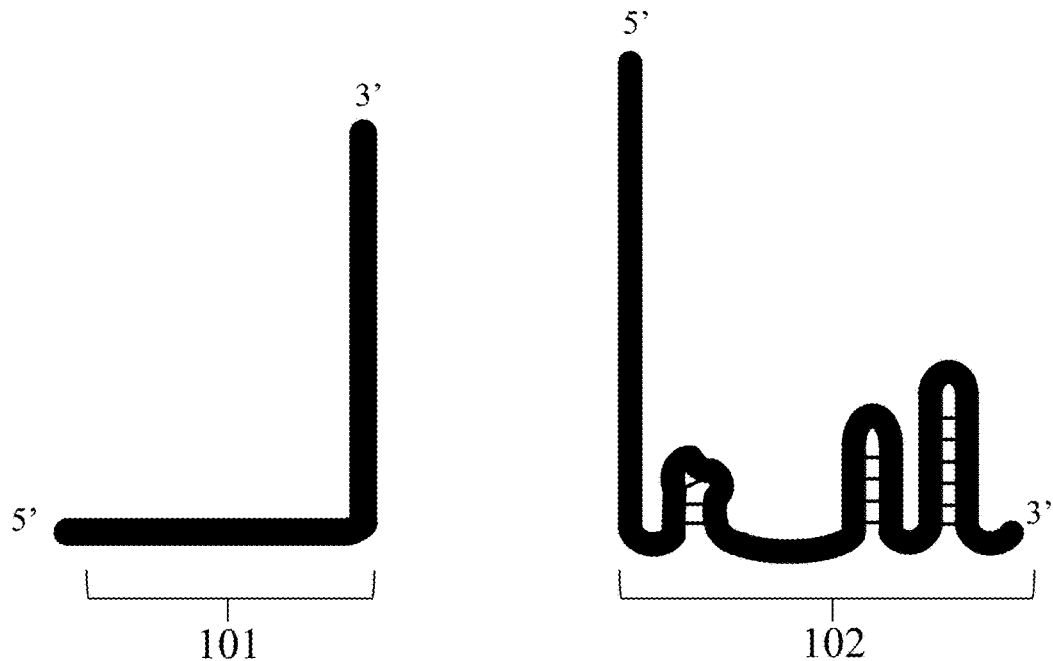
Figure 1D:
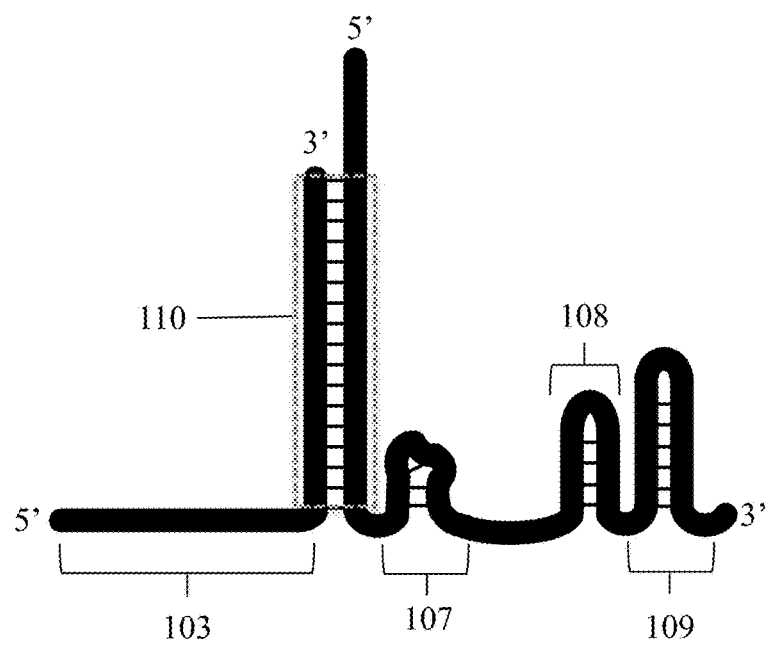

As used herein, "dual-guide RNA" and "Cas9-dual-guide RNA" typically refer to a two-component RNA system for a polynucleotide component capable of associating with a cognate Cas9 protein. FIG. 1A and FIG. 1B present illustrative examples of Class 2 Type II CRISPR-Cas9-associated dual-guide RNAs. FIG. 1A illustrates a Type II CRISPR-Cas9 system two-component RNA comprising a Cas9-crRNA (FIG. 1A, 101) and a Cas9-tracrRNA (FIG. 1A, 102). FIG. 1B illustrates the formation of base-pair hydrogen bonds between the Cas9-crRNA and the Cas9-tracrRNA to form secondary structure (see, e.g., U.S. Published Patent Application No. 2014-0068797, published 6 Mar. 2014; see also Jinek M., et al., Science 337:816-21 (2012)). FIG. 1B presents an overview of and nomenclature for secondary structural elements of the Cas9-crRNA and Cas9-tracrRNA of the *S. pyogenes* Cas9 including the following: a spacer element (FIG. 1B, 103) comprising a spacer sequence (also referred to herein as a nucleic acid target binding sequence); a first stem element (FIG. 1B, 104, 105, 106) comprising a lower stem element (FIG. 1B, 104), a bulge element comprising unpaired nucleotides (FIG. 1B, 105), and an upper stem element (FIG. 1B, 106); a *nexus* element (FIG. 1B, 107) comprising a second stem element; a first 3' hairpin element (FIG. 1B, 108) comprising a third stem element; and a second 3' hairpin element (FIG. 1B, 109) comprising a fourth stem element. In some Class 2 Type II CRISPR-Cas9 systems, the first stem element does not have a bulge element (e.g., *C. jejuni*). FIG. 1C illustrates a Type II CRISPR-Cas9 two-RNA component system comprising a Cas9-crRNA (FIG. 1C, 101) and a Cas9-tracrRNA (FIG. 1C, 102). FIG. 1D illustrates the formation of base-pair hydrogen bonds between the Cas9-crRNA and the Cas9-tracrRNA to form a secondary structure. FIG. 1D presents an overview of and nomenclature for the following: a spacer element (FIG. 1D, 103); a first stem element (FIG. 1D, 110); a nexus element (FIG. 1D, 107) comprising a second stem element; a first 3' hairpin element (FIG. 1D, 108) comprising a third stem element; and a second 3' hairpin element (FIG. 1D, 109) comprising a fourth stem element. A Cas9-dual-guide RNA is capable of forming a nucleoprotein complex with a cognate Cas9 protein, wherein the complex is capable of targeting a nucleic acid target sequence complementary to the spacer sequence. Modifications of Cas9-dual-guides are known in the art, including, deletion of one or more 3' hairpin elements (FIG. 1B, 108, 109; FIG. 1D, 108, 109), modifications of the first stem element (FIG. 1B, 104, 105, 106; FIG. 1D 110), and modifications of the upper stem, bulge, and lower stem (FIG. 1B, 106, 105, 104, respectively) (see, e.g., U.S. Patent Publication No. 2014-0315985, published 23 Oct. 2014; U.S. Patent Publication No. 2015-0376586, published 31 Dec. 2015). As used herein, a "dual-guide Cas9 polynucleotide" refers to a two-component system having a polynucleotide with the same structural elements as a crRNA (FIG. 1A, 101) and a polynucleotide with the same structural elements as a tracr-RNA (FIG. 1A 102). A dual-guide Cas9 polynucleotide system is capable of associating with a cognate Cas9 protein.

As used herein, "single-guide RNA" (sgRNA) and "Cas9-sgRNA" typically refer to a one-component RNA system as further described herein, wherein the system is capable of associating with a cognate Cas9 protein.

Figure 2A:
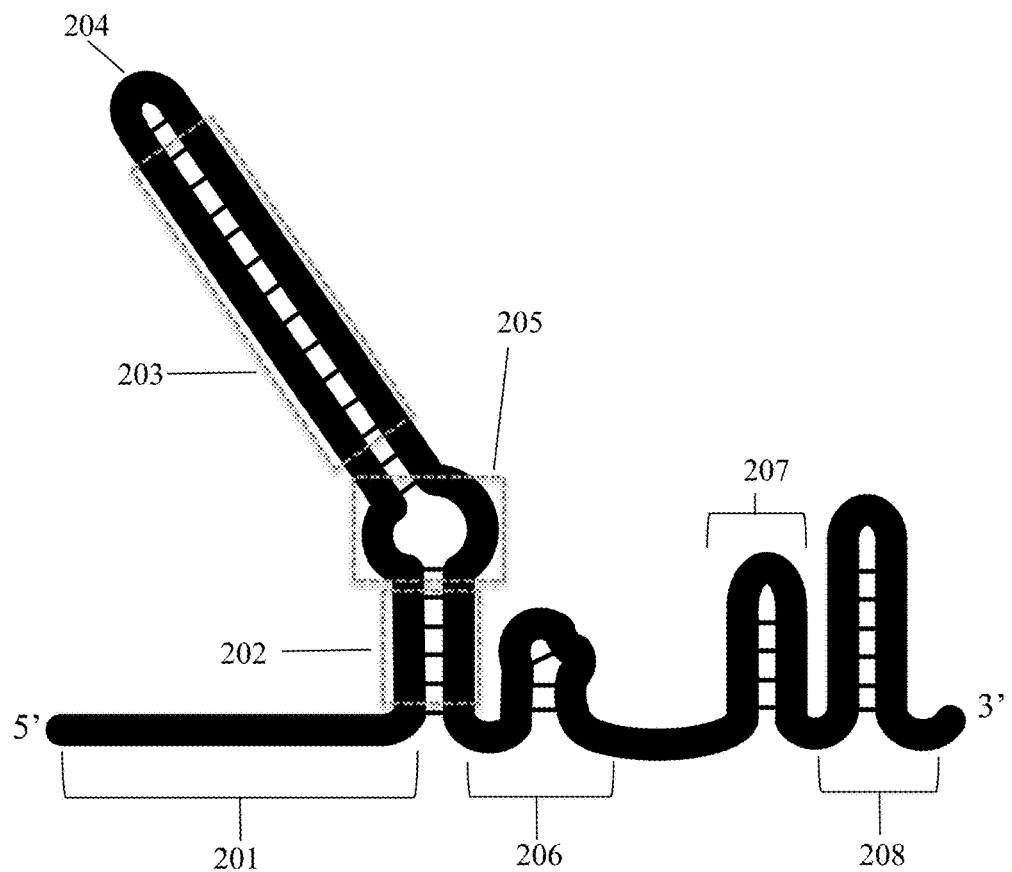
FIG. 2A, FIG. 2B, and FIG. 2C present examples of single-guide Class 2 Type II CRISPR-associated guide RNAs.
Figure 2B:
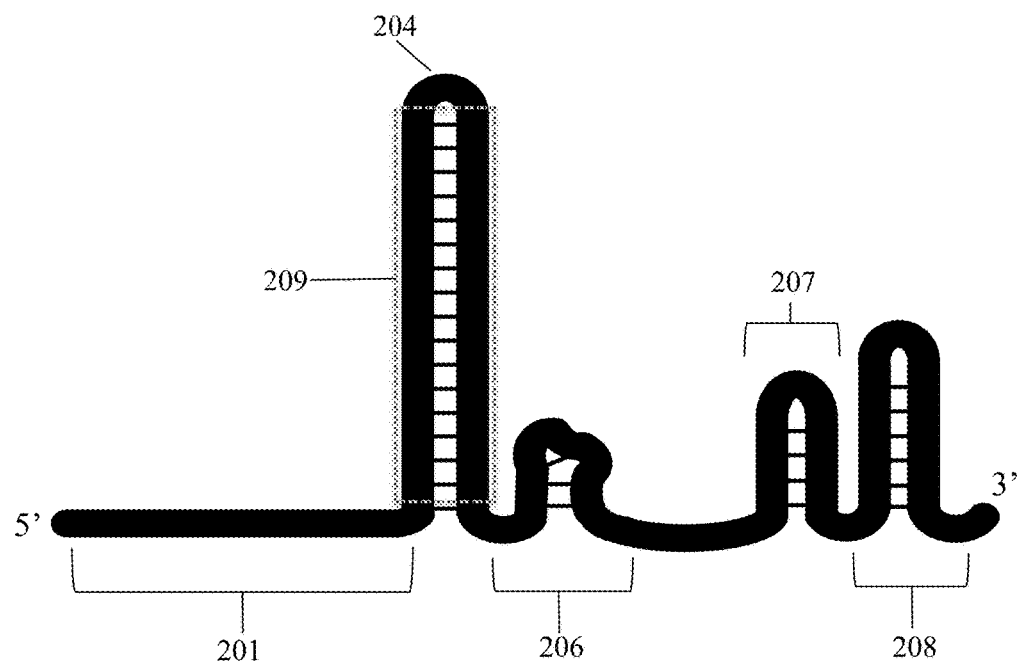
Figure 2C:
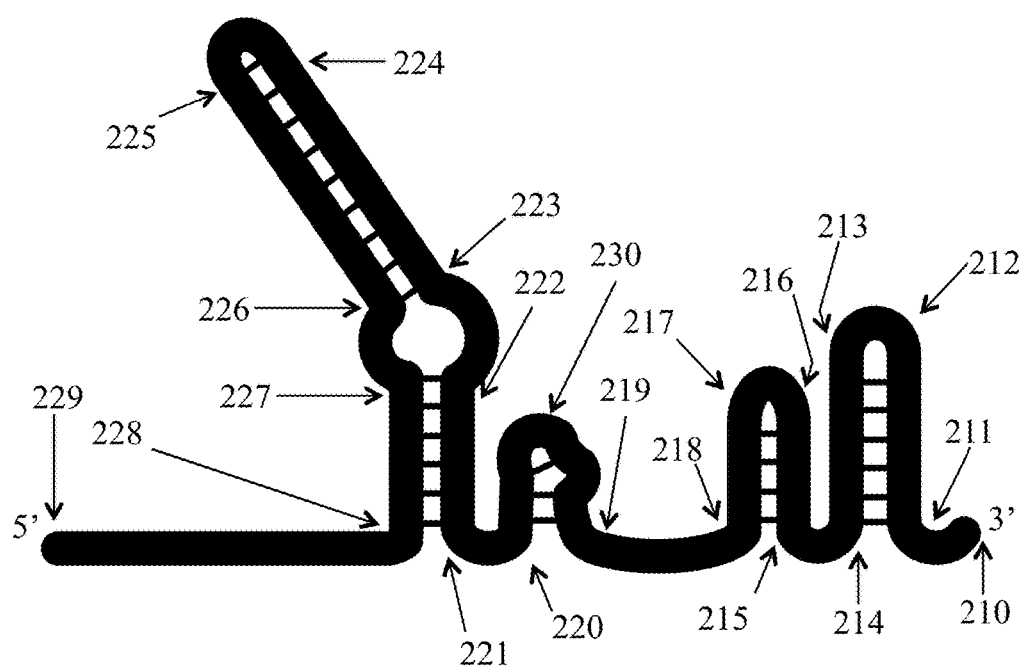

FIG. 2A, FIG. 2B and FIG. 2C show examples of Class 2 Type II CRISPR-Cas9-associated RNA. These figures illustrate Cas9 single-guide RNAs (Cas9-sgRNA) wherein the Cas9-crRNA is covalently joined to the Cas9-tracrRNA, often through a tetraloop, and forms a RNA polynucleotide secondary structure through base-pair hydrogen bonding (see, e.g., U.S. Published Patent Application No. 2014-0068797, published 6 Mar. 2014). FIG. 2A presents an overview of and nomenclature for secondary structural elements of a Cas9-sgRNA for *S. pyogenes* including the following: a spacer element (FIG. 2A, 201) comprising a spacer sequence (also referred to herein as a nucleic acid targeting nucleic acid sequence); a first stem-loop element (FIG. 2A, 202, 205, 203, 204) comprising a lower stem element (FIG. 2A, 202), a bulge element comprising unpaired nucleotides (FIG. 2A, 205), and an upper stem element (FIG. 2A, 203), and a loop element (FIG. 2A, 204) comprising unpaired nucleotides; a nexus element (FIG. 2A, 206) comprising a second stem-loop element; a first 3' hairpin element (FIG. 2A, 207) comprising a third stem-loop element; and a second 3' hairpin element comprising a third stem element (FIG. 2A, 208) comprising a fourth stem-loop element. (See, e.g., FIGS. 1 and 3 of Briner, A. E., et al., Molecular Cell 56(2):333-339 (2014)).

FIG. 2B presents an overview of and nomenclature for secondary structural elements of a Cas9-sgRNA for *C. jejuni* including the following: a spacer element (FIG. 2B, 201); a first stem element (FIG. 2B, 209) and a loop element (FIG. 2B, 204) comprising unpaired nucleotides (i.e., the first stem-loop element comprises the first stem element and the loop element); a nexus element (FIG. 2B, 206) comprising a second stem-loop element; a first 3' hairpin element (FIG. 2B, 207) comprising a third stem-loop element; and a second 3' hairpin element comprising a third stem element (FIG. 2B, 208) comprising a fourth stem-loop element. A Cas9-sgRNA is capable of forming a nucleoprotein complex with a cognate Cas9 protein, wherein the complex is capable of targeting a nucleic acid sequence complementary to the spacer sequence.

Modifications of Cas9 single-guides are known in the art including, but not limited to, deletion of one or more 3' hairpin elements (FIG. 2, 207, 208), modifications of the first stem element (FIG. 1B, 104, 105, 106; FIG. 1D 110), and modifications of the upper stem, bulge, and lower stem (FIG. 1B, 106, 105, 104, respectively) (see, e.g., U.S. Patent Publication No. 2014-0315985, published 23 Oct. 2014; U.S. Patent Publication No. 2015-0376586, published 31 Dec. 2015).

As used herein, a "Cas9 single-guide polynucleotide" refers to a one-component system having the same structural elements as a sgRNA (FIG. 2). A single-guide Cas9 polynucleotide system is capable of associating with a cognate Cas9 protein.

FIG. 2C presents a more detailed illustration of FIG. 2A. Table 1 presents a series of numerical indicators used to illustrate regions of nucleic acid sequences associated with a Class 2 Type II CRISPR-Cas9 sgRNA. In Table 1, ":" is the equivalent of the term "comprising."

TABLE 1

Numerical Indicators Used to Illustrate Regions of Nucleic Acid Sequences in a sgRNA

| Indicator | Corresponding Region |
|---|---|
| | Nucleic acid binding protein binding sequences |
| 210 | a 3' terminus |
| 210-211 | a linker element nucleic acid sequence: a 3' terminal linker element nucleic acid sequence |
| | 3' hairpin elements (compare FIG. 2A, 207, 208) |
| 211-214 | a hairpin nucleic acid sequence 1-2: a 3' hairpin 1-2 element |
| 211-212 | a 3' hairpin 1-2 stem element nucleic acid sequence 2 |
| 212-213 | a 3' hairpin 1-2 loop element nucleic acid sequence |
| 213-214 | a 3' hairpin 1-2 stem element nucleic acid sequence 1 |
| 214-215 | a linker element nucleic acid sequence: a 3' hairpin 1-2 linker element nucleic acid sequence |
| 215-218 | a hairpin nucleic acid sequence 1-1: a 3' hairpin-1-1 element |
| 215-216 | a 3' hairpin 1-1 stem element nucleic acid sequence 2 |
| 216-217 | a 3' hairpin 1-1 loop element nucleic acid sequence |
| 217-218 | a 3' hairpin 1-1 stem element nucleic acid sequence 1 |
| 218-219 | a linker element nucleic acid sequence: a 3' hairpin 1-1 linker element nucleic acid sequence |
| | Nexus element |
| 219-220 | a nexus element nucleic acid sequence |
| 219-230 | a split-nexus stem element nucleic acid sequence 1-1 |
| 230-220 | a split-nexus stem element nucleic acid sequence 1-2 |
| | Stem 1 linker element |
| 220-221 | a connective nucleic acid sequence 1: a linker element nucleic acid sequence 1 |
| 221-228 | first stem-loop element (see also FIG. 2A, 202, 203, 204, 205; FIG. 2B, 204, 209) |
| 221-224/ 225-228 | first stem element (see also, FIG. 1A, 104, 105, 106; FIG. 1D, 110; 2A, 202, 205, 203) |
| 221-222/ 227-228 | a lower stem element 1 |
| 222-223/ 226-227 | a bulge element 1 |
| 223-224/ 225-226 | an upper stem element 1 |
| 221-224 | a first stem element nucleic acid sequence 1-2 |
| 221-222 | a lower stem element nucleic acid sequence 1-2 |
| 222-223 | a bulge element nucleic acid sequence 1-2 |
| 223-224 | an upper stem element nucleic acid sequence 1-2 |
| 224-225 | a loop element nucleic acid sequence 1 |
| 224-225 | an upper stem element nucleic acid sequence 1-1 |
| 224-225 | a bulge element nucleic acid sequence 1-1 |
| 224-225 | a lower stem element nucleic acid sequence 1-1 |
| 225-228 | a first stem element nucleic acid sequence 1-1 |
| 228-229 | a spacer element 1 comprising a nucleic acid sequence 1: a spacer nucleic acid sequence: a nucleic acid target binding sequence (e.g., a DNA target binding sequence) |
| 229 | a 5' end |

Figure 3A:
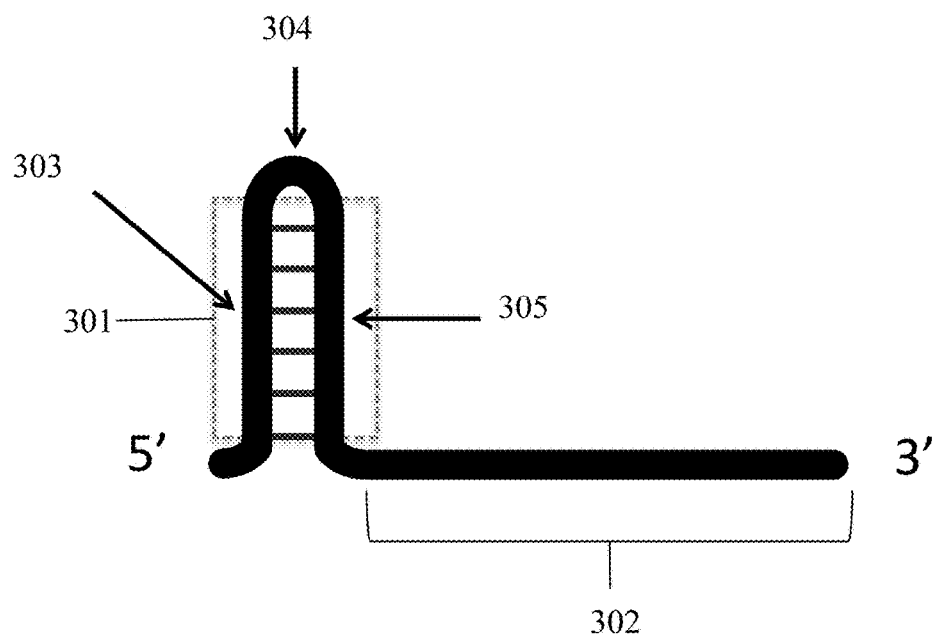
FIG. 3A and FIG. 3B present examples of a Class 2 Type V crRNA guide RNAs.
Figure 3B:
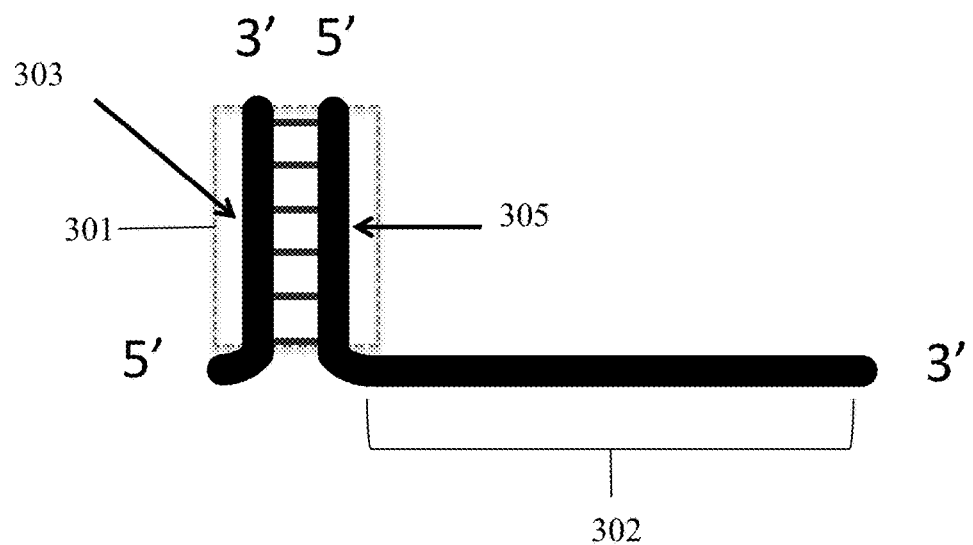

"Class 2 Type V guide crRNA" and "Cpf1-crRNA," as used herein, typically refer to a one-component RNA system for a polynucleotide component capable of associating with a cognate Cpf1 protein (see, e.g., Zetsche, B., et al., Cell 163:1-13 (2015)). FIG. 3A presents an example of a Type V CRISPR-Cpf1-associated RNA (Cpf1-crRNA), as well as an overview of and nomenclature for secondary structural elements of a Cpf1-crRNA as follows: a stem-loop element (FIG. 3A, 301) and a spacer element (FIG. 3A, 302) comprising a nucleic acid target binding sequence. The stem-loop element comprises, in a 5' to 3' direction, a Cpf1-stem RNA sequence 1C (FIG. 3A, 303), a loop element (FIG. 3A, 304), and a complementary Cpf1-stem RNA sequence 1C (FIG. 3A, 305), wherein the Cpf1-stem RNA sequence 1 and the complementary Cpf1-stem RNA sequence 1C form a duplex. FIG. 3B presents a modification of the Cpf1-crRNA wherein the loop element is removed from the stem-loop element of FIG. 3A. FIG. 3B illustrates a stem element (FIG.

3B, 301) comprising, in a 5' to 3' direction, a Cpf1-stem nucleic acid sequence 1 (FIG. 3B, 303); a complementary Cpf1-stem nucleic acid sequence 1C (FIG. 3B, 305), wherein the Cpf1-stem nucleic acid sequence 1 and the complementary Cpf1-stem nucleic acid sequence 1C form a duplex; and a spacer element (FIG. 3A, 302) comprising a nucleic acid target binding sequence. A guide crRNA is capable of forming a nucleoprotein complex with a cognate Cpf1 protein, wherein the complex is capable of targeting a nucleic acid target sequence complementary to the nucleic acid target binding sequence.

As used herein, "a nucleic acid target binding sequence" and "spacer nucleic acid sequence" refer to nucleic acid sequences capable of hybridizing to a nucleic acid target sequence in a polynucleotide. A "spacer element" comprises a nucleic acid target binding sequence.

As used herein, "a nucleic acid scaffold," "NASC," "a NASC polynucleotide composition," "a NASC composition" and "a NASC polynucleotide composition" all refer to a polynucleotide complex forming a scaffold. In preferred embodiments, the scaffold is capable of binding a nucleic acid binding protein. Typically, a NASC polynucleotide composition is a complex of two or more engineered nucleic acid sequences forming a scaffold comprising: (i) a repeat element 1 (e.g., comprising a repeat nucleic acid sequence 1) and a repeat element 2 (e.g., comprising a repeat nucleic acid sequence 2); (ii) a nucleic acid binding protein binding element 1 (e.g., comprising a nucleic acid binding protein binding sequence 1) and a nucleic acid binding protein binding element 2 (e.g., comprising a nucleic acid binding protein binding sequence 2); and (iii) a spacer element 1 (e.g., comprising a nucleic acid target binding sequence 1) and a spacer element 2 (e.g., comprising a nucleic acid target binding sequence 2). In a NASC polynucleotide composition, the repeat element 1 is connected with the repeat element 2.

The NASC polynucleotide composition is capable of associating with a nucleic acid binding protein. In some embodiments, the NASC polynucleotide composition is capable of associating with two or more nucleic acid binding proteins (e.g., nucleic acid binding proteins having similar structural motifs and functional motifs) to form a nucleoprotein complex. Examples of nucleic acid binding proteins are discussed herein below.

In some embodiments of NASC polynucleotide compositions, each of a first NASC polynucleotide component (e.g., a NASC-PC1 comprising a repeat element 1, a nucleic acid binding protein binding element 1, and a spacer element 1) and a second NASC polynucleotide component (e.g., NASC-PC2 comprising a repeat element 2, a nucleic acid binding protein binding element 2, and a spacer element 2) is capable of associating with the same kind of a nucleic acid binding protein (e.g., nucleic acid binding proteins having similar structural motifs and functional motifs) to form a nucleoprotein complex.

In other embodiments of NASC polypeptide compositions, a nucleoprotein complex is capable of being formed by a nucleic acid binding protein binding to a macromolecule comprising a nucleic acid target binding sequence 1, a repeat nucleic acid sequence 1, a repeat nucleic acid sequence 2, and a nucleic acid target binding sequence 1.

A NASC polynucleotide composition/nucleic acid binding protein 1/nucleic acid binding protein 2 complex is capable of preferentially binding a nucleic acid target sequence in a polynucleotide (relative to a polynucleotide that does not comprise the nucleic acid target sequence).

A NASC polynucleotide (NASC-PC) comprising multiple spacer elements is generically referred to herein as "a NASC-PC-MTS," and specifically referred to with reference to the number of spacer elements "a NASC-PC-(number of spacer elements) TS" (e.g., for two spacer elements, the designation used is a NASC-PC-2TS).

The components of a NASC-PC comprising multiple polynucleotides are referred to herein with reference to the number of polynucleotides "a NASC-PC-(number of polynucleotides)" (e.g., for two polynucleotides, the designation used is a NASC-PC1-1 and a NASC-PC1-2).

A NASC-PC polynucleotide component comprising concatenated elements is referred to herein as "NASC-PC-CE." In particular embodiments comprising split-nexus polynucleotides, a NASC polynucleotide component comprising concatenated split-nexus elements is referred to herein as "NASC-PC-SCE."

As used herein, "a nucleic acid brace sequence" is a nucleic acid sequence comprising at least two distinct nucleic acid target sequences: a nucleic acid target sequence 1 complementary to a nucleic acid target binding sequence 1 of a first NASC polynucleotide composition, and a nucleic acid target sequence 2 complementary to a nucleic acid target binding sequence 2 of a second NASC polynucleotide composition. An example of a nucleic acid brace sequence is a DNA brace sequence.

As used herein, "a NASC-Cage Composition (NASC-CC)" comprises at least a first NASC polynucleotide composition connected by nucleic acid brace sequences to a second NASC polynucleotide composition to form a cage-like structure typically having an internal space for packaging molecules.

As used herein, the term "cognate" typically refers to a Cas protein (e.g., Cas9 protein or a Cpf1 protein) and one or more Cas polynucleotides (e.g., Class 2 Type II CRISPR-Cas9-associated NATNA or Class 2 Type V CRISPR-Cpf1-associated NATNAs, respectively) that are capable of forming a nucleoprotein complex capable of site-directed binding to a nucleic acid target sequence complementary to the nucleic acid target binding sequence present in one of the one or more Cas polynucleotides.

The terms "wild-type," "naturally occurring," and "unmodified" are used herein to mean the typical (or most common) form, appearance, phenotype, or strain existing in nature; for example, the typical form of cells, organisms, characteristics, polynucleotides, proteins, macromolecular complexes, genes, RNAs, DNAs, or genomes as they occur in, and can be isolated from, a source in nature. The wild-type form, appearance, phenotype, or strain serve as the original parent before an intentional modification. Thus, mutant, variant, engineered, recombinant, and modified forms are not wild-type forms.

As used herein, the terms "engineered," "genetically engineered," "recombinant," "modified," "non-naturally occurring," "non-natural," and "non-native" are interchangeable and indicate intentional human manipulation.

As used herein, "interrupted," "broken," and "discontinuous" are used interchangeably to mean a break in continuity, for example, in covalent bonds of a polynucleotide backbone. For example, a first polynucleotide and a second polynucleotide that are discontinuous each have a 5' terminus and a 3' terminus (5' terminus-first polynucleotide-3' terminus and 5' terminus-second polynucleotide-3' terminus). For example, the 5' terminus of a DNA or RNA molecule is typically the fifth carbon in the sugar ring and the 3' terminus is typically the hydroxyl group on the third carbon in the sugar ring. Two polynucleotides each having a 5' terminus and a 3' terminus are formed when the backbone of a single polynucleotide is broken at one site. A 5' and/or 3' terminus can be covalently modified, for example, by addition of a moiety (e.g., a moiety providing resistance to the degradative effects of exonucleases).

"Covalent bond," "covalently attached," "covalently bound," "covalently linked," "covalently connected," and "molecular bond" are used interchangeably herein, and refer to a chemical bond that involves the sharing of electron pairs between atoms. Examples of covalent bonds include, but are not limited to, phosphodiester bonds and phosphorothioate bonds.

"Non-covalent bond," "non-covalently attached," "non-covalently bound," "non-covalently linked," "non-covalent interaction," and "non-covalently connected" are used interchangeably herein, and refer to any relatively weak chemical bond that does not involve sharing of a pair of electrons. Multiple non-covalent bonds often stabilize the conformation of macromolecules and mediate specific interactions between molecules. Examples of non-covalent bonds include, but are not limited to hydrogen bonding, ionic interactions (e.g., $Na^+Cl^-$), van der Waals interactions, and hydrophobic bonds.

As used herein, "hydrogen bonding," "hydrogen base pairing," "hydrogen bond base pairing," "hydrogen bonded," and "hydrogen-bonded base pairs" are used interchangeably and refer to canonical hydrogen bonding and non-canonical hydrogen bonding including, but not limited to, "Watson-Crick-hydrogen-bonded base pairs" (W—C-hydrogen-bonded base pairs or W—C hydrogen bonding); "Hoogsteen-hydrogen-bonded base pairs" (Hoogsteen hydrogen bonding); and "wobble-hydrogen-bonded base pairs" (wobble hydrogen bonding). W—C hydrogen bonding, including reverse W—C hydrogen bonding, refers to purine-pyrimidine base pairing, that is adenine:thymine, guanine:cytosine, and uracil:adenine. Hoogsteen hydrogen bonding, including reverse Hoogsteen hydrogen bonding, refers to a variation of base pairing in nucleic acids wherein two nucleobases, one on each strand, are held together by hydrogen bonds in the major groove. This non-W—C hydrogen bonding can allow a third strand to wind around a duplex and form triple-stranded helices. Wobble hydrogen bonding, including reverse wobble hydrogen bonding, refers to a pairing between two nucleotides in RNA molecules that does not follow Watson-Crick base pair rules. There are four major wobble base pairs:guanine:uracil, inosine (hypoxanthine):uracil, inosine-adenine, and inosine-cytosine. Rules for canonical hydrogen bonding and non-canonical hydrogen bonding are known to those of ordinary skill in the art (see, e.g., The RNA World, Third Edition (Cold Spring Harbor Monograph Series), R. F. Gesteland, Cold Spring Harbor Laboratory Press, ISBN 978-0879697396 (2005); The RNA World, Second Edition (Cold Spring Harbor Monograph Series), R. F. Gesteland, et al., Cold Spring Harbor Laboratory Press, ISBN 978-0879695613 (1999); The RNA World (Cold Spring Harbor Monograph Series), R. F. Gesteland, et al., Cold Spring Harbor Laboratory Press, ISBN 978-0879694562 (1993) (see, e.g., Appendix 1: Structures of Base Pairs Involving at Least Two Hydrogen Bonds, I. Tinoco); Principles of Nucleic Acid Structure, W. Saenger, Springer International Publishing AG, ISBN 978-0-387-90761-1 (1988); Principles of Nucleic Acid Structure, First Edition, S. Neidle, Academic Press, ISBN 978-01236950791 (2007)).

"Connect," "connected," and "connecting" are used interchangeably herein, and refer to a covalent bond or a non-covalent bond between two macromolecules (e.g., polynucleotides, proteins, and the like).

As used herein, "complementarity" refers to the ability of a nucleic acid sequence to form hydrogen bond(s) with another nucleic acid sequence (e.g., through canonical Watson-Crick base pairing). A percent complementarity indicates the percentage of residues in a nucleic acid molecule that can form hydrogen bonds with a second nucleic acid sequence. If two polynucleotide sequences have 100% complementarity, the two sequences are perfectly complementary, i.e., all of the contiguous residues of a first polynucleotide hydrogen bond with the same number of contiguous residues in a second polynucleotide.

As used herein, "binding" refers to a non-covalent interaction between macromolecules (e.g., between a protein and a polynucleotide, between a polynucleotide and a polynucleotide, or between a protein and a protein, and the like). Such non-covalent interaction is also referred to as "associating" or "interacting" (e.g., if a first macromolecule interacts with a second macromolecule, the first macromolecule binds to second macromolecule in a non-covalent manner). Some portions of a binding interaction may be sequence-specific. "Sequence-specific binding," as used herein, typically refers to one or more NASC polypeptide compositions capable of forming a complex with one or more proteins (e.g., a Cas9 protein and/or a Cpf1 protein) to cause the proteins to bind a nucleic acid sequence (e.g., a DNA sequence) comprising a nucleic acid target sequence (e.g., a DNA target sequence) preferentially relative to a second nucleic acid sequence (e.g., a second DNA sequence) without the nucleic acid target binding sequence (e.g., the DNA target binding sequence). All components of a binding interaction do not need to be sequence-specific, such as the protein binding with phosphate residues in a DNA backbone. Binding interactions can be characterized by a dissociation constant (Kd). "Binding affinity" refers to the strength of the binding interaction. An increased binding affinity is correlated with a lower Kd.

As used herein, a Cas protein (e.g., a Cas9 protein) is said to "target" a polynucleotide if a site-directed nucleoprotein complex comprising a Cas protein binds or cleaves a polynucleotide at the nucleic acid target sequence within the polynucleotide.

As used herein, "double-strand break" (DSB) refers to both strands of a double-stranded segment of DNA being severed. In some instances, if such a break occurs, one strand can be said to have a "sticky end" wherein nucleotides are exposed and not hydrogen bonded to nucleotides on the other strand. In other instances, a "blunt end" can occur wherein both strands remain fully base paired with each other.

"Donor polynucleotide," "donor oligonucleotide," and "donor template" are used interchangeably herein and can be a double-stranded polynucleotide (e.g., a double-stranded DNA), a single-stranded polynucleotide (e.g., single-stranded DNA), or a combination thereof. Donor polynucleotides comprise homology arms flanking the insertion sequence (e.g., DSBs in the DNA). The homology arms on each side can vary in length. Parameters for the design and construction of donor polynucleotides are well-known in the art (see, e.g., Ran, F., et al., Nature Protocols 8(11):2281-2308 (2013); Smithies, O., et al., Nature 317:230-234 (1985); Thomas, K., et al., Cell 44:419-428 (1986); Wu, S., et al., Nature Protocols 3:1056-1076 (2008); Singer, B., et al., Cell 31:25-33 (1982); Shen, P., et al., Genetics 112:441-457 (1986); Watt, V., et al., Proceedings of the National Academy of Sciences of the United States of America 82:4768-4772 (1985); Sugawara, N., et al., Journal of Molecular Cell Biology 12(2):563-575 (1992); Rubnitz, J., et al., Journal of Molecular Cell Biology 4(11):2253-2258 (1984); Ayares, D., et al., Proceedings of the National Academy of Sciences of the United States of America 83(14):5199-5203 (1986); Liskay, R, et al., Genetics 115 (1):161-167 (1987)).

As used herein, "homology-directed repair" (HDR) refers to DNA repair that takes place in cells, for example, during repair of a DSB in DNA. HDR requires nucleotide sequence homology and uses a donor polynucleotide to repair the sequence wherein the DSB (e.g., within a DNA target sequence) occurred. The donor polynucleotide generally has the requisite sequence homology with the sequence flanking the DSB so that the donor polynucleotide can serve as a suitable template for repair. HDR results in the transfer of genetic information from, for example, the donor polynucleotide to the DNA target sequence. HDR may result in alteration of the DNA target sequence (e.g., insertion, deletion, or mutation) if the donor polynucleotide sequence differs from the DNA target sequence and part or all of the donor polynucleotide is incorporated into the DNA target sequence. In some embodiments, an entire donor polynucleotide, a portion of the donor polynucleotide, or a copy of the donor polynucleotide is integrated at the site of the DNA target sequence. For example, a donor polynucleotide can be used for repair of the break in the DNA target sequence, wherein the repair results in the transfer of genetic information (i.e., polynucleotide sequences) from the donor polynucleotide at the site or in close proximity of the break in the DNA. Accordingly, new genetic information (i.e., polynucleotide sequences) may be inserted or copied at a DNA target sequence.

A "genomic region" is a segment of a chromosome in the genome of a host cell that is present on either side of the nucleic acid target sequence site or, alternatively, also includes a portion of the nucleic acid target sequence site. The homology arms of the donor polynucleotide have sufficient homology to undergo homologous recombination with the corresponding genomic regions. In some embodiments, the homology arms of the donor polynucleotide share significant sequence homology to the genomic region immediately flanking the nucleic acid target sequence site; it is recognized that the homology arms can be designed to have sufficient homology to genomic regions farther from the nucleic acid target sequence site.

As used herein, "non-homologous end joining" (NHEJ) refers to the repair of a DSB in DNA by direct ligation of one end of the break to the other end of the break without a requirement for a donor polynucleotide. NHEJ is a DNA repair pathway available to cells to repair DNA without the use of a repair template. NHEJ in the absence of a donor polynucleotide often results in nucleotides being randomly inserted or deleted at the site of the DSB.

"Microhomology-mediated end joining" (MMEJ) is pathway for repairing a DSB in DNA. MMEJ involves deletions flanking a DSB and alignment of microhomologous sequences internal to the broken ends before joining. MMEJ is genetically defined and requires the activity of, for example, CtIP, Poly(ADP-Ribose) Polymerase 1 (PARP1), DNA polymerase theta (Pol θ), DNA Ligase 1 (Lig 1), or DNA Ligase 3 (Lig 3). Additional genetic components are known in the art (see, e.g., Sfeir, A., et al., Trends in Biochemical Sciences 40:701-714 (2015)).

As used herein, "DNA repair" encompasses any process whereby cellular machinery repairs damage to a DNA molecule contained in the cell. The damage repaired can include single-strand breaks or double-strand breaks. At least three mechanisms exist to repair DSBs: HDR, NHEJ, and MMEJ. "DNA repair" is also used herein to refer to DNA repair resulting from human manipulation, wherein a target locus is modified, e.g., by inserting, deleting, or substituting nucleotides, all of which represent forms of genome editing.

As used herein, "recombination" refers to a process of exchange of genetic information between two polynucleotides.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, transcription start sites, repressor binding sequences, stem-loop structures, translational initiation sequences, internal ribosome entry sites (IRES), translation leader sequences, transcription termination sequences (e.g., polyadenylation signals and poly-U sequences), translation termination sequences, primer binding sites, and the like.

Regulatory elements include those that direct constitutive, inducible, and repressible expression of a nucleotide sequence in many types of host cells and those that direct expression of the nucleotide sequence only in certain host cells (e.g., tissue-specific regulatory sequences). In some embodiments, a vector comprises one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer; see, e.g., Boshart, M., et al., Cell 41:521-530 (1985)), the SV40 promoter, the dihydrofolate reductase promoter, the β-actin promoter, the phosphoglycerol kinase (PGK) promoter, and the EF1α promoter. It will be appreciated by those skilled in the art that the design of an expression vector may depend on such factors as the choice of the host cell to be transformed, the level of expression desired, and the like. A vector can be introduced into host cells to thereby produce transcripts, proteins, or peptides, including fusion proteins or peptides, encoded by nucleic acids as described herein.

"Gene," as used herein, refers to a polynucleotide sequence comprising exon(s) and related regulatory sequences. A gene may further comprise intron(s) and/or untranslated region(s) (UTR(s)).

As used herein, the term "operably linked" refers to polynucleotide sequences or amino acid sequences placed into a functional relationship with one another. For example, regulatory sequences (e.g., a promoter or enhancer) are "operably linked" to a polynucleotide encoding a gene product if the regulatory sequences regulate or contribute to the modulation of the transcription of the polynucleotide. Operably linked regulatory elements are typically contiguous with the coding sequence. However, enhancers can function if separated from a promoter by up to several kilobases or more. Accordingly, some regulatory elements may be operably linked to a polynucleotide sequence but not contiguous with the polynucleotide sequence. Similarly, translational regulatory elements contribute to the modulation of protein expression from a polynucleotide.

As used herein, "expression" refers to transcription of a polynucleotide from a DNA template, resulting in, for example, a messenger RNA (mRNA) or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product(s)." Expression may include splicing the mRNA in a eukaryotic cell, if the polynucleotide is derived from genomic DNA (gDNA).

As used herein, the term "modulate" refers to a change in the quantity, degree or amount of a function. For example, a NASC polynucleotide composition/first nucleic acid binding protein/second nucleic acid binding protein (e.g., Class 2 CRISPR-Cas proteins) complex, as disclosed herein, may modulate the activity of a promoter sequence by binding to two or more a nucleic acid target sequences at or near the promoter. Depending on the action occurring after binding, the NASC polynucleotide composition/first nucleic acid binding protein/second nucleic acid binding protein complex can induce, enhance, suppress, or inhibit transcription of a gene operatively linked to the promoter sequence. Thus, "modulation" of gene expression includes both gene activation and gene repression.

Modulation can be assayed by determining any characteristic directly or indirectly affected by the expression of the target gene. Such characteristics include, e.g., changes in RNA or protein levels, protein activity, product levels, expression of the gene, or activity level of reporter genes. Accordingly, the terms "modulating expression," "inhibiting expression," and "activating expression" of a gene can refer to the ability of a NASC polypeptide composition/nucleic acid binding protein(s) complex to change, activate, or inhibit transcription of a gene.

"Vector" and "plasmid," as used herein, refer to a polynucleotide vehicle to introduce genetic material into a cell. Vectors can be linear or circular. Vectors can contain a replication sequence capable of effecting replication of the vector in a suitable host cell (i.e., an origin of replication). Upon transformation of a suitable host, the vector can replicate and function independently of the host genome or integrate into the host genome. Vector design depends, among other things, on the intended use and host cell for the vector, and the design of a vector of the invention for a particular use and host cell is within the level of skill in the art. The four major types of vectors are plasmids, viral vectors, cosmids, and artificial chromosomes. Typically, vectors comprise an origin of replication, a multicloning site, and/or a selectable marker. An expression vector typically comprises an expression cassette.

As used herein, "expression cassette" refers to a polynucleotide construct generated using recombinant methods or by synthetic means and comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in a vector to form an expression vector.

As used herein, a "targeting vector" is a recombinant DNA construct typically comprising tailored DNA arms, homologous to gDNA, that flank elements of a target gene or nucleic acid target sequence (e.g., a DSB). A targeting vector can comprise a donor polynucleotide. Elements of the target gene can be modified in a number of ways including deletions and/or insertions. A defective target gene can be replaced by a functional target gene, or in the alternative a functional gene can be knocked out. Optionally, the donor polynucleotide of a targeting vector comprises a selection cassette comprising a selectable marker that is introduced into the target gene. Targeting regions (i.e., nucleic acid target sequences) adjacent or within a target gene can be used to affect regulation of gene expression.

As used herein, the terms "nucleic acid," "nucleic acid sequence," "nucleotide sequence," "oligonucleotide," and "polynucleotide" are interchangeable and refer to a polymeric form of nucleotides. The nucleotides may be deoxyribonucleotides (DNA), ribonucleotides (RNA), analogs thereof, or combinations thereof, and may be of any length. Polynucleotides may perform any function and may have any secondary and tertiary structures. The terms encompass known analogs of natural nucleotides and nucleotides that are modified in the base, sugar and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include fluorinated nucleotides, methylated nucleotides, and nucleotide analogs. Nucleotide structure may be modified before or after a polymer is assembled. Following polymerization, polynucleotides may be additionally modified via, for example, conjugation with a labeling component or target binding component. A nucleotide sequence may incorporate non-nucleotide components. The terms also encompass nucleic acids comprising modified backbone residues or linkages, that are synthetic, naturally occurring, and non-naturally occurring, and have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), Locked Nucleic Acid (LNA™) (Exiqon, Inc., Woburn, Mass.) nucleosides, glycol nucleic acid, bridged nucleic acids, and morpholino structures.

Peptide-nucleic acids (PNAs) are synthetic homologs of nucleic acids wherein the polynucleotide phosphate-sugar backbone is replaced by a flexible pseudo-peptide polymer. Nucleobases are linked to the polymer. PNAs have the capacity to hybridize with high affinity and specificity to complementary sequences of RNA and DNA.

In phosphorothioate nucleic acids, the phosphorothioate (PS) bond substitutes a sulfur atom for a non-bridging oxygen in the polynucleotide phosphate backbone. This modification makes the internucleotide linkage resistant to nuclease degradation. In some embodiments, phosphorothioate bonds are introduced between the last 3 to 5 nucleotides at the 5' or 3' end of a polynucleotide sequence to inhibit exonuclease degradation. Placement of phosphorothioate bonds throughout an entire oligonucleotide helps reduce degradation by endonucleases as well.

Threose nucleic acid (TNA) is an artificial genetic polymer. The backbone structure of TNA comprises repeating threose sugars linked by phosphodiester bonds. TNA polymers are resistant to nuclease degradation. TNA can self-assemble by base-pair hydrogen bonding into duplex structures.

Linkage inversions can be introduced into polynucleotides through use of "reversed phosphoramidites" (see, e.g., www.ucalgary.ca/dnalab/synthesis/-modifications/linkages). A 3'-3' linkage at a terminus of a polynucleotide stabilizes the polynucleotide to exonuclease degradation by creating an oligonucleotide having two 5'-OH termini and no 3'-OH terminus. Typically, such polynucleotides have phosphoramidite groups on the 5'-OH position and a dimethoxytrityl (DMT) protecting group on the 3'-OH position. Normally, the DMT protecting group is on the 5'-OH and the phosphoramidite is on the 3'-OH.

Polynucleotide sequences are displayed herein in the conventional 5' to 3' orientation unless otherwise indicated.

As used herein, "sequence identity" generally refers to the percent identity of nucleotide bases or amino acids comparing a first polynucleotide or polypeptide to a second polynucleotide or polypeptide using algorithms having various weighting parameters. Sequence identity between two polynucleotides or two polypeptides can be determined using sequence alignment by various methods and computer programs (e.g., BLAST, CS-BLAST, FASTA, HMMER, L-ALIGN, and the like) available through the worldwide web at sites including, but not limited to, GENBANK (www.ncbi.nlm.nih.gov/genbank/) and EMBL-EBI (www.e-bi.ac.uk.). Sequence identity between two polynucleotides or two polypeptide sequences is generally calculated using the standard default parameters of the various methods or computer programs. A high degree of sequence identity, as used herein, between two polynucleotides or two polypeptides is typically between about 90% identity and 100% identity, for example, about 90% identity or higher, preferably about 95% identity or higher, more preferably about 98% identity or higher. A moderate degree of sequence identity, as used herein, between two polynucleotides or two polypeptides is typically between about 80% identity to about 85% identity, for example, about 80% identity or higher, preferably about 85% identity. A low degree of sequence identity, as used herein, between two polynucleotides or two polypeptides is typically between about 50% identity and 75% identity, for example, about 50% identity, preferably about 60% identity, more preferably about 75% identity. For example, a Cas protein (e.g., a Cas9 comprising amino acid substitutions) can have a low degree of sequence identity, a moderate degree of sequence identity, or a high degree of sequence identity, over its length to a reference Cas protein (e.g., a wild-type Cas9). As another example, a NATNA can have a low degree of sequence identity, a moderate degree of sequence identity, or a high degree of sequence identity, over its length compared to a reference wild-type polynucleotide that complexes with the reference Cas protein (e.g., a sgRNA that forms a complex with Cas9).

As used herein, "hybridization" or "hybridize" or "hybridizing" is the process of combining two complementary single-stranded DNA or RNA molecules so as to form a single double-stranded molecule (DNA/DNA, DNA/RNA, RNA/RNA) through hydrogen base pairing. Hybridization stringency is typically determined by the hybridization temperature and the salt concentration of the hybridization buffer; e.g., high temperature and low salt provide high stringency hybridization conditions. Examples of salt concentration ranges and temperature ranges for different hybridization conditions are as follows: high stringency, approximately 0.01M to approximately 0.05M salt, hybridization temperature 5° C. to 10° C. below $T_m$; moderate stringency, approximately 0.16M to approximately 0.33M salt, hybridization temperature 20'C to 29° C. below $T_m$; and low stringency, approximately 0.33M to approximately 0.82M salt, hybridization temperature 40° C. to 48° C. below $T_m$. $T_m$ of duplex nucleic acids is calculated by standard methods well-known in the art (see, e.g., Maniatis, T., et al., Molecular Cloning: A Laboratory Manual, Cold Spring Harbor Laboratory Press: New York (1982); Casey, J., et al., Nucleic Acids Research 4:1539-1552 (1977); Bodkin, D. K., et al., Journal of Virological Methods 10(1): 45-52 (1985); Wallace, R. B., et al., Nucleic Acids Research 9(4):879-894 (1981)). Algorithm prediction tools to estimate $T_m$ are also widely available. High stringency conditions for hybridization typically refer to conditions under which a polynucleotide complementary to a target sequence predominantly hybridizes with the target sequence, and substantially does not hybridize to non-target sequences. Typically, hybridization conditions are of moderate stringency, preferably high stringency.

As used herein, a "stem element" or "stem structure" refers to a polynucleotide comprising two strands that are known or predicted to form a double-stranded region (the "stem element"). A "stem-loop element" or "stem-loop structure" refers to a stem structure wherein the 3' end of one strand is covalently bonded to the 5' end of the second strand by a nucleotide sequence of typically single-stranded nucleotides ("a stem-loop element nucleotide sequence"). In some embodiments, the loop element comprises a loop element nucleotide sequence of between about 3 and about 20 nucleotides in length, preferably between about 4 and about 10 nucleotides in length. In preferred embodiments, a loop element nucleotide sequence is a single-stranded nucleotide sequence of unpaired nucleic acid bases that do not interact through hydrogen bond formation to create a stem element within the loop element nucleotide sequence. The term "hairpin element" is also used herein to refer to stem-loop structures. Such structures are well known in the art. The base pairing may be exact; however, as is known in the art, a stem element does not require exact base pairing. Thus, the stem element may include one or more base mismatches or non-paired bases.

A "linker element nucleotide sequence" and "linker nucleotide sequence" are used interchangeably herein and refer to a single-stranded sequence of one or more nucleotides covalently attached to a 5' end, a 3' end, or to both the 5' and 3' ends of a first polynucleotide sequence, and typically refer to a single-stranded nucleic acid sequence connecting a first polynucleotide sequence with a second polynucleotide sequence. In preferred embodiments, the linker element nucleotide sequence is a single-stranded nucleotide sequence of unpaired nucleic acid bases that do not interact through hydrogen bond formation to create a stem element within the linker element nucleotide sequence. In some embodiments, a linker element nucleotide sequence is between about 1 and about 20 nucleotides in length, preferably between about 2 and about 10 nucleotides in length.

As used herein, the term "amino acid" refers to natural and synthetic (unnatural) amino acids, including amino acid analogs, modified amino acids, peptidomimetics, glycine, and D or L optical isomers.

As used herein, the terms "peptide," "polypeptide," and "protein" are interchangeable and refer to polymers of amino acids. A polypeptide may be of any length. It may be branched or linear, it may be interrupted by non-amino acids, and it may comprise modified amino acids. The terms also refer to an amino acid polymer that has been modified through, for example, acetylation, disulfide bond formation, glycosylation, lipidation, phosphorylation, pegylation, biotinylation, cross-linking, and/or conjugation (e.g., with a labeling component or ligand). Polypeptide sequences are displayed herein in the conventional N-terminal to C-terminal orientation, unless otherwise indicated.

Polypeptides and polynucleotides can be made using routine techniques in the field of molecular biology (see, e.g., standard texts discussed above). Furthermore, essentially any polypeptide or polynucleotide is available from commercial sources.

The terms "fusion protein" and "chimeric protein," as used herein, refer to a single protein created by joining two or more proteins, protein domains, or protein fragments that do not naturally occur together in a single protein. For example, a fusion protein can contain a first domain from a Cas9 protein and a second domain a Csy4 protein. The modification to include such domains in fusion protein may confer additional activity on the modified site-directed polypeptides. These activities can include nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity) that modifies a polypeptide associated with nucleic acid target sequence (e.g., a histone). A fusion protein can also comprise epitope tags (e.g., histidine tags, FLAG® (Sigma Aldrich, St. Louis, Mo.) tags, Myc tags), reporter protein sequences (e.g., glutathione-S-transferase, beta-galactosidase, luciferase, green fluorescent protein, cyan fluorescent protein, yellow fluorescent protein), and/or nucleic acid binding domains (e.g., a DNA binding domain, an RNA binding domain). A fusion protein can also comprise activator domains (e.g., heat shock transcription factors, NFKB activators) or repressor domains (e.g., a KRAB domain). As described by Lupo, A., et al., Current Genomics 14(4): 268-278 (2013), the KRAB domain is a potent transcriptional repression module and is located in the amino-terminal sequence of most C2H2 zinc finger proteins (see, e.g., Margolin, J., et al., Proceedings of the National Academy of Sciences of the United States of America 91:4509-4513 (1994); Witzgall, R., et al., Proceedings of the National Academy of Sciences of the United States of America 91:4514-4518 (1994)). The KRAB domain typically binds to co-repressor proteins and/or transcription factors via protein-protein interactions, causing transcriptional repression of genes to which KRAB zinc finger proteins (KRAB-ZFPs) bind (see, e.g., Friedman J. R., et al., Genes & Development 10:2067-2678 (1996)). In some embodiments, linker nucleic acid sequences are used to join the two or more proteins, protein domains, or protein fragments.

A "moiety," as used herein, refers to a portion of a molecule. A moiety can be a functional group or describe a portion of a molecule with multiple functional groups (e.g., that share common structural aspects). The terms "moiety" and "functional group" are typically used interchangeably; however, a "functional group" can more specifically refer to a portion of a molecule that comprises some common chemical behavior. "Moiety" is often used as a structural description. In some embodiments, a 5' terminus, a 3' terminus, or a 5' terminus and a 3' terminus (e.g., a non-native 5' terminus and/or a non-native 3' terminus in a first stem element).

The term "affinity tag," as used herein, typically refers to one or more moieties that increases the binding affinity of a polynucleotide component of a NASC polynucleotide composition, for example, to facilitate formation of a NASC complex. Some embodiments of the present invention use an "affinity sequence," which is a polynucleotide sequence comprising one or more affinity tags. In some embodiments of the present invention, a polynucleotide component further comprises an affinity sequence located at the 5' end, the 3' end, or located between the 5' end and the 3' end. Some embodiments of the present invention introduce one or more affinity tags to the N-terminal of a Cas protein sequence (e.g., a Cas9 protein sequence), to the C-terminal of a Cas protein sequence, to a position located between the N-terminal and C-terminal of a Cas protein sequence, or to combinations thereof. In some embodiments of the invention, the Cas-polypeptide is modified with an affinity tag or an affinity sequence. A wide variety of affinity tags are disclosed in U.S. Published Patent Application No. 2014-0315985, published 23 Oct. 2014.

As used herein, a "cross-link" is a bond that links one polymer chain (e.g., a polynucleotide or polypeptide) to another. Such bonds can be covalent bonds or ionic bonds. In some embodiments, one polynucleotide can be bound to another polynucleotide by cross linking the polynucleotides. In other embodiments, a polynucleotide can be cross linked to a polypeptide. In additional embodiments, a polypeptide can be cross linked to a polypeptide.

The term "cross-linking moiety," as used herein, typically refers to a moiety suitable to provide cross linking between polynucleotide components of a NASC polynucleotide composition. A cross-linking moiety is another example of an affinity tag.

The terms "ligand" and "ligand-binding moiety," as used herein, refer to moieties that facilitate the binding of polynucleotide components to form a NASC polynucleotide composition. Ligands and ligand-binding moieties are paired affinity tags.

As used herein, a "host cell" generally refers to a biological cell. A cell is the basic structural, functional and/or biological unit of an organism. A cell can originate from any organism having one or more cells. Examples of host cells include, but are not limited to, a prokaryotic cell, eukaryotic cell, a bacterial cell, an archaeal cell, a cell of a single-cell eukaryotic organism, a protozoal cell, a cell from a plant (e.g., cells from plant crops (such as soy, tomatoes, sugar beets, pumpkin, hay, cannabis, tobacco, plantains, yams, sweet potatoes, cassava, potatoes, wheat, sorghum, soybean, rice, corn, maize, oil-producing *Brassica* (e.g., oil-producing rapeseed and canola), cotton, sugar cane, sunflower, millet, and alfalfa), fruits, vegetables, grains, seeds, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. agardh,* and the like), seaweeds (e.g., kelp), a fungal cell (e.g., a yeast cell or a cell from a mushroom), an animal cell, a cell from an invertebrate animal (e.g., fruit fly, cnidarian, echinoderm, nematode, and the like), a cell from a vertebrate animal (e.g., fish, amphibian, reptile, bird, or mammal), a cell from a mammal (e.g., a pig, a cow, a goat, a sheep, a rodent, a rat, a mouse, a non-human primate, a human, and the like). Furthermore, a cell can be a stem cell or a progenitor cell.

As used herein, "stem cell" refers to a cell that has the capacity for self-renewal, i.e., the ability to go through numerous cycles of cell division while maintaining the undifferentiated state. Stem cells can be totipotent, pluripotent, multipotent, oligopotent, or unipotent. Stem cells can be embryonic, fetal, amniotic, adult, or induced pluripotent stem cells.

As used herein, "induced pluripotent stem cells" refers to a type of pluripotent stem cell that is artificially derived from a non-pluripotent cell, typically an adult somatic cell, by inducing expression of specific genes.

"Plant," as used herein, refers to whole plants, plant organs, plant tissues, germplasm, seeds, plant cells, and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to, roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. "Plant organ" refers to plant tissue or a group of tissues that constitute a morphologically and functionally distinct part of a plant.

"Subject," as used herein, refers to any member of the phylum Chordata, including, without limitation, humans and other primates, including non-human primates such as rhesus macaques, chimpanzees and other monkey and ape species; farm animals, such as cattle, sheep, pigs, goats and horses; domestic mammals, such as dogs and cats; laboratory animals, including rabbits, mice, rats and guinea pigs; birds, including domestic, wild, and game birds, such as chickens, turkeys and other gallinaceous birds, ducks, and geese; and the like. The term does not denote a particular age or gender. Thus, the term includes adult, young, and newborn individuals as well as male and female. In some embodiments, a host cell is derived from a subject (e.g., stem cells, progenitor cells, or tissue-specific cells). In some embodiments, the subject is a non-human subject.

As used herein, "transgenic organism" refers to an organism whose genome is genetically modified. The term includes the progeny (any generation) of a transgenic organism, provided that the progeny has the genetic modification.

As used herein, "isolated" can refer to a nucleic acid or polypeptide that, by human intervention, exists apart from its native environment and is therefore not a product of nature. An isolated nucleic acid or polypeptide can exist in a purified form and/or can exist in a non-native environment such as, for example, in a recombinant cell.

In a general aspect of the present invention, a NASC polynucleotide composition comprises a repeat element 1 connected with a repeat element 2, a nucleic acid binding protein binding element 1 and a nucleic acid binding protein binding element 2, and a spacer element 1 and a spacer element 2.

Repeat element 1 and repeat element two are typically connected by covalent bonds, non-covalent bonds, or a combination of covalent and non-covalent bonds. In some embodiments, repeat element 1 and repeat element 2 are connected by hydrogen-bonded base pairs.

The NASC polynucleotide composition is capable of associating with nucleic acid binding protein(s) to form a nucleoprotein complex. In some embodiments, two or more nucleic acid binding proteins having similar structural motifs and functional motifs are used to form nucleoprotein complexes with NASC polynucleotide compositions. In preferred embodiments, the nucleic acid binding proteins are Class 2 CRISPR-Cas proteins. In some embodiments, the nucleic acid binding protein binds a double-stranded nucleic acid binding protein binding sequence ("a double-stranded nucleic acid binding protein").

A NASC polynucleotide composition/nucleic acid binding protein 1/nucleic acid binding protein 2 complex is capable of preferentially binding a nucleic acid target sequence in a polynucleotide (relative to a polynucleotide that does not comprise the nucleic acid target sequence).

FIG. 4A, FIG. 4B, FIG. 4C, FIG. 4D, FIG. 4E, FIG. 4F, FIG. 4G, FIG. 4H, FIG. 4I, FIG. 4J, FIG. 4K, FIG. 4L, FIG. 4M, FIG. 4N, and FIG. 4O illustrate generic examples of different types of nucleic acid scaffolds of the present invention. These figures present relative locations of different elements in engineered nucleic acid sequences for forming scaffolds.

In some embodiments, a complex of two or more engineered nucleic acid sequences forming a scaffold comprises:

a first engineered nucleic acid comprising (i) a nucleic acid binding protein binding element 1 comprising a nucleic acid binding protein binding sequence 1 (e.g., a double-stranded nucleic acid binding protein binding sequence 1) having a first end and a second end, (ii) a repeat element 1 comprising a repeat nucleic acid sequence 1 having a first end and a second end, and (iii) a spacer element 1 comprising a nucleic acid target binding sequence 1; and a second engineered nucleic acid comprising (i) a nucleic acid binding protein binding element 1C comprising a nucleic acid binding protein binding sequence 2 (e.g., a double-stranded nucleic acid binding protein binding sequence 2) having a first end and a second end, (ii) a repeat element 2 comprising a repeat nucleic acid sequence 2 having a first end and a second end, and (iii) a spacer element 2 comprising a nucleic acid target binding sequence 2.

Repeat nucleic acid sequence 1 and repeat nucleic acid sequence 1C are complementary. Repeat nucleic acid sequence 1C is also referred to as a repeat nucleic acid sequence 2. The repeat nucleic acid sequence 1 is connected with the repeat nucleic acid sequence 1C through hydrogen-bonded base pairs.

Figure 4A:
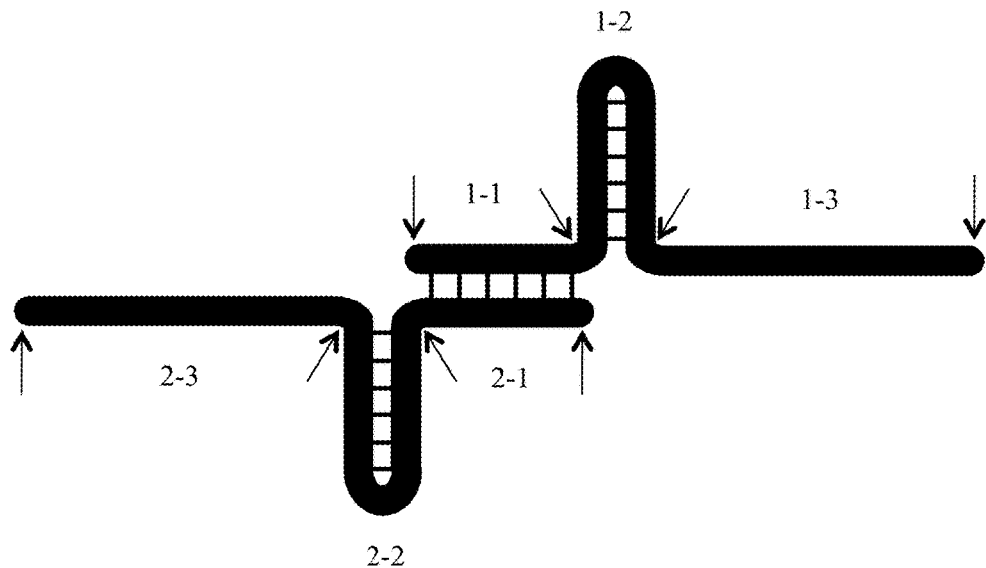
FIG. 4A, FIG. 4B, FIG. 4C, FIG. 4D, FIG. 4E, FIG. 4F, FIG. 4G, FIG. 4H, FIG. 4I, FIG. 4J, FIG. 4K, FIG. 4L, FIG. 4M, FIG. 4N, and FIG. 4O (this lattermost figure is FIG. 4 "O" and not FIG. 4 "zero") illustrate examples of generic arrangements of engineered nucleic acid scaffold polynucleotide compositions of the present invention. The illustrated sequences are not rendered in a 5' to 3' or 3' to 5' orientation and do not have polarity.
Figure 4B:
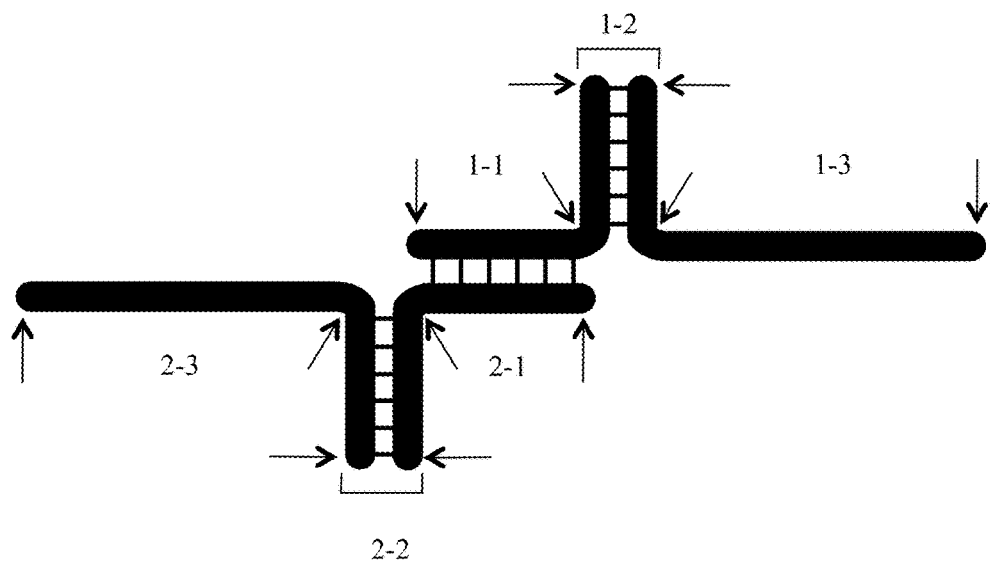
Figure 4C:
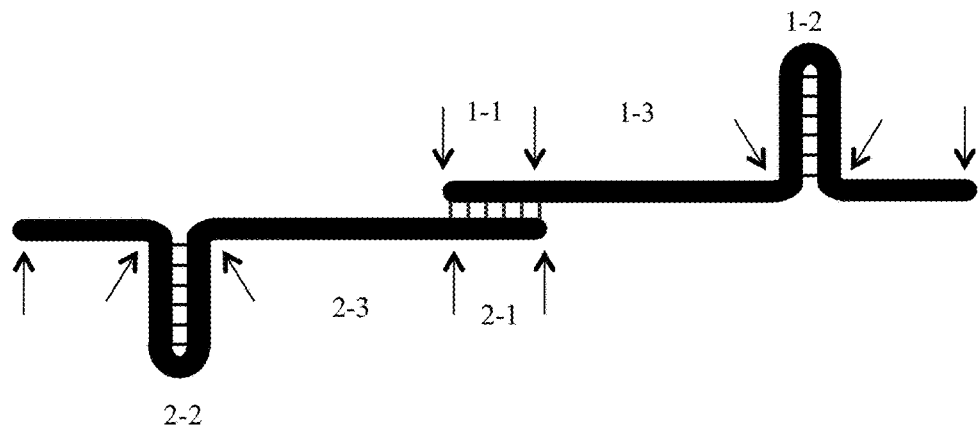
Figure 4D:
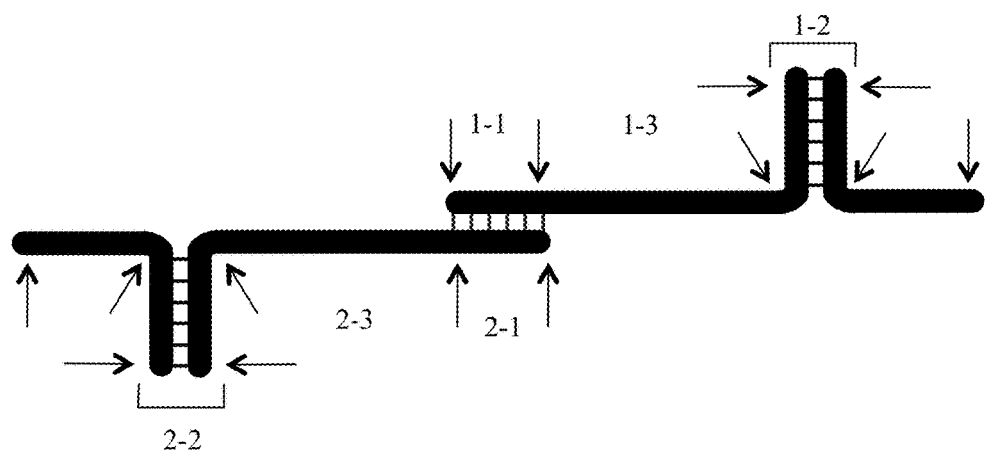
Figure 4E:
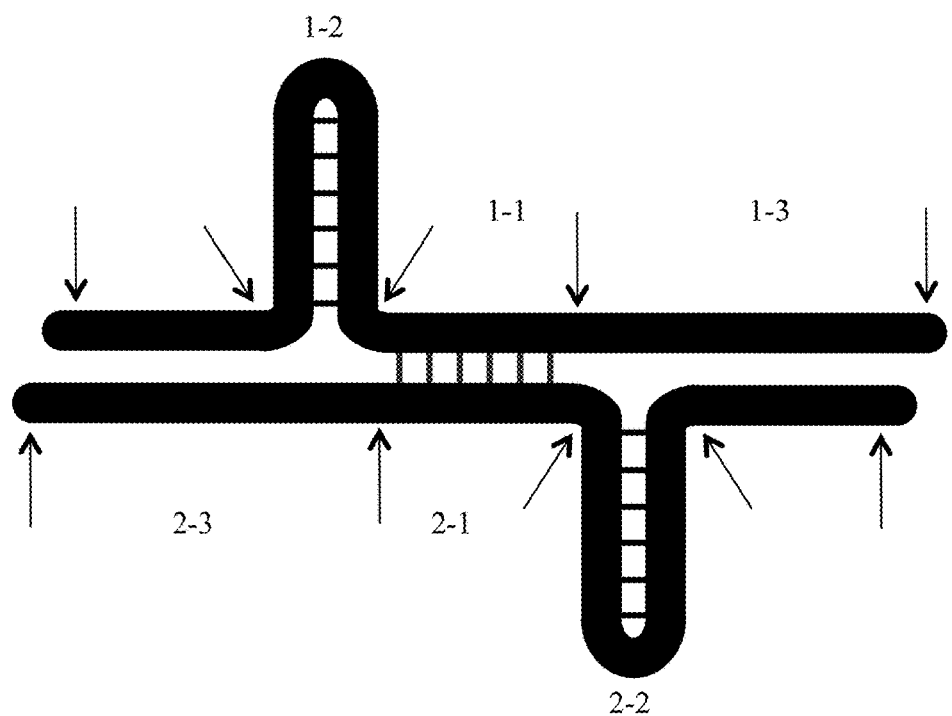
Figure 4F:
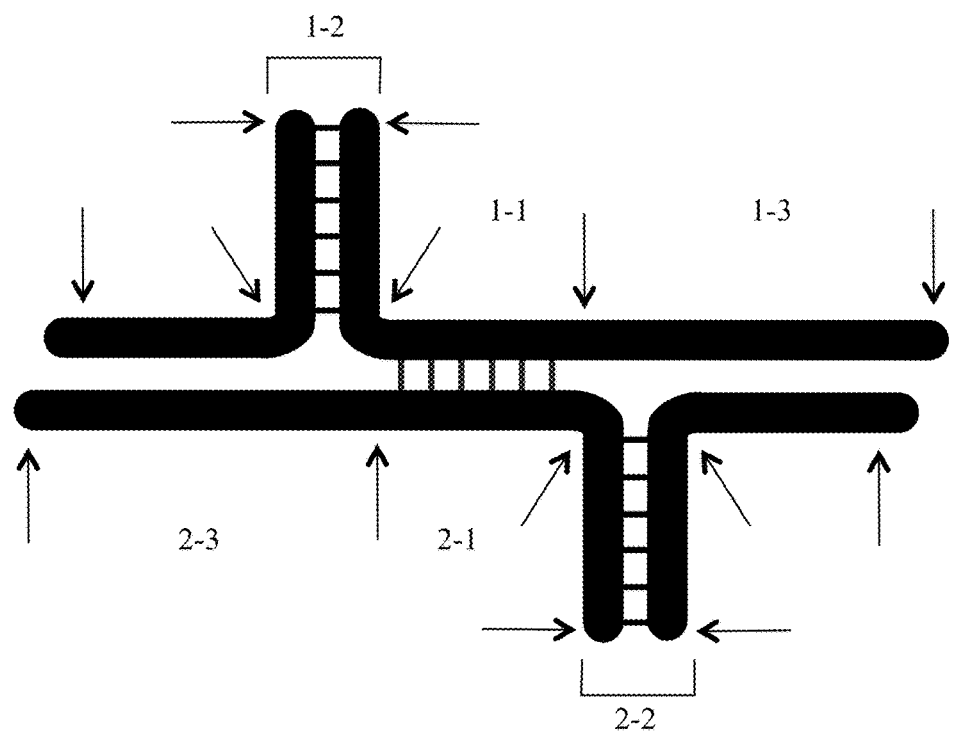
Figure 4G:
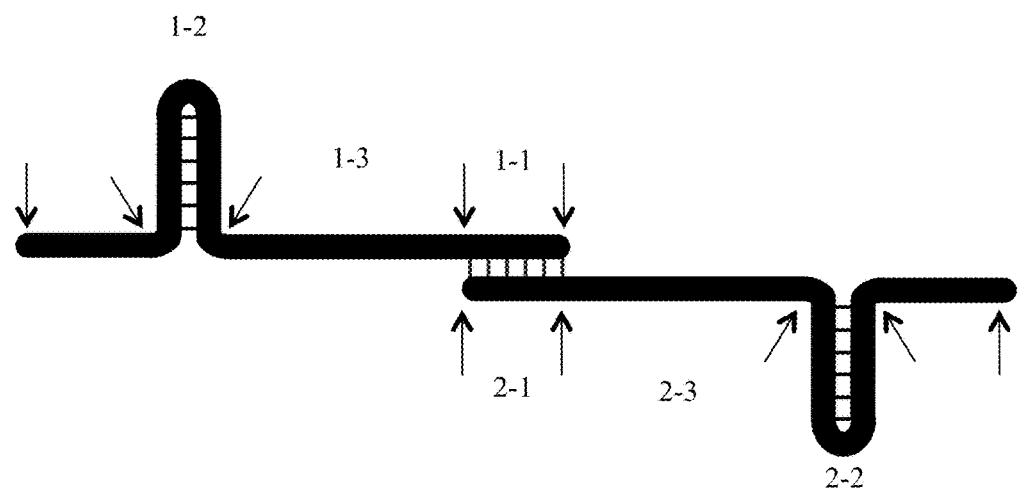
Figure 4H:
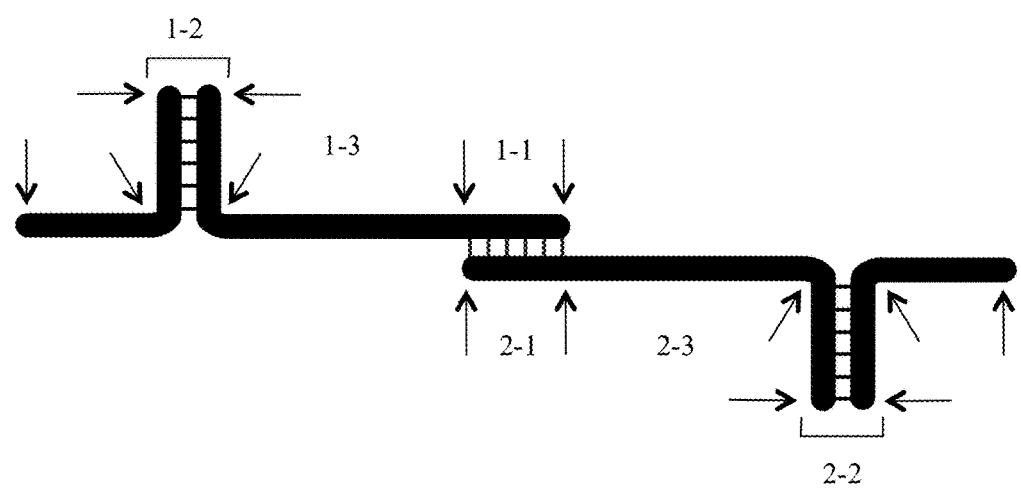
Figure 4I:
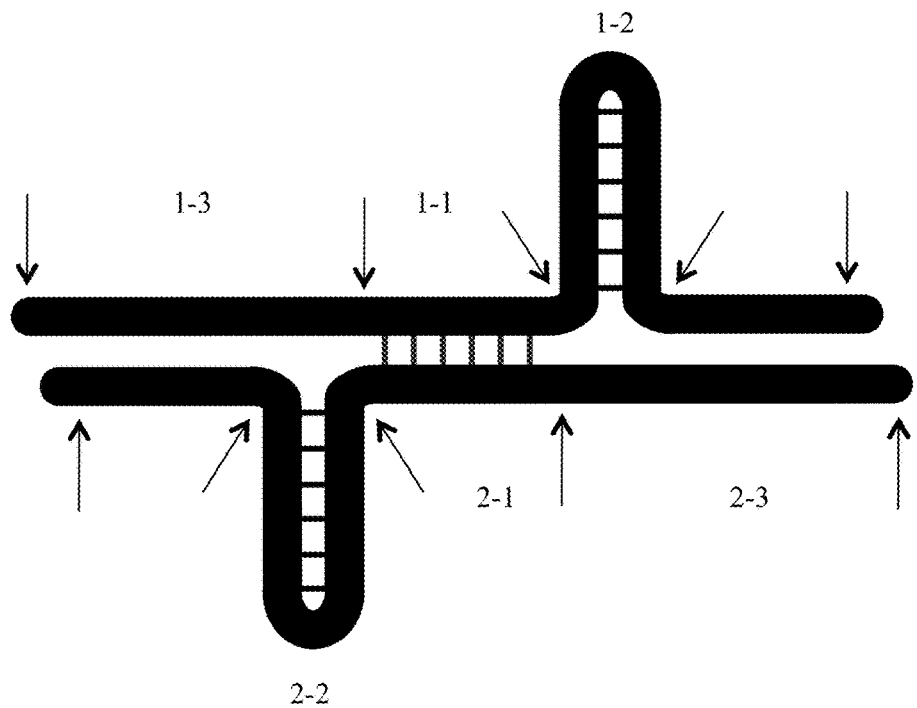
Figure 4J:
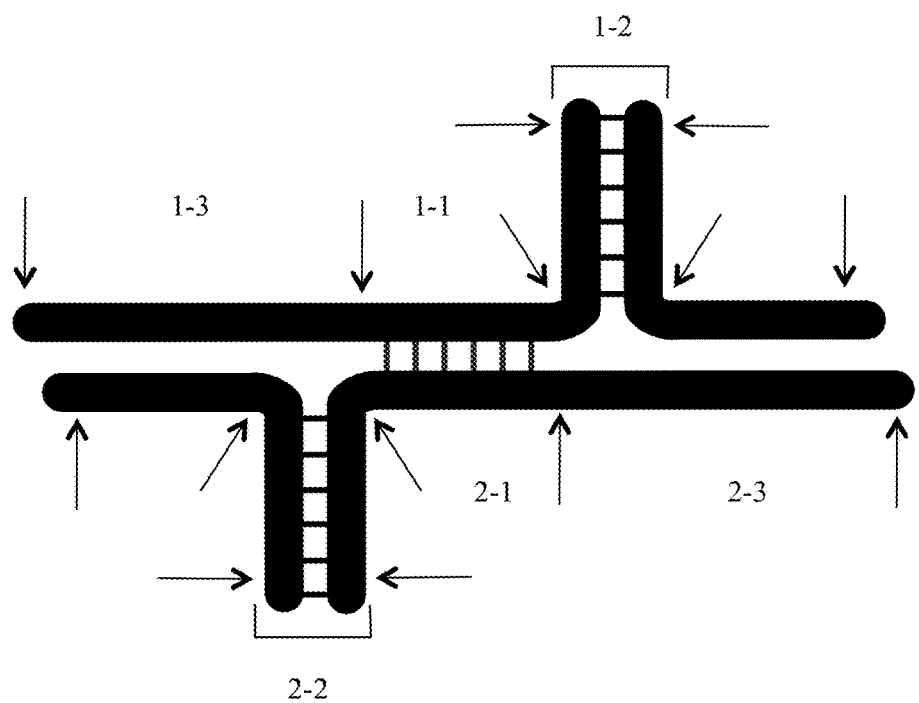
Figure 4K:
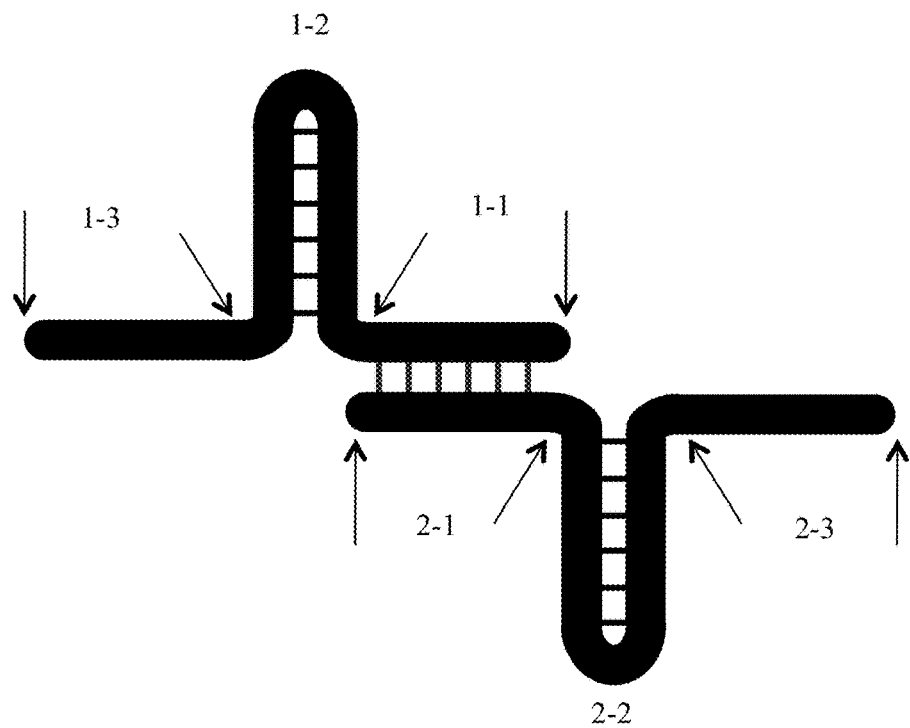
Figure 4L:
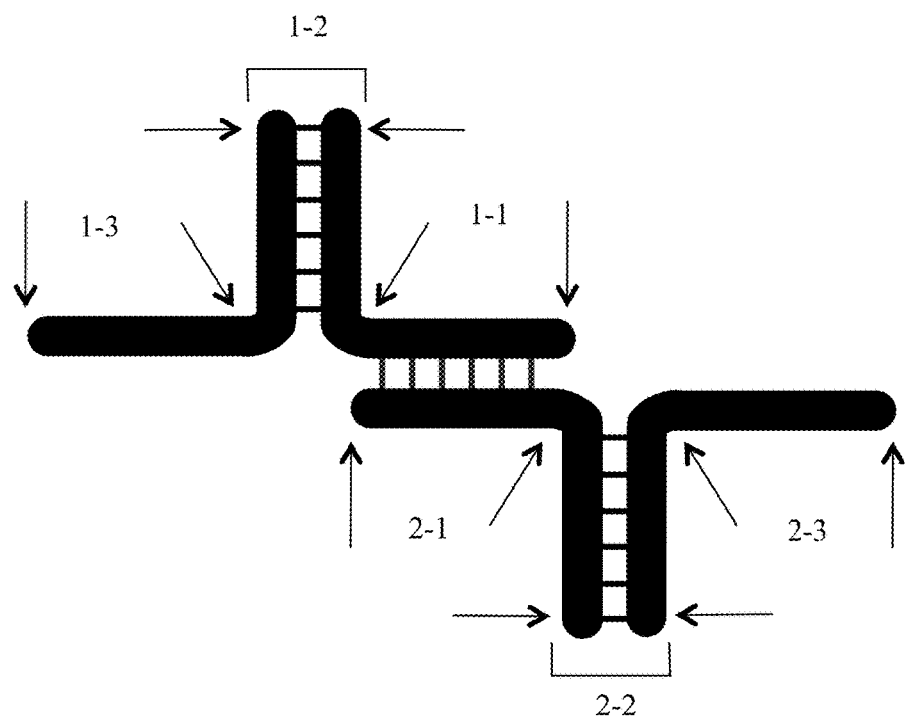
Figure 4M:
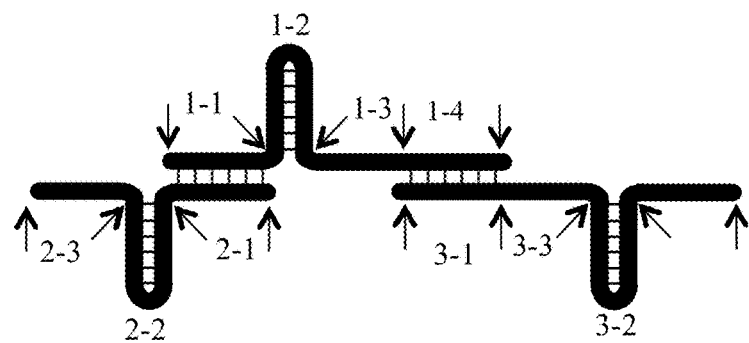
Figure 4N:
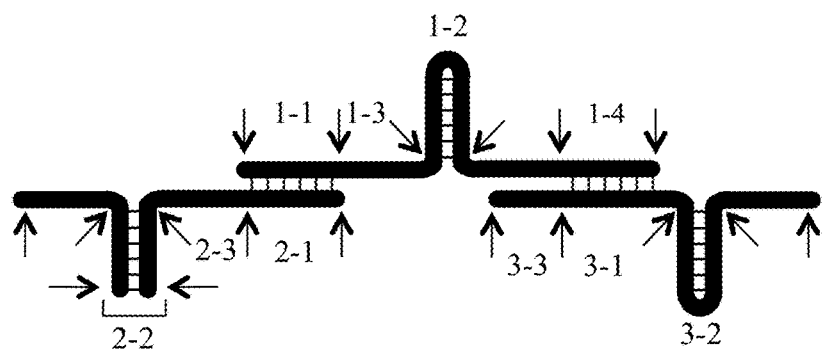
Figure 4O:
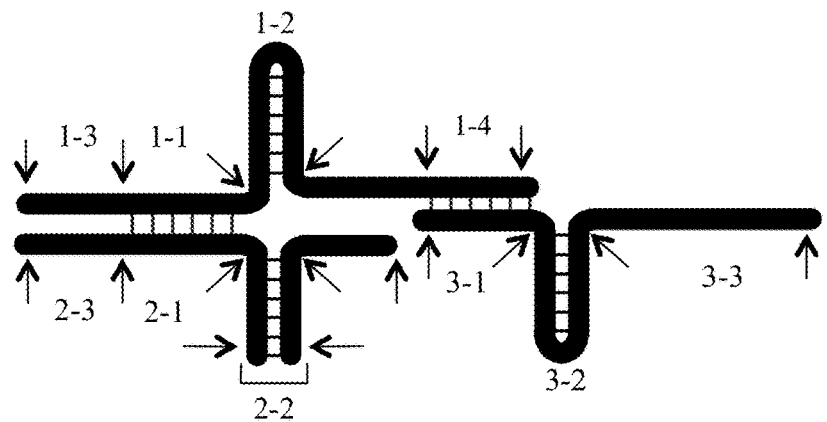

Table 2 presents a series of indicators used consistently in FIG. 4A through 4O.

TABLE 2

Numerical Indicators Used to Illustrate Regions of Complexes of Two or More Engineered Nucleic Acid Sequences for Forming a Scaffold
Indicator and Corresponding Region

| Nucleic acid sequence | General element | Element comprises | Example of element component |
|---|---|---|---|
| a first engineered nucleic acid | | | |
| 1-1 | a repeat element 1 | a repeat nucleic acid sequence 1 | a repeat nucleic acid sequence |
| 1-2 | a nucleic acid binding protein binding element 1 | a nucleic acid binding protein binding sequence 1 | a double-stranded nucleic acid binding protein binding sequence 1 |
| 1-3 | a spacer element 1 | a nucleic acid sequence 1 | a nucleic acid target binding sequence 1 |

TABLE 2-continued

Numerical Indicators Used to Illustrate Regions of Complexes of Two or More Engineered Nucleic Acid Sequences for Forming a Scaffold
Indicator and Corresponding Region

| Nucleic acid sequence | General element | Element comprises | Example of element component |
|---|---|---|---|
| a second engineered nucleic acid | | | |
| 2-1 | a repeat element 2 | a repeat nucleic acid sequence 2 | a repeat nucleic acid sequence |
| 2-2 | a nucleic acid binding protein binding element 2 | a nucleic acid binding protein binding sequence 2 | a double-stranded nucleic acid binding protein binding sequence 2 |
| 2-3 | a spacer element 2 | a nucleic acid sequence 2 | a nucleic acid target binding sequence 2 |
| a third engineered nucleic acid | | | |
| 3-1 | a repeat element 3 | a repeat nucleic acid sequence 3 | a repeat nucleic acid sequence |
| 3-2 | a nucleic acid binding protein binding element 3 | a nucleic acid binding protein binding sequence 3 | a double-stranded nucleic acid binding protein binding sequence 3 |
| 3-3 | a spacer element 3 | a nucleic acid sequence 3 | a nucleic acid target binding sequence 3 |
| additional engineered nucleic acids | | | |
| #-1 | a repeat element # | a repeat nucleic acid sequence # | a repeat nucleic acid sequence |
| #-2 | a nucleic acid binding protein binding element # | a nucleic acid binding protein binding sequence # | a double-stranded nucleic acid binding protein binding sequence # |
| #-3 | a spacer element # | a nucleic acid sequence # | a nucleic acid target binding sequence # |

An arrow in the figure corresponds to a site that can comprise additional nucleic acid sequences, such as a linker element nucleic acid sequence, and a pair of arrows illustrates boundaries of a particular element (e.g., the arrows flanking region 1-1 in FIG. 4A).
# = for additional engineered nucleic acids, sequential numbering following the number 3

FIG. 4A, FIG. 4C, FIG. 4E, FIG. 4G, FIG. 4I, and FIG. 4K, each presents one example from a collection of six different arrangements of region 1-1, region 1-2, and region 1-3 within a first engineered nucleic acid, and region 2-1, region 2-2, and region 2-3 within a second engineered nucleic acid, wherein the repeat nucleic acid sequence 1-1 is associated with the repeat nucleic acid sequence 2-1 through hydrogen bonding between the repeat nucleic acid sequence 1-1 and the repeat nucleic acid sequence 2-1. In these figures, the first engineered nucleic acid is a single polynucleotide and the second engineered nucleic acid is a single polynucleotide. Each polynucleotide has a first end and a second end. In some embodiments, the first end is a 5' end and the second end is a 3' end. In other embodiments, the first end is a 3' end and the second end is a 5' end.

FIG. 4B, FIG. 4D, FIG. 4F, FIG. 4H, FIG. 4J, and FIG. 4L each presents the same arrangement as FIG. 4A, FIG. 4C, FIG. 4E, FIG. 4G, FIG. 4I, and FIG. 4K, respectively, wherein the first engineered nucleic acid comprises multiple polynucleotides associated by hydrogen bonding (indicated in these figures as multiple straight lines between nucleic acid sequences) and the second engineered nucleic acid comprises multiple polynucleotides associated through hydrogen bonding. Each polynucleotide has a first end and a second end. In some embodiments, the first end is a 5' end and the second end is a 3' end, wherein standard 5' to 3' orientation among the polynucleotides is maintained. In other embodiments, the first end is a 3' end and the second end is a 5' end, wherein standard 5' to 3' orientation among the polynucleotides is maintained.

FIG. 4M illustrates an example of a complex of three engineered nucleic acid sequences forming a scaffold. In this figure, the first, second, and third engineered nucleic acids are each a single polynucleotide. The first and second engineered nucleic acids correspond to the first and second engineered nucleic acids presented in FIG. 4A, and the third engineered nucleic acid corresponds to the second engineered nucleic acid of FIG. 4G.

FIG. 4N illustrates an example of a complex of three engineered nucleic acid sequences forming a scaffold. In this figure, the first and third engineered nucleic acids are each a single polynucleotide. The second engineered nucleic acid comprises multiple polynucleotides associated through hydrogen bonding. The first engineered nucleic acid corresponds to the first engineered nucleic acid presented in FIG. 4C. The second engineered nucleic acid corresponds to the second engineered nucleic acid presented in FIG. 4D. The third engineered nucleic acid corresponds to the second engineered nucleic acid of FIG. 4E.

FIG. 4O illustrates an example of a complex of three engineered nucleic acid sequences forming a scaffold. In this figure, the first and third engineered nucleic acids are each a single polynucleotide. The second engineered nucleic acid comprises multiple polynucleotides associated through hydrogen bonding. The first engineered nucleic acid corresponds to the first engineered nucleic acid presented in FIG. 4I. The second engineered nucleic acid corresponds to the second engineered nucleic acid presented in FIG. 4F. The third engineered nucleic acid corresponds to the second engineered nucleic acid of FIG. 4K.

The present invention comprises a wide variety of nucleic acid-based scaffolds that are composed of a complex of two or more engineered nucleic acid sequences. In preferred embodiments, the engineered nucleic acid sequences comprise elements of Class 2 CRISPR nucleic acid targeting nucleic acids, for example, elements encoding nucleic acid sequences based on the sequences of Type 2-crRNAs, Type 2 CRISPR-tracrRNAs, and Type 2 CRISPR single-guide RNAs. Examples of Class 2 CRISPR-associated elements include, but are not limited to, the elements presented in FIG. 1A, FIG. 1B, FIG. 1C, FIG. 1D, FIG. 2A, FIG. 2B, FIG. 3A, and FIG. 3B.

In some embodiments, the nucleic acid scaffolds comprise nucleic acid protein binding sequences including, but not limited to, those associated with genome editing systems (e.g., zinc finger nucleases (ZFNs), transcription activator-like effector-based nucleases (TALENs), meganucleases, and CRISPR-Cas). Examples of nucleic acid protein binding sequences include, but are not limited to, those associated with the following nucleic acid binding proteins: Type 2 CRISPR nucleic acid binding proteins (e.g., Cpf1 protein, dCpf1 protein (catalytically inactive), Cas9 protein, and/or dCas9 protein (catalytically inactive)); Argonaute proteins; double-stranded nucleic acid binding proteins (e.g., Csy4 protein and/or Csy4* protein (catalytically inactive); see, e.g., Haurwitz, R., et al., Science 329(5997):1355-1358 (2010); Sternberg, S., et al., RNA 18(4):661-672 (2012); U.S. Pat. No. 9,115,348); single-stranded RNA binding proteins (e.g., p19 siRNA Binding Protein); single-stranded DNA binding proteins (e.g., adenovirus DBP, Extreme Thermostable SSB (single-stranded DNA binding protein); double-stranded RNA binding proteins (e.g., DICER); double-stranded DNA binding proteins (e.g., ZFNs); and double-stranded RNA/DNA hybrids (e.g., Ribonuclease H); as well as catalytically inactive versions thereof. In additional embodiments, the nucleic acid scaffolds and the associated nucleic acid binding proteins are in nucleic acid scaffold/nucleic acid binding protein complexes, for example, nucleoprotein complexes and ribonucleoprotein complexes.

In some embodiments, each of the nucleic acid binding protein binding sequences of 1-2, 2-2, and/or 3-2, is, for example, a double-stranded DNA binding protein binding sequence, a single-stranded DNA binding protein binding sequence, a double-stranded RNA binding protein binding sequence, a single-stranded RNA binding protein binding sequence, or a double-stranded DNA/RNA hybrid binding protein binding sequence. In preferred embodiments, the nucleic acid binding protein that binds the nucleic acid binding protein binding sequence is a Cas9 protein or a Cpf1 protein.

In particular embodiments, each of the nucleic acid sequence 1-1, nucleic acid sequence 1-2, and/or nucleic acid sequence 1-3 comprises a nucleic acid sequence that binds to a target nucleic acid sequence (e.g., a spacer element).

In a first aspect of the present invention, a NASC polynucleotide composition comprises a NASC-PC1 and NASC-PC2. A NASC-PC1/NASC-PC2 complex comprises a repeat element 1 connected with a repeat element 2, a double-stranded nucleic acid binding protein binding element 1 and a double-stranded nucleic acid binding protein binding element 2, and a spacer element 1 and a spacer element 2. The double-stranded nucleic acid binding proteins that are capable of binding the NASC are one or more Class 2 Type V CRISPR-Cpf1 proteins.

The NASC polynucleotide composition is capable of associating with two Class 2 Type V CRISPR-Cpf1 proteins to form a nucleoprotein complex. In some embodiments, each of NASC-PC1 and NASC-PC2 of the NASC polynucleotide compositions is capable of associating with two Class 2 Type V CRISPR-Cpf1 proteins to form a nucleoprotein complex (e.g., FIG. 5A, FIG. 5B, FIG. 5C, FIG. 5D, FIG. 5E, FIG. 5F, and FIG. 5G).

In the first aspect of the present invention, the repeat element 1 comprises a repeat nucleic acid sequence 1, the repeat element 2 comprises a repeat nucleic acid sequence 1C, the nucleic acid binding protein binding element 1 comprises a double-stranded nucleic acid binding protein binding sequence 1, the nucleic acid binding protein binding element 2 comprises a double-stranded nucleic acid binding protein binding sequence 2, the spacer element 1 comprises a nucleic acid target binding sequence 1, and the spacer element 2 comprises a nucleic acid target binding sequence 2.

The arrangements of the elements are typically as follows: (i) the repeat element 1 is 5' of the nucleic acid binding protein binding element 1, the nucleic acid binding protein binding element 1 is 5' of the spacer element 1, and the repeat element 2 is 5' of the nucleic acid binding protein binding element 2, and the nucleic acid binding protein binding element 2 is 5' of the spacer element 2; or (ii) the nucleic acid binding protein binding element 1 is 5' of the repeat element 1, the repeat element 1 is 5' of the spacer element 1, the nucleic acid binding protein binding element 2 is 5' of the repeat element 2, and the repeat element 2 is 5' of the spacer element 2; or (iii) the nucleic acid binding protein binding element 1 is 5' of the spacer element 1, the spacer element 1 is 5' of the repeat element 1, the nucleic acid binding protein binding element 2 is 5' of the spacer element 2, and the spacer element 2 is 5' of the repeat element 2.

Figure 5A:
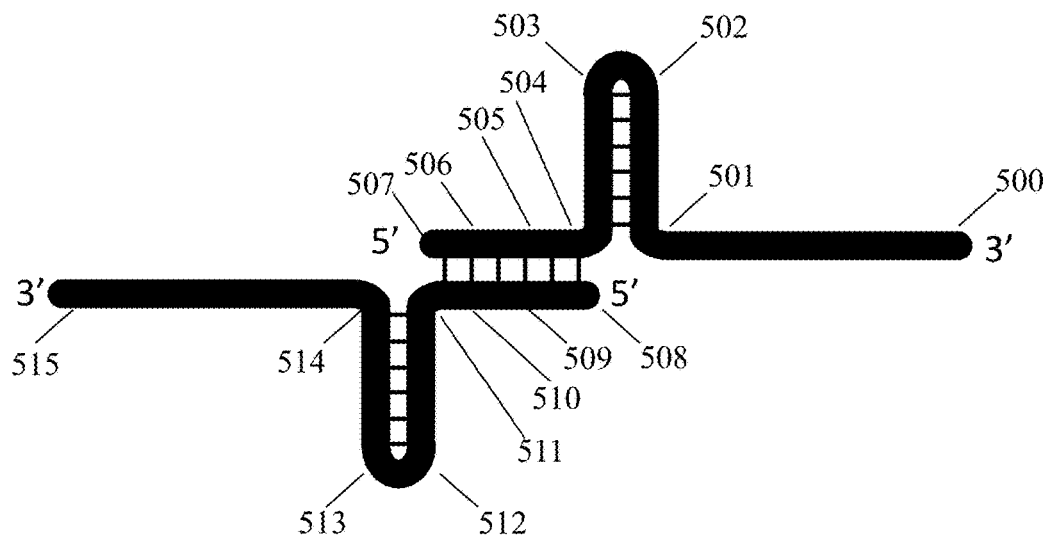
FIG. 5A, FIG. 5B, FIG. 5C, FIG. 5D, FIG. 5E, FIG. 5F, FIG. 5G, FIG. 5H, and FIG. 5I illustrate examples and elements of engineered nucleic acid scaffold polynucleotide compositions of the present invention.
Figure 5B:
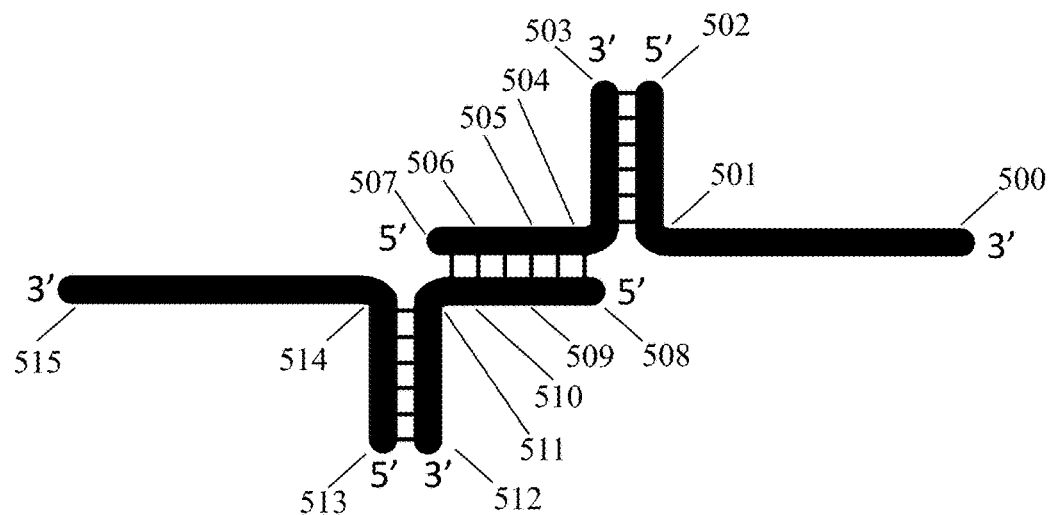
Figure 5C:
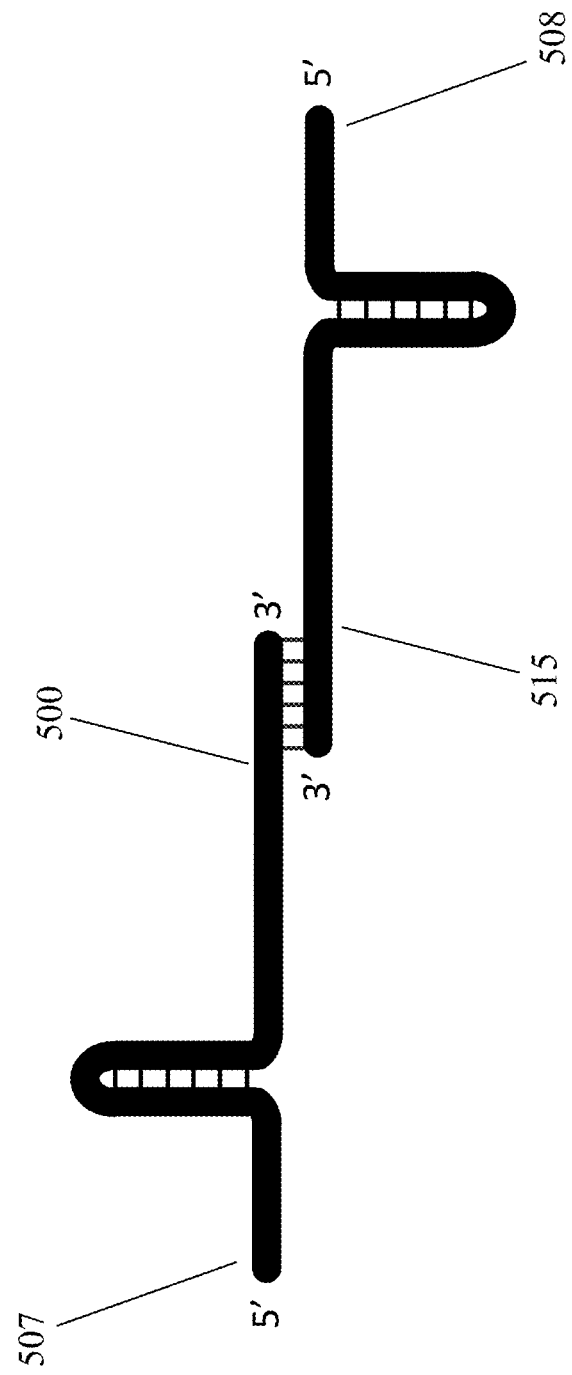
Figure 5D:
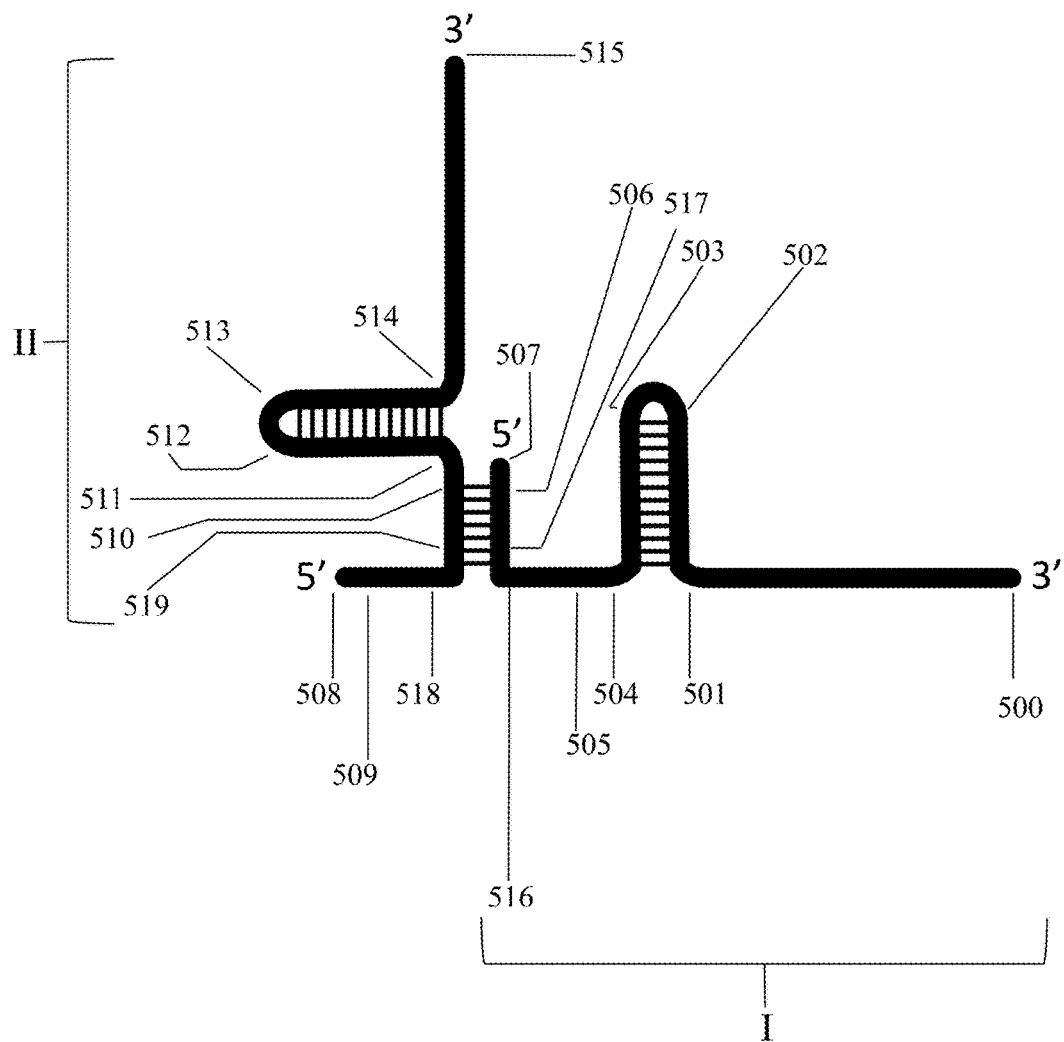
Figure 5E:
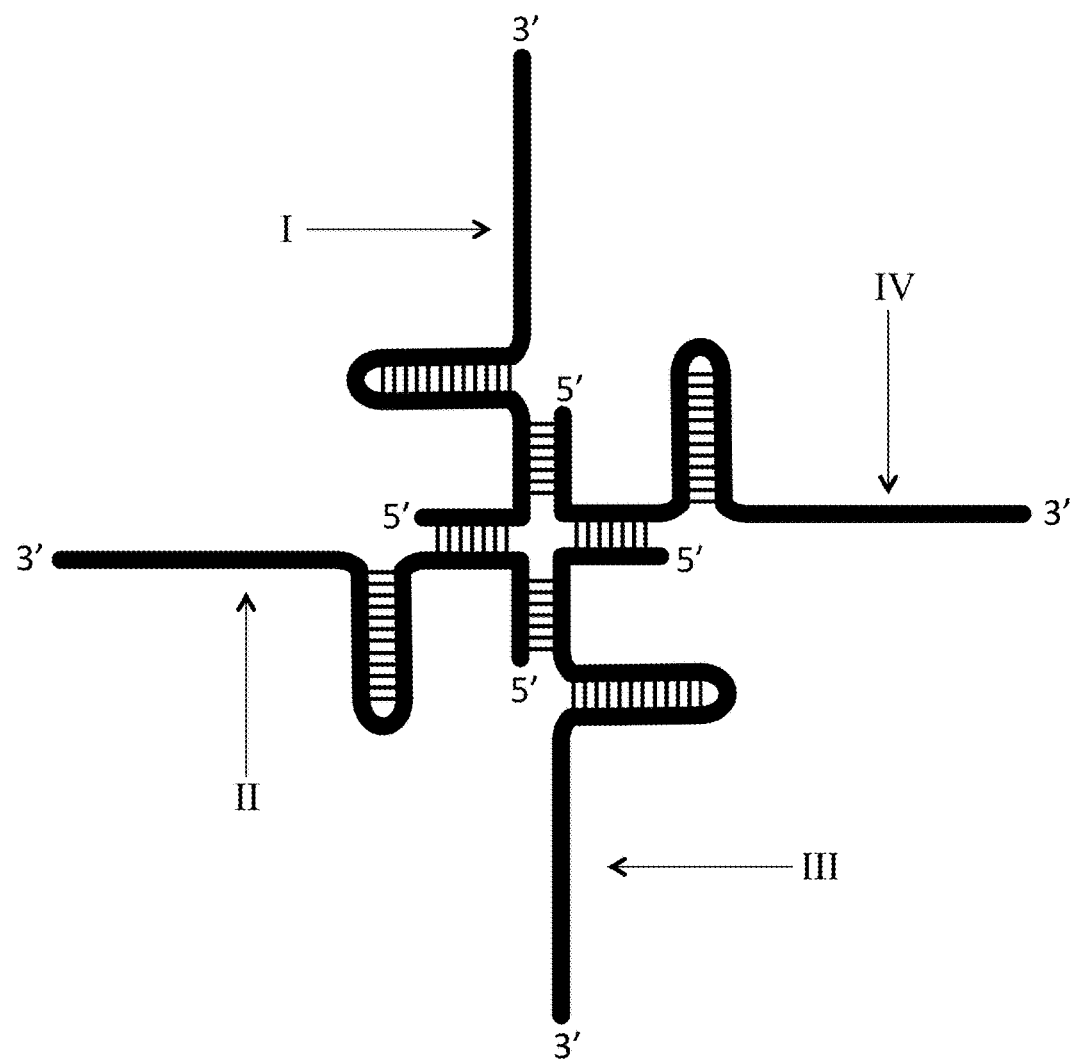
Figure 5F:
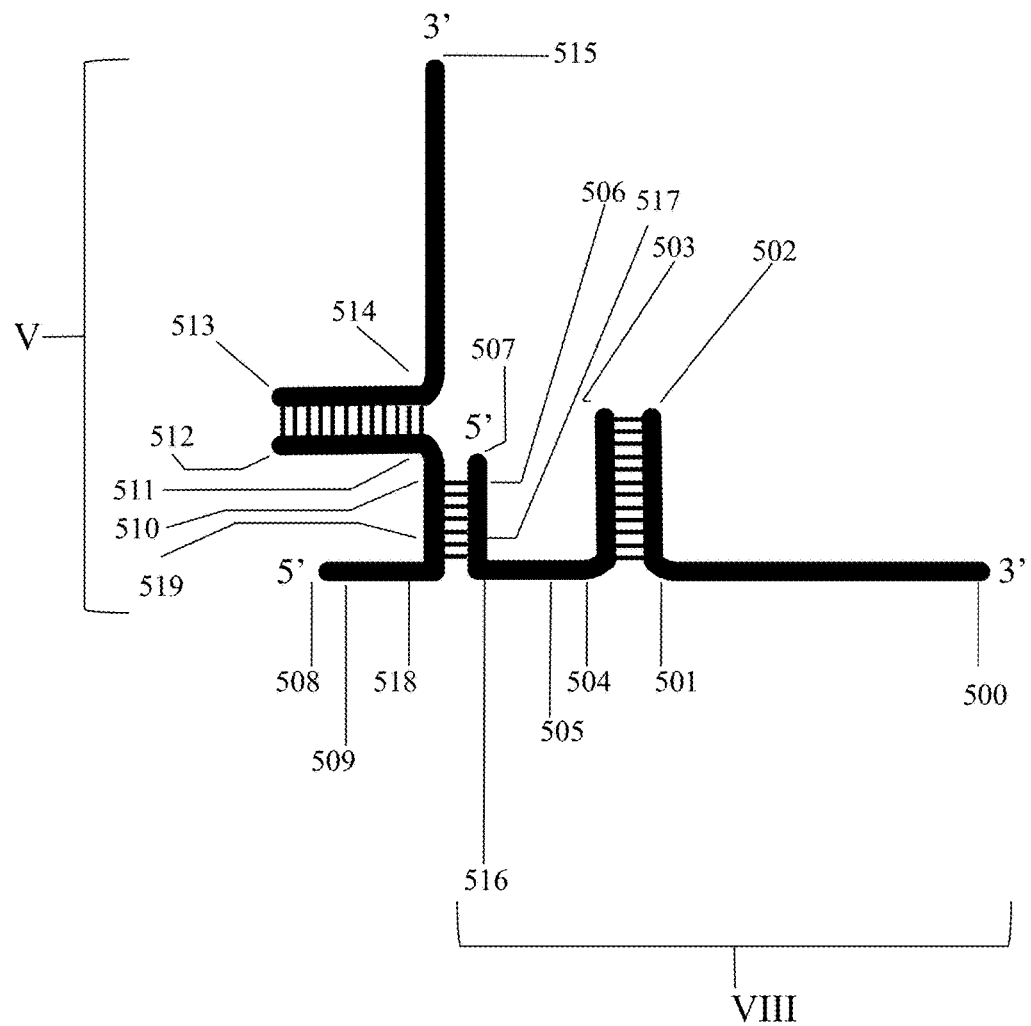
Figure 5G:
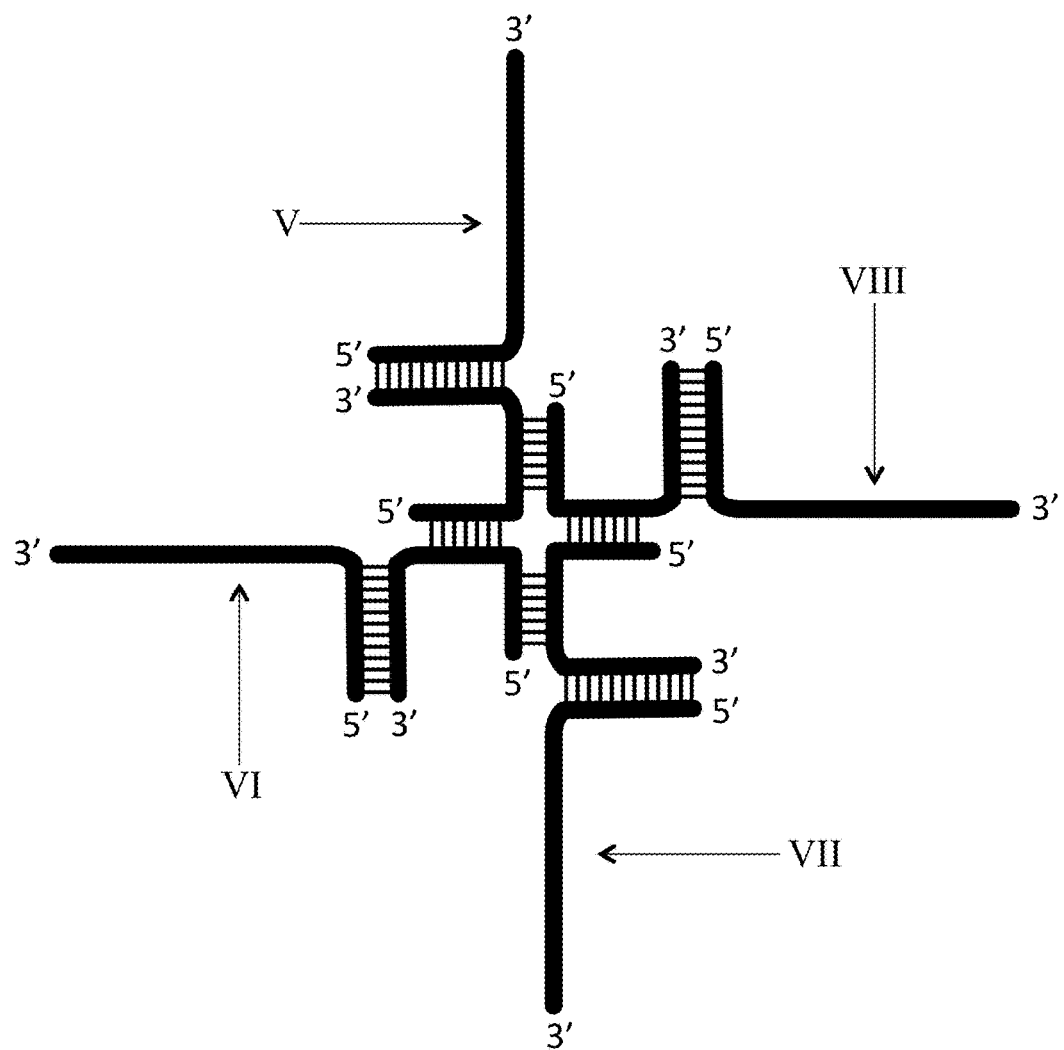

In some embodiments of the first aspect, (i) the nucleic acid binding protein binding element 1 comprises a first stem element nucleic acid sequence 1-1 and a first stem element nucleic acid sequence 1-2, and the first stem element nucleic acid sequence 1-1 and the first stem element nucleic acid sequence 1-2 form a first stem element 1 through hydrogen-bonded base pairs, and/or (ii) the nucleic acid binding protein binding element 2 comprises a first stem element nucleic acid sequence 2-1 and a first stem element nucleic acid sequence 2-2, and the first stem element nucleic acid sequence 2-1 and the first stem element nucleic acid sequence 2-2 form a first stem element 1 through hydrogen-bonded base pairs (e.g., FIG. 5B, FIG. 5F, FIG. 5G). In further embodiments, the first stem element nucleic acid sequence 1-1 and the first stem element nucleic acid sequence 1-2 are connected by a loop element nucleic acid sequence 1 to form a first stem-loop element 1, and/or the first stem element nucleic acid sequence 2-1 and the first stem element nucleic acid sequence 2-2 are connected by a loop element nucleic acid sequence 2 to form a first stem-loop element 2 (e.g., FIG. 5A, FIG. 5C, FIG. 5D, FIG. 5E).

In additional embodiments, the repeat nucleic acid sequence 1 is connected with the repeat nucleic acid sequence 1C through hydrogen-bonded base pairs between the repeat nucleic acid sequence 1 and the repeat nucleic acid sequence 1C.

In other embodiments, the repeat nucleic acid sequence 1 further comprises an affinity tag 1 and the repeat nucleic acid sequence 2 further comprises an affinity tag 2, and the affinity tag 1 is connected with affinity tag 2. For example, the repeat nucleic acid sequence 1 further comprises an effector protein binding site nucleic acid sequence 1 and the repeat nucleic acid sequence 2 further comprises an effector protein binding site nucleic acid sequence 2, and an effector binding site 1 is formed by hydrogen base-pair bonding between the effector protein binding site nucleic acid sequence 1 and the effector protein binding site nucleic acid sequence 2. One example of an effector binding site is a Csy4 protein binding site.

Table 3 presents a series of indicators used consistently in FIG. 5A, FIG. 5B, FIG. 5C, FIG. 5D, FIG. 5E, FIG. 5F, FIG. 5G, FIG. 5H, and FIG. 5I.

first nucleic acid binding Class 2 Type V CRISPR protein binding sequence (FIG. 5A, 504 to 501), a nucleic acid target binding sequence 1 (FIG. 5A, 500 to 501) that is located 3' of the first nucleic acid binding Class 2 Type V CRISPR protein binding sequence, and a first repeat sequence 1 (FIG. 5A, 504-507) that is located 5' of the first nucleic acid binding Class 2 Type V CRISPR protein binding sequence. FIG. 5A, 508 to 515, illustrates a second engineered nucleic acid that comprises a second nucleic acid binding Class 2 Type V CRISPR protein binding sequence (FIG. 5A, 514 to 511), a nucleic acid target binding sequence 2 (FIG. 5A, 515 to 514) that is located 3' of the second nucleic acid binding Class 2 Type V CRISPR protein binding sequence, and a first repeat sequence 2 (FIG. 5A, 511-508) that is located 5' of the second nucleic acid binding Class 2 Type V CRISPR protein binding sequence.

TABLE 3

Numerical Indicators Used to Illustrate Regions of Complexes of Two or More Engineered Nucleic Acid Sequences for Forming a Scaffold Indicator and Corresponding Region 500-507 corresponds to a first engineered nucleic acid sequence
  first engineered nucleic acid component
    a nucleic acid binding protein binding element 1
      a double-stranded nucleic acid binding protein binding element 1
        501-502 corresponds to a first stem element nucleic acid sequence 1-1
          501-520 corresponds to a Class 2 Type V CRISPR protein binding site half stem sequence 1-1a
          520-502 corresponds to a Class 2 Type V CRISPR protein binding site half stem sequence 1-1b
        502-503 corresponds to a loop element nucleic acid sequence 1
        503-504 corresponds to a first stem element nucleic acid sequence 1-2
    a repeat element 1[1]
      504-507 corresponds to a repeat nucleic acid sequence 1
        504-505 corresponds to a linker element nucleic acid sequence 1-1
        505-516 corresponds to a repeat nucleic acid sequence 1a
        516-517 corresponds to a linker element nucleic acid sequence 1-2
        517-506 corresponds to a repeat nucleic acid sequence 1b
        506-507 corresponds to a linker element nucleic acid sequence 1-3
    a spacer element 1
      501-500 corresponds to a nucleic acid target binding sequence 1
508-515 corresponds to a second engineered nucleic acid sequence
  a second engineered nucleic acid component
  a nucleic acid binding protein binding element 2
    a double-stranded nucleic acid binding protein binding element 2
      514-513 corresponds to a first stem element nucleic acid sequence 2-1
        521-513 corresponds to a Class 2 Type V CRISPR protein binding site half stem sequence 2-1c
        514-521 corresponds to a Class 2 Type V CRISPR protein binding site half stem sequence 2-1b
      513-512 corresponds to a loop element nucleic acid sequence 2
      512-511 corresponds to a first stem element nucleic acid sequence 2-2
    a repeat element 2
      511-508 corresponds to a repeat nucleic acid sequence 1C[2]
        510-511 corresponds to a linker element nucleic acid sequence 1C-1
        519-510 corresponds to a repeat nucleic acid sequence 1bC
        518-519 corresponds to a linker element nucleic acid sequence 1C-2
        509-518 corresponds to a repeat nucleic acid sequence 2a
        508-509 corresponds to a linker element nucleic acid sequence 1C-3
    a spacer element 2
  514-515 corresponds to a nucleic acid target binding sequence 2

[1] = repeat element can include an effector protein binding site
[2] = "C" indicates a complementary sequence FIG. 5A presents an example of two engineered nucleic acids forming a scaffold of the present invention (NASC-PC1 and NASC-PC2). In some embodiments, the engineered nucleic acids are Class 2 Type V CRISPR nucleic acid targeting nucleic acids, for example, a Cpf1 nucleic acid targeting nucleic acid comprising a repeat nucleic acid sequence covalently attached to the 5' end of the Cpf1 nucleic acid targeting nucleic acid. FIG. 5A, 500 to 507, illustrates a first engineered nucleic acid that comprises a The first engineered nucleic acid and the second engineered nucleic acid can comprise additional elements such as effector protein binding sequences, for example, a double-stranded nucleic acid binding protein binding site (e.g., a Csy4 protein binding site) created by the association of the repeat nucleic acid sequence 1 (FIG. 5A, 505-506) and the repeat nucleic acid sequence 1C (FIG. 5A, 509-510) through hydrogen bond interactions.

FIG. 5B illustrates a modification of the example shown in FIG. 5A, wherein the loop element nucleic acid sequence 1 (FIG. 5A, 502 to 503) of the first engineered nucleic acid and the loop element nucleic acid sequence 2 (FIG. 5A, 513 to 512) of the second engineered nucleic acid are absent.

FIG. 5C presents an example of two engineered nucleic acids forming a scaffold of the present invention (NASC-PC1 and NASC-PC2). In some embodiments, the engineered nucleic acids are Class 2 Type V CRISPR nucleic acid targeting nucleic acids, for example, a Cpf1 nucleic acid targeting nucleic acid comprising a repeat nucleic acid sequence covalently attached to the 3' end of the Cpf1 nucleic acid targeting nucleic acid. FIG. 5C illustrates a modification of the engineered nucleic acids, wherein a repeat sequence is added to the 3' end (FIG. 5C, 500) of a first engineered nucleic acid (FIG. 5C, 500 to 507) and a complementary repeat sequence is added to the 3' end (FIG. 5C, 515) of the second engineered nucleic acid (FIG. 5C, 508 to 515). The repeat sequence of the first engineered nucleic acid and the complementary repeat sequence of the second nucleic acid interact through hydrogen base-pair bonding.

FIG. 5D presents a modification of NASC-PC1 and NASC-PC2 depicted in FIG. 5A. In FIG. 5D the repeat nucleic acid sequence covalently attached to the 5' end of each Cpf1 nucleic acid targeting nucleic acid comprises two repeat elements separated by a linker element nucleic acid sequence, wherein only one of the two repeat elements of FIG. 5D, I, is complementary to and capable of forming hydrogen bonds with one of the repeat elements of FIG. 5D, II. FIG. 5D illustrates a version of two engineered nucleic acid forming a scaffold, wherein the repeat sequence 1b (FIG. 5D, 506-517) of the first engineered nucleic acid (FIG. 5D, 500 to 507) is capable of hydrogen base-pair bonding with the complementary repeat sequence 1bC (FIG. 5D, 519 to 510) of the second engineered nucleic acid (FIG. 5D, 515 to 508), wherein the repeat sequence 1b of the first engineered nucleic acid and the complementary repeat sequence 1bC of the second engineered nucleic acid interact through hydrogen base-pair bonding.

FIG. 5E presents an example of four engineered nucleic acids forming a scaffold based on two sets of the two engineered nucleic acids of FIG. 5D. In this FIG. 5E, I, and FIG. 5E, II, provide points of reference to facilitate comparison to the two engineered nucleic acids shown in FIG. 5D (i.e., FIG. 5D, I, and II). FIG. 5E illustrates a modified version of the example shown in FIG. 5D wherein a repeat element of the first engineered nucleic acid (FIG. 5E, I; NASC-PC-1) interacts with a repeat element of the second engineered nucleic acid (FIG. 5E, II; NASC-PC-2) through hydrogen base-pair bonding, and a repeat element of the second engineered nucleic acid (FIG. 5E, II) interacts with a repeat element of the third engineered nucleic acid (FIG. 5E, III; NASC-PC-3) through hydrogen base-pair bonding, and a repeat element of the third engineered nucleic acid (FIG. 5E, III) interacts with a repeat element of a fourth engineered nucleic acid (FIG. 5E, IV; NASC-PC-4) through hydrogen base-pair bonding, and a repeat element of the fourth engineered nucleic acid (FIG. 5E, IV) interacts with a repeat element of the first engineered nucleic acid (FIG. 5E, I) through hydrogen base-pair bonding.

FIG. 5F illustrates a modified version of the example shown in FIG. 5D, wherein the loop element nucleic acid sequences (FIG. 5D, 502 to 503 and FIG. 5D, 513 to 512) are not present in the first engineered nucleic acid sequence (FIG. 5F, VIII and FIG. 5F, V), the second engineered nucleic acid sequence (FIG. 5G, VI), the third engineered nucleic acid sequence (FIG. 5G, VI), and the fourth engineered nucleic acid sequence (FIG. 5G, VII).

FIG. 5G presents an example of four engineered nucleic acids forming a scaffold based on two sets of the two engineered nucleic acids of FIG. 5F. In this figure, 5G, V, and FIG. 5G, VIII, provide points of reference to facilitate comparison to the two engineered nucleic acids shown in FIG. 5F (i.e., FIG. 5F, V and VIII). FIG. 5G illustrates a modified version of the example shown in FIG. 5F wherein a repeat element of the first engineered nucleic acid (FIG. 5G, V; NASC-PC-1) interacts with a repeat element of the second engineered nucleic acid (FIG. 5G, VI; NASC-PC-2) through hydrogen base-pair bonding, and a repeat element of the second engineered nucleic acid (FIG. 5G, VI; NASC-PC-2) interacts with a repeat element of the third engineered nucleic acid (FIG. 5G, VII; NASC-PC-3) through hydrogen base-pair bonding, and a repeat element of the third engineered nucleic acid (FIG. 5G, VII) interacts with a repeat element of a fourth engineered nucleic acid (FIG. 5G, VIII; NASC-PC-4) through hydrogen base-pair bonding, and a repeat element of the fourth engineered nucleic acid (FIG. 5G, VIII) interacts with a repeat element of the first engineered nucleic acid (FIG. 5G, V) through hydrogen base-pair bonding.

Figure 5H:
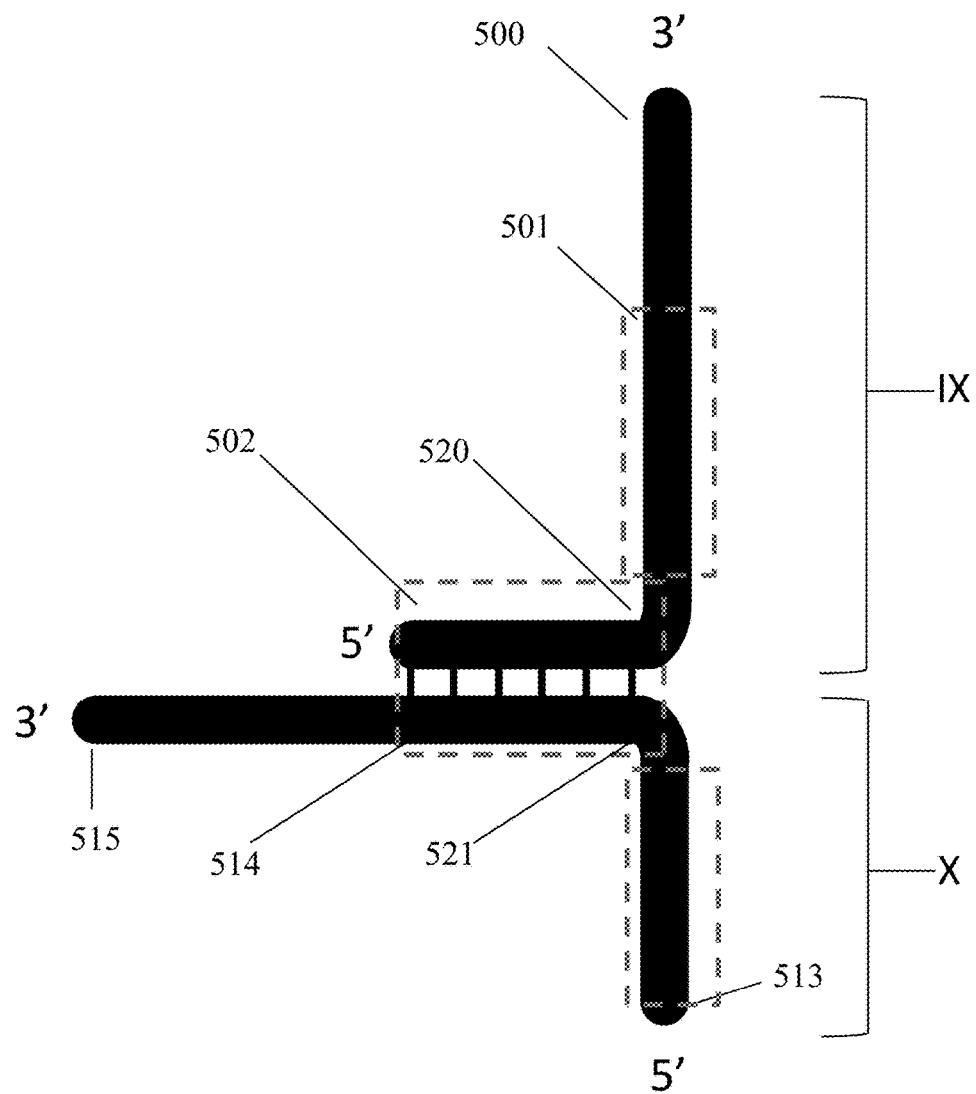
Figure 5I:
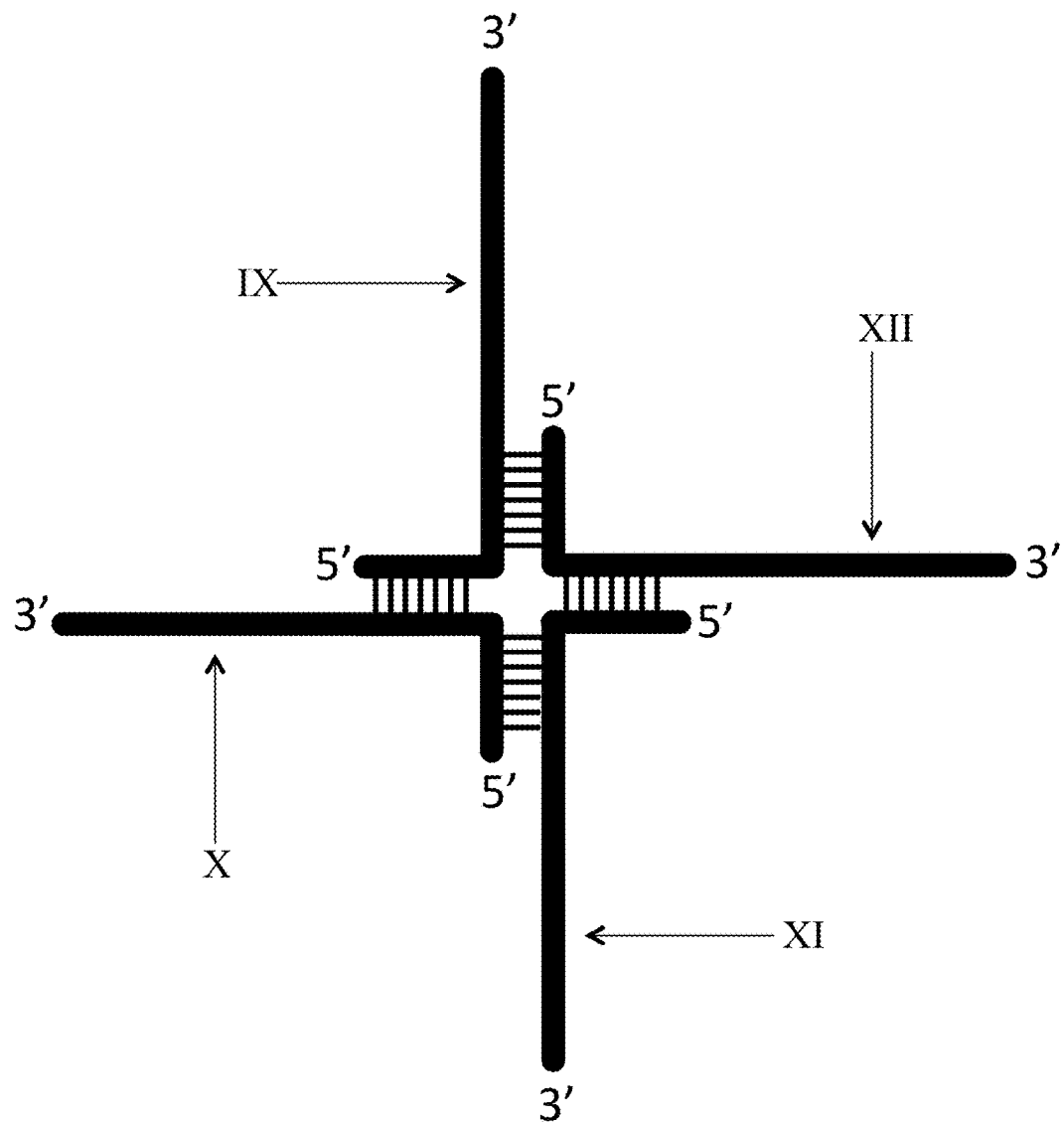

In other embodiments of the first aspect of the present invention, a nucleoprotein complex can be formed by a nucleic acid binding protein binding to a macromolecule comprising a nucleic acid target binding sequence 1, a repeat nucleic acid sequence 1, a repeat nucleic acid sequence 2, and a nucleic acid target binding sequence 1 (e.g., FIG. 5H, FIG. 5I).

FIG. 5H illustrates a version of two engineered nucleic acids forming a scaffold, wherein a Class 2 Type V CRISPR protein binding site half stem sequence 1-1b (FIG. 5H, 520-502) of a first engineered nucleic acid IX (FIG. 5H, 500 to 502; NASC-PC1) is capable of hydrogen base-pair bonding with the complementary Class 2 Type V CRISPR protein binding site half stem sequence 2-1b (FIG. 5H, 514 to 521) of a second engineered nucleic acid X (FIG. 5H, 515 to 513; NASC-PC2), and wherein the Class 2 Type V CRISPR protein binding site half stem sequence 1-1b of the first engineered nucleic acid and the complementary Class 2 Type V CRISPR protein binding site half stem sequence 2-1b of the second engineered nucleic acid interact through hydrogen base-pair bonding. Sequence variation between the half stem sequences that is sufficient to provide sequence specific hybridization between specific pairs of half stem sequences is possible because Class 2 Type V CRISPR protein binding site recognition is tolerant of such sequence variation, provided the secondary structure is maintained.

FIG. 5I illustrates a modified version of the example shown in FIG. 5H, wherein a Class 2 Type V CRISPR protein binding site half stem sequence of the first engineered nucleic acid (FIG. 5I, IX) interacts with a Class 2 Type V CRISPR protein binding site half stem sequence of the second engineered nucleic acid (FIG. 5I, X); a Class 2 Type V CRISPR protein binding site half stem sequence of the second engineered nucleic acid (FIG. 5I, X) interacts with a Class 2 Type V CRISPR protein binding site half stem sequence of the third engineered nucleic acid (FIG. 5I, XI); a Class 2 Type V CRISPR protein binding site half stem sequence of the third engineered nucleic acid (FIG. 5I, XI) interacts with a Class 2 Type V CRISPR protein binding site half stem sequence of the fourth engineered nucleic acid (FIG. 5I, XII); and a Class 2 Type V CRISPR protein binding site half stem sequence of the fourth engineered nucleic acid (FIG. 5I, XII) interacts with the Class 2 Type V CRISPR protein binding site half stem sequence of the first engineered nucleic acid (FIG. 5I, IX).

In a second aspect of the present invention, a NASC polynucleotide composition comprises at least NASC-PC1 and NASC-PC2. A NASC-PC1/NASC-PC2 complex comprises a repeat element 1 connected to a repeat element 2, a double-stranded nucleic acid binding protein binding element 1 and a double-stranded nucleic acid binding protein binding element 2, and a spacer element 1 and a spacer element 2. Embodiments of the present invention include NASC polynucleotide composition comprising double-stranded nucleic acid binding protein binding elements corresponding to one or more Class 2 CRISPR-Cas proteins.

In some embodiments, the NASC polynucleotide composition is capable of associating with two Class 2 Type II CRISPR-Cas9 proteins to form a nucleoprotein complex. FIG. 6A, FIG. 6B, FIG. 6C, FIG. 6D, FIG. 6E, FIG. 6F, FIG. 6G, FIG. 6H, FIG. 6I, FIG. 6K, FIG. 6L, and FIG. 6M illustrate elements and examples of engineered nucleic acid scaffolds of the present invention typically comprising a nucleic acid binding Class 2 CRISPR protein binding sequence.

Table 4 presents a series of indicators used consistently in FIG. 6A, FIG. 6B, FIG. 6C, FIG. 6D, FIG. 6E, FIG. 6F, and FIG. 6G.

TABLE 4

Numerical Indicators Used to Illustrate Regions of Complexes of Two or More Engineered Nucleic Acid Sequences for Forming a Scaffold
Indicator and Corresponding Region a first engineered nucleic acid component
    a first engineered nucleic acid sequence (corresponds to 601-611)
        a nucleic acid binding protein binding element 1
            a double-stranded nucleic acid binding protein binding element 1
                601-602 corresponds a linker element nucleic acid sequence
                602-603 corresponds to a hairpin nucleic acid sequence 1-2
                603-604 corresponds to a linker element nucleic acid sequence
                604-605 corresponds to a hairpin nucleic acid sequence 1-1
                605-606 corresponds to a linker element nucleic acid sequence
                606-607 corresponds to a nexus element nucleic acid sequence 1-1
                607-608 corresponds to a linker element nucleic acid sequence
        a repeat element 1[1]
            608-609 corresponds to a repeat nucleic acid sequence 1
                608-623 corresponds to a linker element nucleic acid sequence 1-1
                      623-624 corresponds to a repeat nucleic acid sequence 1a
                          623-631 corresponds to a repeat nucleic acid sequence 1a1
                          631-632 corresponds to a bulge nucleic acid sequence 1a1
                          632-624 corresponds to a repeat nucleic acid sequence 1a2
                  624-625 corresponds to a linker element nucleic acid sequence 1-2
                      624-647 corresponds to a linker element nucleic acid sequence 1-2-1
                      647-648 corresponds to a repeat nucleic acid sequence 1-2a
                      648-625 corresponds to a linker element nucleic acid sequence 1-2-2
                  625-626 corresponds to a repeat nucleic acid sequence 1b
                      625-633 corresponds to a repeat nucleic acid sequence 1b1
                      633-634 corresponds to a bulge nucleic acid sequence 1b1
                      634-626 corresponds to a repeat nucleic acid sequence 1b2
                626-609 corresponds to a linker element nucleic acid sequence 1-3
            609-610 corresponds to a linker element nucleic acid sequence
        a spacer element 1
            610-611 corresponds to a nucleic acid target binding sequence 1
a second engineered nucleic acid component
    a second engineered nucleic acid sequence (corresponds to 612-622)
        a nucleic acid binding protein binding element 2
            a double-stranded nucleic acid binding protein binding element 2
                612-613 corresponds a linker element nucleic acid sequence
                613-614 corresponds to a hairpin nucleic acid sequence 2-2
                614-615 corresponds to a linker element nucleic acid sequence
                615-616 corresponds to a hairpin nucleic acid sequence 2-1
                616-617 corresponds to a linker element nucleic acid sequence
                617-618 corresponds to a nexus element nucleic acid sequence 2-1
                618-619 corresponds to a linker element nucleic acid sequence
        a repeat element 2
            619-620 corresponds to a repeat nucleic acid sequence 1C[2]
                619-627 corresponds to a linker element nucleic acid sequence 2-3
                    627-628 corresponds to a repeat nucleic acid sequence 1bC
                      627-635 corresponds to a repeat nucleic acid sequence 1b2C
                      635-636 corresponds to a bulge nucleic acid sequence 2b2
                      636-628 corresponds to a repeat nucleic acid sequence 1b1C
                628-629 corresponds to a linker element nucleic acid sequence 2-2
                    628-649 corresponds to a linker element nucleic acid sequence 2-2-2
                    649-650 corresponds to a repeat nucleic acid sequence 1-2aC
                    650-629 corresponds to a linker element nucleic acid sequence 2-2-1
                629-630 corresponds to a repeat nucleic acid sequence 1aC
                    629-637 corresponds to a repeat nucleic acid sequence 1a2C
                    637-638 corresponds to a bulge nucleic acid sequence 2a2

TABLE 4-continued

Numerical Indicators Used to Illustrate Regions of Complexes of Two or
More Engineered Nucleic Acid Sequences for Forming a Scaffold
Indicator and Corresponding Region 638-630 corresponds to a repeat nucleic acid sequence 1a1C
630-620 corresponds to a linker element nucleic acid sequence 2-1
620-621 corresponds to a linker element nucleic acid sequence
a spacer element 2
621-622 corresponds to a nucleic acid target binding sequence 2

[1]= repeat element can include an effector protein binding site
[2]= "C" indicates a complementary sequence Each of a first, a second and a third element can comprise additional nucleic acid sequences, for example, 5' of the element, 3' of the element, or both 5' of the element and 3' of the element.

Each of a first, a second and a third element can comprise additional nucleic acid sequences, for example, 5' of the element, 3' of the element, or both 5' of the element and 3' of the element.

Figure 6A:
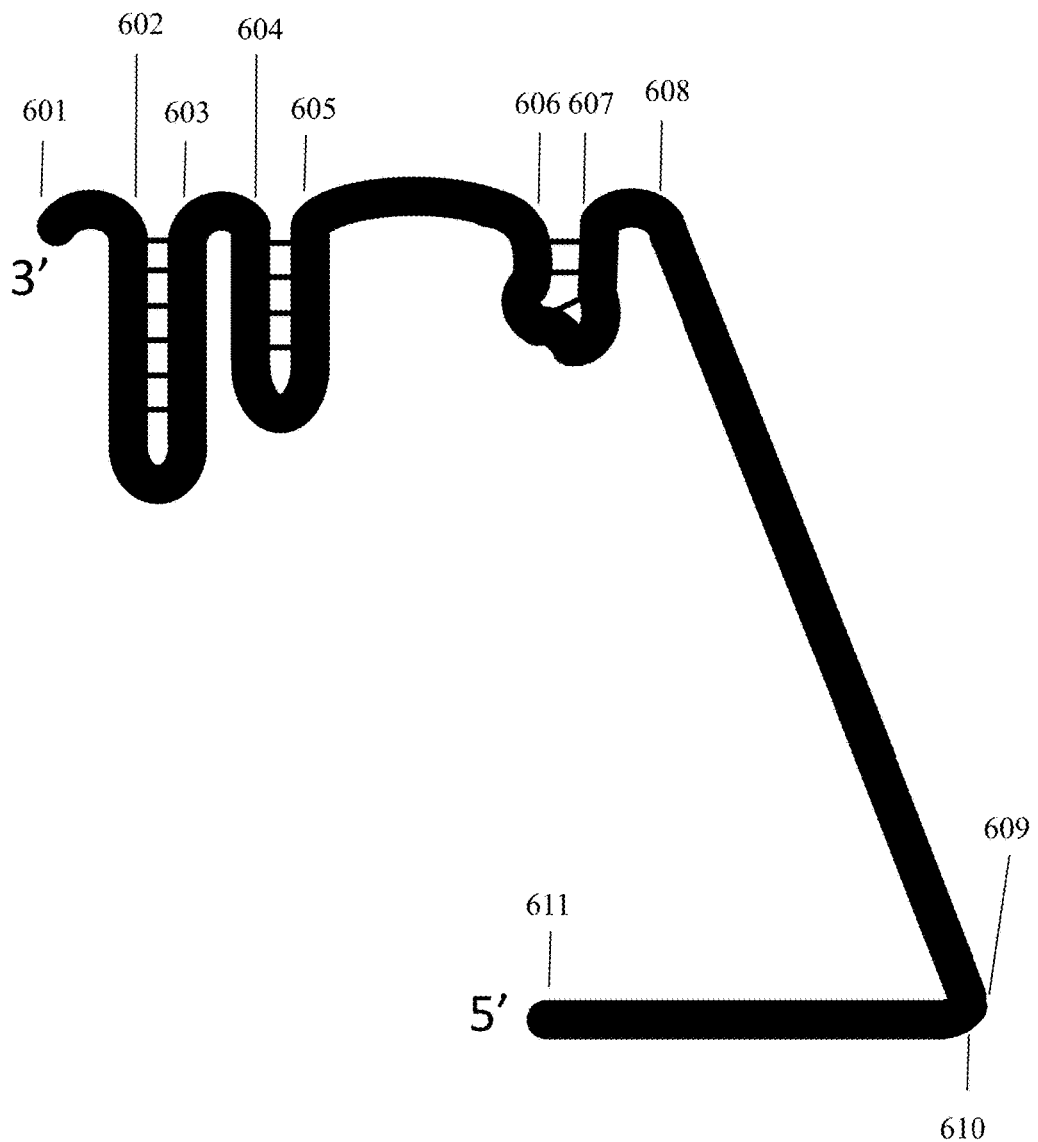
FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, and FIG. 6M illustrate examples and elements of engineered nucleic acid scaffold polynucleotide compositions of the present invention.

FIG. 6A, 601-611, illustrates an example of first engineered nucleic acid that comprises a first element comprising a Class 2 Type II CRISPR binding protein sequence (FIG. 6A, 601-607), a second element comprising a repeat nucleic acid sequence 1 (FIG. 6A, 608-609), and a third element comprising a nucleic acid sequence 1 (FIG. 6A, 610-611). No nucleic acid sequence within the repeat nucleic acid sequence 1 associates with any nucleic acid sequence within the repeat nucleic acid sequence 1 to form a stem element through hydrogen bonding capable of binding to a Class 2 Type II CRISPR-Cas protein.

Figure 6B:
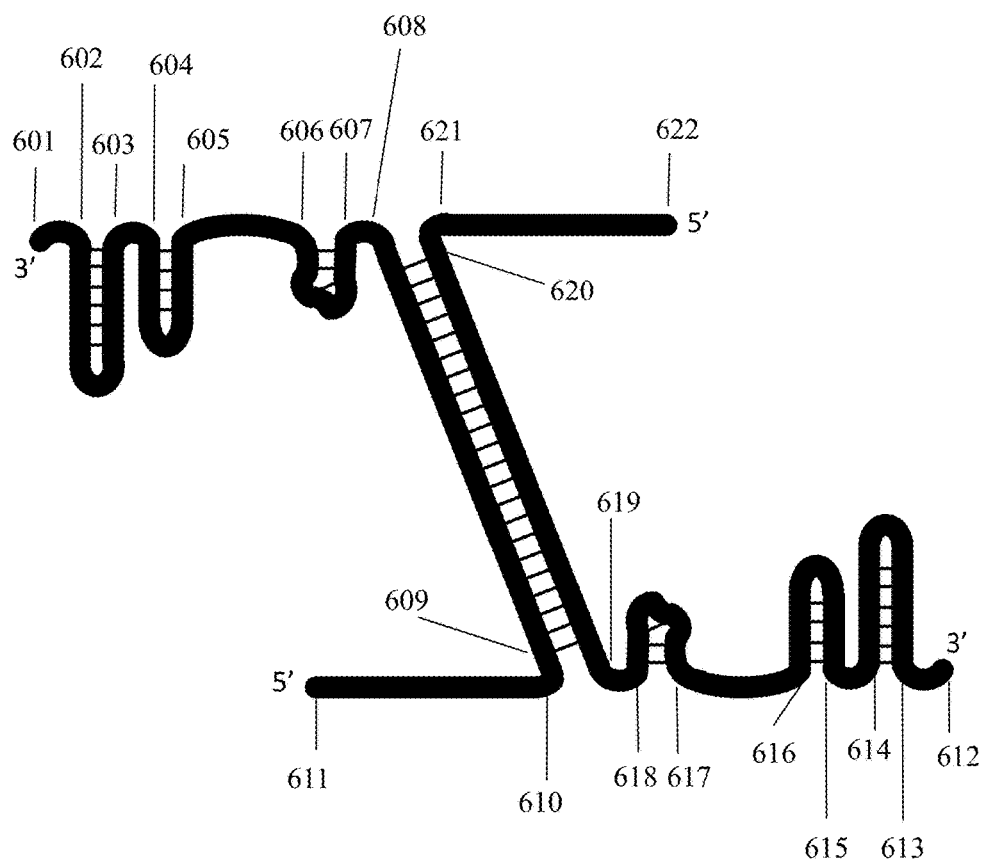

FIG. 6B illustrates a modification to FIG. 6A, wherein the first engineered nucleic acid (FIG. 6B, 601-611) is associated with the second engineered nucleic acid (FIG. 6B, 612-622) through hydrogen base-pair bonding between the repeat nucleic acid sequence 1 (FIG. 6A, 608-609) and the repeat nucleic acid sequence 1C (FIG. 6A, 619-620).

Figure 10:
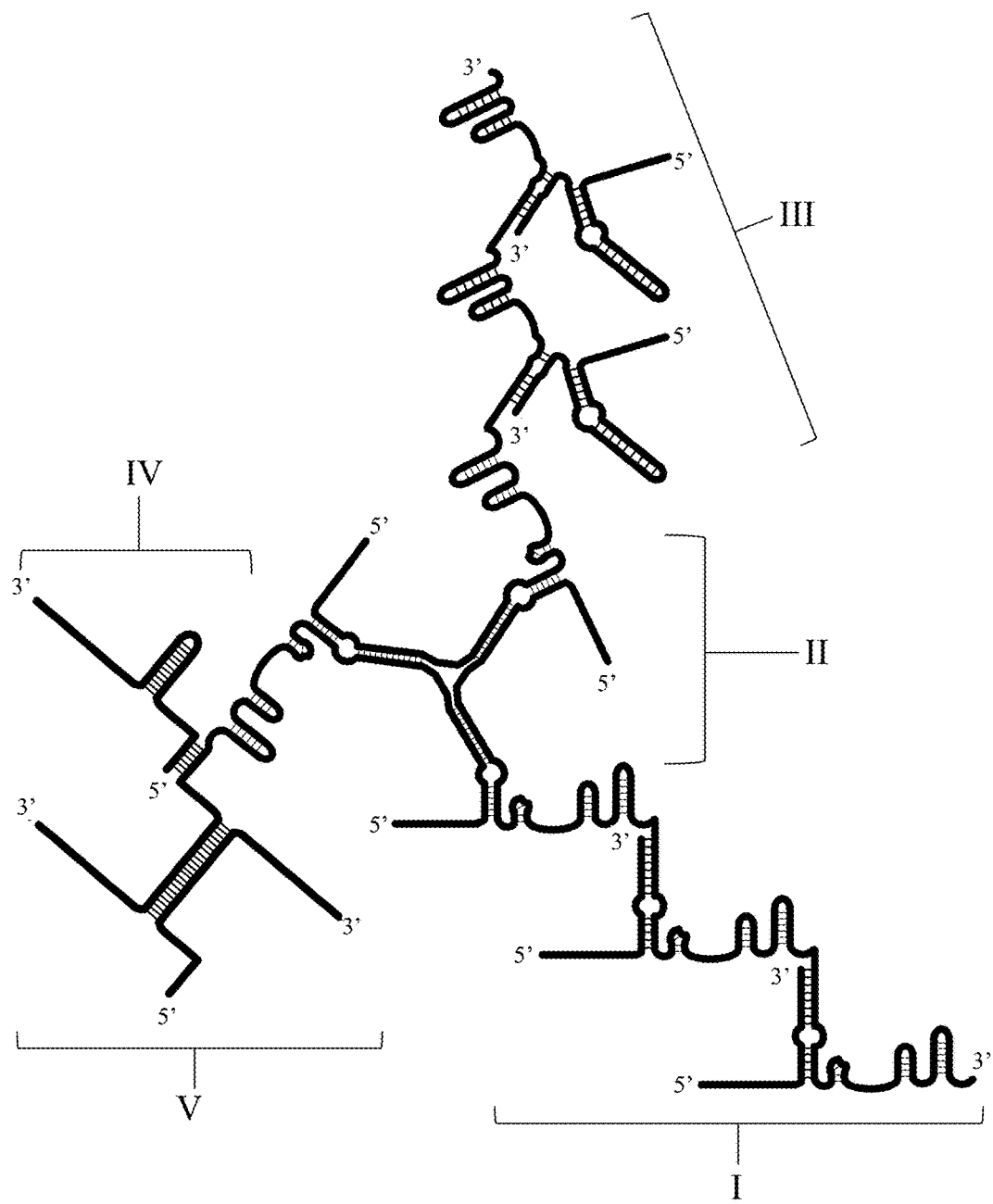
FIG. 10 illustrates an example and elements of an engineered nucleic acid scaffold polynucleotide composition of the present invention.

A NASC polynucleotide composition similar to the composition illustrated in FIG. 6B can be constructed for use with Class 2 Type V CRISPR-Cas proteins to form a nucleoprotein complex. An example of this type of NASC polynucleotide composition is illustrated in FIG. 10, V.

Figure 6C:
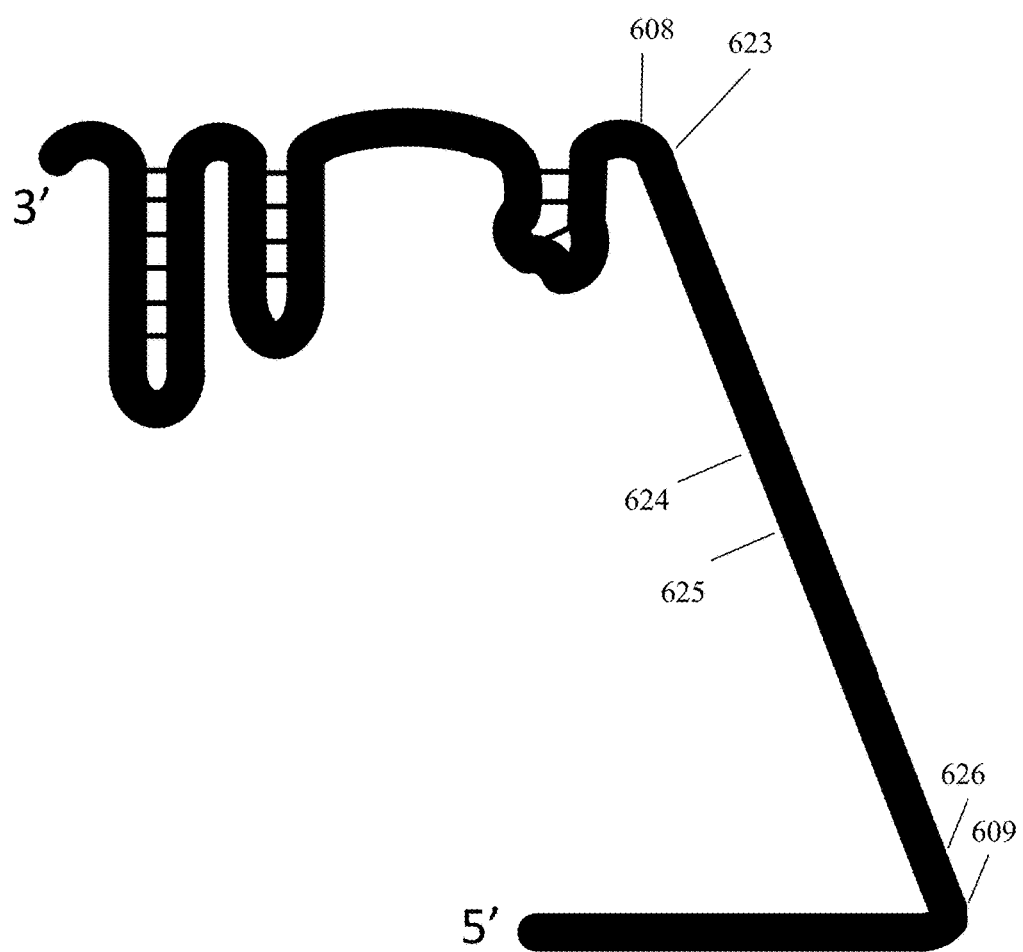

FIG. 6C illustrates an example of a first engineered nucleic acid, wherein the second element further comprises, in a 3' to 5' orientation, a linker element nucleic acid sequence 1-1 (FIG. 6C, 608-623), a repeat nucleic acid sequence 1a (FIG. 6C, 623-624), a linker element nucleic acid sequence 1-2 (FIG. 6C, 624-625), a repeat nucleic acid sequence 1b (FIG. 6D, 625-626), and a linker element nucleic acid sequence 1-3 (FIG. 6C, 626-609). No nucleic acid sequence within the repeat nucleic acid sequence 1 associates with any nucleic acid sequence within the repeat nucleic acid sequence 1 to form a stem element through hydrogen bonding capable of binding to a Class 2 Type II CRISPR-Cas protein.

Figure 6D:
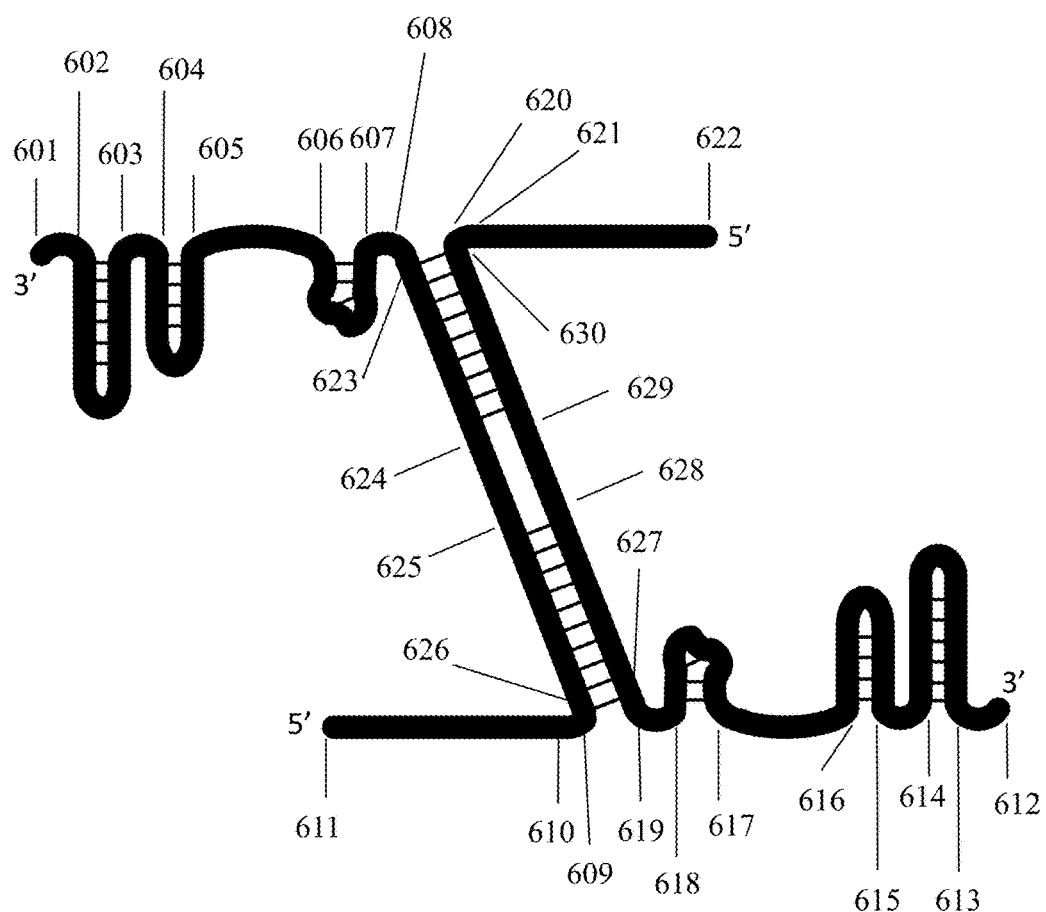

FIG. 6D illustrates a modification to FIG. 6C in which two engineered nucleic acids form a scaffold, wherein the first engineered nucleic acid is associated with the second engineered nucleic acid through hydrogen base-pair bonding between the repeat nucleic acid sequence 1a (FIG. 6D, 623-624) and the repeat nucleic acid sequence 1aC (FIG. 6D, 629-630) and through hydrogen base-pair bonding between the repeat nucleic acid sequence 1b (FIG. 6D, 625-626) and the repeat nucleic acid sequence 1bC (FIG. 6D, 627-628).

Figure 6E:
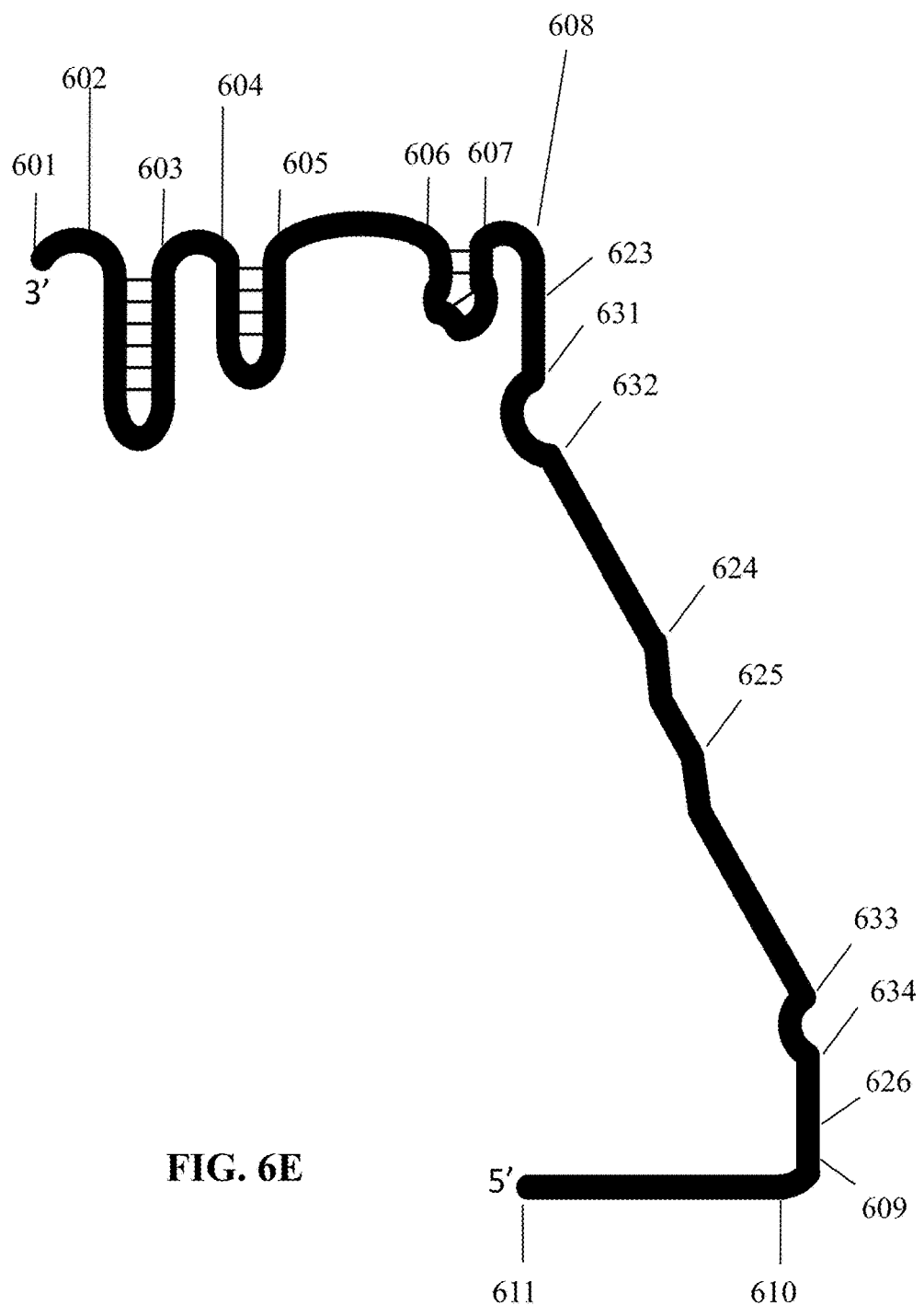

FIG. 6E, illustrates an example of a first engineered nucleic acid, wherein the second element further comprises, in a 3' to 5' orientation, a linker element nucleic acid sequence 1-1 (FIG. 6C, 608-623), a repeat nucleic acid sequence 1a1 (FIG. 6C, 623-631), a bulge nucleic acid sequence (FIG. 6E, 631-632), a repeat nucleic acid sequence 1a2 (FIG. 6E, 632-624), a linker element nucleic acid sequence 1-2 (FIG. 6C, 624-625), a repeat nucleic acid sequence 1b1 (FIG. 6D, 625-633), a bulge nucleic acid sequence 1b1 (FIG. 6E, 633-634), and a repeat nucleic acids sequence 1b2 (FIG. 6E, 634-626). No nucleic acid sequence within the repeat nucleic acid sequence 1 associates with any nucleic acid sequence within the repeat nucleic acid sequence 1 to form a stem element through hydrogen bonding capable of binding to a Class 2 Type II CRISPR-Cas protein.

Figure 6F:
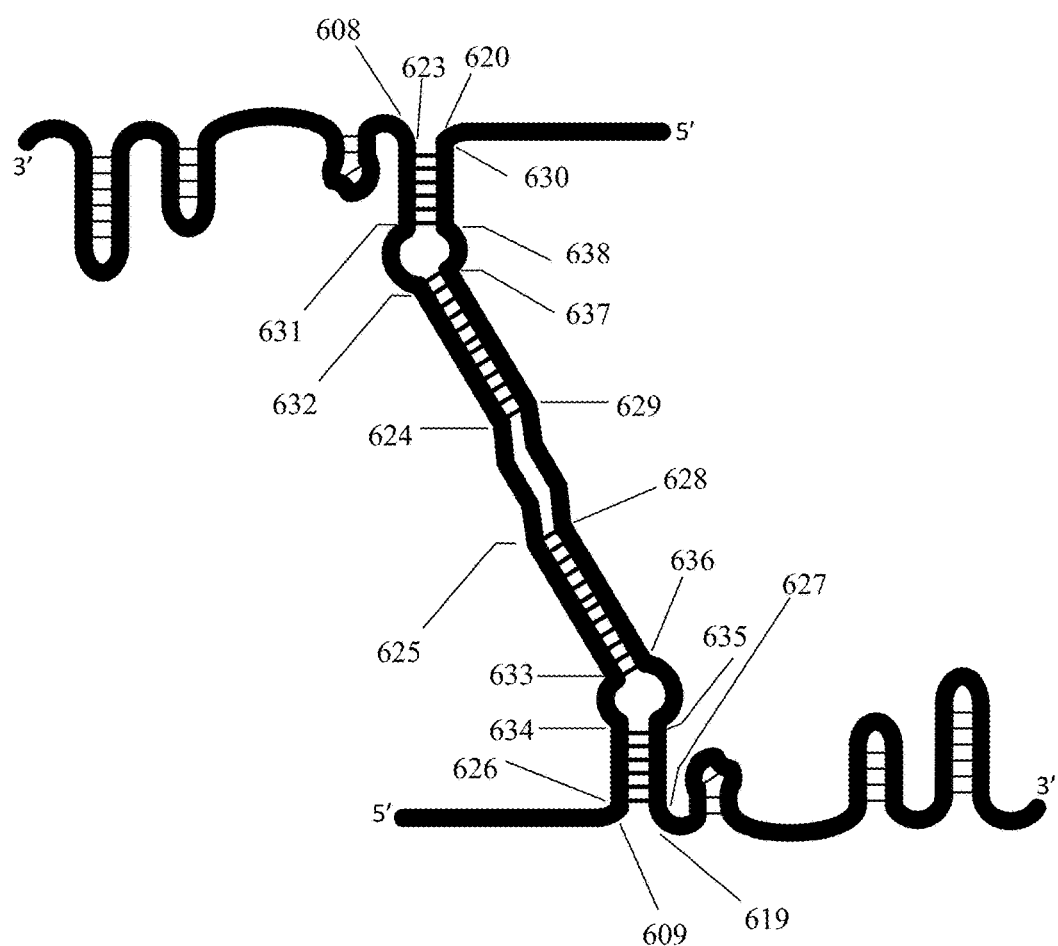

FIG. 6F illustrates a modification to FIG. 6E in which two engineered nucleic acids form a scaffold, wherein the first engineered nucleic acid is associated with the second engineered nucleic acid through hydrogen base-pair bonding between the repeat nucleic acid sequence 1a1 (FIG. 6F, 623-631) and the repeat nucleic acid sequence 1a1C (FIG. 6F, 638-630), through hydrogen base-pair bonding between the repeat nucleic acid sequence 1a2 (FIG. 6F, 632-624) and the repeat nucleic acid sequence 1a2C (FIG. 6F, 629-637), through hydrogen base-pair bonding between the repeat nucleic acid sequence 1b1 (FIG. 6F, 625-633) and the repeat nucleic acid sequence 1b1C (FIG. 6F, 636-628), and through hydrogen base-pair bonding between the repeat nucleic acid sequence 1b2 (FIG. 6E, 634-626) and repeat nucleic acid sequence 1b2C (FIG. 6E, 627-635).

Figure 6G:
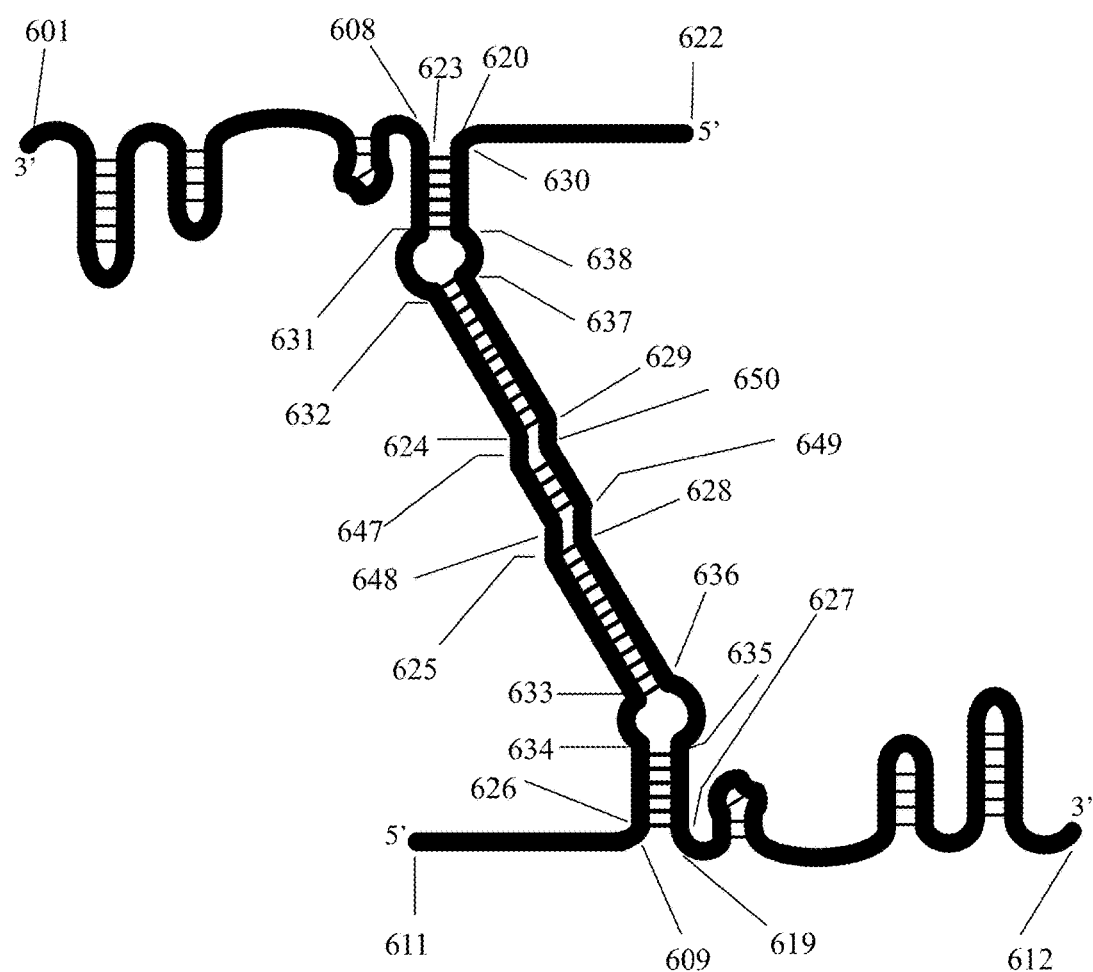

FIG. 6G is a variation of the NASC polynucleotide composition illustrated in FIG. 6F. The linker element nucleic acid sequence 1-2 is modified by insertion of an effector protein binding site nucleic acid sequence 1 (FIG. 6G, 647-648) and the linker element nucleic acid sequence 2-2 is modified by insertion of an effector protein binding site nucleic acid sequence 2 (FIG. 6G, 649-650). The effector protein binding site nucleic acid sequence 1 and the effector protein binding site nucleic acid sequence 2 connect to form an effector protein binding site through hydrogen-bonded base pairs. In one embodiment, the effector protein binding site is a Csy4 binding site. An enzymatically inactive form of the Csy4 protein can bind the site to further stabilize the NASC polynucleotide composition structure. An enzymatically active form of the Csy4 protein can bind the site to destabilize (e.g., through endoribonuclease activity) the NASC polynucleotide composition structure (e.g., to induce disruption of NASC polynucleotide composition/nucleic acid binding proteins-based closed cage structures).

Figure 6H:
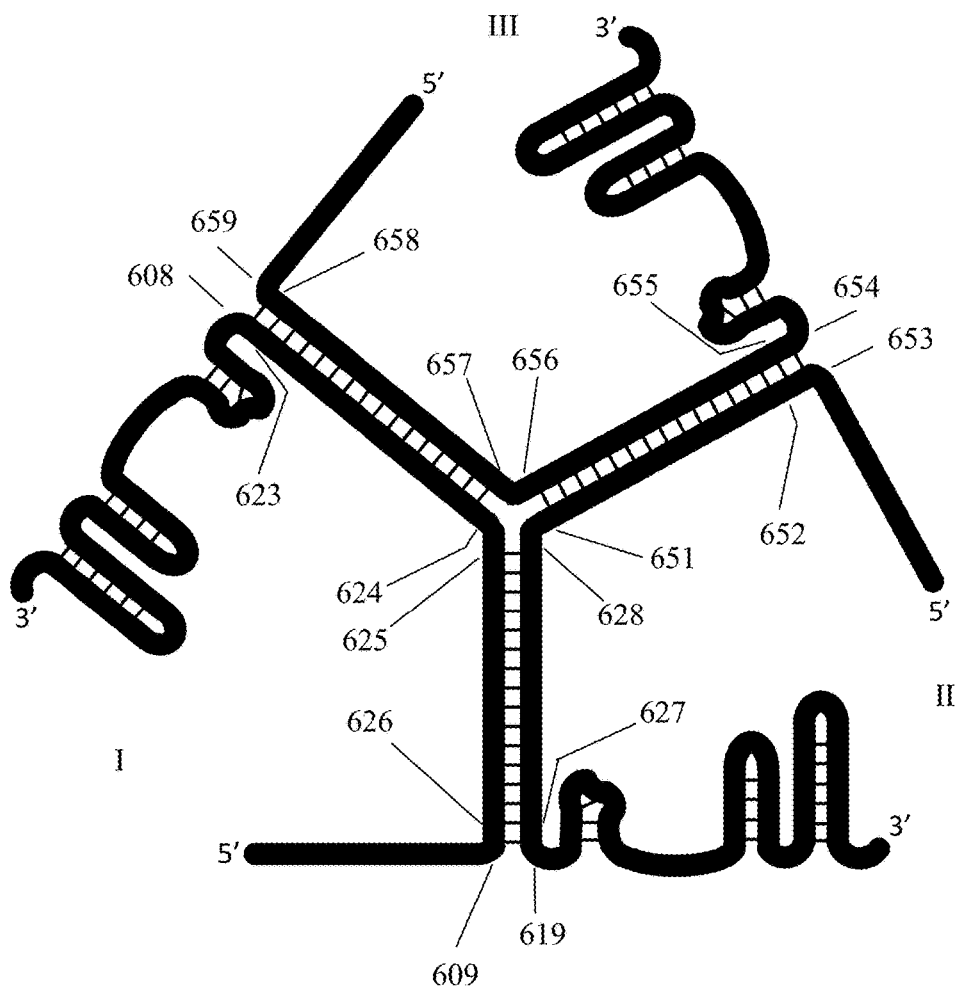
Figure 6I:
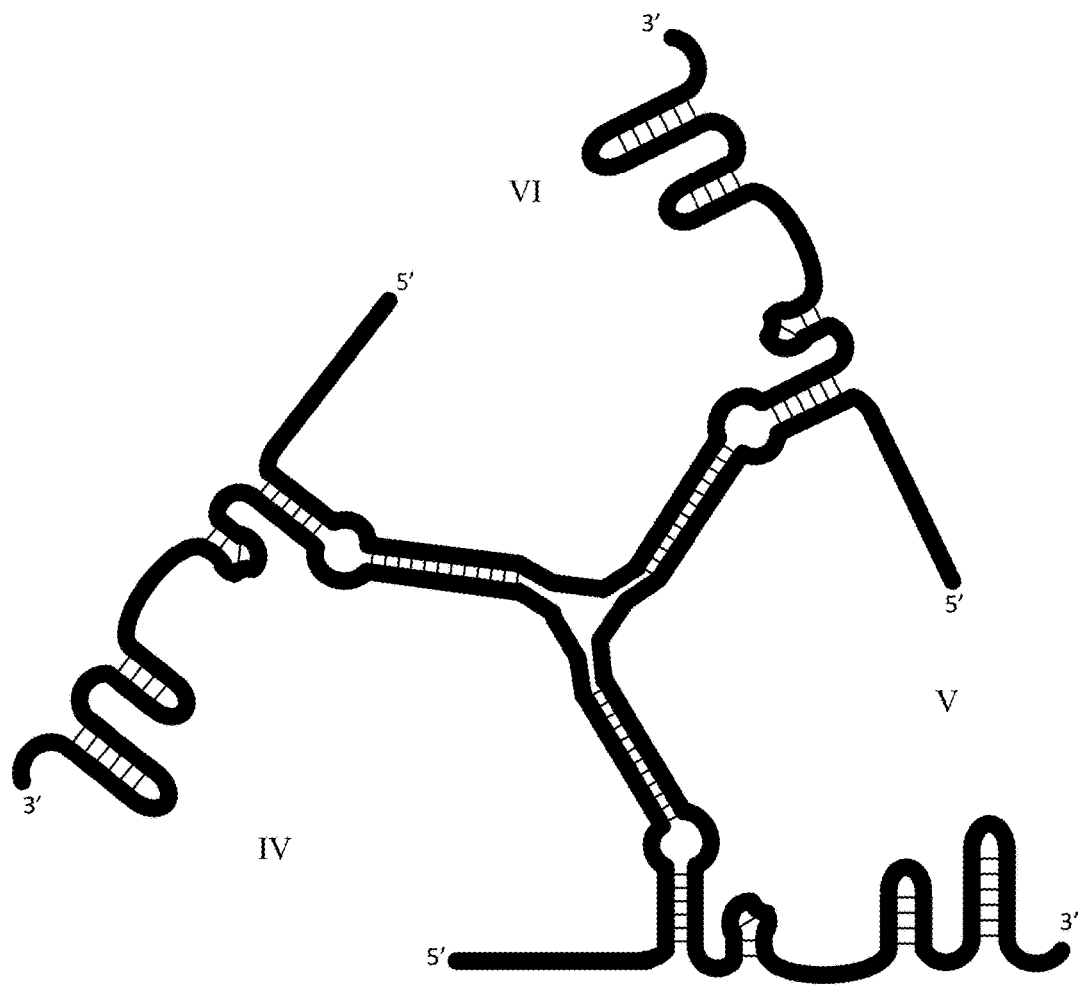
Figure 6J:
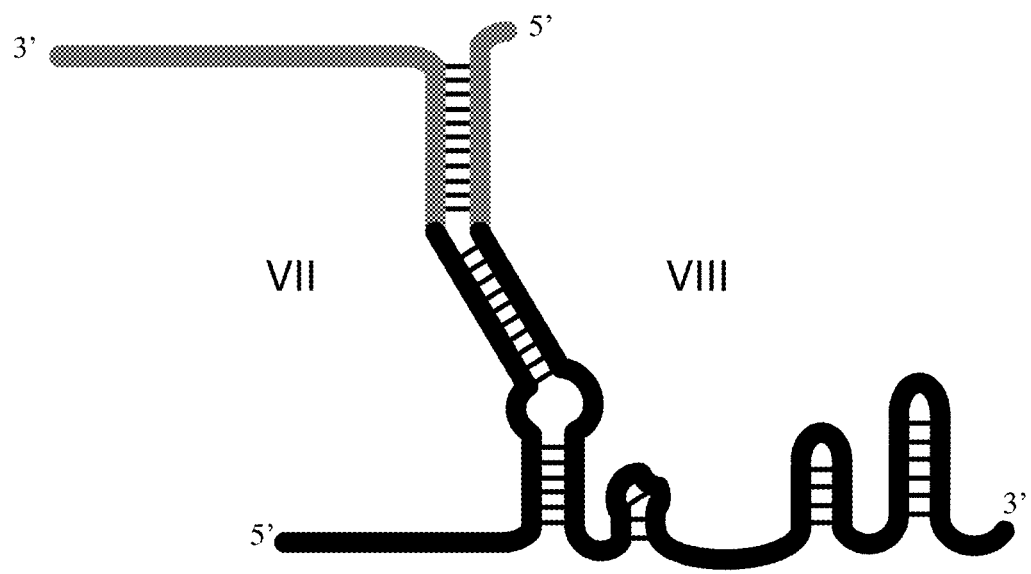
Figure 6K:
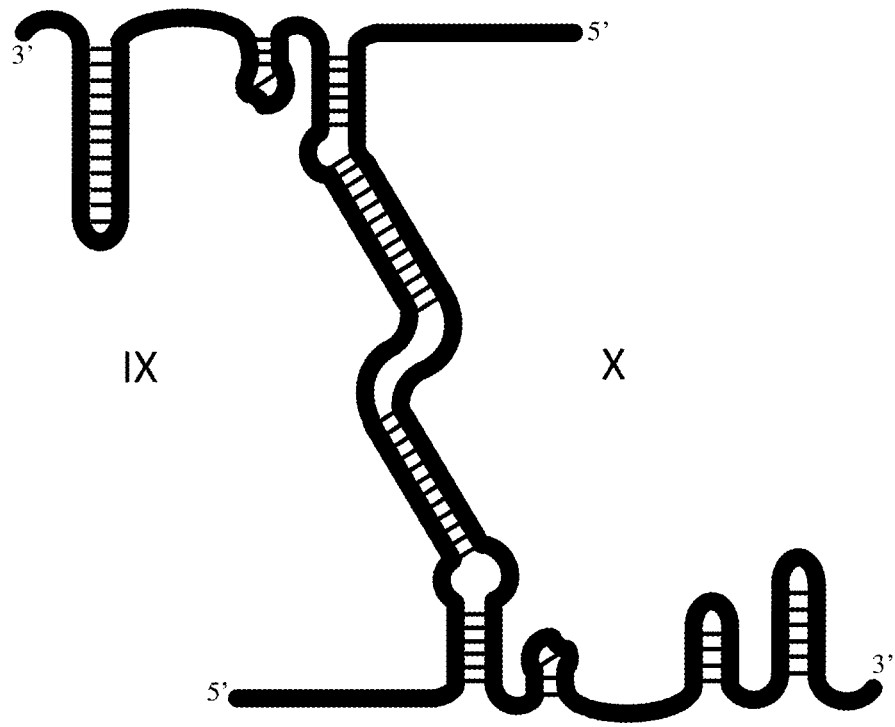

FIG. 6K illustrates a NASC polynucleotide composition capable of associating with a first Class 2 Type II CRISPR-Cas9 ortholog protein and a second Class 2 Type II CRISPR-Cas9 ortholog protein to form a nucleoprotein complex.

FIG. 6K illustrates a NASC polynucleotide composition comprising a NASC-PC1 and a NASC-PC2. The NASC-PC1 (FIG. 6K, IX) comprises, in a 5' to 3' direction: a nucleic acid target binding sequence 1; a linker nucleic acid sequence 1 comprising, a repeat nucleic acid sequence 1a, a repeat nucleic acid sequence 1b, a repeat nucleic acid 1c, and a repeat nucleic acid 1d; and S. thermophilus Class 2 Type II CRISPR-Cas9 nucleic acid binding protein binding sequence 1. The NASC-PC2 (FIG. 6K, X) comprises, in a 5' to 3' direction: a nucleic acid target binding sequence 2; a linker nucleic acid sequence 1 comprising, a repeat nucleic acid sequence 1dC, a repeat nucleic acid sequence 1cC, a repeat nucleic acid 1bC, and a repeat nucleic acid sequence 1aC; and a S. pyogenes Class 2 Type II CRISPR-Cas9 nucleic acid binding protein binding sequence 1. The NASC-PC1 and the NASC-PC2 connected through hydrogen-bonded base pairs between the repeat nucleic acid sequence 1a/the repeat nucleic acid sequence 1aC, the repeat nucleic acid sequence 1b/the repeat nucleic acid sequence 1bC, the repeat nucleic acid sequence 1c/the repeat nucleic acid 1cC, and the repeat nucleic acid sequence 1d/the repeat nucleic acid 1dC to form a macromolecule. The macromolecule is capable of binding a S. thermophilus Class 2 Type II CRISPR-Cas9 protein (around the repeat nucleic acid sequence 1 d/the repeat nucleic acid sequence 1 dC region and the repeat nucleic acid sequence 1c/the repeat nucleic acid sequence 1cC region) and a S. pyogenes Class 2 Type II CRISPR-Cas9 protein (around the repeat nucleic acid sequence 1b/the repeat nucleic acid sequence 1bC region, the repeat nucleic acid sequence 1a/the repeat nucleic acid sequence 1aC region). Use of such NASC polynucleotide composition/Cas9 ortholog protein complexes provides, for example, an increased number of available target sequences in view of PAM variability between the Cas9 ortholog proteins (versus use of one guide nucleic acid/Cas9 protein complex comprising either Cas9 ortholog alone). Further, NASC polynucleotide composition/Cas9 ortholog protein complexes may improve specificity of targeting of a polynucleotide region by providing greater flexibility in choosing nearby target sequences in view of PAM variability between the Cas9 ortholog proteins (versus use of one guide nucleic acid/Cas9 protein complex comprising either Cas9 ortholog alone). In view of the teachings of the present specification, one of ordinary skill in the art can apply this use of two or more different Cas9 ortholog proteins by combining different components of the NASC polynucleotide compositions described herein.

In a further embodiment, the NASC-PC1 (FIG. 6K, IX) and NASC-PC2 (FIG. 6K, X) are capable of associating with the same Class 2 Type II CRISPR-Cas9 ortholog protein (see, e.g., Fonfara, I., et al., Nucleic Acids Research 42(4):2577-2590 (2014)). In this embodiment, the repeat nucleic acid sequence 1d/the repeat nucleic acid sequence 1dC region, and the repeat nucleic acid sequence 1c/the repeat nucleic acid sequence 1cC region are capable of associating with a S. mutans Class 2 Type II CRISPR-Cas9 protein and are also capable of associating with a S. pyogenes Class 2 Type II CRISPR-Cas9 protein. The repeat nucleic acid sequence 1b/the repeat nucleic acid sequence 1bC region, and the repeat nucleic acid sequence 1a/the repeat nucleic acid sequence 1aC region are capable of associating with a S. pyogenes Class 2 Type II CRISPR-Cas9 protein and are also capable of associating with a S. mutans Class 2 Type II CRISPR-Cas9 protein. For example, although the repeat regions of NASC-PC1 (FIG. 6K, IX) and the NASC-PC2 (FIG. 6K, X) are derived from different species containing Class 2 Type II CRISPR loci (e.g., S. pyogenes or S. mutans), only one Class 2 Type II CRISPR-Cas9 protein (e.g., a S. pyogenes Class 2 Type II CRISPR-Cas9 protein or a S. mutans Class 2 Type II CRISPR-Cas9 protein) is used to form a NASC polynucleotide composition/Cas9 complex. One advantage of this type of NASC polynucleotide composition is the flexibility to use either of two Cas9 proteins with the same NASC polynucleotide composition, and each of the Cas9 proteins recognize different PAM sequences. Thus, the number of possible binding sites that can be targeted by the NASC polynucleotide composition is increased.

In some embodiments of the second aspect of the present invention, a NASC polynucleotide composition comprises at least three polynucleotides, wherein the complex comprises a repeat element 1 connected to a repeat element 1C, the repeat element 2 connected to a repeat element 2C, the repeat element 3 connected to a repeat element 3C, a double-stranded nucleic acid binding protein binding element 1 a spacer element 1, a spacer element 2, and a spacer element 3, wherein the NASC polynucleotide composition is capable of binding three nucleic acid binding proteins. In some embodiments, the nucleic acid binding proteins are double-stranded nucleic acid binding proteins. In preferred embodiments, the nucleic acid binding proteins Class 2 CRISPR-Cas proteins.

Table 5 presents a series of additional indicators used in FIG. 6H and FIG. 6I.

TABLE 5

Numerical Indicators Used to Illustrate Regions of Complexes of Two or More Engineered Nucleic Acid Sequences for Forming a Scaffold
Indicator and Corresponding Region a first engineered nucleic acid component (I)
a first engineered nucleic acid sequence
  a nucleic acid binding protein binding element 1
    a repeat element 1[1]
      608-609 corresponds to a repeat nucleic acid sequence 1
        608-623 corresponds to a linker element nucleic acid sequence 1-1
          623-624 corresponds to a repeat nucleic acid sequence 1a
        624-625 corresponds to a linker element nucleic acid sequence 1-2
          625-626 corresponds to a repeat nucleic acid sequence 1b
        626-609 corresponds to a linker element nucleic acid sequence 1-3
  a spacer element 1
a second engineered nucleic acid component (II)
a second engineered nucleic acid sequence
  a nucleic acid binding protein binding element 2
    a repeat element 2
      619-653 corresponds to a repeat nucleic acid sequence 2

TABLE 5-continued

Numerical Indicators Used to Illustrate Regions of Complexes of Two or More Engineered Nucleic Acid Sequences for Forming a Scaffold Indicator and Corresponding Region 619-627 corresponds to a linker element nucleic acid sequence 2-3
   627-628 corresponds to a repeat nucleic acid sequence 1bC²
  628-651 corresponds to a linker element nucleic acid sequence 2-2
   651-652 corresponds to a repeat nucleic acid sequence 2a
  652-653 corresponds to a linker element nucleic acid sequence 2-4
 a spacer element 2
a third engineered nucleic acid component (III)
 a third engineered nucleic acid sequence
  a nucleic acid binding protein binding element 3
  a repeat element 3
   654-659 corresponds to a repeat nucleic acid sequence 1
    654-655 corresponds to a linker element nucleic acid sequence 3-3
     655-656 corresponds to a repeat nucleic acid sequence 2aC
    656-657 corresponds to a linker element nucleic acid sequence 3-2
     657-658 corresponds to a repeat nucleic acid sequence 1aC
    658-659 corresponds to a linker element nucleic acid sequence 3-1
 a spacer element 3

[1] = repeat element can include an effector protein binding site
[2] = "C" indicates a complementary sequence FIG. 6H illustrates a modification to FIG. 6C where three engineered nucleic acids form a scaffold, wherein a first engineered nucleic acid (FIG. 6H, I) is associated with a second engineered nucleic acid (FIG. 6H, II) through hydrogen base-pair bonding between repeat nucleic acid sequence 1b (FIG. 6H, 625-626) and repeat nucleic acid sequence 1bC (FIG. 6H, 627-628), and the second engineered nucleic acid (FIG. 6H, II) is associated with the third engineered nucleic acid (FIG. 6H, III) through hydrogen base-pair bonding between repeat nucleic acid sequence 2a (FIG. 6H, 638-639) and repeat nucleic acid sequence 2aC (FIG. 6H, 642-643), and the third engineered nucleic acid (FIG. 6H, III) is associated with the first engineered nucleic acid (FIG. 6H, I) through hydrogen base-pair bonding between repeat nucleic acid sequence 1aC (FIG. 6H, 644-645) and repeat nucleic acid sequence 1a (FIG. 6H, 623-624).

FIG. 6I illustrates a modification to FIG. 6E where three engineered nucleic acids form a scaffold using the engineered nucleic acid described in FIG. 6E, wherein the first engineered nucleic acid (FIG. 6I, IV) is associated with the second engineered nucleic acid (FIG. 6I, V) through hydrogen base-pair bonding between repeat sequences, and the second engineered nucleic acid (FIG. 6I, V) is associated with the third engineered nucleic acid (FIG. 6I, VI) through hydrogen base-pair bonding between repeat sequences, and the third engineered nucleic acid (FIG. 6I, VI) is associated with the first engineered nucleic acid (FIG. 6I, IV) through hydrogen base-pair bonding between repeat sequences.

FIG. 6J illustrates a NASC polynucleotide composition capable of associating with a Class 2 Type II CRISPR-Cas protein and a Class 2 Type V CRISPR-Cpf1 protein to form a nucleoprotein complex.

FIG. 6J illustrates a NASC polynucleotide composition capable of associating with a Class 2 Type II CRISPR-Cas9 protein and a Class 2 Type V CRISPR-Cpf1 protein to form a nucleoprotein complex. FIG. 6J illustrates a NASC polynucleotide composition comprising a NASC-PC1 comprising a spacer element 1 and a spacer element 2 (NASC-PC-2TS; FIG. 6J, VII). The NASC-PC-2TS comprising, in a 5' to 3' direction: a Class 2 Type II CRISPR-Cas9 nucleic acid target binding sequence 1; a linker nucleic acid binding sequence 1 comprising a repeat nucleic acid sequence 1a, a repeat nucleic acid sequence 1b, and a repeat nucleic acid sequence 1c; and a Class 2 Type V CRISPR-Cpf1 nucleic acid target binding sequence 1. The NASC polynucleotide composition further comprises a NASC-PC2 comprising a concatenate comprising a Class 2 Type II CRISPR-Cas9 nucleic acid binding protein binding sequence 1 and a Class 2 Type V CRISPR-Cpf1 nucleic acid binding protein binding sequence 2 (NASC-PC-CE; FIG. 6J, VIII). The NASC-PC-CE further comprises a repeat nucleic acid sequence 1aC, a repeat nucleic acid sequence 1bC, and a repeat nucleic acid sequence 1cC through which the NASC-PC-CE is connected to the NASC-PC-2TS through hydrogen-bonded base pairs to form a macromolecule that is capable of binding a Class 2 Type II CRISPR-Cas9 protein and a Class 2 Type V CRISPR-Cpf1 protein. Use of such NASC polynucleotide composition/Cas9 protein/Cpf1 protein complexes provides, for example, an increased number of available target sequences in view of PAM variability and target sequence length differences between the Cas9 protein and the Cpf1 protein (versus use of one guide nucleic acid/Cas protein complex comprising either Cas9 protein or Cpf1 protein alone). Furthermore, NASC polynucleotide composition/Cas9 protein/Cpf1 protein complexes may improve specificity of targeting of a polynucleotide region by providing greater flexibility in choosing nearby target sequences in view of PAM variability and target sequence lengths between the Cas9 protein and the Cpf1 protein (versus use of one guide nucleic acid/Cas protein complex comprising either Cas9 protein or Cpf1 protein alone). In view of the teachings of the present specification, one of ordinary skill in the art can apply this use of two or more different Cas proteins by combining different components of the NASC polynucleotide compositions described herein.

In other embodiments, a first repeat nucleic acid sequence of a pair further comprises a first affinity tag and a second repeat nucleic acid sequence of the pair further comprises a second affinity tag, and the first affinity tag is connected with the second affinity tag. For example, the repeat nucleic acid sequence 1 further comprises an effector protein binding site nucleic acid sequence 1 and the repeat nucleic acid sequence 2 further comprises an effector protein binding site nucleic acid sequence 2, and an effector binding site 1 is formed by hydrogen base-pair bonding between the effector protein binding site nucleic acid sequence 1 and the effector protein binding site nucleic acid sequence 2. One example of an effector binding site is a Csy4 protein binding site.

In a third aspect of the present invention, NASC polynucleotide composition comprises an engineered concatenated nucleic acid component ("NASC-PC-CT") and at least a NASC-PC1 and a NASC-PC2.

In one embodiment of the third aspect of the present invention, an engineered NASC polynucleotide concatenated element (NASC-PC-CE) comprises, in a 3' to 5' direction: a first concatenate element 1 comprising a nucleic acid binding protein binding element 1, and a second concatenate element 1 comprising a repeat element A1, wherein the repeat element A1 comprises a repeat nucleic acid sequence A1; a first concatenate element 2 comprising a nucleic acid binding protein binding element 2; and a second concatenate element 2 comprising a repeat element 2, wherein the repeat element 2 comprises a repeat nucleic acid sequence A2. The first concatenate element 1 is connected to the second concatenate element 1, the second concatenate element 1 is connected to the first concatenate element 2, and the first concatenate element 2 is connected to the second concatenate element 2 to form the NASC-PC-CE.

A third concatenate element 1 (NASC-PC-CE3-1) comprises, in a 3' to 5' direction a repeat element A1C comprising a repeat nucleic acid sequence A1C, and a spacer element 1 comprising a nucleic acid target binding sequence 1. A third concatenate element 2 (NASC-PC-CE3-2) comprises, in a 3' to 5' direction a repeat element A2C comprising a repeat nucleic acid sequence A2C, and a spacer element 2 comprising a nucleic acid target binding sequence 2. The repeat nucleic acid sequence A1 is connected with the repeat nucleic acid sequence A1-C, the repeat nucleic acid sequence A2 is connected with the repeat nucleic acid sequence A2-C to form the NASC-PC-CE.

A first nucleic acid binding protein is capable of binding the nucleic acid binding protein binding element 1 and a second nucleic acid binding protein is capable of binding the nucleic acid binding protein binding element 2. In some embodiments, the nucleic acid binding protein binding element is a double-stranded nucleic acid binding protein binding element that binds a double-stranded nucleic acid binding protein.

In additional embodiments, a first repeat nucleic acid sequence of a pair is connected with the second repeat nucleic acid sequence of the pair through hydrogen-bonded base pairs.

FIG. 7A, FIG. 7B, FIG. 7C, FIG. 7D, FIG. 7E, FIG. 7F, FIG. 7G, FIG. 7H, and FIG. 7I, illustrate elements and examples of engineered concatenated nucleic acid scaffolds of the present invention.

Table 6 presents a series of indicators used consistently in FIG. 7A, FIG. 7B, FIG. 7C, FIG. 7D, FIG. 7E, FIG. 7F, FIG. 7G, FIG. 7H, and FIG. 7I.

TABLE 6

Numerical Indicators Used to Illustrate Regions of Complexes of Two or More Engineered Nucleic Acid Sequences for Forming a Scaffold Indicator and Corresponding Region an engineered NASC polynucleotide concatenated element (corresponds-700-717) (NASC-PC-CE)
    a first concatenate element 1 (NASC-PC-CE1-1)
        a nucleic acid binding protein binding element 1
            700-701 corresponds to a linker element nucleic acid sequence 1-5
            701-702 corresponds to a hairpin nucleic acid sequence 1-2
            702-703 corresponds to a linker element nucleic acid sequence 1-4
            703-704 corresponds to a hairpin nucleic acid sequence 1-1
            704-705 corresponds to a linker element nucleic acid sequence 1-3
            705-706 corresponds to a nexus element 1
            706-707 corresponds to a linker element nucleic acid sequence 1-2
    a second concatenate element 1 (NASC-PC-CE1-2)
        a repeat element A1[1]
            707-708 corresponds to a repeat nucleic acid sequence A1
                707-728 corresponds to a linker element nucleic acid sequence A1-1
                    707-726 corresponds to a linker element nucleic acid sequence A1-4
                    726-727 corresponds to a repeat nucleic acid sequence A1-1
                    727-728 corresponds to a bulge nucleic acid sequence A1-1
                728-708 corresponds to a linker element nucleic acid sequence A1-2
                    728-729 corresponds to a repeat nucleic acid sequence A1-2
                    729-730 corresponds to a linker element nucleic acid sequence A1-3
                    730-708 corresponds to a linker nucleic sequence A1-4 that can comprise an effector protein binding site nucleic acid sequence A1
            708-709 corresponds to a linker element nucleic acid sequence A1
    a first concatenate element 2 (NASC-PC-CE-1-2)
        a nucleic acid binding protein binding element 2 (NASC-PC-CE2)
            709-710 corresponds to a linker element nucleic acid sequence 2-5
            710-711 corresponds to a hairpin nucleic acid sequence 2-1
            711-712 corresponds to a linker element nucleic acid sequence 2-4
            712-713 corresponds to a linker element nucleic acid sequence 2-3
            713-714 corresponds to a nexus element 2
            714-715 corresponds to a linker element nucleic acid sequence 2-2
    a second concatenate element 2 (NASC-PC-CE2-2)
        a repeat element A2
            715-716 corresponds to a repeat nucleic acid sequence A2
                715-731 corresponds to a linker element nucleic acid sequence A2-4
                    715-733 corresponds to a linker element nucleic acid sequence A2-1
                    731-732 corresponds to a repeat nucleic acid sequence A2-1
                    732-733 corresponds to a bulge nucleic acid sequence A2-1

TABLE 6-continued

Numerical Indicators Used to Illustrate Regions of Complexes of Two or
More Engineered Nucleic Acid Sequences for Forming a Scaffold
Indicator and Corresponding Region 733-716 corresponds to a linker element nucleic acid sequence A2-2
    733-734 corresponds to a repeat nucleic acid sequence A2-2
    734-735 corresponds to a linker element nucleic acid A2-3
    716-735 corresponds to a linker nucleic sequence A2-4 that can comprise an effector protein binding site nucleic acid sequence A2
716-717 corresponds to linker element nucleic acid sequence A2
a third concatenate element 1 (NASC-PC-CE3-1)
  a repeat element A1C[2]
    718-719 corresponds to a repeat nucleic acid sequence A1C
      719-737 corresponds to a linker element nucleic acid sequence A1-1n
        719-736 corresponds to a repeat nucleic acid sequence A1-1C[2]
        736-737 corresponds to a bulge nucleic acid sequence A1-1n[3]
      737-718 corresponds to a linker element nucleic acid sequence A1-2n
        737-748 corresponds to a repeat nucleic acid sequence A1-2C
        738-748 corresponds to a linker element nucleic acid A1-3n
        738-718 corresponds to a linker nucleic sequence A1-4n that can comprise an effector protein binding site nucleic acid sequence A1C
    719-720 corresponds to a linker element nucleic acid sequence A1-4n
  a spacer element 1
    720-721 corresponds a nucleic acid target binding sequence 1
a third concatenate element 2 (NASC-PC-CE3-2)
  a repeat element A2C
    722-723 corresponds to a repeat nucleic acid sequence A2-1C2
      723-740 corresponds to a linker element nucleic acid sequence A2-1n
        723-739 corresponds to a repeat nucleic acid sequence A2-1C
        739-740 corresponds to a bulge nucleic acid sequence A2-1n
    722-740 corresponds to a linker element nucleic acid sequence A2-2n
      740-741 corresponds to a repeat nucleic acid sequence A2-2C
      741-749 corresponds to a a linker element nucleic acid A2-3n
      749-722 corresponds to a linker nucleic sequence A2-4 that can comprise an effector protein binding site nucleic acid sequence A2C
    723-724 corresponds to a linker element nucleic acid sequence A2-4n
  a spacer element 2
    724-725 corresponds to a nucleic acid target binding sequence 2

[1] = repeat element can include an effector protein binding site
[2] = "C" indicates a complementary sequence
[3] = "n" indicates an opposite strand sequence (e.g., A2-1/A2-1n)

Each of a first, a second and a third element can comprise additional nucleic acid sequences, for example, 5' of the element, 3' of the element, or both 5' of the element and 3' of the element.

Figure 7A:
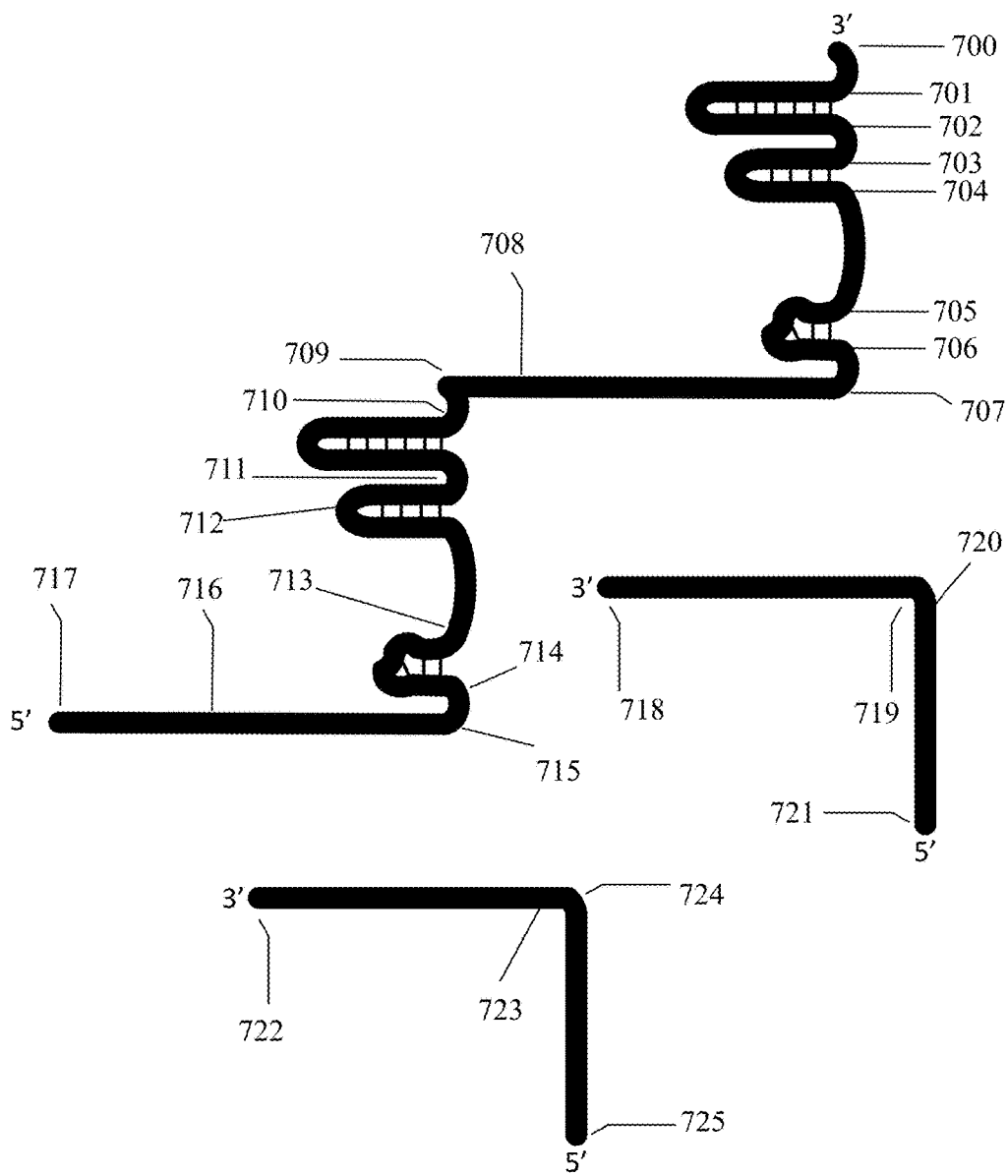
FIG. 7A, FIG. 7B, FIG. 7C, FIG. 7D, FIG. 7E, FIG. 7F, FIG. 7G, FIG. 7H, and FIG. 7I illustrate examples and elements of engineered concatenated nucleic acid scaffold polynucleotide compositions of the present invention.

FIG. 7A, 700-717, illustrates an example of a NASC-PC-CE that comprises a first concatenate element 1 comprising a Class 2 Type II CRISPR binding protein sequence (FIG. 7A, 700-706), a second concatenate element 1 (FIG. 7A, 707-708) comprising a repeat nucleic acid sequence A1, a first concatenate element 2 (FIG. 7A, 709-714) comprising a Class 2 Type II CRISPR binding protein sequence (FIG. 7A, 710-714), a second concatenate element 2 (FIG. 7A, 715-717) comprising a repeat nucleic acid sequence A2 (FIG. 7A, 715-716), and a third concatenate element 1 (NASC-PC-CE3-1; FIG. 7A, 718-721) comprising a repeat nucleic acid sequence A1C (FIG. 7A, 718-719) and a nucleic acid target binding sequence 1 (FIG. 7A, 720-721), and a third concatenate element 2 (NASC-PC-CE3-2; FIG. 7A, 722-725) comprising a repeat nucleic acid sequence A2C (FIG. 7A, 722-723) and a nucleic acid target binding sequence 2 (FIG. 7A, 724-725). One or more of the repeat nucleic acid sequences is a Class II Type II CRISPR protein binding sequence (e.g., a Cas9 protein binding sequence). Repeat nucleic acid sequence A1 is connected to repeat nucleic acid sequence A1C. In one embodiment, repeat nucleic acid sequence A1 is connected through hydrogen-bonded base pairs to repeat nucleic acid sequence.

Figure 7B:
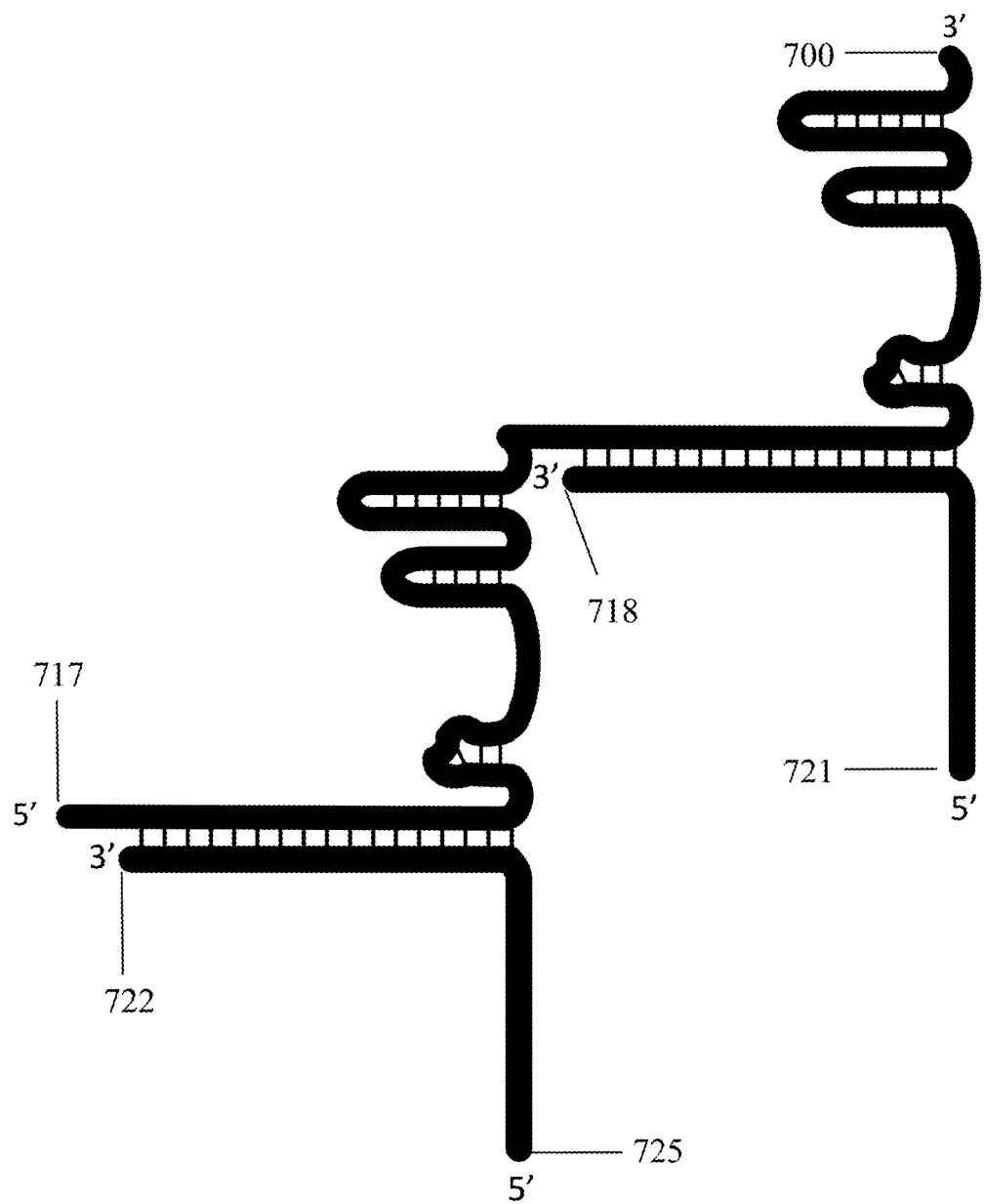

FIG. 7B illustrates an example of the formation of a scaffold through association of the NASC-PC-CE (FIG. 7A, 700-717) with the third concatenate element 1 (FIG. 7A, 718-721) through hydrogen base-pair bonding between repeat nucleic acid sequence A1 (FIG. 7A, 707-708) and repeat nucleic acid sequence A1C (FIG. 7A, 718-719), and the association of the NASC-PC-CE (FIG. 7A, 700-717) with the third concatenate element 2 (FIG. 7A, 722-725) through hydrogen base-pair bonding between repeat nucleic acid sequence A2 (FIG. 7A, 715-716) and repeat nucleic acid sequence A2C (FIG. 7A, 722-723).

Figure 7C:
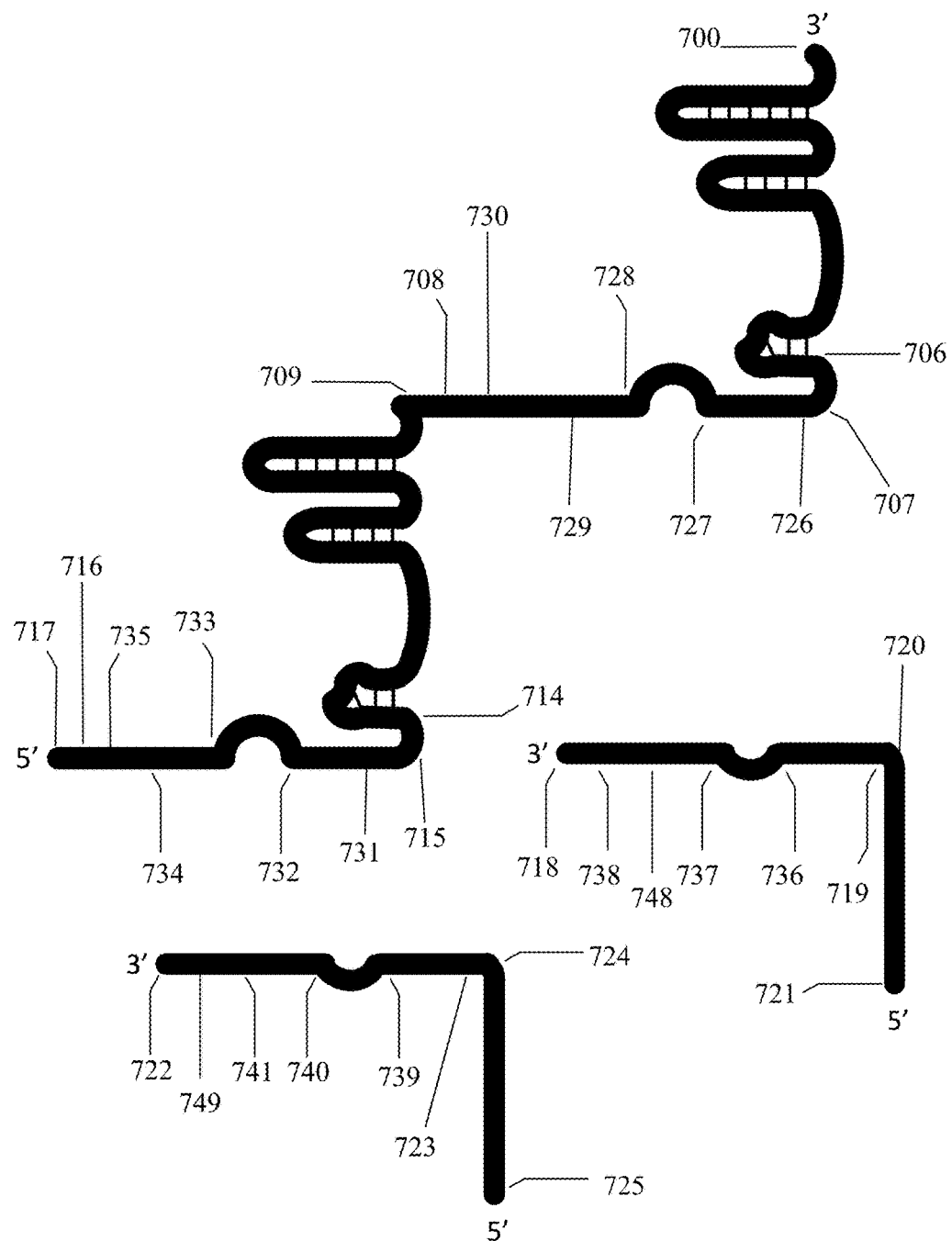

FIG. 7C illustrates a modification of a NASC-PC-CE wherein the NASC-PC-CE (FIG. 7A, 700-717) further comprises a repeat nucleic acid sequence A1-1 (FIG. 7C, 726-727), a bulge nucleic acid sequence A1-1 (FIG. 7C, 727-728), a repeat nucleic acid sequence A1-2 (FIG. 7C, 728-729) and a repeat nucleic acid sequence A2-1 (FIG. 7C, 731-732), a bulge nucleic acid sequence A2-1 (FIG. 7C, 732-733), and a repeat nucleic acid sequence A2-2 (FIG. 7C, 733-734). The third concatenate element 1 (FIG. 7C, 718-721) further comprises a repeat nucleic acid sequence A1-1C (FIG. 7C, 719-736), a bulge nucleic acid sequence A1-1 (FIG. 7C, 736-737), and a repeat nucleic acid sequence A1-2C (FIG. 7C, 737-748). The third concatenate element 2 (FIG. 7C, 722-725) further comprises a repeat nucleic acid sequence A2-1C (FIG. 7C, 723-739), a bulge nucleic acid sequence A2-1 (FIG. 7C, 739-740), and a repeat nucleic acid sequence A2-2C (FIG. 7C, 740-741).

Figure 7D:
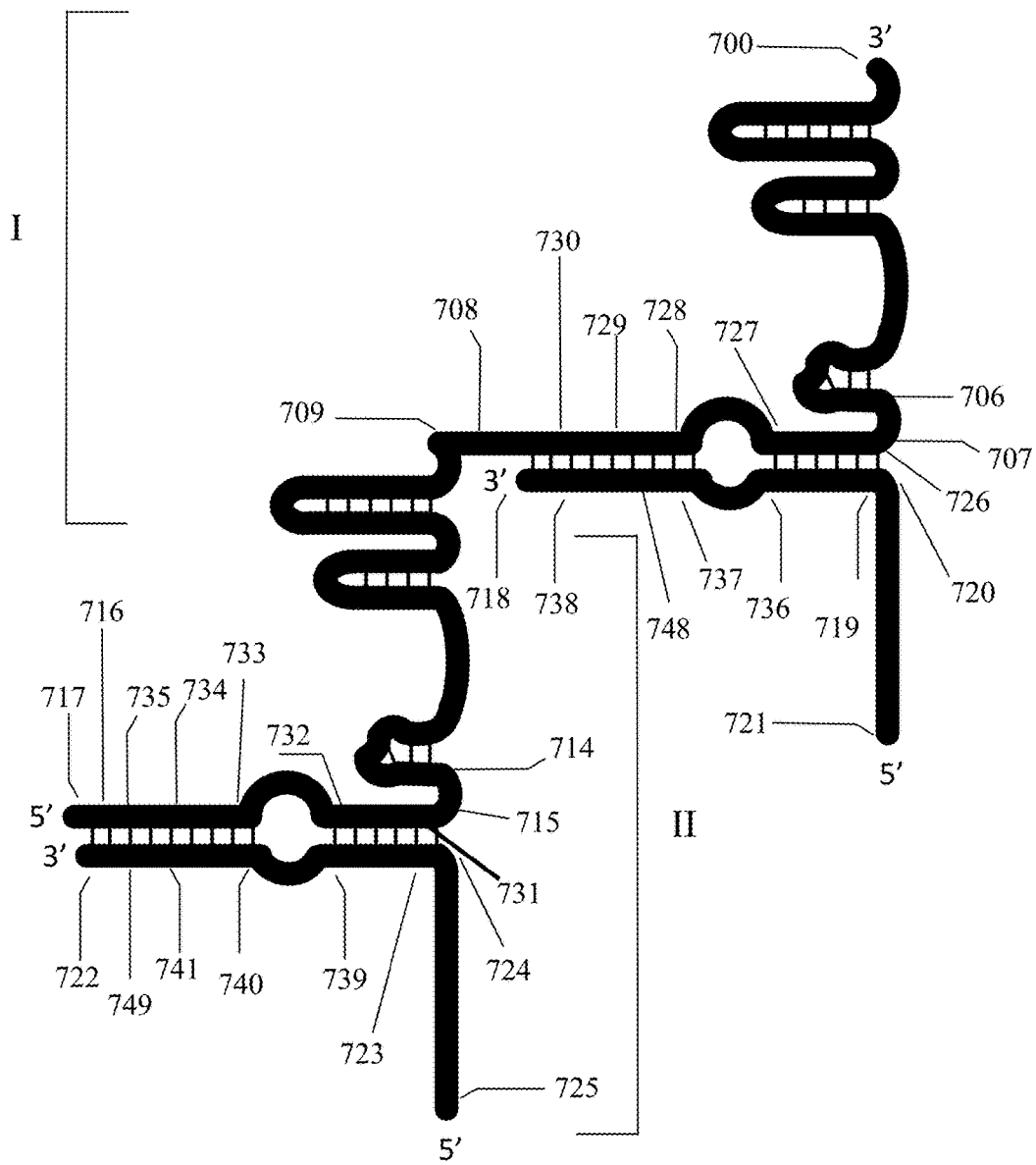

FIG. 7D illustrates an example of the formation of a scaffold through association of the NASC-PC-CE (FIG. 7D, 700-717) with the third concatenate element 1 (FIG. 7D, 721-718) through hydrogen base-pair bonding between: repeat nucleic acid sequence A1-1 (FIG. 7C, 726-727) and repeat nucleic acid sequence A1-1C (FIG. 7C, 719-736), and hydrogen base-pair bonding between repeat nucleic acid sequence A1-2 (FIG. 7C, 728-729) and repeat nucleic acid sequence A1-2C (FIG. 7C, 737-748); association of the engineered concatenated element 1 (FIG. 7D, 700-717) with the third concatenate element 2 (FIG. 7C, 722-725) through hydrogen base-pair bonding between repeat nucleic acid sequence A2-1 (FIG. 7C, 731-732) and repeat nucleic acid sequence A2-1C (FIG. 7C, 723-739), and through hydrogen base-pair bonding between repeat nucleic acid sequence A2-2 (FIG. 7C, 733-734) and repeat nucleic acid sequence A2-2C (FIG. 7C, 740-741).

Figure 7E:
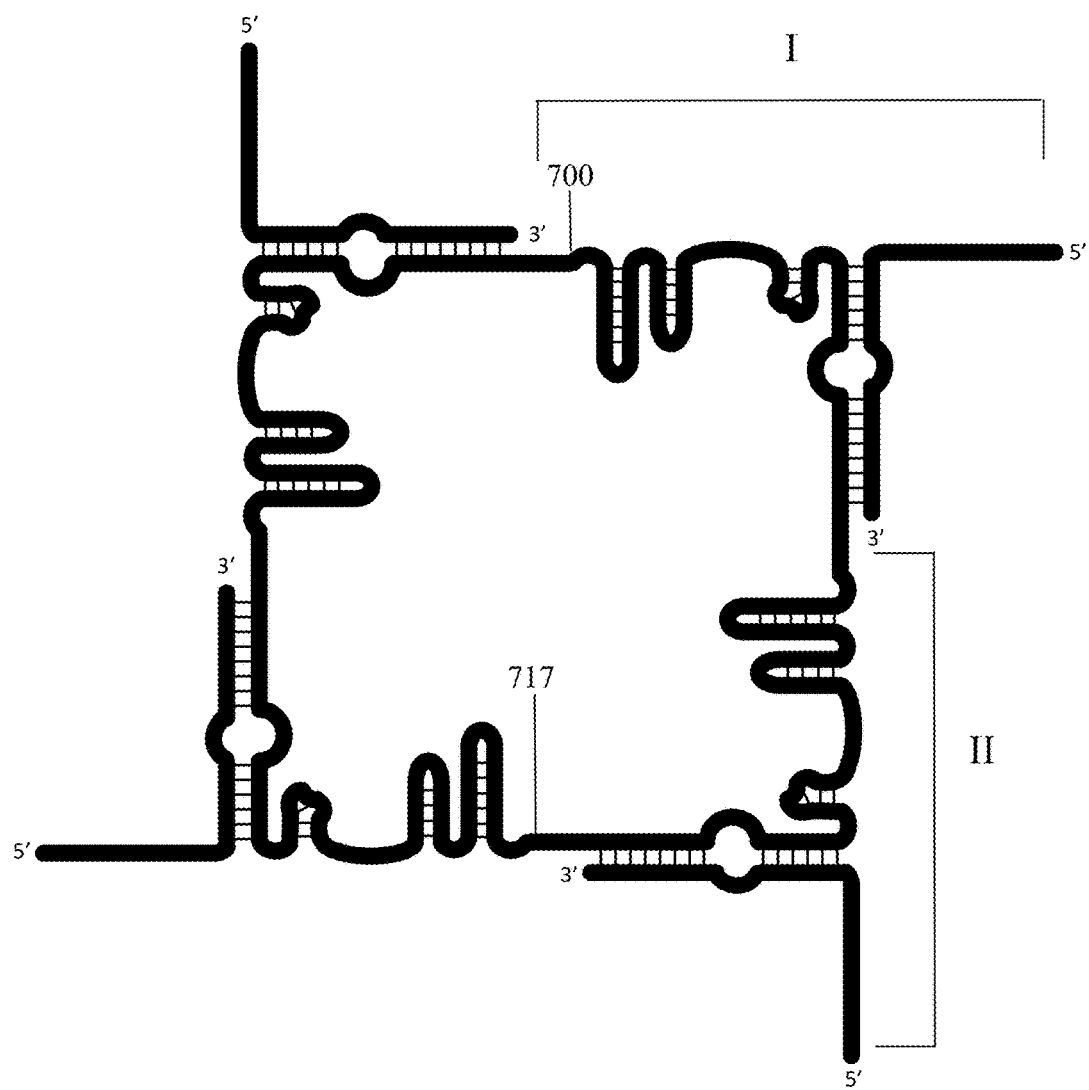

FIG. 7E presents an example of a complex formed from four engineered nucleic acid sequences to make a scaffold comprising a circular NASC-PC-CE. In this figure, the NASC-PC-CE comprises two copies of the NASC-PC-CE shown in FIG. 7D, 700-717 that are joined 5' end to 3' end to form the circular NASC-PC-CE. In this figure, reference numbers relative to FIG. 7D are shown to help illustrate the components of the circular concatenated nucleic acid element.

Figure 7F:
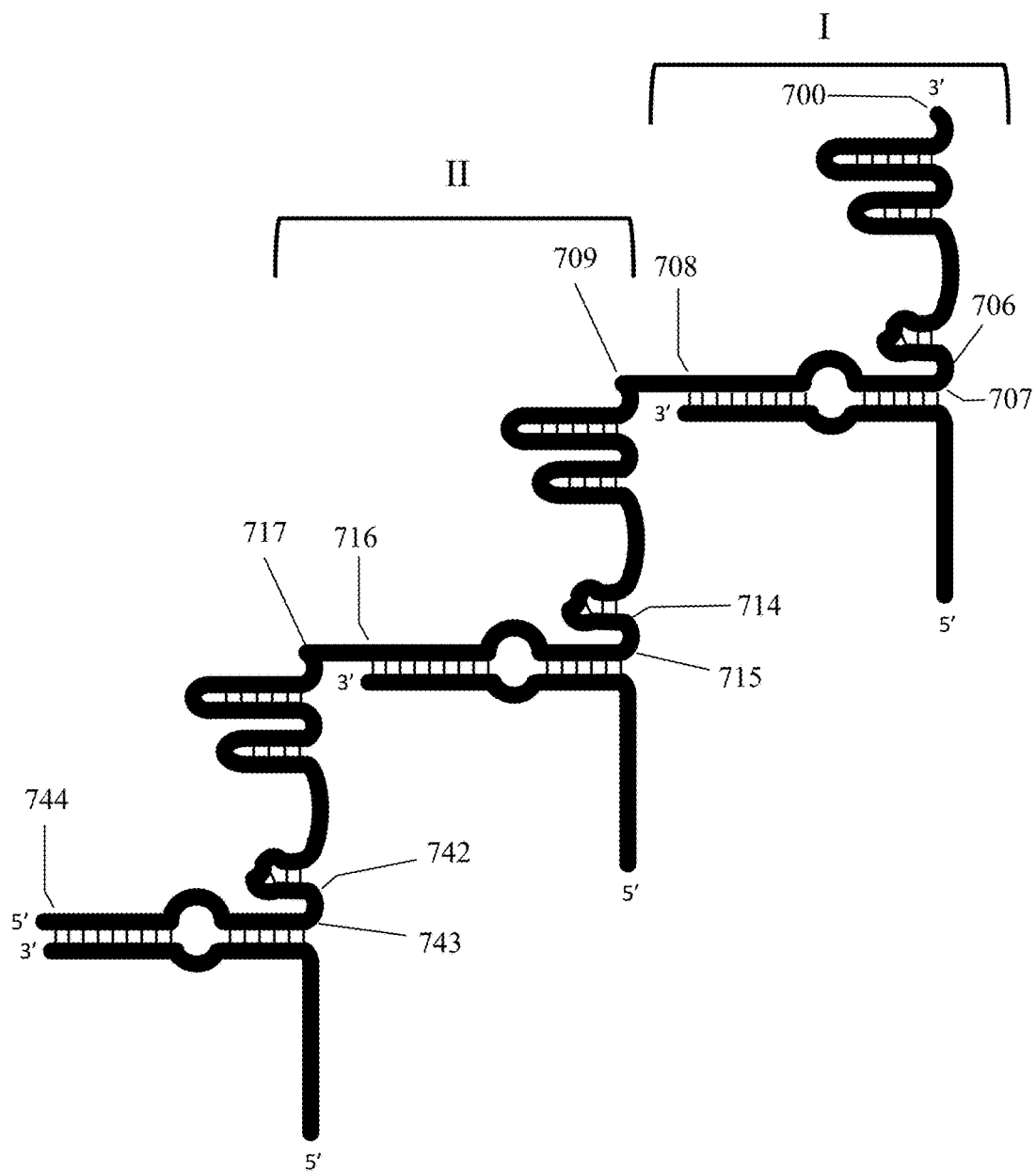

FIG. 7F is an illustration of a modification to the example shown in FIG. 7D, wherein the NASC-PC-CE (FIG. 7F, 700-717) further comprises a first concatenate element 3 (FIG. 7F, 717-744) covalently linked to the 5' end (FIG. 7F, 700-744). A second concatenate element 3 is associated with the first concatenate element 3 (FIG. 7F, 743-744).

Figure 7G:
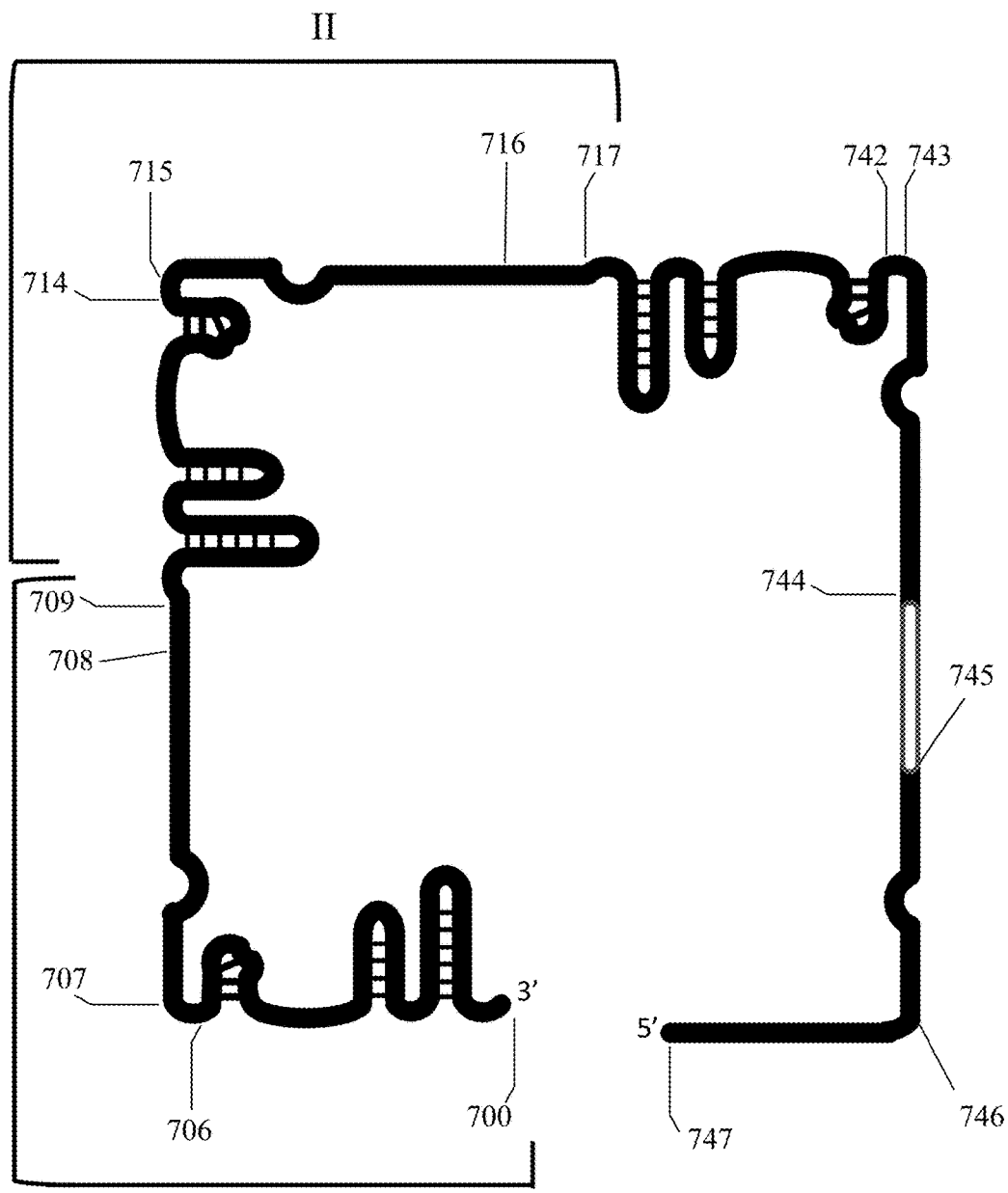

FIG. 7G illustrates an example of a modification to the NASC-PC-CE (FIG. 7F, 700-744) depicted in FIG. 7F, wherein the NASC-PC-CE comprises a fourth concatenate element (FIG. 7G, 744-747) covalently linked to the 5' end (FIG. 7F, 700-747). In this figure, the region, FIG. 7G, 744-745, is illustrated as a white box to make the cross-over lines in FIG. 7H and FIG. 7I more apparent. This region can also comprise a linker element nucleic acid sequence.

FIG. 7H, 700-747, illustrate an example of a NASC-PC-CE, wherein the second concatenate element 1 (FIG. 7H, 707-708) is associated with the third concatenate element 1 (FIG. 7H, 744-747) through hydrogen base-pair bonding.

Figure 7H:
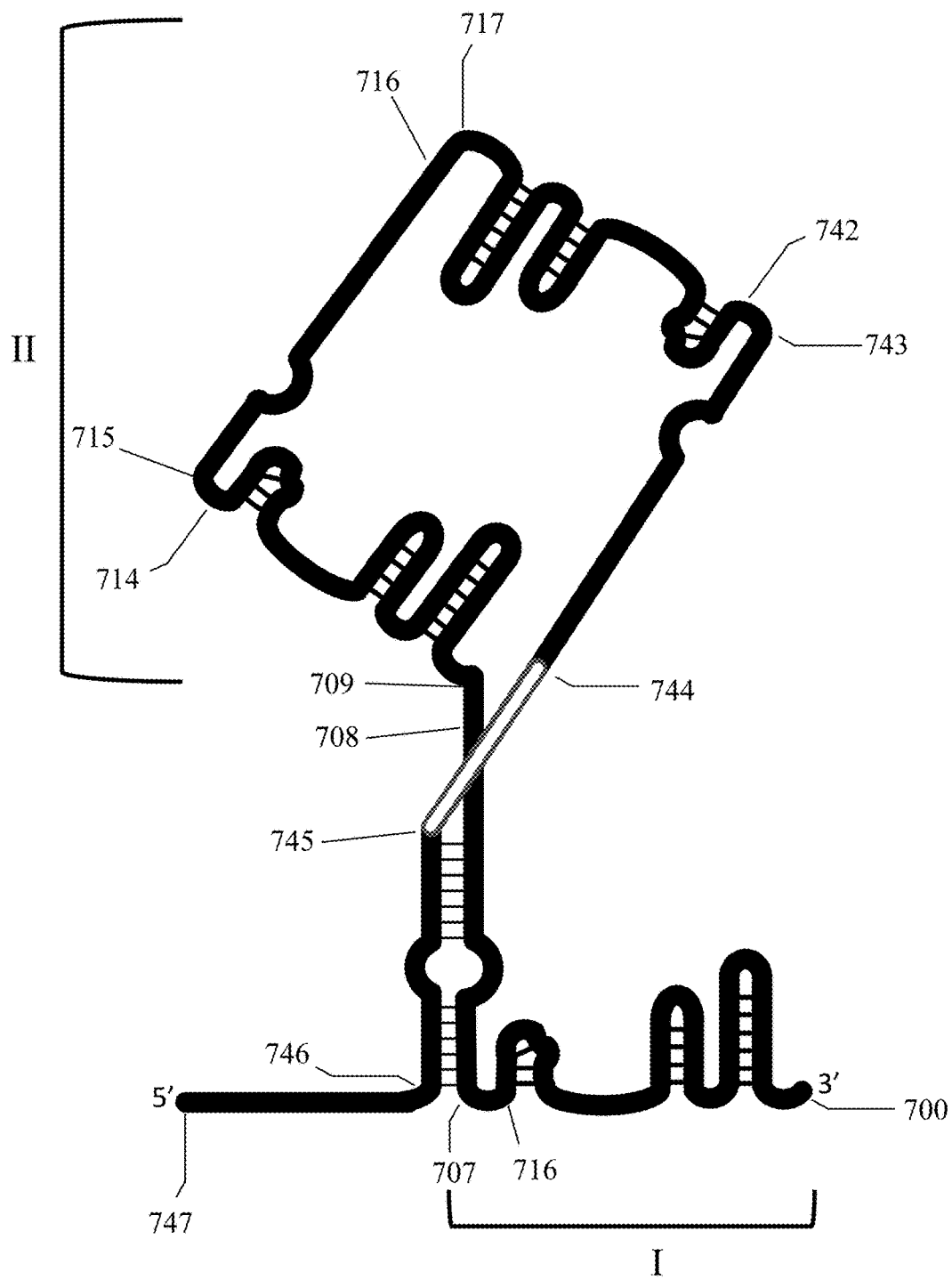
Figure 7I:
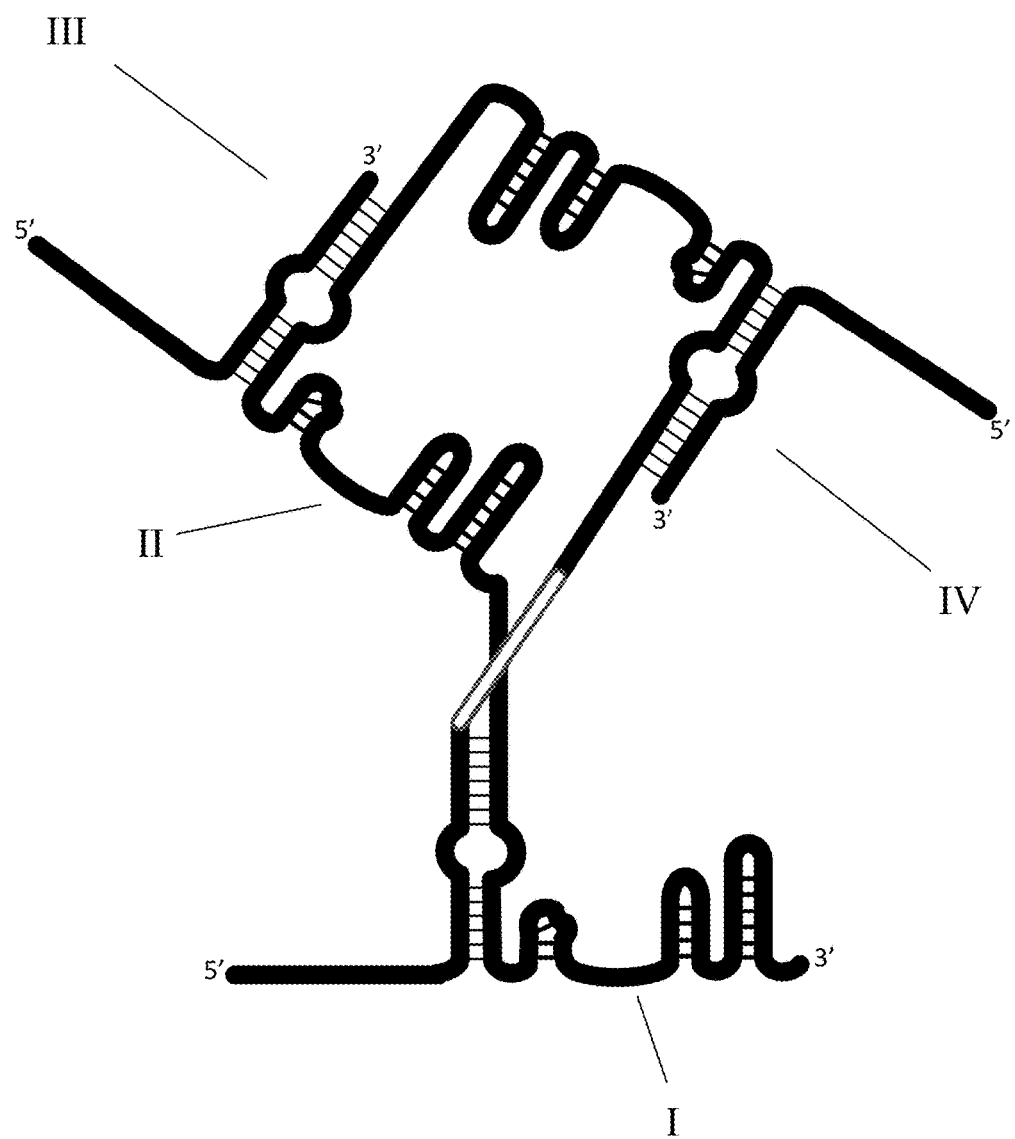

FIG. 7I illustrates a modification to the example shown in FIG. 7H, wherein a third concatenated element I associates with the NASC-PC-CE though hydrogen base-pair bonding to form element III (FIG. 7I, III) and a fourth concatenate element associates with the NASC-PC-CE though hydrogen base-pair bonding to form element IV (FIG. 7I, IV).

In other embodiments of the third aspect of the present invention, the NASC-PC-CE comprises split-nexus polynucleotides.

FIG. 8A, FIG. 8B, FIG. 8C, FIG. 8D, FIG. 8E, FIG. 8F, FIG. 8G, FIG. 8H, FIG. 8I, FIG. 8J, FIG. 8K, FIG. 8L, FIG. 8M, and FIG. 8N illustrate elements and examples of engineered concatenated split-nexus nucleic acid scaffolds of the present invention.

Figure 8A:
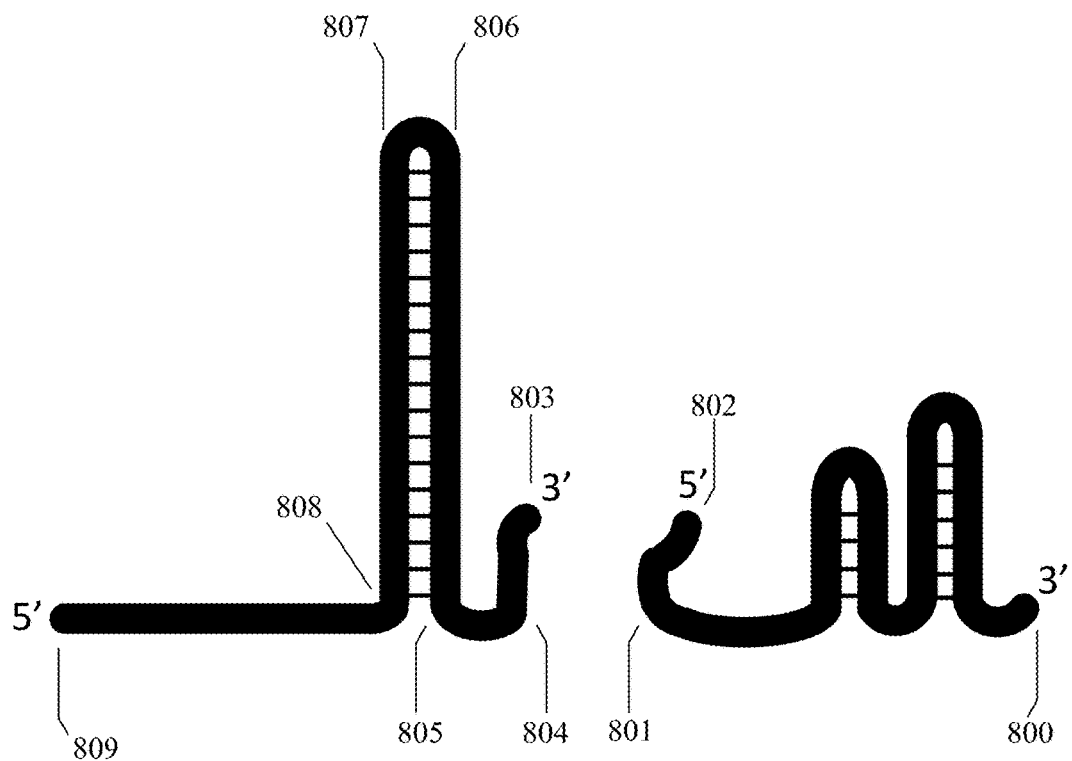
FIG. 8A, FIG. 8B, FIG. 8C, FIG. 8D, FIG. 8E, FIG. 8F, FIG. 8G, FIG. 8H, FIG. 8I, FIG. 8J, FIG. 8K, FIG. 8L, FIG. 8M, and FIG. 8N illustrate examples and elements of engineered concatenated split-*nexus* nucleic acid scaffold polynucleotide compositions of the present invention.
Figure 8B:
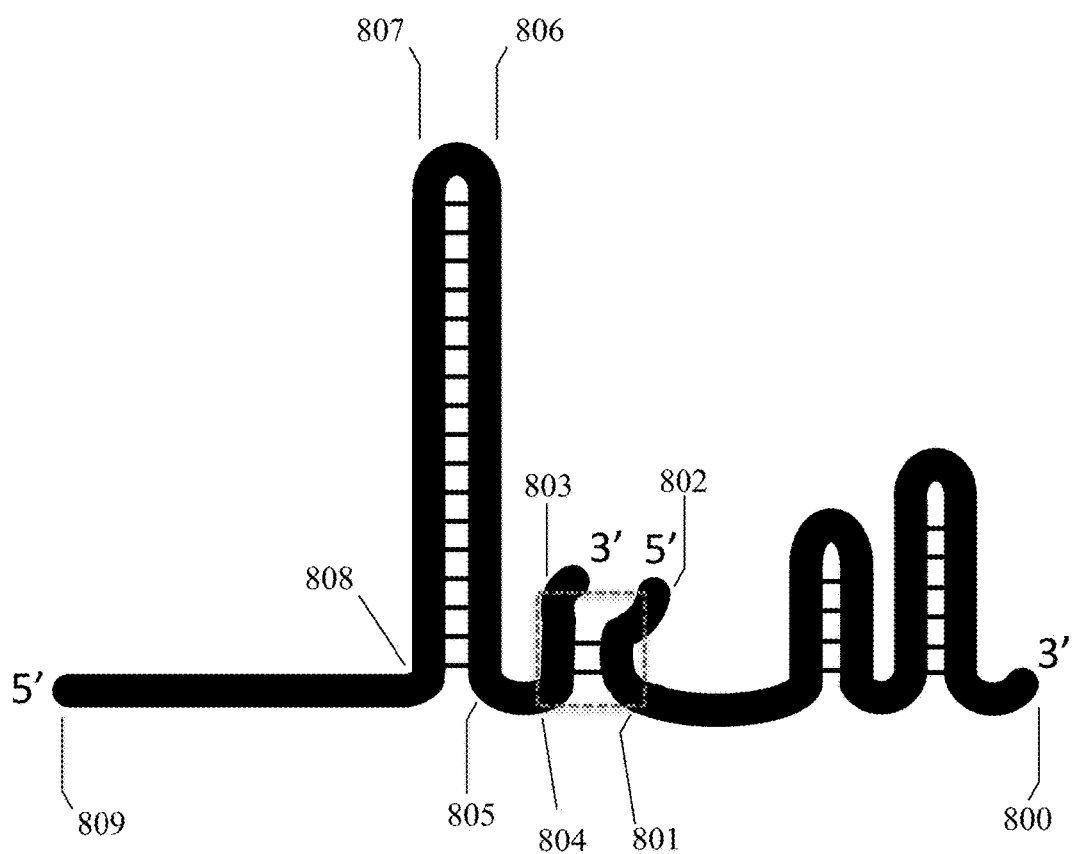
Figure 8C:
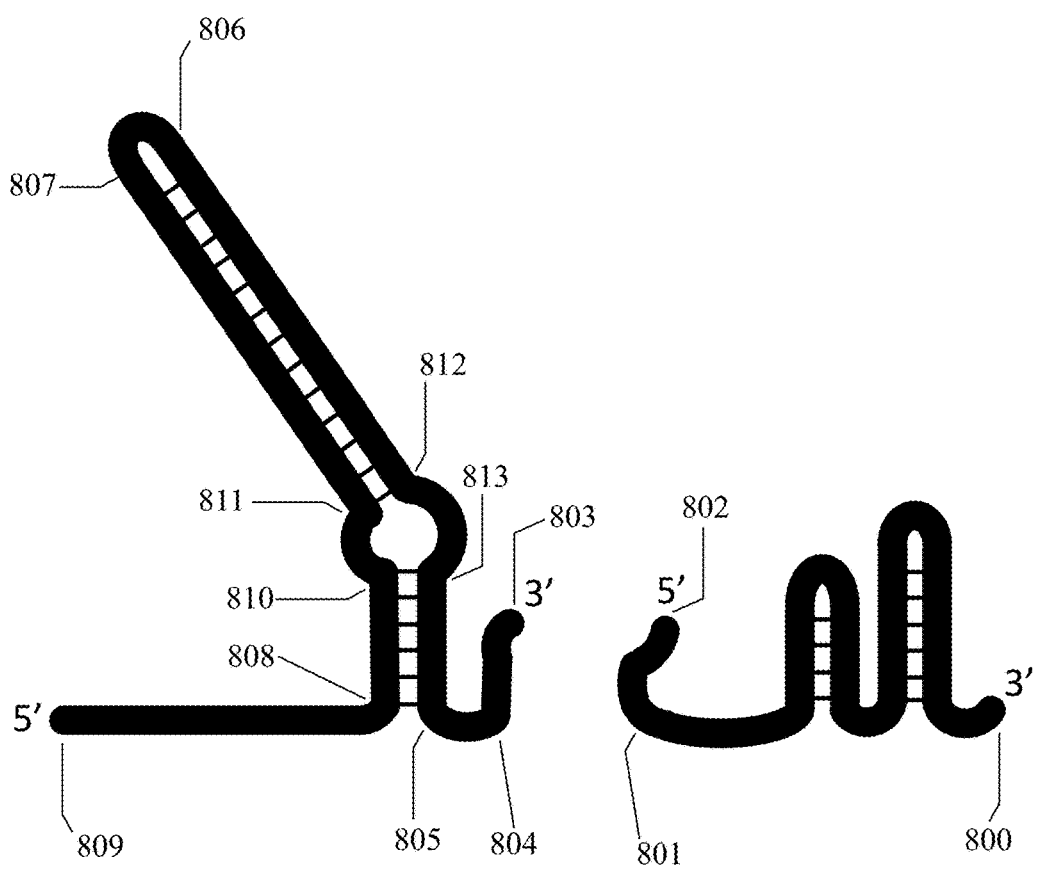
Figure 8D:
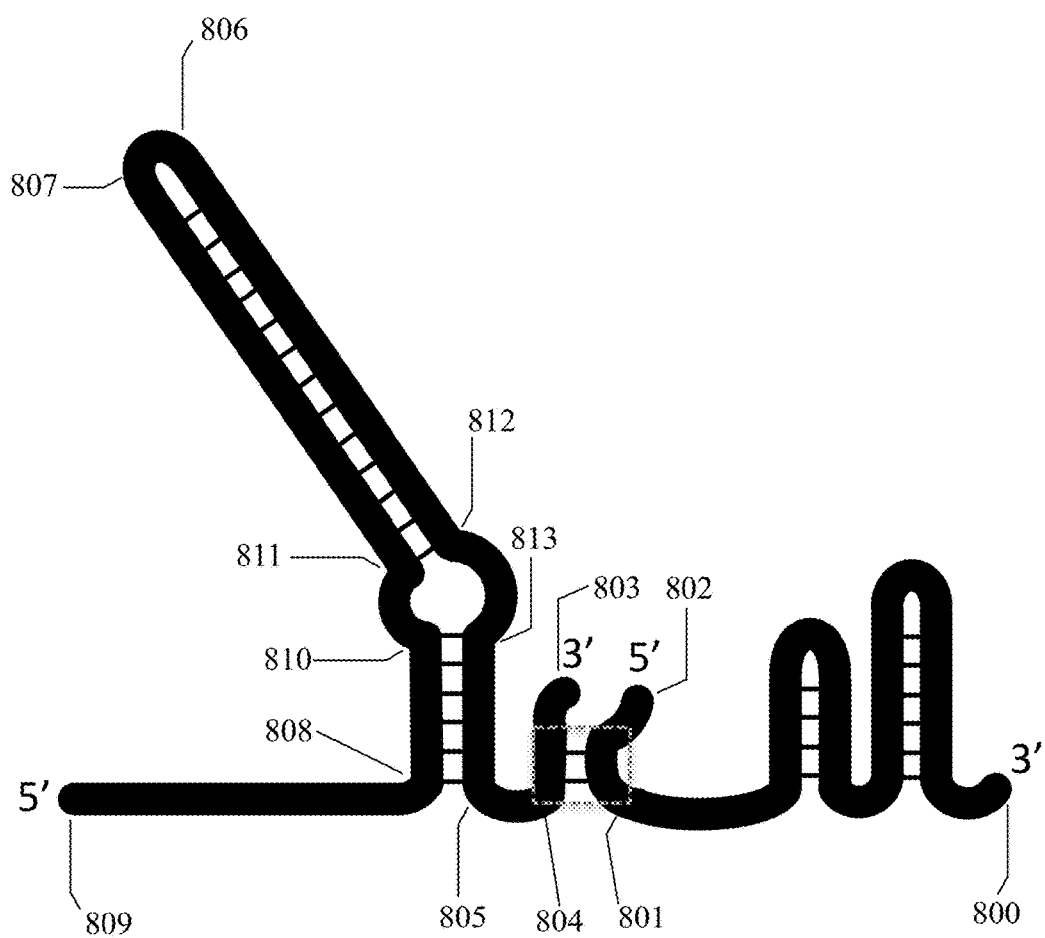
Figure 8E:
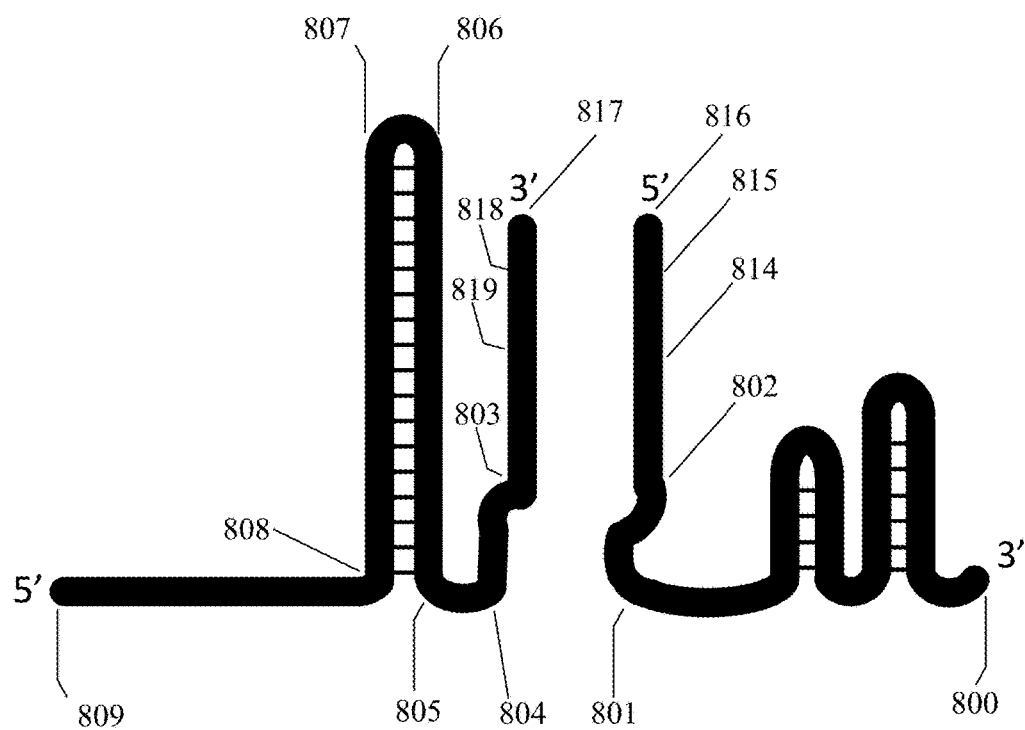
Figure 8F:
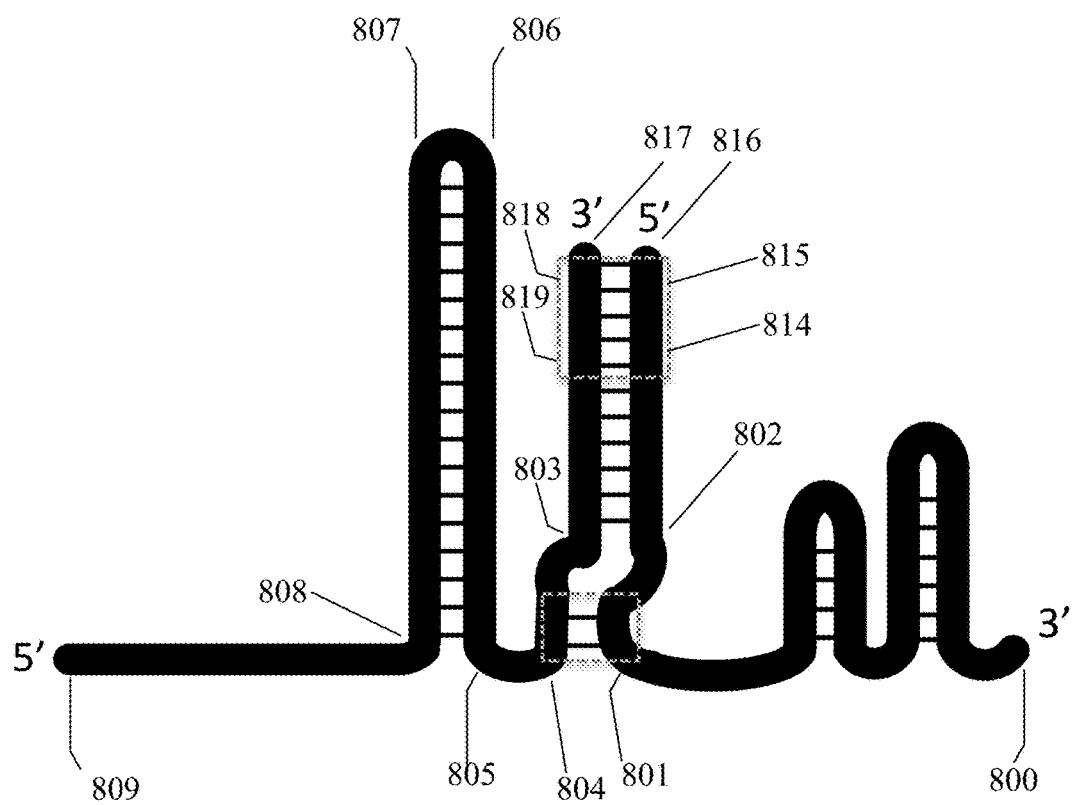
Figure 8G:
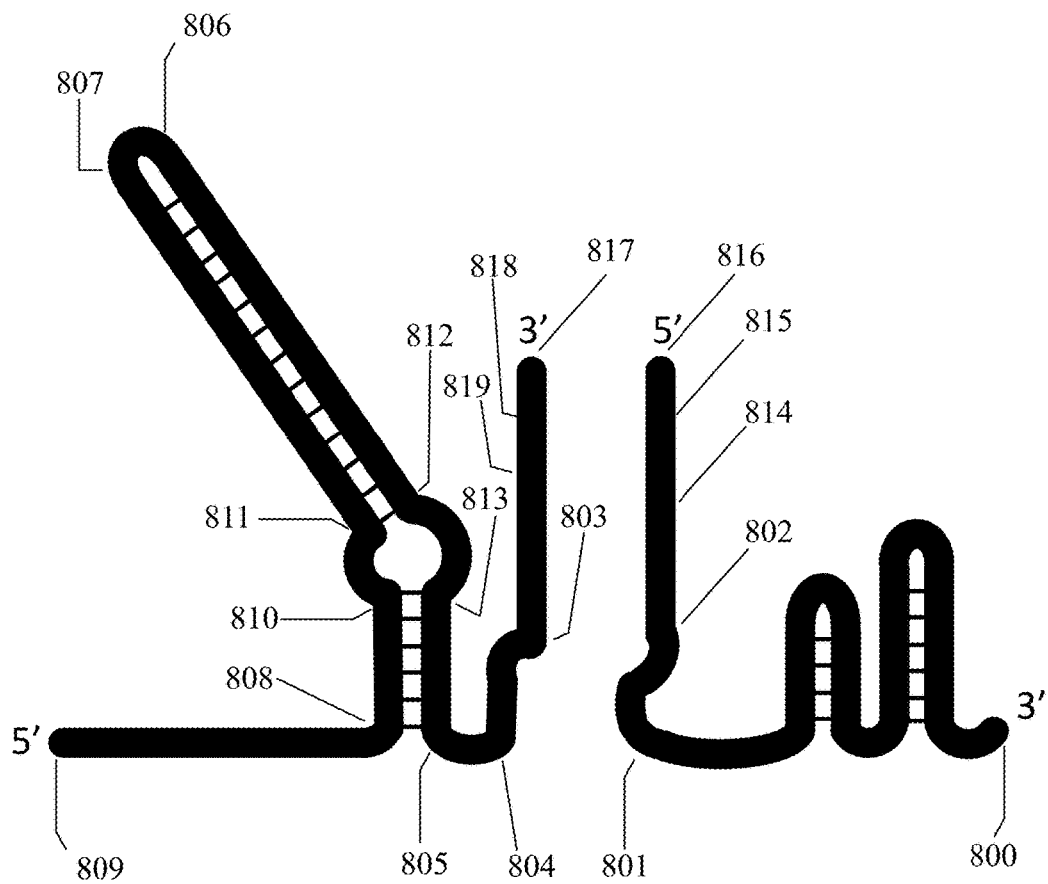
Figure 8H:
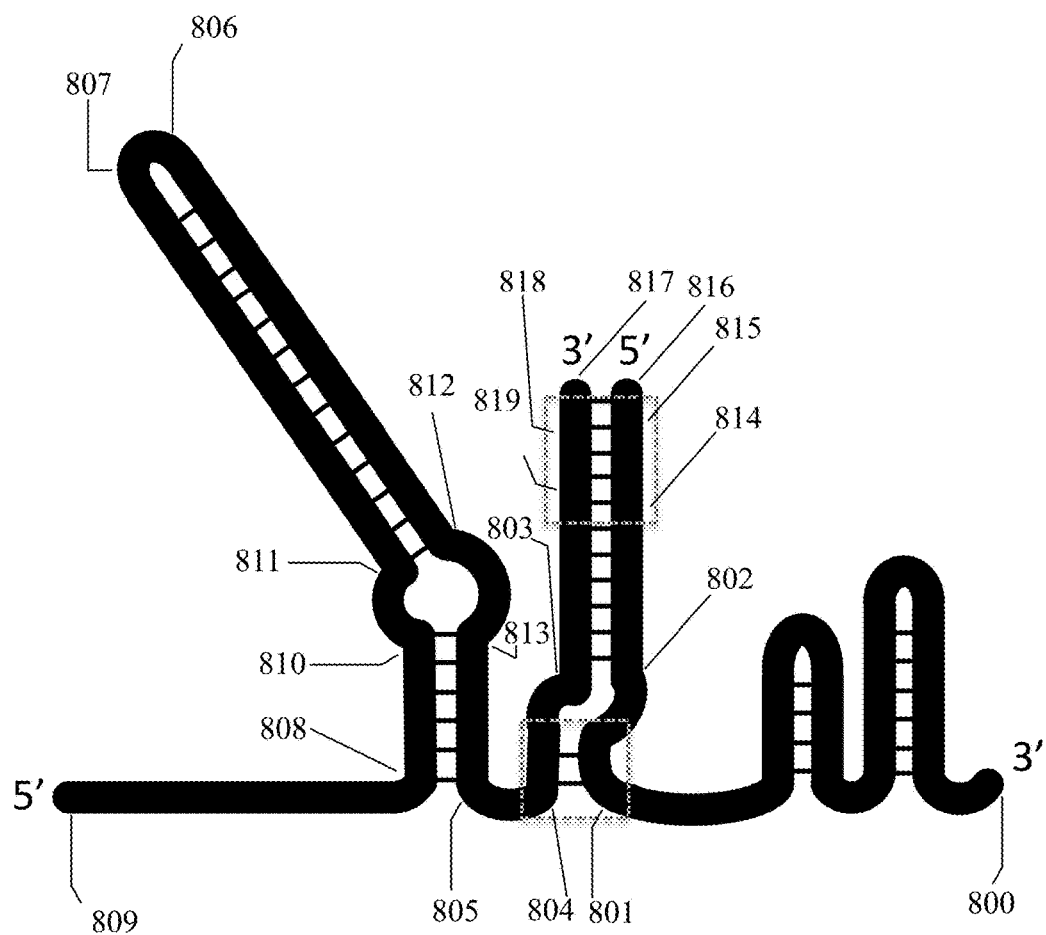
Figure 8I:
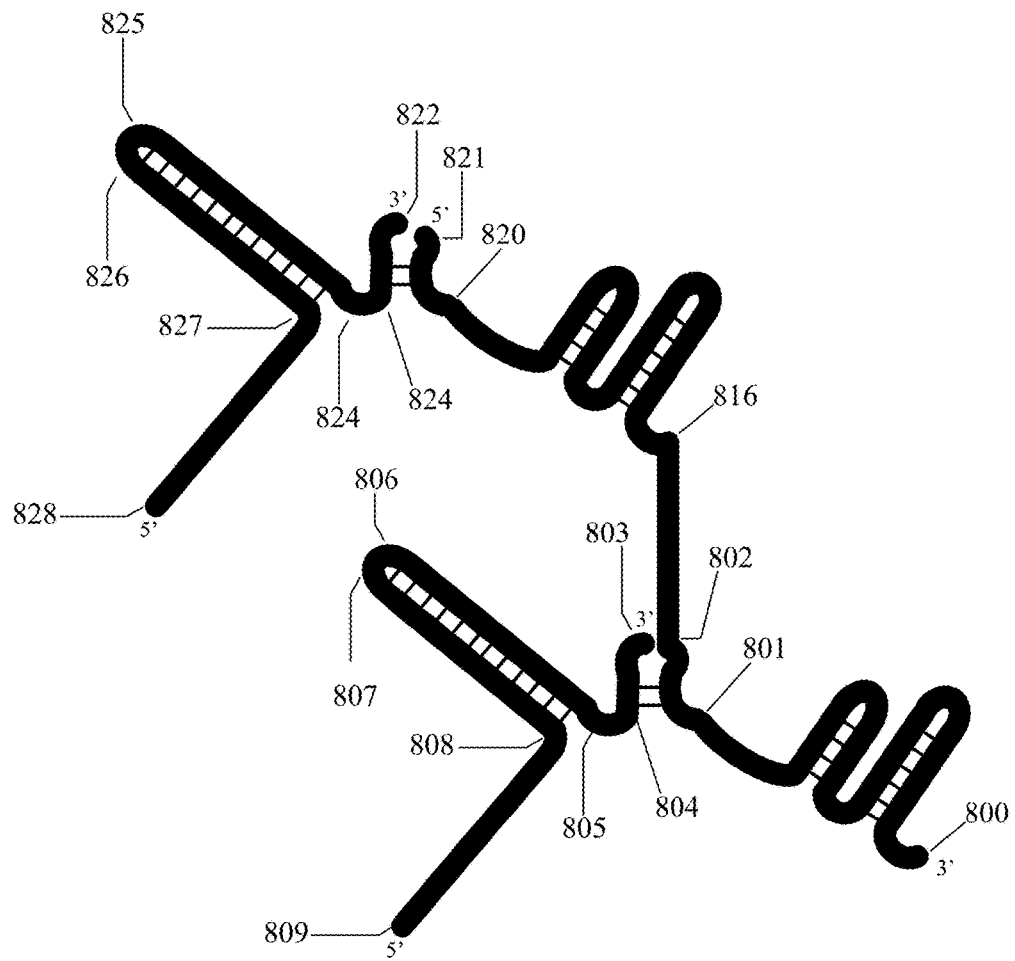
Figure 8J:
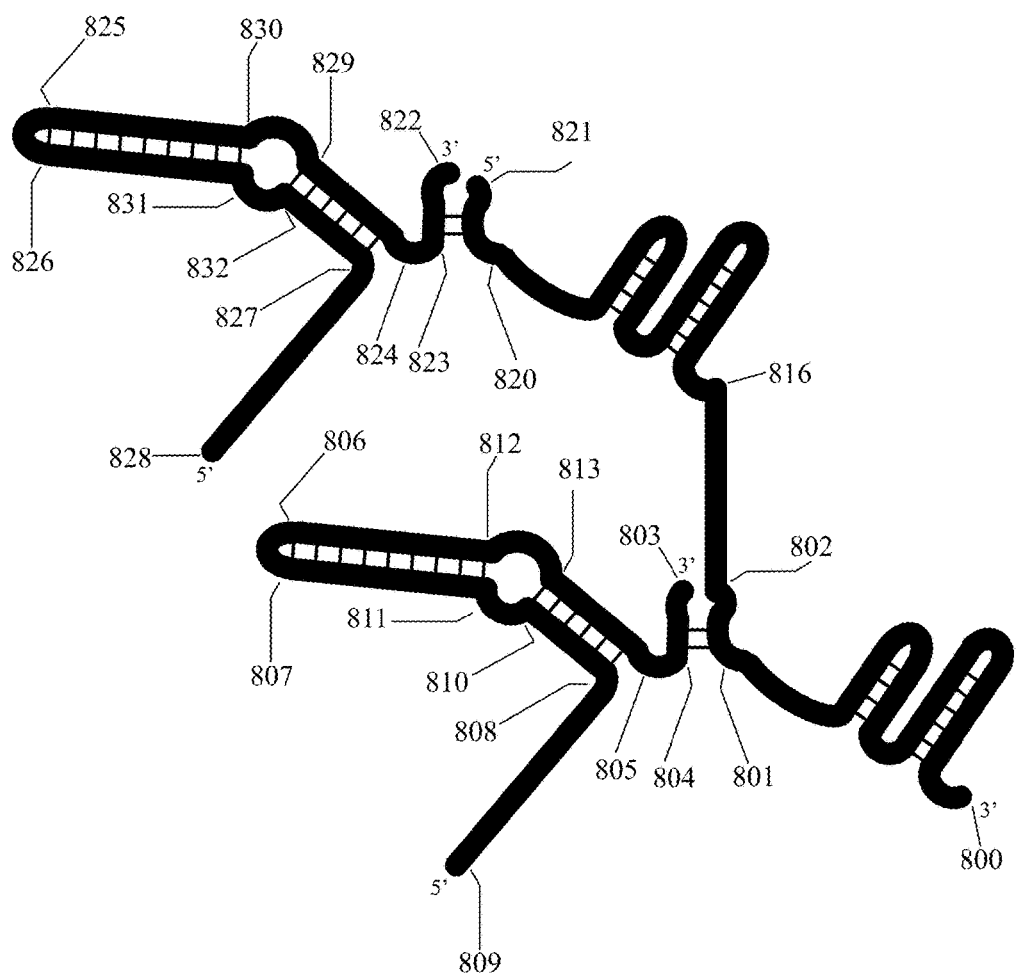
Figure 8K:
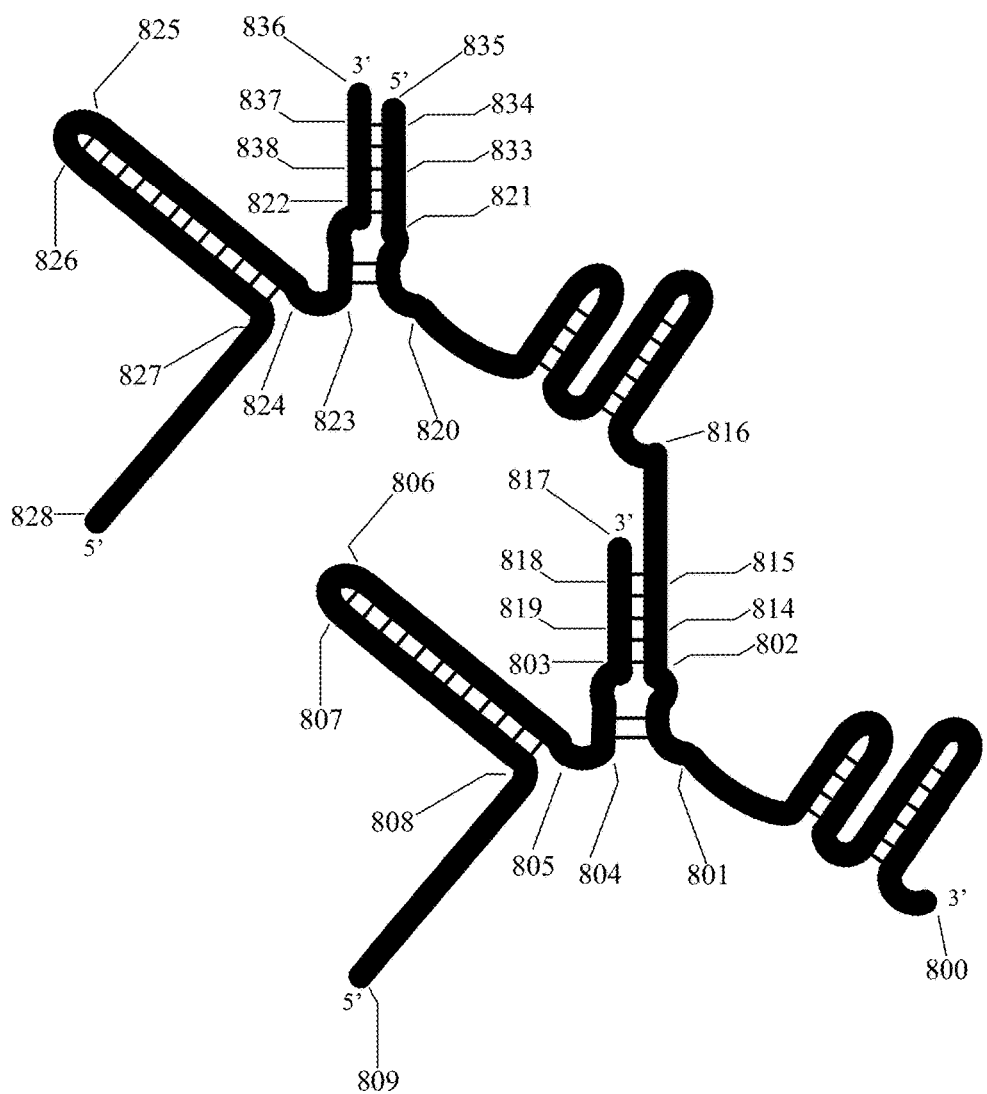
Figure 8L:
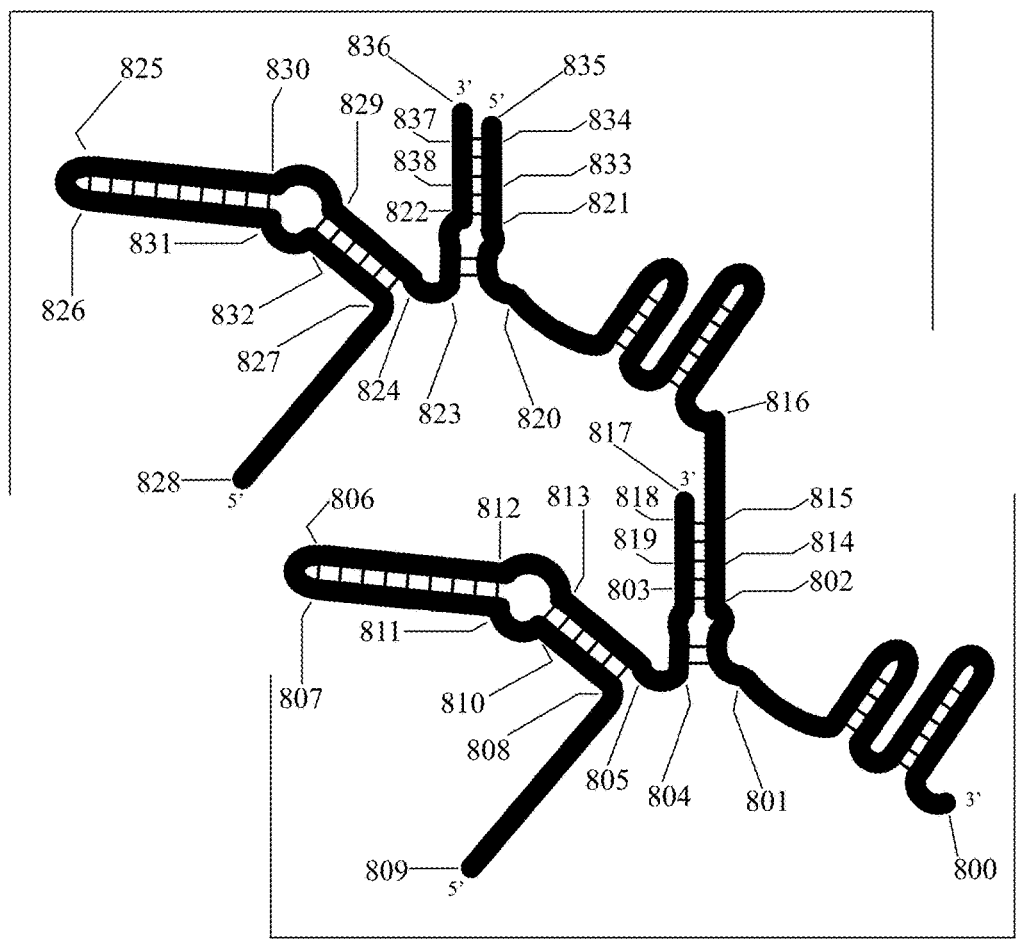
Figure 8M:
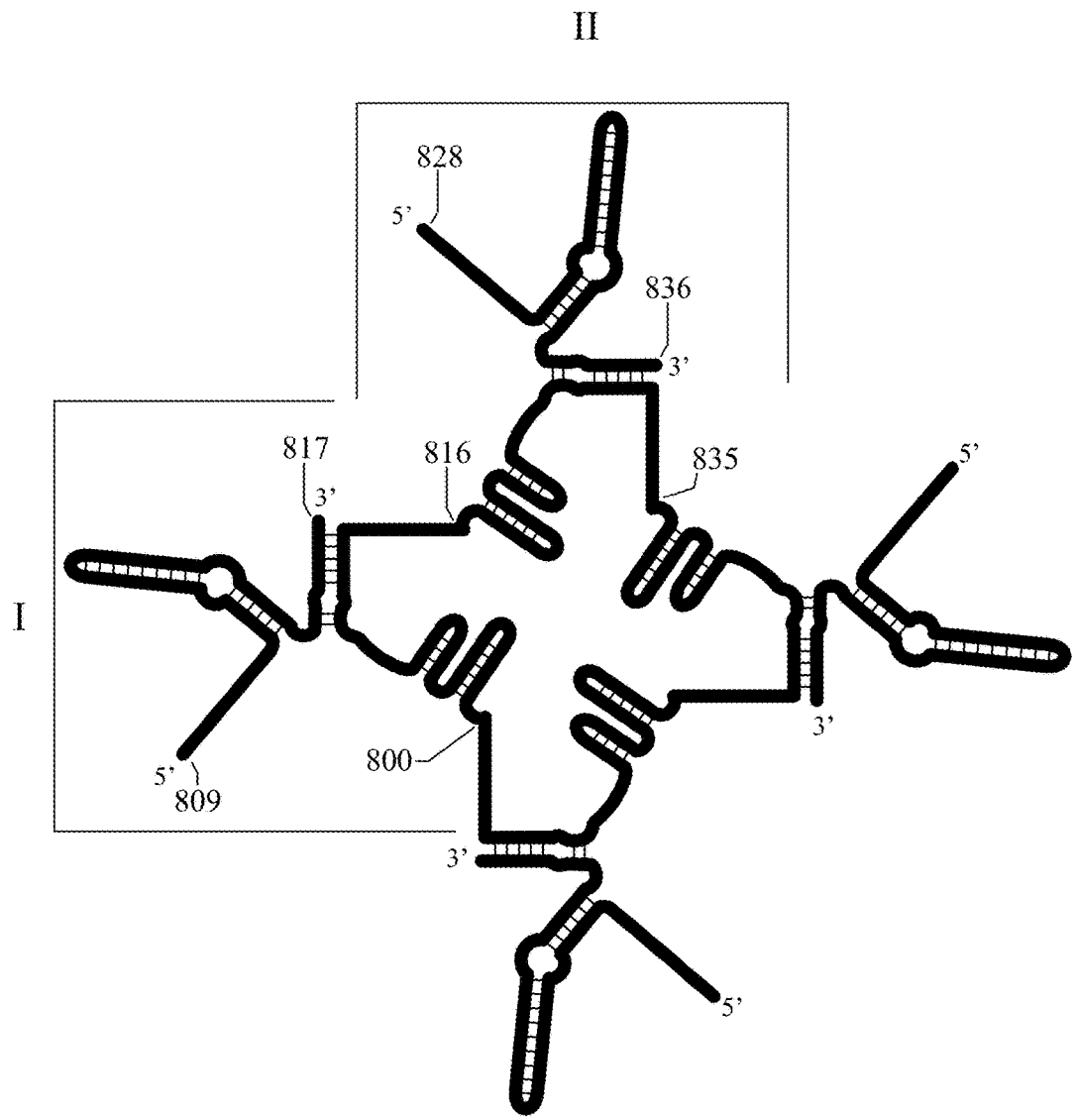
Figure 8N:
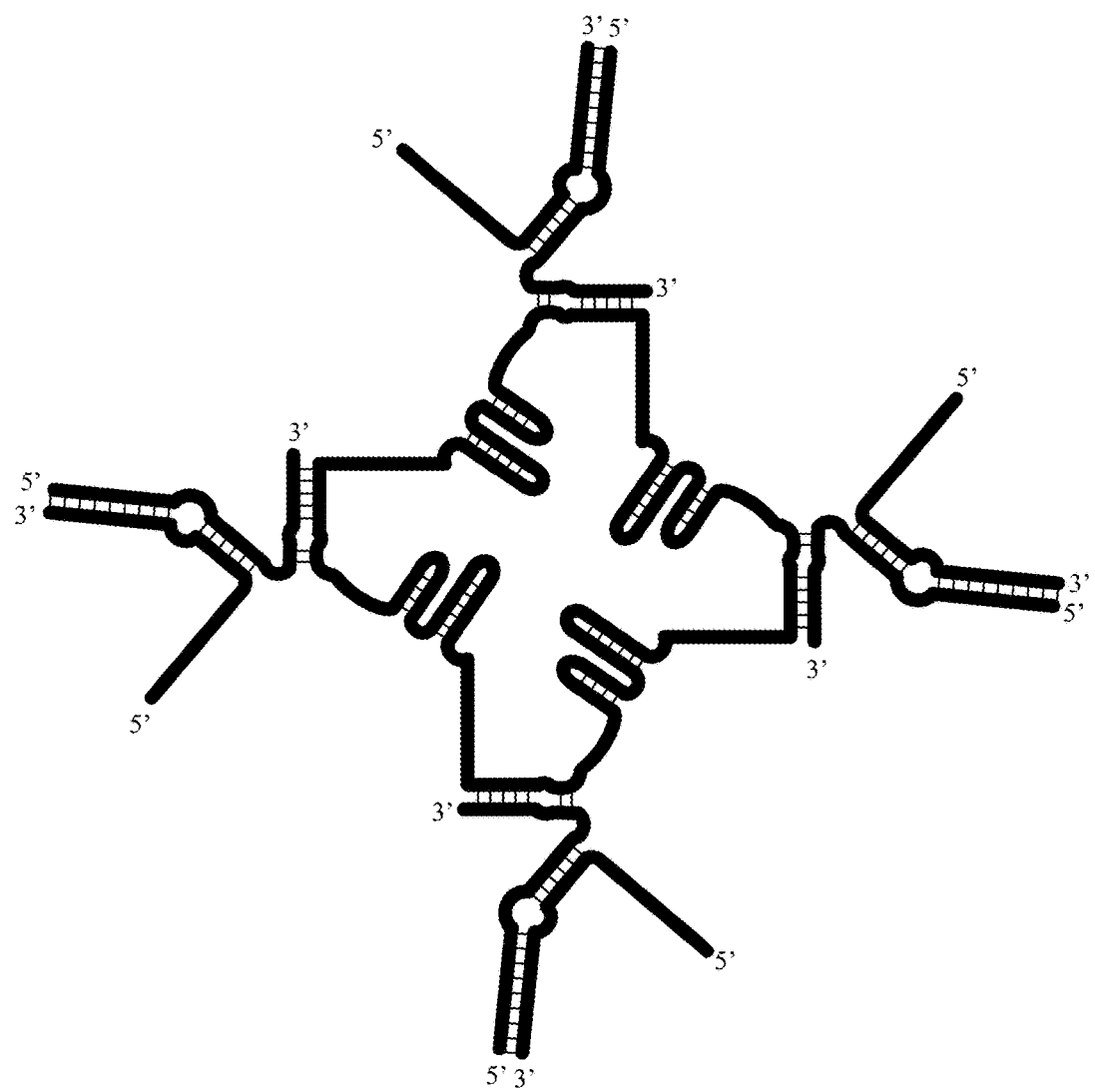

Table 7 presents a series of indicators used consistently in FIG. 8A through 8N.

TABLE 7

Numerical Indicators Used to Illustrate Regions of Complexes of Two or More Engineered Nucleic Acid Sequences for Forming a Scaffold Indicator and Corresponding Region an engineered NASC split-nexus polynucleotide concatenated element (corresponds to 800-835) (NASC-PC-SCE)
    a first concatenate element 1 (NASC-PC-SCE1-1)
        a nucleic acid binding protein binding element 1
            800-801 corresponds to a nucleic acid binding protein binding nucleic acid 1
            801-802 corresponds to a split-nexus stem element nucleic acid sequence 1-1
        a repeat element 1-1[1]
            802-816 corresponds an auxiliary polynucleotide 1-1
                802-815 corresponds to a repeat nucleic acid sequence 1-1
                      814-815 corresponds to a double-stranded nucleic acid binding effector protein binding site nucleic acid sequence 1
    a second concatenate element 1 (NASC-PC-SCE1-2)
        a nucleic acid binding protein binding element 2
            816-820 corresponds to a nucleic acid binding protein binding nucleic acid 2
            820-821 corresponds to a split-nexus stem element nucleic acid sequence 2-1
        a repeat element 2-1
            821-835 corresponds an auxiliary polynucleotide 2-1
                821-834 corresponds to a repeat nucleic acid sequence 2-1
                      833-834 corresponds to a double-stranded nucleic acid binding effector protein binding site nucleic acid sequence 2
    a second concatenate element 1 (NASC-PC-SCE2-1)
        a repeat element 1
            808-807 corresponds to a first stem element nucleic acid sequence 1-1
                808-810 corresponds to a lower stem element nucleic acid sequence 1-1
                810-811 corresponds to a bulge element nucleic acid sequence 1-1
                811-807 corresponds to an upper stem element nucleic acid sequence 1-1
            807-806 corresponds to a loop element nucleic acid sequence 1
            806-805 corresponds to a first stem element nucleic acid sequence 1-2
                806-812 corresponds to an upper stem element nucleic acid sequence 1-2
                812-813 corresponds to a bulge element nucleic acid sequence 1-2
                813-805 corresponds to a lower stem element nucleic acid sequence 1-2
            805-804 corresponds to a connective nucleic acid sequence 1
                [805-806/808-807 corresponds a first stem element 1]
                [811-807/806-812 corresponds to an upper stem element 1]
                [810-811/812-813 corresponds to a bulge element 1]
                [808-810/813-805 corresponds to a lower stem element 1]

TABLE 7-continued

Numerical Indicators Used to Illustrate Regions of Complexes of Two or More Engineered Nucleic Acid Sequences for Forming a Scaffold Indicator and Corresponding Region 804-803 corresponds to a split-nexus stem element nucleic acid sequence 1-2
[803-804/801-802 corresponds to a nexus element 1]
803-817 corresponds to an auxiliary polynucleotide 1-2
803-818 corresponds to a repeat nucleic acid sequence 1-2 (in some embodiments complementary to the repeat nucleic acid sequence 1-1)
818-819 corresponds to a double-stranded nucleic acid binding effector protein binding site nucleic acid sequence 1C²
[the site 814-815/818-819 corresponds to a double-stranded nucleic acid binding effector protein binding site 1]
a spacer element 1
808-809 corresponds to a nucleic acid target binding sequence 1
a second concatenate element 1 (NASC-PC-SCE2--2)
a repeat element 2
827-826 corresponds to a first stem element nucleic acid sequence 2-1
832-827 corresponds to a lower stem element nucleic acid sequence 2-1
831-832 corresponds to a bulge element nucleic acid sequence 2-1
831-826 corresponds to an upper stem element nucleic acid sequence 2-1
825-826 corresponds to a loop element nucleic acid sequence 2
824-825 corresponds to a first stem element nucleic acid sequence 2-2
825-830 corresponds to an upper stem element nucleic acid sequence 2-2
829-830 corresponds to a bulge element nucleic acid sequence 2-2
829-824 corresponds to a lower stem element nucleic acid sequence 2-2
823-824 corresponds to a connective nucleic acid sequence 2
[826-827/824-825 corresponds a first stem element 2]
[826-831/825-830 corresponds to an upper stem element 2]
[831-832/829-830 corresponds to a bulge element 2]
[827-832/824-829 corresponds to a lower stem element 2]
822-823 corresponds to a split-nexus stem element nucleic acid sequence 2-2
[822-823/820-821 corresponds to a nexus element 2]
822-836 corresponds to an auxiliary polynucleotide 2-2
822-837 corresponds to a repeat nucleic acid sequence 2-2 (in some embodiments complementary to the repeat nucleic acid sequence 2-1)
837-838 corresponds to a double-stranded nucleic acid binding effector protein binding site nucleic acid sequence 2C
[the site 837-838/833-834 corresponds to a double-stranded nucleic acid binding effector protein binding site 2]
a spacer element 2
827-828 corresponds to a nucleic acid target binding sequence 2

[1] = a repeat element can include an effector protein binding site
[2] = "C" indicates a complementary sequence FIG. 8A illustrates an example of split-nexus Cas9-associated polynucleotides. FIG. 2B presents an example of a Cas9-associated single-guide polynucleotide. The split-nexus Cas9-associated polynucleotides of FIG. 8A are generated by splitting the polynucleotide backbone within the nexus element (FIG. 2B, 206) of a Cas9-associated single-guide polynucleotide. FIG. 8A shows the two resulting split-nexus polynucleotides when not associated through hydrogen bond interactions. FIG. 8B presents a view of the split-nexus polynucleotides when associated through hydrogen bond interactions. The region of the hydrogen bond interactions is illustrated by a broken-dash box in FIG. 8B.

FIG. 8C illustrates another example of split-nexus Cas9-associated polynucleotides. FIG. 2A presents an example of a Cas9-associated single-guide polynucleotide. The split-nexus Cas9-associated polynucleotides of FIG. 8C are generated by splitting the polynucleotide backbone within the nexus element (FIG. 2A, 206) of a Cas9-associated single-guide polynucleotide. FIG. 8C shows the two resulting split-nexus polynucleotides when not associated through hydrogen bond interactions. FIG. 8D presents a view of the split-nexus polynucleotides when associated through hydrogen bond interactions. The region of the hydrogen bond interactions is illustrated by a broken-dash box in FIG. 8D.

FIG. 8E illustrates the addition of an auxiliary polynucleotide to the split-nexus Cas9-associated polynucleotide illustrated in FIG. 8A. In this figure, the 5' end of a first auxiliary polynucleotide (FIG. 8E, 803-817) is covalently attached to the 3' end of one half of the split-nexus element (FIG. 8E, 803) and the 3' end of a second auxiliary polynucleotide (FIG. 8E, 802-816) is covalently attached to the 5' end of the other half of the split-nexus element (FIG. 8E, 802). In some embodiments, only one auxiliary polynucleotide is included. In other embodiments, two auxiliary polynucleotides of the same or different lengths are included. FIG. 8E shows the two split-nexus polynucleotides when not associated through hydrogen bond interactions.

FIG. 8F presents a view of the split-nexus polynucleotides when associated through hydrogen bond interactions. The region of the hydrogen bond interactions is illustrated by the broken-dash box at FIG. 8D, 803-804/801-802. An auxiliary polynucleotide can comprise additional elements such as effector protein binding sequences, for example, a double-stranded nucleic acid binding protein binding site can be created by the association of two auxiliary polynucleotides through hydrogen bond interactions (e.g., such region of the hydrogen bond interactions is illustrated by the broken-dash box at FIG. 8D, 818-819-804/814-815).

FIG. 8G illustrates another example of the addition of an auxiliary polynucleotide to the split-nexus Cas9-associated polynucleotide illustrated in FIG. 8C. In this figure, the 5' end of a first auxiliary polynucleotide (FIG. 8G, 803-817) is covalently attached to the 3' end of one half of the split-nexus element (FIG. 8E, 803) and the 3' end of a second auxiliary polynucleotide (FIG. 8G, 802-816) is covalently attached to the 5' end of the other half of the split-nexus element (FIG. 8G, 802). In some embodiments, only one auxiliary polynucleotide is included. In other embodiments, two auxiliary polynucleotides of the same or different lengths are included. FIG. 8G shows the two split-nexus polynucleotides when not associated through hydrogen bond interactions. FIG. 8H presents a view of the split-nexus polynucleotides when associated through hydrogen bond interactions. The region of the hydrogen bond interactions is illustrated by the broken-dash box at FIG. 8H, 803-804/801-802. An auxiliary polynucleotide can comprise additional elements such as effector protein binding sequences, for example, a double-stranded nucleic acid binding protein binding site can be created by the association of two auxiliary polynucleotides through hydrogen bond interactions (e.g., such region of the hydrogen bond interactions is illustrated by the broken-dash box at FIG. 8H, 818-819-804/814-815).

In one embodiment, the third aspect of the present invention is directed to an engineered NASC split-nexus polynucleotide concatenated element (NASC-PC-SCE) polynucleotide composition comprising, in a 3' to 5' direction, a first concatenate element 1 (NASC-PC-SCE1-1) comprising a nucleic acid binding protein binding element 1, a split-nexus stem element nucleic acid sequence 1-1, and a repeat element comprising a repeat nucleic acid sequence 1-1, and a second concatenate element 1 (NASC-PC-SCE1-2) comprising a nucleic acid binding protein binding element 2, a split-nexus stem element nucleic acid sequence 2-1, and a repeat element comprising a repeat nucleic acid sequence 2-1. The NASC-PC-SCE1-1 and the NASC-PC-SCE1-2 are connected to form the NASC-PC-SCE. A second concatenate element 1 (NASC-PC-SCE2-1) comprises a repeat element 1 comprising, in a 3' to 5' direction, a repeat nucleic acid sequence 1-2, a split-nexus stem element nucleic acid sequence 1-2, and a first stem element, and a spacer element 1 comprising a nucleic acid target binding sequence 1. A second concatenate element 2 (NASC-PC-SCE2-2) comprises a repeat element 2 comprising, in a 3' to 5' direction, a repeat nucleic acid sequence 2-2, a split-nexus stem element nucleic acid sequence 2-2, and a first stem element, and a spacer element 2 comprising a nucleic acid target binding sequence 2.

The repeat element 1-1 is connected to the repeat element 1-2, and the repeat element 2-1 is connected to the repeat element 2-2 to form the NASC-PC-SCE, and the NASC-PC-SCE is capable of binding two nucleic acid binding proteins. In some embodiments, the nucleic acid binding protein binding element is a double-stranded nucleic acid binding protein binding element that binds a double-stranded nucleic acid binding protein. In additional embodiments, a first repeat nucleic acid sequence of a pair is connected with the second repeat nucleic acid sequence of the pair through hydrogen-bonded base pairs.

FIG. 8I presents an example of a NASC-PC-SCE comprising two copies of the split-nexus polynucleotide shown in FIG. 8B, 800-802 forming a scaffold. In this figure, the NASC-PC-SCE is a first split-nexus polynucleotide (FIG. 8I, 800-802) covalently attached to a second split-nexus polynucleotide (FIG. 8I, 816-821) through an auxiliary polynucleotide (FIG. 8I, 802-816). Each first half of a split-nexus element (FIG. 8I, 801-802 and 820-821) is connected with the complementary second half of its split-nexus element (FIG. 8I, 803-804, and 822-823, respectively), for example, through hydrogen-bonded base pairs.

FIG. 8J presents an example of a NASC-PC-SCE comprising two copies of the split-nexus polynucleotide shown in FIG. 8D, 800-802 forming a scaffold. In this figure, the NASC-PC-SCE is a first split-nexus polynucleotide (FIG. 8J, 800-802) covalently attached to a second split-nexus polynucleotide (FIG. 8J, 816-821) through an auxiliary polynucleotide (FIG. 8J, 802-816). Each first half of a split-nexus element (FIG. 8J, 801-802 and 820-821) is connected with the complementary second half of its split-nexus element (FIG. 8J, 803-804, and 822-823, respectively), for example, through hydrogen-bonded base pairs.

FIG. 8K presents an example of a NASC-PC-SCE comprising two copies of the split-nexus polynucleotide shown in FIG. 8F, 800-816, each comprising an auxiliary sequence, forming a scaffold. In this figure, the NASC-PC-SCE is a first split-nexus polynucleotide (FIG. 8K, 800-816) covalently attached to a second split-nexus polynucleotide (FIG. 8J, 816-835) through an auxiliary polynucleotide (FIG. 8J, 802-816). Each first half of a split-nexus element (FIG. 8K, 801-802 and 820-821) is connected with the complementary second half of its split-nexus element (FIG. 8K, 803-804, and 822-823, respectively) and is also connected by the auxiliary sequences (FIG. 8K, 802-815 and 803-818; FIG. 8K, 821-834 and 822-836). The connections are made, for example, through hydrogen-bonded base pairs.

FIG. 8L presents an example of a NASC-PC-SCE comprising two copies of the split-nexus polynucleotide shown in FIG. 8H, 800-816, each comprising an auxiliary sequence, forming a scaffold. In this figure, the NASC-PC-SCE is a first split-nexus polynucleotide (FIG. 8H, 800-816) covalently attached to a second split-nexus polynucleotide (FIG. 8H, 816-835) through an auxiliary polynucleotide (FIG. 8H, 802-816). Each first half of a split-nexus element (FIG. 8H, 801-802 and 820-821) is connected with the complementary second half of its split-nexus element (FIG. 8H, 803-804, and 822-823, respectively) and is also connected by the auxiliary sequences (FIG. 8H, 802-815 and 803-818; FIG. 8K, 821-834 and 822-836). The connections are made, for example, through hydrogen-bonded base pairs. The two components of the NASC-PC-SCE are indicated in this figure as I and II.

FIG. 8M presents an example of a NASC-PC-SCE comprising elements I and II as shown in FIG. 8L. NASC-PC-SCE comprises a circular NASC-PC-SCE. In this figure, two sets of elements I and II, shown in FIG. 8L, 800-835, are joined 5' end to 3' end to form the circular NASC-PC-SCE. In this figure, reference numbers relative to FIG. 8L are shown to help illustrate the components of the circular NASC-PC-SCE.

FIG. 8N presents an example of a NASC-PC-SCE comprising elements I and II as shown in FIG. 8L, with the exception that the first stem element nucleic acid sequences are not joined by loop element nucleic acid sequences (see, e.g., FIG. 8L, 806-807, 825-826). NASC-PC-SCE comprises a circular NASC-PC-SCE.

In other embodiments, a first repeat nucleic acid sequence of a pair further comprises first affinity tag and the second repeat nucleic acid sequence of the pair further comprises a second affinity tag, and the first affinity tag is connected with the second affinity tag. For example, the first repeat nucleic acid sequence further comprises an effector protein binding site nucleic acid sequence 1 and the second repeat nucleic acid sequence further comprises an effector protein binding site nucleic acid sequence 2. The effector protein binding site nucleic acid sequence 1 is connected by hydrogen-bonded base pairs to the effector protein binding site nucleic acid sequence 2 to form an effector protein binding site 1. One example of an effector binding site is a Csy4 protein binding site.

In a fourth aspect of the present invention, a NASC polynucleotide composition comprises a combination of nucleic acid binding protein binding elements for two or more different nucleic acid binding proteins. In some embodiments, one or more of the nucleic acid binding protein binding elements is a double-stranded nucleic acid binding protein binding element that binds a double-stranded nucleic acid binding protein (e.g., a Class 2 CRISPR-Cas protein). Embodiments of the fourth aspect of the present invention include a first NATNA covalently connected to a second NATNA to form a NASC polynucleotide composition. In some embodiments, a first NATNA covalently is connected to a second NATNA to form a NASC-PC component and two or more NASC-PC components are connected either covalently or non-covalently to form a NASC polynucleotide composition. The NASC polynucleotide composition is capable of binding at least two nucleic acid binding proteins. Non-covalent connections include connecting the NASC-PC components through hydrogen-bonded base pairs.

Figure 9A:
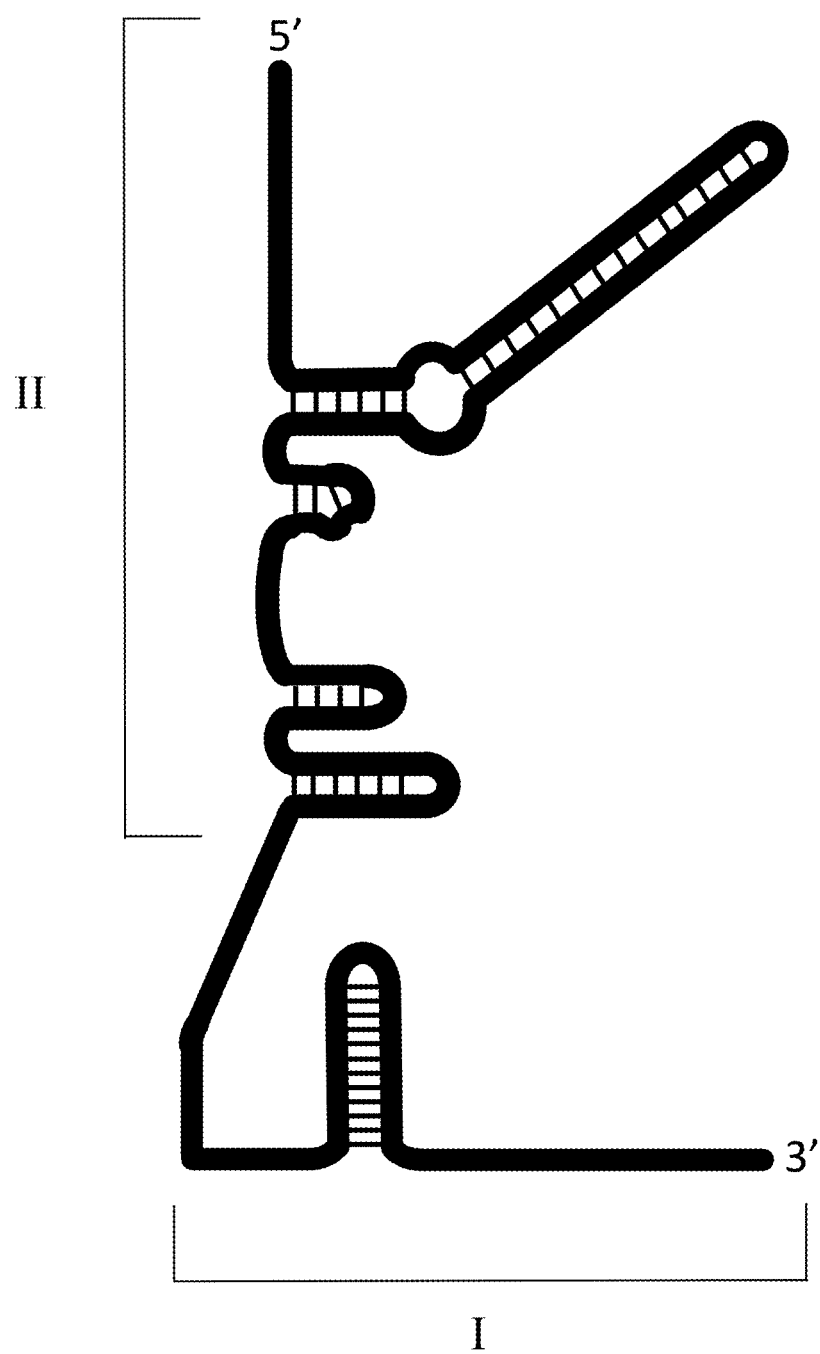
FIG. 9A and FIG. 9B illustrate examples and elements of engineered nucleic acid scaffold polynucleotide compositions of the present invention.

FIG. 9A presents an example of two NATNAs joined to form a NASC polynucleotide composition comprising (i) a copy of the engineered nucleic acid sequence shown in FIG. 5D, I, 500-507 (FIG. 9A, I), and (ii) a copy of an engineered nucleic acid sequence corresponding to the single-guide polynucleotide shown in FIG. 2A further comprising a linker element nucleic acid sequence covalently attached to the 3' end of the single-guide polynucleotide (FIG. 9A, II), wherein the linker element nucleic acid sequence is covalently attached to the 5' end of the engineered nucleic acid sequence shown in FIG. 5D, I, 500-507, forming a scaffold.

Figure 9B:
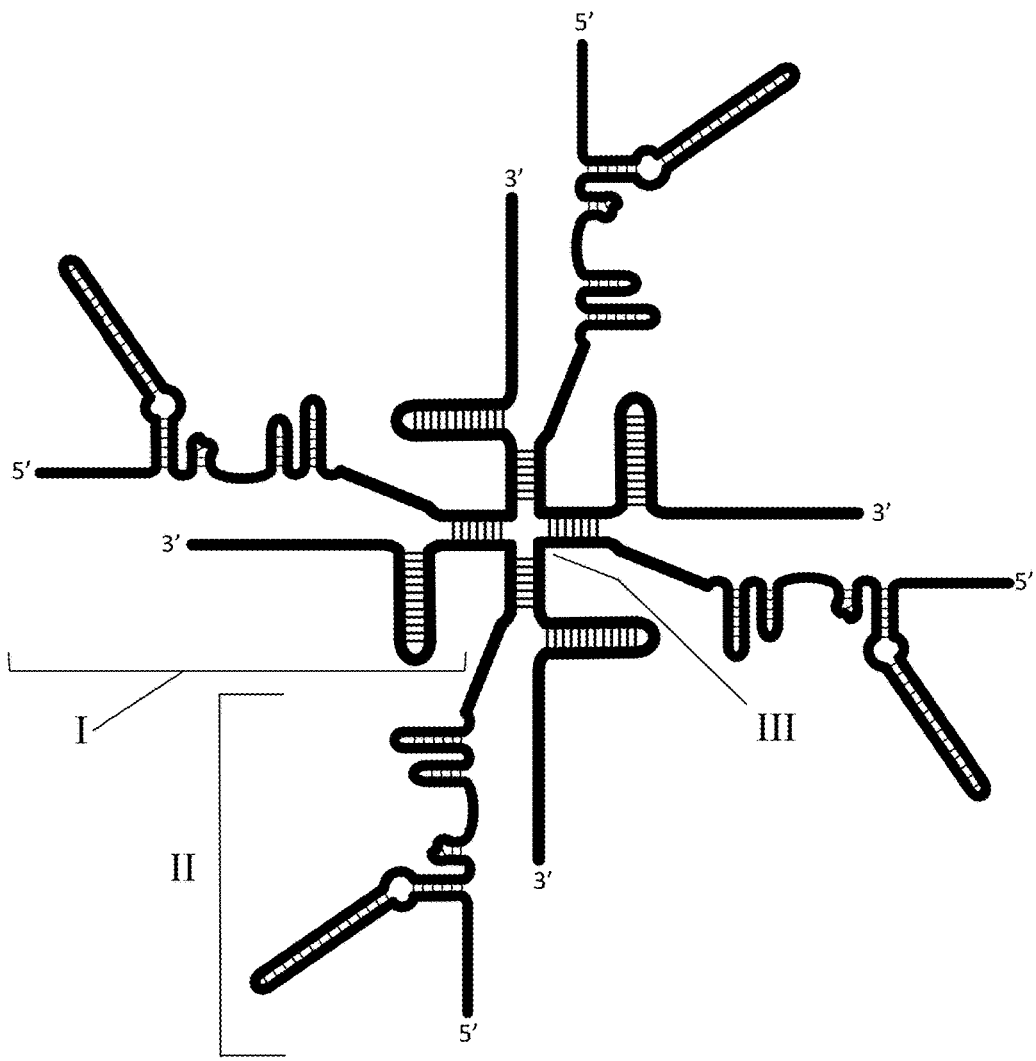

FIG. 9B presents an example of a complex of two sets of the components shown in FIG. 9A. In this figure, reference numbers relative to FIG. 9A, I and II, are shown to help illustrate the components. Furthermore, FIG. 9A, III, is provided to facilitate comparison of the core structure of the complex of FIG. 9A to the complex presented in FIG. 5D.

FIG. 10 presents a complex of a number of different engineered nucleic acid sequences forming a scaffold. In this figure, reference numbers are provided to help illustrate the components of the scaffold: FIG. 10, I, compare to FIG. 7F; FIG. 10, II, compare to FIG. 6H; FIG. 10, III, compare to FIG. 8L; and FIG. 10, IV, compare to FIG. 9A, wherein I and II are connected through hydrogen-bonded base pairs instead of a covalent connection; and FIG. 10, V compare to FIG. 5H.

The types of connections between one or more polynucleotide components of a NASC polynucleotide composition include, for example, covalent linkages and non-covalent linkages.

One example of a non-covalent linkage is hydrogen bonding. Types of hydrogen bonds are discussed above. Embodiments of the present invention include, but are not limited to, the following types of hydrogen bonds in pairs of hydrogen-bonded nucleotides: W—C hydrogen bonding, reverse W—C hydrogen bonding, Hoogsteen hydrogen bonding, reverse Hoogsteen hydrogen bonding, wobble hydrogen bonding, reverse wobble hydrogen bonding, or combinations thereof.

NASC polynucleotide components are typically designed such that paired repeat elements intended to connect with each other, particularly if the connection is through hydrogen-bonded base pairs, and only form connections (e.g., hydrogen bonds) between the paired repeat elements. Formation of internal structures within each repeat element that interfere with the two repeat elements connecting typically avoided. Furthermore, connections (e.g., formation of hydrogen-bonded base pairs) between the repeat elements and other regions of component NASC polynucleotides are also avoided.

In addition to covalent linkages and non-covalent linkages, other types of connections between one or more polynucleotide components of a NASC polynucleotide composition can be used including, but not limited to, ligand/ligand binding moiety pairings, and/or cross-linking. Ligand/ligand binding moiety pairings include, but are not limited to, a selected nucleic acid sequence and a corresponding aptamer; and a nucleic acid secondary structure/a small molecule, ion, or protein that binds to the nucleic acid secondary structure. Typically, a first polynucleotide component of a NASC polynucleotide composition is adapted to comprise a ligand (e.g., the first polynucleotide component of a NASC polynucleotide composition comprises at its 3' end a selected nucleic acid sequence) and a second polynucleotide component of the NASC polynucleotide composition is adapted to comprise a ligand binding moiety (e.g., the second polynucleotide component of the NASC polynucleotide composition comprises an aptamer at its 5' end that binds the selected nucleic acid sequence).

Cross-linking agents useful to form connections between one or more polynucleotide components of a NASC polynucleotide composition include, but are not limited to, alkylating agents (e.g., 1, 3-bis(2-chloroethyl)-1-nitrosourea) and nitrogen mustard); cisplatin (cis-diamminedichloroplatinum(II)) and its derivatives); ionizing radiation; nitrous acid; reactive chemicals (e.g., malondialdehyde); psoralens (activated in the presence of UV); and aldehydes (e.g., acrolein and crotonaldehyde).

In some embodiments of the present invention, affinity tags are introduced into two or more polynucleotide components of a NASC polynucleotide composition. For example, a nucleic acid sequence within one polynucleotide component of a NASC polynucleotide composition can be modified to comprise an affinity sequence. Nucleic acid binding effector proteins and their corresponding effector protein binding sequences are examples of affinity tags. An affinity tag can be introduced into a first polynucleotide components of a NASC polynucleotide composition. An affinity tag can be an affinity sequences such as MS2 binding sequence, U1A binding sequence, stem-loop sequence (e.g., a Csy4 protein binding sequence, or Cas6 protein binding sequence), eIF4A binding sequence, Transcription Activator-Like Effector (TALE) binding sequence (see, e.g., Valton, J., et al., Journal of Biological Chemistry 287(46): 38427-38432 (2012)), or zinc finger domain binding sequence (see, e.g., Font, J., et al., Methods Molecular Biology 649:479-491 (2010); Isalan, M., et al., Nature Biotechnology 19(7):656-660 (2001)). A second polynucleotide component of the NASC polynucleotide composition can be modified to comprise a corresponding affinity tag: an MS2 coding sequence, U1A coding sequence, stem-loop binding protein coding sequence (e.g., an enzymatically (endoribonuclease) inactive Csy4 protein that binds the Csy4 protein sequence), eIF4A coding sequence, TALE coding sequence, or a zinc finger domain coding sequence, respectively. Typically, enzymatically inactive nucleic acid binding proteins that retain sequence specific nucleic acid binding are used (e.g., an endoribonuclease-inactive Csy4 protein (dCsy4)); however, in some embodiments enzymatically active nucleic acid binding proteins or nucleic acid proteins with altered enzymatic activity are used. When more than two polynucleotide components of a NASC polynucleotide composition are modified with an affinity sequence, in preferred embodiments, the two affinity sequences typically are not the same; thus, there are two different affinity sequences associated with the Cas protein.

Example 1 describes production of exemplary components of engineered NASC polynucleotide compositions. Example 1 describes in silico design of NASC polynucleotide components corresponding to a number of embodiments of the NASC polynucleotide compositions described herein. Table 9 sets forth a correlation between NASC polynucleotide components and structures illustrated in the figures.

Example 2 describes production of NASC polynucleotide components of the present invention. The NASC polynucleotide components described in this Example were used in in vitro Cas cleavage assays to evaluate cleavage percentages of nucleic acid target sequences by the NASC polynucleotide compositions. Example 5 describes performance of in vitro Cas protein-mediated cleavage assays. Example 3 and Example 4 describe methods that can be used for production of double-stranded DNA target sequences for use in in vitro Cas cleavage assays.

Example 6 presents a deep sequencing analysis for detection of target modifications in eukaryotic cells using NASC polynucleotide compositions/first nucleic acid binding protein/second nucleic acid binding protein compositions (comprising, for example, Class 2 CRISPR-Cas proteins) of the present invention.

Example 9 presents an alternative analysis, the T7E1 assay, for detection of target modifications in eukaryotic cells using NASC polynucleotide composition/first nucleic acid binding protein/second nucleic acid binding protein compositions (comprising, for example, Class 2 CRISPR-Cas proteins).

Example 7 describes identification and screening of Class 2 crRNAs that can be engineered to make NASC polynucleotide components of the present invention.

Example 8 describes identification and screening of Class 2 tracrRNAs that can be used to engineer NASC polynucleotide components.

Example 10 describes the generation and testing of various modifications of Class 2 Type V guide crRNAs and their suitability for use in constructing NASC polynucleotide components.

Example 11 describes the generation and testing of various modifications of Class 2 Type II guide RNAs and their suitability for use in constructing NASC polynucleotide components.

Example 12 describes the use of NASC polynucleotide compositions to modify nucleic acid target sequences present in human gDNA and measure the level of cleavage activity and specificity of cleavage at those sites. Measurement of the level of cleavage percentage and/or cleavage specificity at a particular site can provide options to identify the nucleic acid target sequences having a desired cleavage percentage and/or specificity.

In a fifth aspect, the present invention is directed to nucleic acid/protein compositions comprising a NASC polynucleotide composition complexed with a first nucleic acid binding protein and a second nucleic acid binding protein. The first nucleic acid binding protein can comprise one or more nuclease activities, and the second nucleic acid binding protein can comprise one or more nuclease activities. In some embodiments, the first nucleic acid binding protein is catalytically inactive for one or more of the nuclease activities, the second nucleic acid binding protein is catalytically inactive for one or more of the nuclease activities, or both the first nucleic acid binding protein is catalytically inactive for one or more of the nuclease activities and the second nucleic acid binding protein is catalytically inactive for one or more of the nuclease activities. In other embodiments of the NASC polynucleotide composition/first nucleic acid binding protein/second nucleic acid binding protein complexes, either the first nucleic acid binding protein or the second nucleic acid binding protein is catalytically inactive, and the complexes can further be connected with a donor polynucleotide via the catalytically inactive protein. In preferred embodiments, the first nucleic acid binding protein and the second nucleic acid binding protein are Class 2 CRISPR-Cas proteins (e.g., a Cas9 protein, a Cpf1 protein, or a Cas9 protein and a Cpf1 protein).

In some embodiments of the NASC polynucleotide composition/first nucleic acid binding protein/second nucleic acid binding protein composition, either the Cas9 protein or the Cpf1 protein is catalytically inactive (dCas9 or dCpf1) and the NASC polynucleotide composition/first nucleic acid binding protein/second nucleic acid binding protein composition further comprises a donor polynucleotide wherein the donor polynucleotide comprises a nucleotide sequence complementary to the Cpf1 spacer element, or the regions adjacent to the Cpf1 spacer element, or a nucleotide sequence complementary to the spacer element, or the regions adjacent to the Cas9 spacer element. The donor polynucleotide is capable of associating with the spacer element, or the regions adjacent to the spacer element, through hydrogen bonding between the donor polynucleotide nucleotide sequence complementary to the spacer element, or the sequence adjacent to the spacer element.

Mutations of the Cas9 protein that are enzymatically inactive for RuvC-1-related nuclease activity, HNH-related nuclease activity, and both RuvC-1-related nuclease activity and HNH-related nuclease activity are known in the art. Mutations of the Cpf1 protein that are enzymatically inactive are known in the art (see, e.g., Yamano, T., et al., Cell 165(4):949-962 (2016)); Zetsche, B., et al., Cell 163:1-13 (2015)).

Across CRISPR systems, "guide biogenesis" (also referred to as "guide processing") involves endonuclease or exonuclease truncation of the guide RNA sequence following transcription of the CRISPR array. Enzymatic processing of the guide RNA can be carried out by RNases encoded by the Cas operon (e.g., Cas6 of Class 1 Type I-E systems) or by endogenous RNases (e.g., RNase III of Class 2 Type II-A systems).

In Class 2 Type V systems, guide biogenesis is performed by the Cpf1 protein nuclease. The Cpf1 protein is also responsible for sequence-specific double-stranded DNA target cleavage.

In the Type V system, cleavage of the pre-crRNA occurs in an upstream region (e.g., in a 5' direction) from the pseudo-knot secondary structure (see, e.g., FIG. 3A, 303) and results in the generation of a guide Cpf1 crRNA. In some embodiments of the present invention, preventing the Cpf1 protein from cleaving 5' of the guide crRNA stem element is useful, for example, to prevent separation of a NASC polynucleotide composition/Cas9 protein/Cpf1 protein complex by Cpf1-mediated cleavage. It has been demonstrated that the sequence of Type V pre-crRNA can be modified to prevent guide RNA processing by the Type V CRISPR Cpf1 protein (see Fonfara, I., et al., Nature 532 (7600):517-521 (2016)).

One method to prevent Cpf1 cleavage of sequences 5' of the guide crRNA stem element is by modification (e.g., base mutations, insertions, deletions, or chemical modifications) of the bases in the region upstream of the pseudo-knot or within the pseudo-knot of the pre-crRNA to prevent the processing of the pre-crRNA by the Cpf1 protein. To evaluate the effect of such modifications on guide processing, the modified pre-crRNA can be incubated in the presence of a cognate Cpf1 protein for a period of time in a suitable buffer. The mixture can be treated with Proteinase K (Denville Scientific, South Plainfield, N.J.) to remove the protein and the mixture can be analyzed by polyacrylamide gel electrophoresis to evaluate whether cleavage of the modified pre-crRNA occurs. A pre-crRNA not incubated in the presence of a cognate Cpf1 protein can serve as a positive control (i.e., a control for the absence of guide processing). If no single modification in the pre-crRNA is sufficient to ablate guide processing, then combinations of modifications exhibiting reduced processing of the pre-crRNA can be combined into a pre-crRNA design and re-tested for the absence of guide processing activity. Modifications of pre-crRNA that result in the inability of the modified pre-crRNA to be processed can be further evaluated for the ability of the Cpf1-pre-crRNA/Cpf1 protein complex to maintain sequence-specific binding and/or cleavage of a DNA target nucleic acid comprising the pre-crRNA spacer element.

A second method to prevent Cpf1 cleavage of sequences 5' of the guide crRNA stem element is by modification of the Cpf1 protein. In this method, the amino acid residues of the Cpf1 protein are modified to perturb guide processing. X-ray crystallography of guide crRNA/Cpf1 protein complexes has shown that the pseudo-knot is bound by the interface of two protein domains designated the wedge domain (WED) and the RuvC domain (see Yamano, T., et al., Cell 165(4): 949-962 (2016). Amino acid residues of Cpf1 proximal to the region binding the 5' end of the guide crRNA and/or the pseudo-knot structure are likely to be involved in endonuclease catalysis of pre-crRNAs. Mutagenesis strategies, such as alanine screening (see, e.g., Lefèvre, F., et al., Nucleic Acids Research 25(2):447-448 (1997); Lee, et al., Molecular Pharmacology 50(1):140-148 (1996)) can be used to modify regions within the WED and RuvC domain, or other domains within the Cpf1 protein, to identify residues in the protein responsible for guide crRNA processing. In this method, Cpf1 proteins comprising alanine mutations can be expressed and incubated with a cognate pre-crRNA in a suitable buffer. After incubation, Proteinase K can be added to the reaction mix to remove the Cpf1 protein and the reaction mix can be analyzed by polyacrylamide gel electrophoresis to evaluate whether cleavage of the modified pre-crRNA occurred. A pre-crRNA not incubated in the presence of a cognate Cpf1 protein can serve as a positive control (i.e., a control for the absence of guide processing). If no single mutation in the Cpf1 protein is sufficient to ablate guide processing, then combinations of mutations exhibiting reduced processing of the pre-crRNA can be combined into a single Cpf1 protein construct and re-tested for the absence of guide processing activity. Candidate mutations or combinations of mutations in the Cpf1 protein can be further evaluated for the ability of the Cpf1-pre-crRNA complex to maintain sequence-specific binding and/or cleavage of a DNA target nucleic acid comprising the pre-crRNA spacer element.

In a sixth aspect, the present invention relates to nucleic acid sequences encoding one or more polynucleotide components of a NASC polynucleotide composition, as well as expression cassettes, vectors, and recombinant cells comprising nucleic acid sequences encoding one or more polynucleotide components of a NASC polynucleotide composition. In some embodiments, such expression cassettes, vectors, and recombinant cells further comprise sequences encoding one or more nucleic acid binding proteins (e.g., Class 2 CRISPR-Cas proteins) with which the NASC polynucleotide composition is capable of forming a complex.

A further embodiment of the present invention relates to vectors, including expression vectors, comprising one or more nucleic acid sequences encoding one or more polynucleotide components of a NASC polynucleotide composition, and optionally one or more nucleic acid sequences encoding nucleic acid binding proteins (e.g., Class 2 CRISPR-Cas proteins) capable of forming a complex with the NASC polynucleotide composition. Vectors can also include sequences encoding selectable or screenable markers. Furthermore, nuclear targeting sequences can also be added, for example, to Cas9 protein and Cpf1 protein coding sequences. Vectors can also include polynucleotides encoding protein tags (e.g., poly-His tags, hemagglutinin tags, fluorescent protein tags, bioluminescent tags). The coding sequences for such protein tags can be fused to, for example, one or more nucleic acid sequences encoding a Cas9 protein and/or a Cpf1 protein.

General methods for construction of expression vectors are known in the art; furthermore, expression vectors for host cells are commercially available. There are several commercial software products designed to facilitate selection of appropriate vectors and construction thereof, such as insect cell vectors for insect cell transformation and gene expression in insect cells, bacterial plasmids for bacterial transformation and gene expression in bacterial cells, yeast plasmids for cell transformation and gene expression in yeast and other fungi, mammalian vectors for mammalian cell transformation and gene expression in mammalian cells or mammals, and viral vectors (including lentivirus, retrovirus, adenovirus, herpes simplex virus I or II, parvovirus, reticuloendotheliosis virus, and adeno-associated virus (AAV) vectors) for cell transformation and gene expression and methods to easily allow cloning of such polynucleotides. Illustrative plant transformation vectors include those derived from a Ti plasmid of *Agrobacterium tumefaciens* (Lee, L. Y., et al., Plant Physiology 146(2): 325-332 (2008)). Also useful and known in the art are *Agrobacterium rhizogenes* plasmids. For example, SNAPGENE™ (GSL Biotech LLC, Chicago, Ill.; snapgene.com/resources/plasmid_files/your_time_is_valuable/) provides an extensive list of vectors, individual vector sequences, and vector maps, as well as commercial sources for many of the vectors.

Lentiviral vectors are examples of vectors useful for introduction into mammalian cells of one or more nucleic acid sequences encoding one or more polynucleotide components of a NASC polynucleotide composition, and optionally one or more nucleic acid sequences encoding one or more nucleic acid binding proteins (e.g., Class 2 CRISPR-Cas proteins) with which the NASC polynucleotide composition is capable of forming a complex. Lentivirus is a member of the Retroviridae family and is a single-stranded RNA virus, which can infect both dividing and non-dividing cells as well as provide stable expression through integration into the genome. To increase the safety of lentivirus, components necessary to produce a viral vector are split across multiple plasmids. Transfer vectors are typically replication incompetent and may additionally contain a deletion in the 3'LTR, which renders the virus self-inactivating after integration. Packaging and envelope plasmids are typically used in combination with a transfer vector. For example, a packaging plasmid can encode combinations of the Gag, Pol, Rev, and Tat genes. A transfer plasmid can comprise viral LTRs and the psi packaging signal. The envelope plasmid comprises an envelope protein (usually vesicular stomatitis virus glycoprotein, VSV-GP, because of its wide infectivity range).

Lentiviral vectors based on human immunodeficiency virus type-1 (HIV-1) have additional accessory proteins that facilitate integration in the absence of cell division. HIV-1 vectors have been designed to address a number of safety concerns. These include separate expression of the viral genes in trans to prevent recombination events leading to the generation of replication-competent viruses. Furthermore, the development of self-inactivating vectors reduces the potential for transactivation of neighboring genes and allows the incorporation of regulatory elements to target gene expression to particular cell types (see, e.g., Cooray, S., et al., Methods in Enzymology 507:29-57 (2012)).

Transformed host cells (or recombinant cells) are cells or the progeny of cells that have been transformed or transfected, using recombinant DNA techniques, with one or more nucleic acid sequences encoding one or more polynucleotide components of a NASC polynucleotide composition, and optionally one or more nucleic acid sequences encoding one or more nucleic acid binding proteins (e.g., Class 2 CRISPR-Cas proteins) with which the NASC polynucleotide composition is capable of forming a complex. Methods of introducing polynucleotides (e.g., an expression vector) into host cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, ballistic gene transfer technology (e.g., using a gene gun or a biolistic particle delivery system), direct microinjection, and nanoparticle-mediated delivery.

As an alternative to expressing one or more nucleic acid sequences encoding one or more polynucleotide components of a NASC polynucleotide composition, and optionally one or more nucleic acid sequences encoding one or more nucleic acid binding proteins (e.g., Class 2 CRISPR-Cas proteins) with which the NASC polynucleotide composition is capable of forming a complex, a NASC polynucleotide composition and/or the one or more nucleic acid binding proteins (e.g., Class 2 CRISPR-Cas proteins) can be directly introduced into a cell, for example. Alternatively, one or more components can be expressed by a cell and the other component(s) directly introduced. Methods to introduce the components into a cell include electroporation, lipofection, and ballistic gene transfer technology.

A variety of host cells are disclosed herein that can be used to produce recombinant cells by introduction of one or more nucleic acid sequences encoding one or more polynucleotide components of a NASC polynucleotide composition, and optionally one or more nucleic acid sequences encoding one or more nucleic acid binding proteins (e.g., Class 2 CRISPR-Cas proteins) with which the NASC polynucleotide composition is capable of forming a complex. Such host cells include, but are not limited to a plant cell, a yeast cell, a bacterial cell, an insect cell, an algal cell, or a mammalian cell.

Methods of introducing polynucleotides (e.g., an expression vector) into host cells to produce recombinant cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, ballistic gene transfer technology, direct microinjection, and nanoparticle-mediated delivery. For ease of discussion, "transfection" is used below to refer to any method of introducing polynucleotides into a host cell.

Preferred methods for introducing polynucleotides plant cells include microprojectile bombardment and *Agrobacterium*-mediated transformation. Alternatively, other non-*Agrobacterium* species (e.g., *Rhizobium*) and other prokaryotic cells that are able to infect plant cells and introduce heterologous polynucleotides into the genome of the infected plant cell can be used. Other methods include electroporation, liposome-mediated transfection, transformation using pollen or viruses, and chemicals that increase free DNA uptake, or free DNA delivery using microprojectile bombardment. See, e.g., Narusaka, Y., et al., Chapter 9, in Transgenic Plants—Advances and Limitations, edited by Yelda, O., ISBN 978-953-51-0181-9 (2012).

In some embodiments, a host cell is transiently or non-transiently transfected. In some embodiments, a cell is transfected as it naturally occurs in a subject. In some embodiments, a cell that is transfected is taken from a subject, e.g., a primary cell or progenitor cell. In some embodiments, the primary cell or progenitor cell is cultured and/or is returned after ex vivo transfection to the same subject (autologous treatment) or to a different subject.

The NASC polynucleotide composition/first nucleic acid binding protein/second nucleic acid binding protein (comprising, for example, Class 2 CRISPR-Cas proteins) complexes described herein can be used to generate non-human transgenic organisms by site-specifically introducing a selected polynucleotide sequence at a DNA target locus in the genome to generate a modification of the gDNA. The transgenic organism can be an animal or a plant.

A transgenic animal is typically generated by introducing the system into a zygote cell. A basic technique, described with reference to making transgenic mice (Cho, A., et al., "Generation of Transgenic Mice," Current Protocols in Cell Biology, CHAPTER. Unit-19.11 (2009)), involves five basic steps: first, preparation of a system, as described herein, including a suitable donor polynucleotide; second, harvesting of donor zygotes; third, microinjection of the system into the mouse zygote; fourth, implantation of microinjected zygotes into pseudo-pregnant recipient mice; and fifth, performing genotyping and analysis of the modification of the gDNA established in founder mice. The founder mice will pass the genetic modification to any progeny. The founder mice are typically heterozygous for the transgene. Mating between these mice will produce mice that are homozygous for the transgene 25% of the time.

Methods for generating transgenic plants are also well known. A transgenic plant generated, e.g., using *Agrobacterium* transformation methods, typically contains one transgene inserted into one chromosome. It is possible to produce a transgenic plant that is homozygous with respect to a transgene by sexually mating (i.e., selfing) an independent segregant transgenic plant containing a single transgene to itself, for example an F0 plant, to produce F1 seed. Plants formed by germinating F1 seeds can be tested for homozygosity. Typical zygosity assays include, but are not limited to, single nucleotide polymorphism assays and thermal amplification assays that distinguish between homozygotes and heterozygotes.

As an alternative to using a system described herein for the direct transformation of a plant, transgenic plants can be formed by crossing a first plant that has been transformed with a system with a second plant that has never been exposed to the system. For example, a first plant line containing a transgene can be crossed with a second plant line to introgress the transgene into the second plant line, thus forming a second transgenic plant line.

Further aspects of the present invention relate to methods of using nucleoprotein compositions comprising NASC polynucleotide compositions and a nucleic acid binding protein (e.g., Class 2 CRISPR-Cas proteins) complexes. Embodiments of such nucleoprotein compositions are described herein. Numerous uses of the engineered nucleic acid sequences described herein, include, but are not limited to, forming a scaffold of a complex of two or more engineered nucleic acid sequences comprising a nucleic acid binding Class 2 CRISPR protein binding sequence and a spacer nucleic acid sequence complementary to a target nucleic acid sequence; precise editing of gDNA regions (e.g., excision, insertion, modification); tethering a donor polynucleotide in close proximity to a cut-site (e.g., cleavage using a Cas9 protein or a Cpf1 protein); excision of a gDNA region and simultaneous donor polynucleotide tethering at the excision site; forming an artificial histone or introduction of heterochromatin structure, for example, using dCas9; and tight transcriptional control of gene expression (e.g., blocking transcription of a gene). Additional uses of the engineered nucleic acid sequence scaffolds described herein include, but are not limited to, methods of use and methods of manufacturing nucleoprotein particle sheets; flexible biomaterials, for example, for use in tissue engineering; caged drug delivery vehicles; vaccine delivery vehicles, for example, DNA or RNA vaccines; size-gated porous membranes, for example, making and using membranes having holes of fixed size; nanoparticles of selected sizes; and protein nucleic acid polymers.

In one embodiment, the present invention includes a method of binding a nucleic acid sequence (e.g., DNA) comprising contacting a first nucleic acid target sequence in the nucleic acid (e.g., DNA) and a second, nucleic acid target sequence in the nucleic acid sequence (e.g., DNA) with a NASC polynucleotide composition/first nucleic acid binding protein/second nucleic acid binding protein composition (comprising, for example, Class 2 CRISPR-Cas proteins), thereby facilitating binding of the nucleoprotein to the first nucleic acid target sequence in the nucleic acid sequence and the second nucleic acid target sequence in the nucleic acid. The NASC polynucleotide composition/first nucleic acid binding protein/second nucleic acid binding protein composition (comprising, for example, Class 2 CRISPR-Cas proteins) comprises a first spacer element that is complementary to the first nucleic acid target sequence (e.g., DNA) and a second spacer element that is complementary to the second nucleic acid target sequence (e.g., DNA). In some embodiments, the nucleic acid target sequence is gDNA. Such methods of binding a nucleic acid target sequence can be carried in vitro (a biochemical assay), in cell (in cultured cells), ex vivo (cells removed from a subject), or in vivo (cells in an organism).

A variety of methods are known in the art to evaluate and/or quantitate protein-nucleic acid interactions including, but not limited to, the following: immunoprecipitation (ChIP) assays, DNA electrophoretic mobility shift assays (EMSA), DNA pull-down assays, and microplate capture and detection assays. Commercial kits, materials, and reagents are available to practice many of these methods from, for example, Thermo Scientific (Wilmington, Del.), Signosis (Santa Clara, Calif.), Bio-Rad (Hercules, Calif.), and Promega (Madison, Wis.). A common approach to detect protein-nucleic acid interactions is EMSA (see, e.g., Hellman L. M., et al., Nature Protocols 2(8):1849-1861 (2007)).

In another embodiment, the present invention includes a method of cutting a nucleic acid sequence (e.g., DNA) comprising contacting a first nucleic acid target sequence in the nucleic acid (e.g., DNA) and a second nucleic acid target sequence in the nucleic acid sequence (e.g., DNA) with a nucleoprotein composition comprising a NASC polynucleotide composition/first nucleic acid binding protein/second nucleic acid binding protein composition (comprising, for example, Class 2 CRISPR-Cas proteins), thereby facilitating binding of the nucleoprotein composition to the first nucleic acid target sequence in the nucleic acid sequence and the second nucleic acid target sequence in the nucleic acid. The nucleoprotein composition comprises a first spacer element that is complementary to the first nucleic acid target sequence (e.g., DNA) and a second spacer element that is complementary to the second nucleic acid target sequence (e.g., DNA). The first nucleic acid binding protein (e.g., Class 2 CRISPR-Cas protein) of the bound nucleoprotein composition cuts the first nucleic acid target sequence, and the second nucleic acid binding protein (e.g., Class 2 CRISPR-Cas protein) of the bound nucleic acid/protein composition cuts the second nucleic acid target sequence. In some embodiments, the nucleic acid target sequence is gDNA. Such methods of binding a nucleic acid target sequence can be carried in vitro, in cell, ex vivo, or in vivo.

Figure 16A:
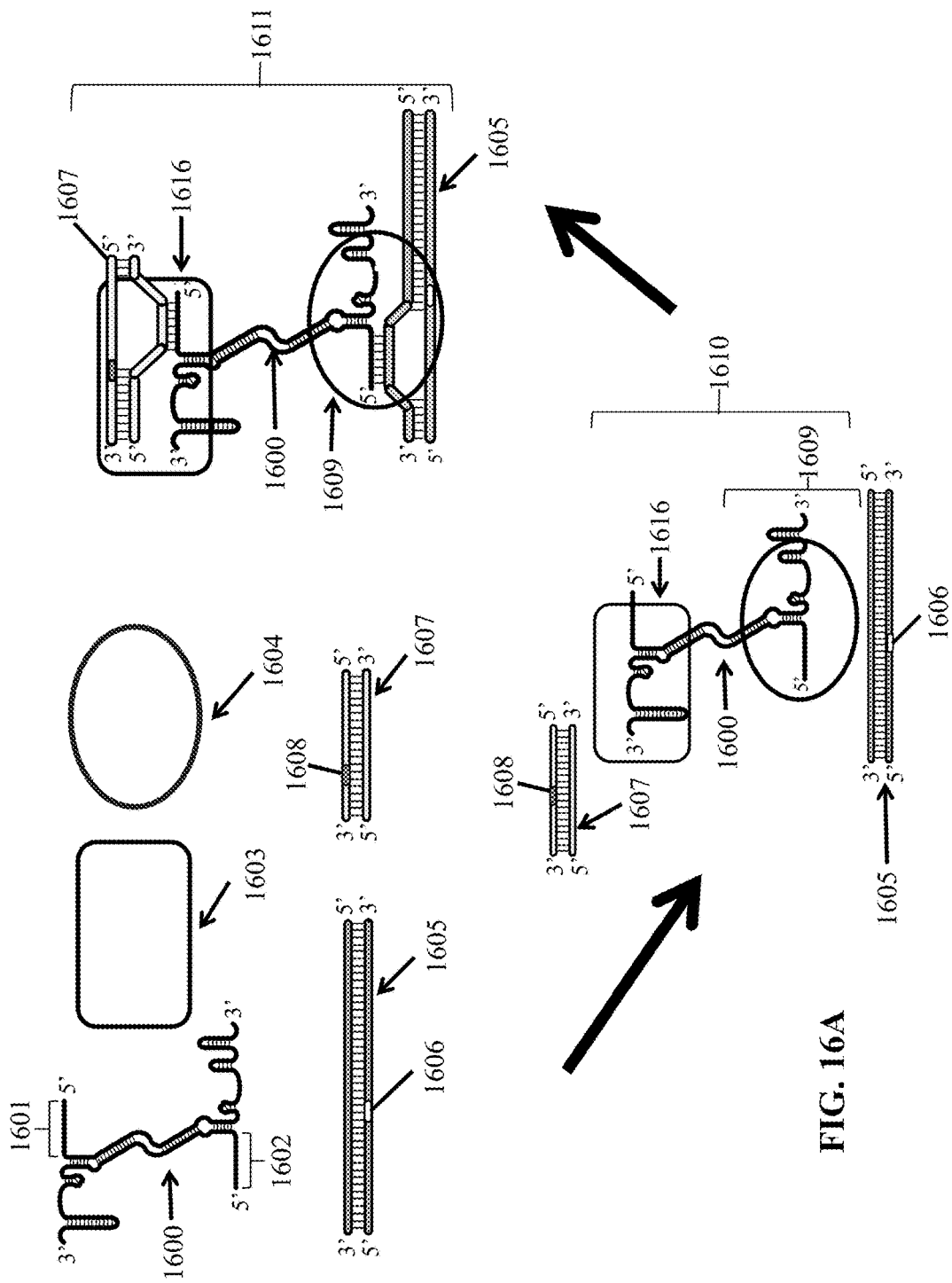
FIG. 16A, FIG. 16B, and FIG. 16C illustrate an engineered nucleic acid scaffold polynucleotide composition of the present invention forming a nucleoprotein complex with two different proteins and binding to a first nucleic acid target sequence in a first polynucleotide and a second nucleic acid sequence in a second polynucleotide. Three combinations of binding and cleaving outcomes are illustrated.
Figures 16B, 16C:
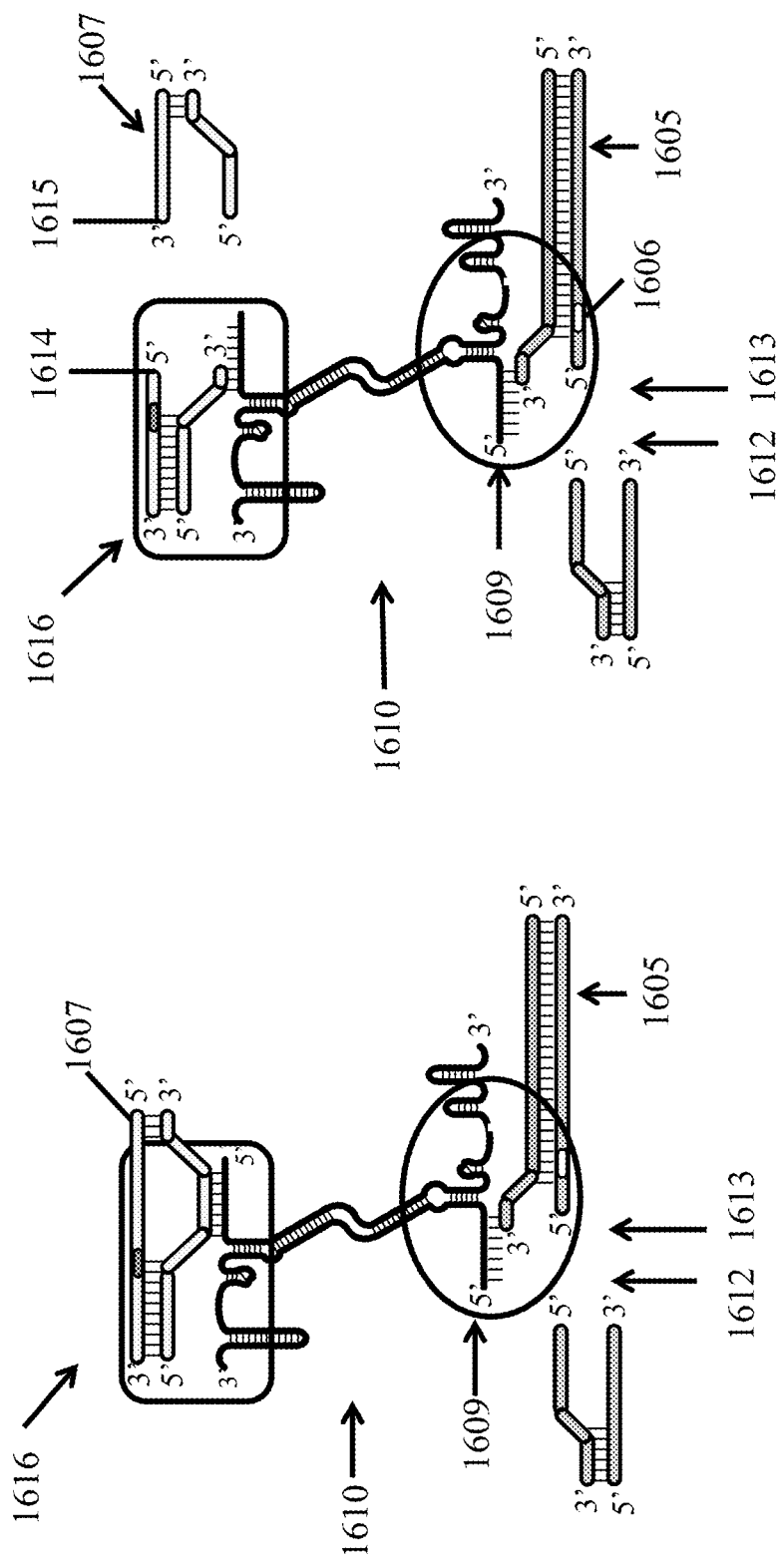

Methods of binding and of binding and cutting nucleic acid target sequences using a NASC-PC1/NASC-PC2/S. thermophilus Cas9 protein/S. pyogenes protein composition are exemplified in FIG. 16A, FIG. 16B, and FIG. 16C. FIG. 16A illustrates a S. pyogenes Cas9 protein (FIG. 16A, 1604) and a S. thermophilus Cas9 protein (FIG. 16A, 1603), a NASC-PC1/NASC-PC2 composition (FIG. 16A,1600) (generally having the structure shown in FIG. 6K), a double-stranded nucleic acid (FIG. 16A, 1605) comprising a first DNA target binding sequence complementary to the NASC-PC1/NASC-PC2 S. pyogenes Cas9 spacer element (FIG. 16A, 1602), and a double-stranded nucleic acid (FIG. 16A, 1607) comprising a second DNA target binding sequence complementary to the NASC-PC1/NASC-PC2 S. thermophilus Cas9 spacer element (FIG. 16A, 1601). FIG. 16A, 1606, indicates the location of the S. pyogenes Cas9 PAM. FIG. 16A, 1608, indicates the location of the S. thermophilus Cas9 PAM.

FIG. 16A illustrates the formation of the S. pyogenes Cas9 protein (FIG. 16A, 1604; complex 1609) and S. thermophilus Cas9 protein (FIG. 16A, 1603; complex 1616) in complex with the NASC-PC1/NASC-PC2 composition (FIG. 11A, 1600; complex 1610).

FIG. 16A illustrates hydrogen bonding of the nucleoprotein complex to the double-stranded DNA target sequences (FIG. 16A, 1611). FIG. 16A, 1611, illustrates the binding of the NASC-PC1/NASC-PC2/S. thermophilus Cas9 protein/S. pyogenes Cas9 protein composition to the double-stranded nucleic acid (FIG. 16A, 1605) comprising a first DNA target binding sequence complementary to the NASC-PC1/NASC-PC2 S. pyogenes Cas9 spacer element (FIG. 16A, 1602) and a double-stranded nucleic acid (FIG. 16A, 1607) comprising a second DNA target binding sequence complementary to the NASC-PC1/NASC-PC2 S. thermophilus Cas9 spacer element (FIG. 16A, 1601). If the S. pyogenes Cas9 protein and the S. thermophilus Cas9 protein are enzymatically inactive, the nucleoprotein complex (FIG. 16A, 1610) may be used, for example, to bring two DNA sequences (FIG. 16A, 1605, 1607) into proximity (e.g., FIG. 16A, 1607).

FIG. 16B illustrates cleavage of the FIG. 16B, 1605, DNA by an enzymatically active *S. pyogenes* Cas9 protein and the tethering of the FIG. 16B, 1607, DNA using an enzymatically inactive *S. thermophilus* Cas9 protein to maintain DNA (FIG. 16B, 1607) in proximity to the cleavage site (FIG. 16B, 1612, 1613). Such a nucleoprotein complex may help improve the frequency of HDR using a donor polynucleotide (FIG. 16B, 1607).

FIG. 16C illustrates cleavage of the FIG. 16C, 1605, DNA by an enzymatically active *S. pyogenes* Cas9 protein to break both strands of the FIG. 16C, 1605, DNA (FIG. 16C, 1612, 1613) and cleavage of the FIG. 16C, 1607, DNA by an enzymatically active *S. thermophilus* Cas9 protein to break both strands in the FIG. 16C, 1607, DNA (FIG. 16C, 1614, 1615). Such a nucleoprotein complex may be used to facilitate chromosomal rearrangement (e.g., translocations).

In yet another embodiment, the present invention includes a method of modifying DNA in a cell comprising contacting a first DNA target sequence in the DNA and a second DNA target sequence in the DNA with a NASC polynucleotide composition/first nucleic acid binding protein/second nucleic acid binding protein composition (comprising, for example, Class 2 CRISPR-Cas proteins such as Cas9 protein and/or Cpf1 protein), thereby facilitating binding of the nucleoprotein complex to the first nucleic acid target sequence in the nucleic acid sequence and the second nucleic acid target sequence in the nucleic acid. The NASC polynucleotide composition/first nucleic acid binding protein/second nucleic acid binding protein composition (comprising, for example, Class 2 CRISPR-Cas proteins) comprises a first spacer element that is complementary to the first nucleic acid target sequence and a second spacer element that is complementary to the second nucleic acid target sequence (e.g., DNA). The first protein of the bound nucleoprotein complex cuts the first DNA target sequence, and the second protein of the bound nucleoprotein complex cuts the second DNA target sequence. The cell repairs both the first cut site and the second cut site. Exemplary cell DNA repair pathways include HDR, NHEJ, and MMEJ. In some embodiments, the nucleic acid target sequence is gDNA. Such methods of binding a nucleic acid target sequence can be carried out in vitro, in cell, ex vivo, or in vivo. The contracting step may further comprise a donor polynucleotide being present, wherein at least a portion of the donor polynucleotide is incorporated between the first cut site and the second cut site.

In another embodiment, the invention relates to a method to bring a donor polynucleotide into proximity of a DSB in a nucleic acid target, typically DNA, in a cell. The method comprises contacting a first DNA target sequence in the DNA and a second DNA target sequence in a donor polynucleotide with NASC polynucleotide composition/first DNA binding protein/second DNA binding protein composition (comprising, for example, Class 2 CRISPR-Cas proteins such as Cas9 protein and/or Cpf1 protein) having a first DNA target binding sequence complementary to the first DNA target and a second DNA target binding sequence complementary to the second DNA target. The first DNA binding protein is catalytically active and is associated with the first DNA target binding sequence. The second DNA binding protein is enzymatically inactive and is associated with the second DNA target binding sequence. Contacting the nucleoprotein complex with the first and second DNA target sequences facilitates the binding of the nucleoprotein complex to the first DNA target sequence in the DNA and the second DNA target sequence in the donor polynucleotide. The catalytically active DNA binding protein of the nucleoprotein complex cuts the first DNA target sequence to form a cut site. The donor polynucleotide is in proximity to the cut site (e.g., the DSB) because the catalytically active DNA binding protein and the catalytically inactive DNA binding protein are complexed with the NASC polynucleotide composition, that is, they are part of the same nucleoprotein complex. In some embodiments, at least a portion of the donor polynucleotide is introduced into the cut site in the DNA (e.g., by an HDR repair process) resulting in modifying the DNA.

Figure 12:
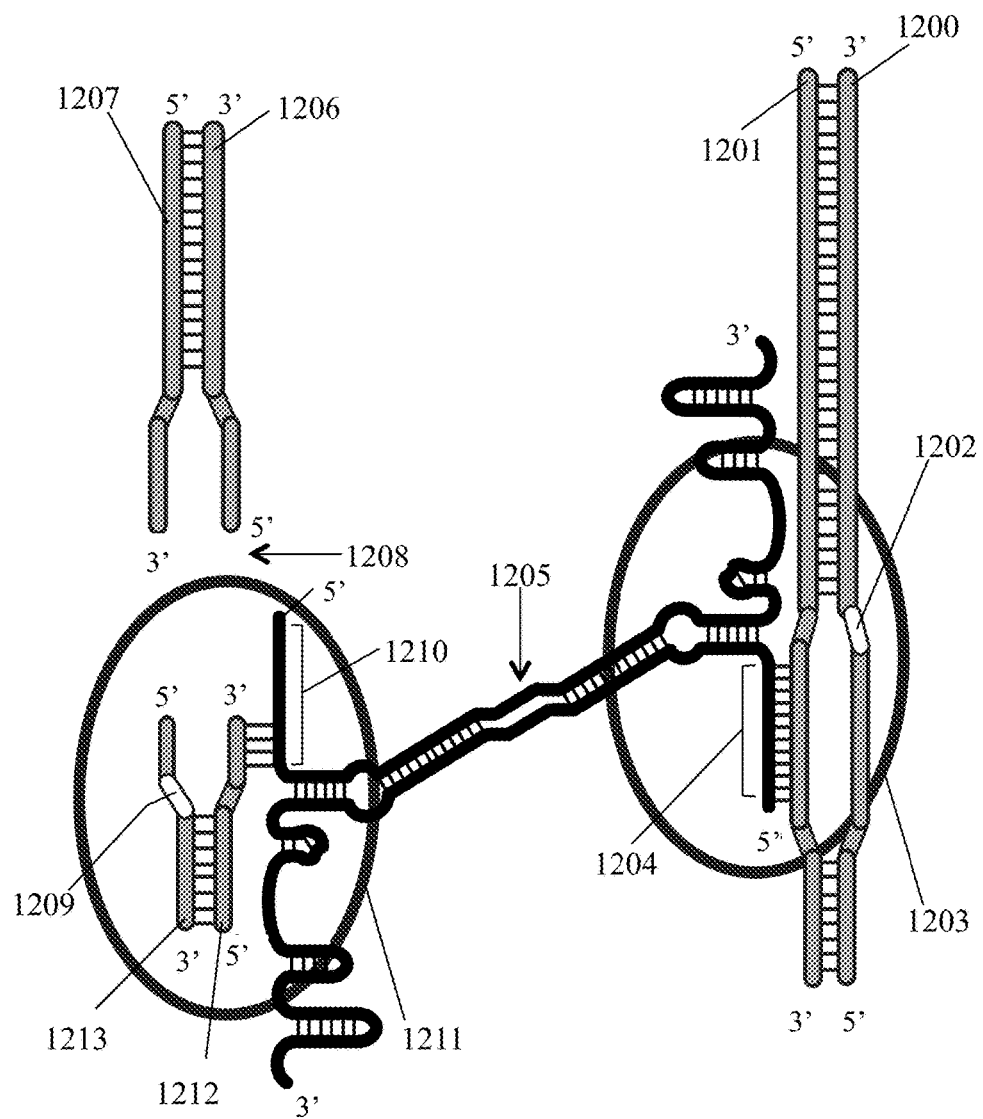
FIG. 12 illustrates a nucleoprotein complex comprising an engineered nucleic acid scaffold polynucleotide composition of the present invention binding to a first nucleic acid target sequence and binding to a second nucleic acid target sequence that is cut by a nuclease of the complex.

FIG. 12 illustrates using NASC-PC1/NASC-PC2/active Cas9 protein/dCas9 protein composition, wherein endonuclease domains of the active Cas9 are active and the endonuclease domains of the dCas9 are inactive, to bring a donor polynucleotide into proximity of a DSB in a nucleic acid target sequence. FIG. 12 illustrates the active Cas9 protein (FIG. 12, 1211) and the dCas9 protein (FIG. 12, 1203), NASC-PC1/NASC-PC2 composition (FIG. 12, 1205; see also FIG. 6F); a double-stranded nucleic acid (FIG. 12, 1206/1207) comprising a first DNA target binding sequence complementary to the active Cas9-NASC-PC1/NASC-PC2 composition spacer element (FIG. 12, 1210); and a donor polynucleotide (FIG. 12, 1200/1201) comprising a second DNA target binding sequence complementary to the dCas9-NASC-PC1/NASC-PC2 composition spacer element (FIG. 12, 1204). FIG. 12 illustrates the NASC-PC1/NASC-PC2/active Cas9 protein/dCas9 protein in complex and the hydrogen bonding of the first DNA target binding sequence to the first DNA target sequence upstream of a first Cas9 PAM (FIG. 12, 1209) and the second DNA target binding sequence to the second target sequence upstream of a second Cas9 PAM (FIG. 12, 1202) in the donor polynucleotide. FIG. 12, 1208, illustrates double-strand blunt-end cuts made by Cas9 at the first DNA target binding sequence, resulting in a second double-stranded nucleic acid (FIG. 12, 1213/1212), and shows the donor polynucleotide (FIG. 12, 1200/1201) in proximity to the double-strand blunt-end cuts. Having the donor polynucleotide in close proximity to the double-strand cuts increases the likelihood of integration of the donor polynucleotide sequences, or portions thereof, into the DNA comprising the first nucleic acid target.

In a further embodiment, the invention relates to a method bringing a first nucleic acid target site, typically DNA, into the proximity of a second nucleic acid target site, typically DNA, in a cell. The method comprises contacting a first nucleic target sequence and a second nucleic target sequence with a nucleoprotein complex comprising NASC polynucleotide composition in a complex with a nucleic acid binding protein, and a second nucleic acid binding protein, thereby facilitating binding of the nucleoprotein complex to the first nucleic acid target sequence and the second nucleic acid target sequence. The first DNA target sequence is complementary to a first nucleic acid binding sequence of the NASC polynucleotide composition, wherein the associated first protein is a catalytically inactive nucleic acid binding protein (e.g., a dCpf1 protein or a dCas9 protein). The second DNA target sequence is complementary to a second nucleic acid binding sequence of the NASC polynucleotide composition, wherein the associated second protein is a catalytically inactive nucleic acid binding protein (e.g., a dCpf1 protein or a dCas9 protein). The first nucleic acid target site is brought into proximity of a second nucleic acid target site because the first and second catalytically inactive nucleic acid binding proteins are complexed with the NASC polynucleotide composition, that is, they are part of the same nucleic acid/protein composition. In some embodiments, the first nucleic acid target sequence and the second nucleic acid target sequence are on separate polynucleotides (e.g., different chromosomes) or a single polynucleotide comprises the first nucleic acid target sequence and the second nucleic acid target sequence (e.g., different sections of the same chromosome).

Figure 13:
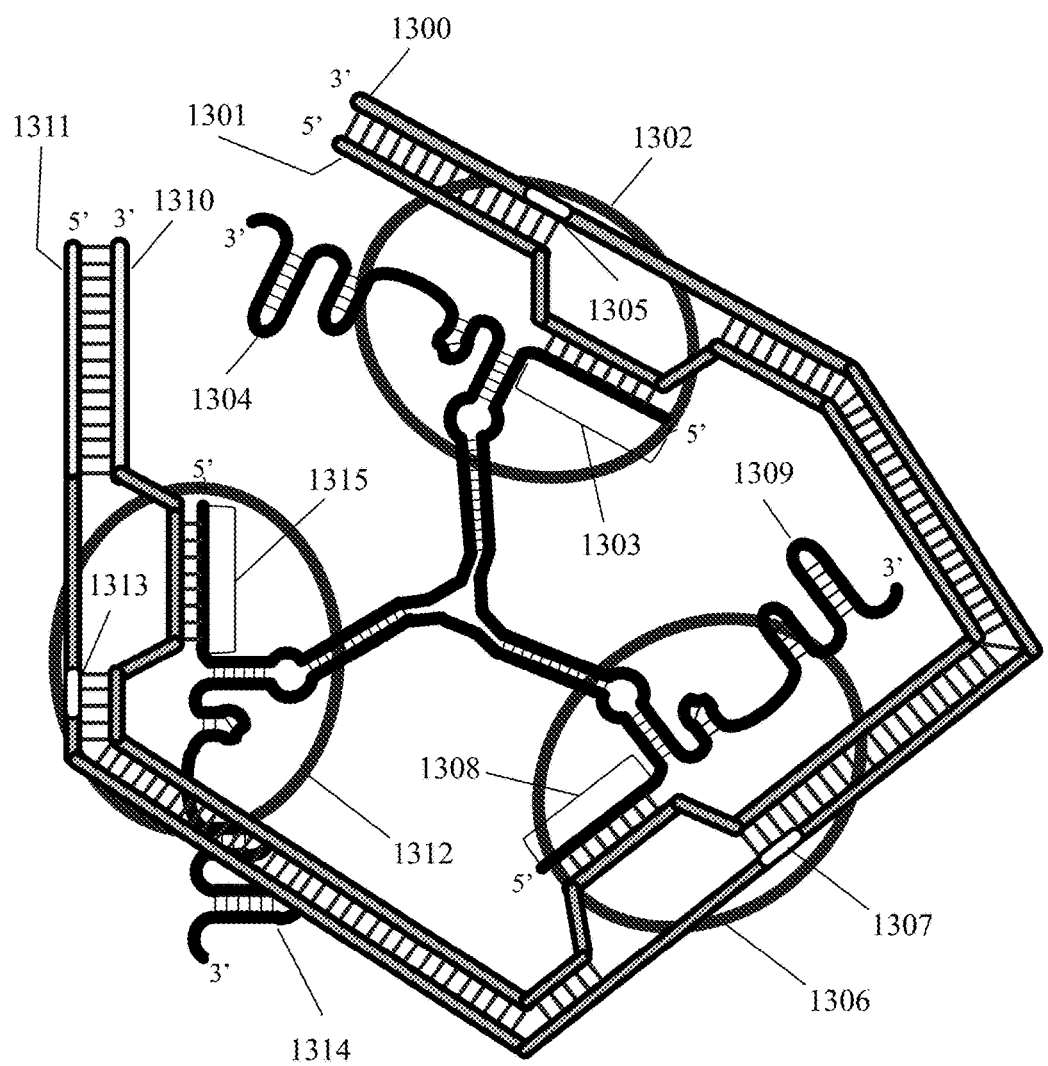
FIG. 13 illustrates a nucleoprotein complex comprising an engineered nucleic acid scaffold polynucleotide composition of the present invention binding to three nucleic acid target sequences in a polynucleotide.

FIG. 13 illustrates an example of a NASC polynucleotide composition/a first dCas9 protein/second dCas9 binding protein/a third dCas9 protein composition binding to three sites within a single DNA polynucleotide. The NASC polynucleotide composition is also illustrated in FIG. 6I. This nucleoprotein complex can be used to in a method of bringing a first nucleic acid target site, typically DNA, into the proximity of a second nucleic acid target site, typically DNA, into the proximity of a third nucleic acid target site, typically DNA, in a cell. This method also can be applied, for example, to detection of nucleic acid target sites in proximity and modulating in vitro or in vivo transcriptional modulation of a gene adjacent the three target sites. Indicators of the components illustrated in FIG. 13 are presented in Table 8.

Figure 14:
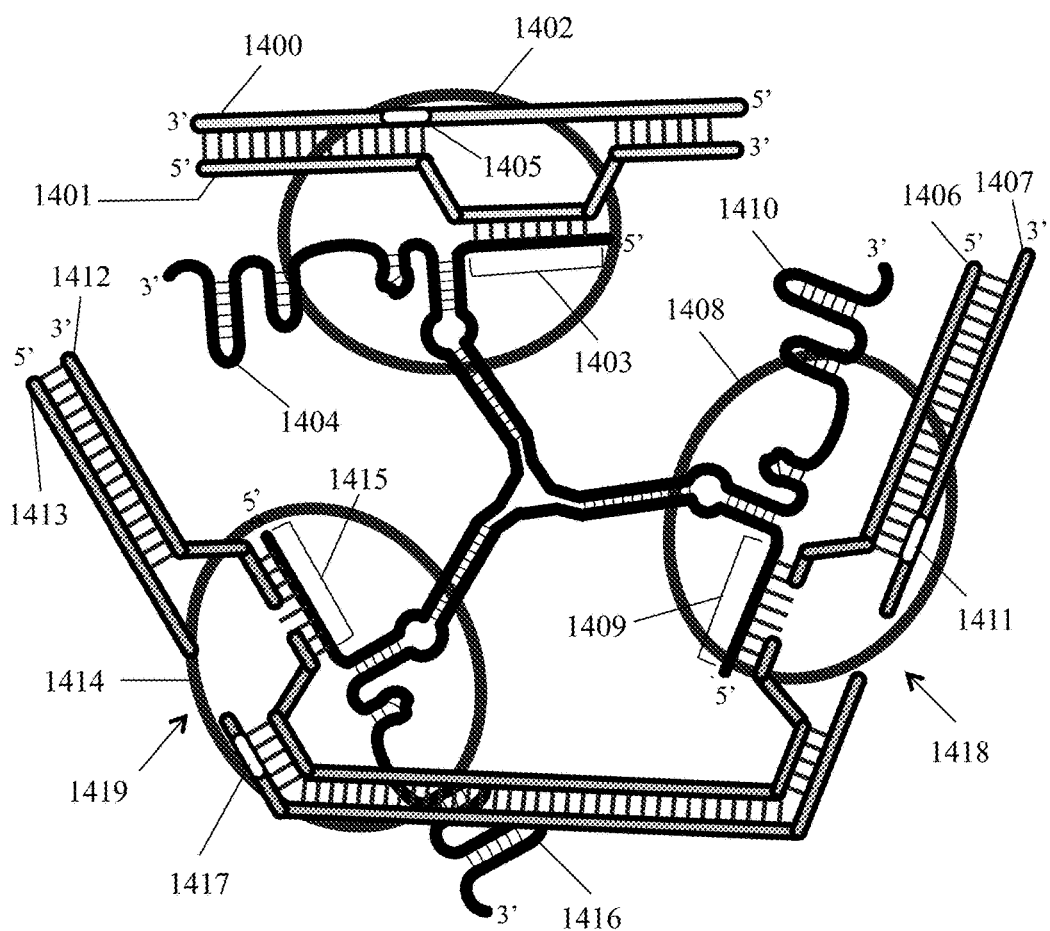
FIG. 14 illustrates a nucleoprotein complex comprising an engineered nucleic acid scaffold polynucleotide composition of the present invention binding to a first nucleic acid target sequence in a first polynucleotide and binding to a second nucleic acid target sequence and a third nucleic acid target sequence in a second polynucleotide, wherein the second and third nucleic acid target sequences are cut by a nuclease of the complex.

FIG. 14 illustrates an example of a NASC polynucleotide composition/a first dCas9 protein/second active Cas9 binding protein/a third active Cas9 protein composition binding to three sites of multiple DNA polynucleotides. The NASC polynucleotide composition is also illustrated in FIG. 6I. This nucleoprotein complex can be used, for example, in a method to bring a donor polynucleotide into proximity of two DSBs in a nucleic acid target, typically DNA, in a cell to facilitate HDR integration of the donor polynucleotide or portions of the donor polynucleotide into the region between the two DNA target cleavage sites. Indicators of the components illustrated in FIG. 14 are presented in Table 8. The NASC polynucleotide composition is also illustrated in FIG. 6I.

Figure 15:
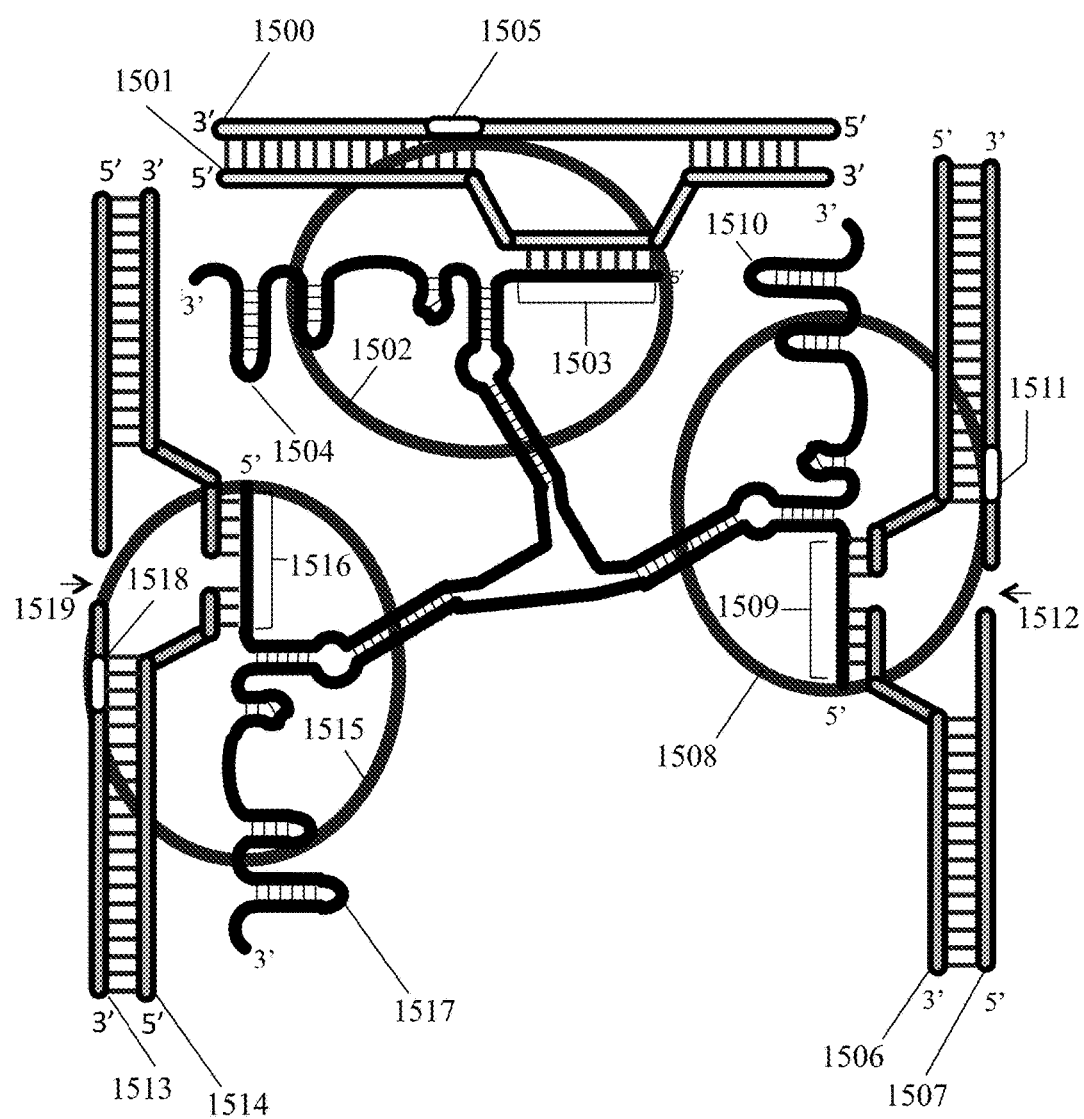
FIG. 15 illustrates a nucleoprotein complex comprising an engineered nucleic acid scaffold polynucleotide composition of the present invention binding to a first nucleic acid target sequence in a first polynucleotide, binding to a second nucleic acid target sequence in a second polynucleotide, and binding a third nucleic acid target sequence in a third polynucleotide, wherein the second and third nucleic acid target sequences are cut by a nuclease of the complex.

FIG. 15 illustrates an example of a NASC polynucleotide composition/a first dCas9 protein/second active Cas9 binding protein/a third active Cas9 protein composition binding to three sites in three different DNA polynucleotides. The NASC polynucleotide composition is also illustrated in FIG. 6I. This nucleoprotein complex can be used, for example, in a method to improve ligation frequency of two DNA polynucleotides to the 5' and 3' ends of a third DNA polynucleotide. Indicators of the components illustrated in FIG. 15 are presented in Table 8. The NASC polynucleotide composition is also illustrated in FIG. 6I.

TABLE 8

Indicators and Corresponding Regions for FIG. 13, FIG. 14, and FIG. 15

| FIG. 13 | | FIG. 14 | | FIG. 15 | |
|---|---|---|---|---|---|
| Indicator | Component | Indicator | Component | Indicator | Component |
| 1300 | a 3' end of a first strand of a DNA | 1400 | a 3' end of a first strand of a first DNA | 1500 | a 3' end of a first strand of a first DNA |
| 1301 | a 5' end of a first strand of a DNA | 1401 | a 3' end of a second strand of a first DNA | 1501 | a 3' end of a second strand of a first DNA |
| 1302 | a first Cas9 protein | 1402 | a first Cas9 protein | 1502 | a first Cas9 protein |
| 1303 | a first DNA target binding sequence | 1403 | a first DNA target binding sequence | 1503 | a first DNA target binding sequence |
| 1304 | a first nucleic acid binding protein binding sequence | 1404 | a first nucleic acid binding protein binding sequence | 1504 | a first nucleic acid binding protein binding sequence |
| 1305 | a first Cas9 PAM | 1405 | a first Cas9 PAM | 1505 | a first Cas9 PAM |
| 1306 | a second Cas9 protein | 1408 | a second Cas9 protein | 1508 | a second Cas9 protein |
| 1307 | a second Cas9 PAM | 1411 | a second Cas9 PAM | 1511 | a second Cas9 PAM |
| 1308 | a second DNA target binding sequence | 1409 | a second DNA target binding sequence | 1509 | a second DNA target binding sequence |
| 1309 | a second nucleic acid binding protein binding sequence | 1410 | a second DNA target binding sequence protein binding sequence | 1510 | a second DNA target binding sequence protein binding sequence |
| 1310 | a 3' end of a first strand of a DNA | 1406/1412 | 5'/3' ends of a first strand of a second DNA | 1507/1506 | 5'/3' ends of a second DNA |
| 1311 | a 5' end of a first strand of a DNA | 1413/1407 | 5'/3' ends of a second strand of a second DNA | 1514/1513 | 5'/3' ends of a third DNA |

TABLE 8-continued

Indicators and Corresponding Regions for FIG. 13, FIG. 14, and FIG. 15

| FIG. 13 | | FIG. 14 | | FIG. 15 | |
|---|---|---|---|---|---|
| Indicator | Component | Indicator | Component | Indicator | Component |
| 1312 | a third Cas9 protein | 1414 | a third Cas9 protein | 1515 | a third Cas9 protein |
| 1313 | a third Cas9 PAM | 1417 | a third Cas9 PAM | 1518 | a third Cas9 PAM |
| 1314 | a third nucleic acid binding protein binding sequence | 1416 | a third nucleic acid binding protein binding sequence | 1517 | a third nucleic acid binding protein binding sequence |
| 1315 | a third nucleic acid target binding sequence | 1415 | a third nucleic acid target binding sequence | 1516 | a third nucleic acid target binding sequence |
| | a first double-strand break in the second DNA | 1418 | a double-strand break in the second DNA | 1512 | a double-strand break in the second DNA |
| | a second double-strand break in the second DNA | 1419 | a double-strand break in the third DNA | 1519 | a double-strand break in the third DNA |

In yet another embodiment, the present invention also includes methods of modulating in vitro or in vivo transcription, for example, transcription of a gene comprising regulatory element sequences. The method comprises contacting at least a first nucleic target sequence and a second nucleic target sequence with a NASC polynucleotide composition/first nucleic acid binding protein/second nucleic acid binding protein composition (comprising, for example, catalytically inactive Class 2 CRISPR-Cas proteins such as dCas9 and/or dCpf1), thereby facilitating binding of the nucleoprotein composition to the first nucleic acid target sequence and the second nucleic acid target sequence. At least one of the first DNA target sequence and the second DNA target sequence comprises the regulatory element sequences. The first DNA target binding sequence of the NASC polynucleotide composition/first nucleic acid binding protein/second nucleic acid binding protein composition is complementary to a first nucleic acid target sequence. The second DNA target binding sequence of the NASC polynucleotide composition/first nucleic acid binding protein/second nucleic acid binding protein composition is complementary to a second DNA target sequence. In addition, the first and/or second protein can be fusion proteins, for example, dCas9 fused to a repressor or activator domain, and/or dCpf1 fused to a repressor or activator domain. The binding of the nucleic acid/protein composition to the first DNA target sequence and the second DNA target sequence modulates transcription of the gene. In some embodiments, the first DNA target sequence and the second DNA target sequence comprise the regulatory element sequences, and the first DNA target sequence comprises a promoter and the second DNA target sequence comprises a transcription start site.

Figure 11:
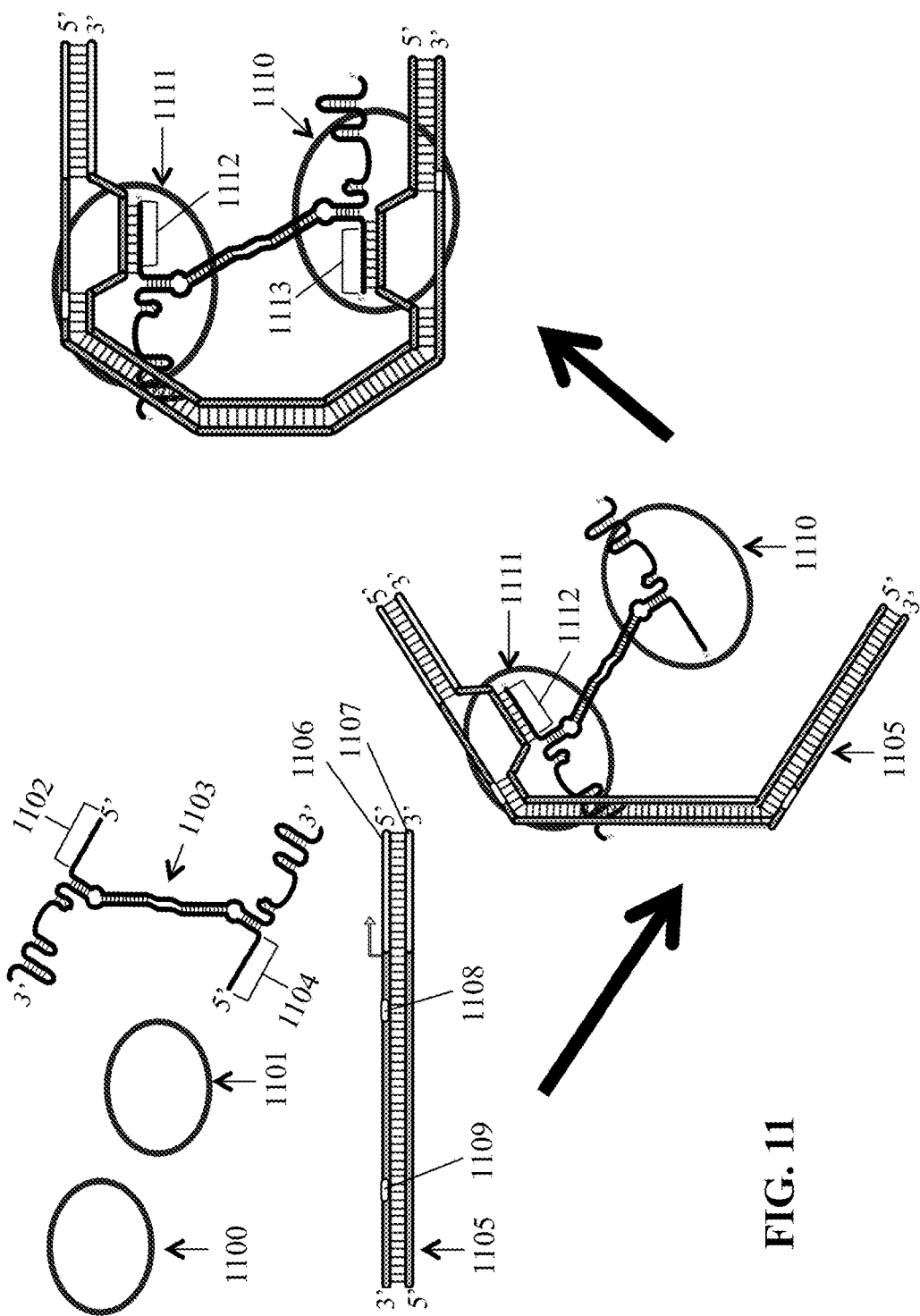
FIG. 11 illustrates a nucleoprotein complex comprising an engineered nucleic acid scaffold polynucleotide composition of the present invention, formation of a nucleoprotein complex, and the nucleoprotein complex binding two nucleic acid target sequences.

FIG. 11 illustrates a method of modulating in vitro or in vivo transcription using NASC polynucleotide compositions of the present invention. In this figure, a NASC polynucleotide composition/a first dCas9 protein/a second dCsa9 protein complex is formed (FIG. 11, 1111, 1110, 1103) by the association of a NASC polynucleotide composition (FIG. 11, 1103) with a first dCas9 protein (FIG. 11, 1100) and a second dCsa9 protein (FIG. 11, 1101). The complex comprises a first DNA target binding sequence (FIG. 11, 1102) complementary to a first nucleic target sequence that is adjacent a first Cas9 PAM (FIG. 11, 1108) and a second DNA target binding sequence (FIG. 11, 1104) that is complementary to a second nucleic target sequence that is adjacent a second Cas9 PAM (FIG. 11, 1109) in a DNA polynucleotide (FIG. 11, 1105). The NASC polynucleotide composition/first dCas9 protein/second dCsa9 protein complex is contacted with the DNA polynucleotide comprising the DNA target sequences, thereby facilitating binding of the nucleoprotein composition through hydrogen-bonded base pairs (FIG. 11, 1112, 1113) to the first nucleic acid target sequence and the second nucleic acid target sequence. At least one of the first DNA target sequence and the second DNA target sequence comprise the regulatory element sequences. The first DNA target binding sequence of the NASC polynucleotide composition/first dCas9 protein/second dCsa9 protein composition is complementary to a first nucleic acid target sequence. The second DNA target binding sequence of the NASC polynucleotide composition/a first dCas9 protein/a second dCsa9 protein composition is complementary to a second DNA target sequence.

Figure 6L:
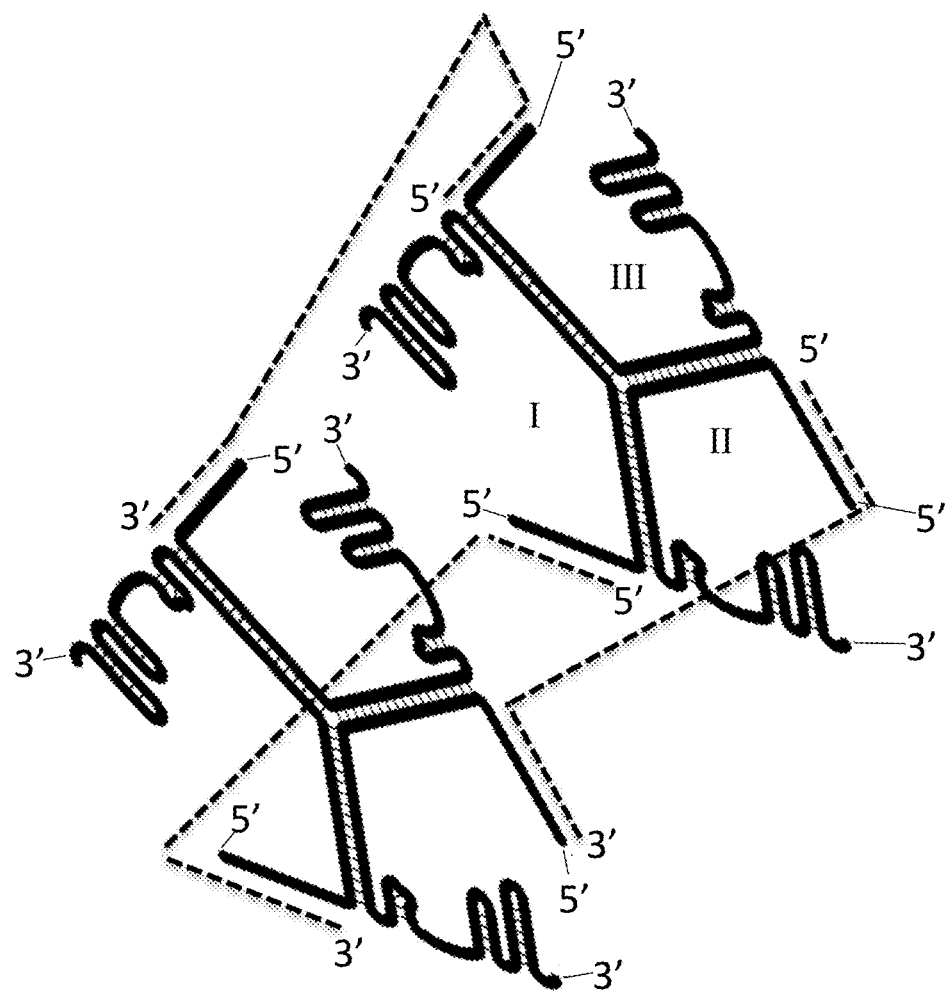
Figure 6M:
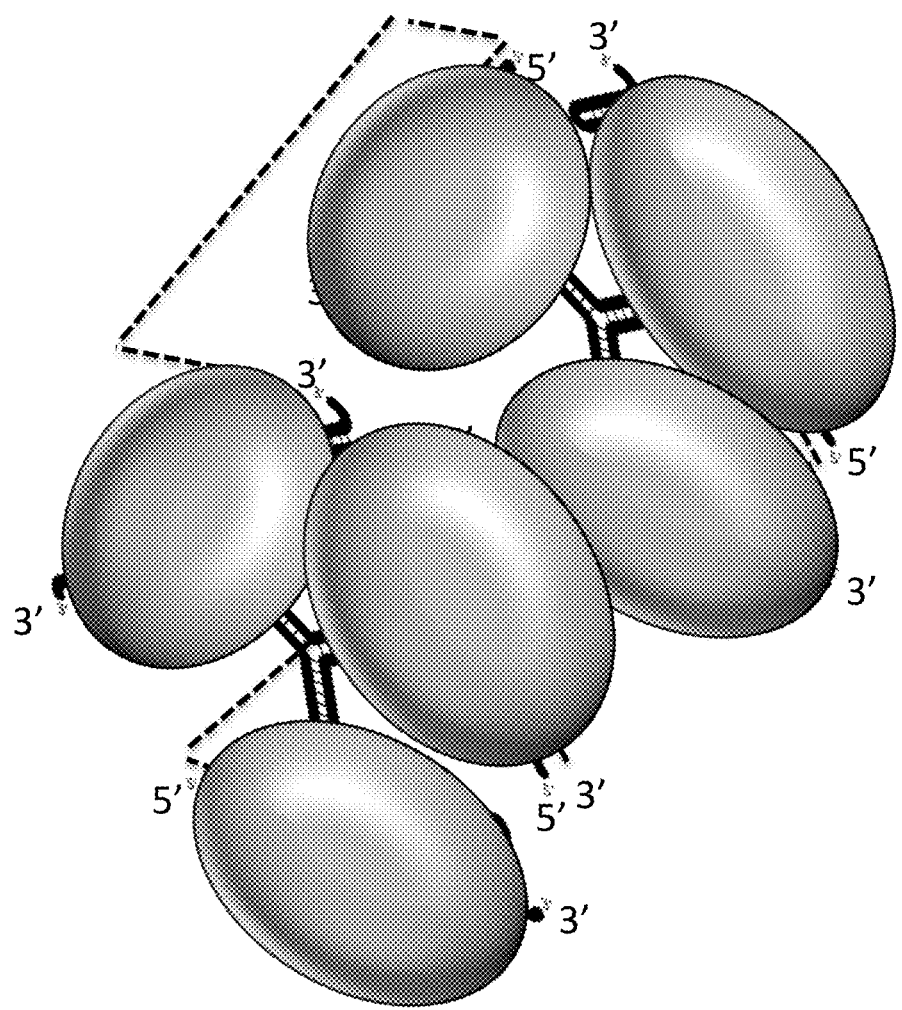

The NASC polynucleotide compositions of the present invention can be used to design nucleic acid/protein macromolecules that self-assemble into complex architectures. Such macromolecules have many uses in nanobiotechnology including, but not limited to, drug delivery, design of nucleic acid/protein nanomaterials, and formation of nanostructures such as nanotubes and closed-cage structures. Example 13 illustrates the use of NASC polynucleotide compositions of the present invention for formation of NASC closed-cage compositions (NASC-CCs). NASC-CCs may be used for packaging of small molecules. Example 14 describes methods that can be used for characterization of NASC-CC/dCas protein complexes to verify proper assembly and assess the size and volume of assembled NASC-CC/dCas protein complexes. The NASC-CC described in Example 13 and Example 14 is illustrated in FIG. 6L. Two NASC polynucleotide compositions corresponding to the NASC polynucleotide composition illustrated in FIG. 6A (referred to in the Example as a NASC-PC1-triplex) can be connected using double-stranded DNA brace nucleic acid sequences. The double-stranded DNA brace nucleic acid sequence can comprise a first DNA target sequence and a second DNA target sequence. As described in Example 13, the NASC-CC is self-assembling because a first NASC-PC1-triplex/dCas9 protein nucleoprotein complex comprises DNA target binding sequences that will specifically bind the first DNA target sequence of the brace nucleic acid sequence. A second NASC-PC1-triplex/dCas9 protein comprising DNA target binding sequences will specifically bind the second DNA target sequence of the brace nucleic acid sequence to form a closed cage structure. FIG. 6M illustrates the NASC-CC with six associated Cas9 proteins forming a nucleoprotein cage.

A wide variety of molecules are candidates for incorporation into NASC-CC polynucleotide compositions to facilitate delivery of the molecules include, but not limited to, vaccines (e.g., inactivated vaccines, attenuated vaccines, protein subunit vaccines, and nucleic acid vaccines); monoclonal antibodies; antibiotics; small molecule drugs; cancer therapeutics; recombinant proteins, biologics, and the like. Such molecules are also referred to herein as "payload."

Fusions of targeting proteins and nucleic acid binding proteins (e.g., Cas9, Cpf1) can be used to achieve tissue, organ, or cell type targeted delivery of NASC-CC polynucleotide compositions. For example, landscape phage peptides specific for specific tumors can be obtained by affinity selection and purified peptides specific for specific tumors can be fused to a Cas9 protein. The Cas9 fusion protein can then be used to assemble a NASC-CC polynucleotide composition to obtain tumor-targeted nanocarriers. Production of phage peptides specific for specific tumors has been described by Jayanna, P., et al., Nanomedicine. 5(1):83 (2009).

Alternative modes of delivery of NASC-CC to cells can be achieved through the linkage, packaging, or association of NASC-CC RNAs, DNAs, or proteins ("NASC-CC/Cas") components with various ligands or chemical agents. Packaging techniques include NASC-CC/Cas packaging into self-assembling liposomes, micelles, dendrimers, nanospheres, or nanocapsules.

Covalent and noncovalent attachment of polyethelyne glycol (PEG; PEGylation) to molecules and macrostructures has been employed for the packaging of payloads for target delivery to cells and can be adapted for the encapsulation of NASC-CC/Cas by one of ordinary skill in the art in view of the teachings of the present specification. Furthermore, protein PEGylation is a widely practiced form of conjugation chemistry for delivery of macromolecules to tissues, cells, and organelles. PEGylated structures can be further modified with molecular attachment of moieties that facilitate cellular uptake (e.g., a folate moiety). Selection of these moieties relies on the unique properties of cells targeted for directed delivery of NASC-CC/Cas and the encapsulated payload (i.e., extracellular matrix, receptors, or antibody composition). These moieties can be attached to the NASC-CC/Cas, NASC-CC packaging agent, or both the NASC-CC/Cas and NASC-CC packaging agent. Moieties that can be used include, but are not limited to, antibodies, ligands, transferrins, glycoproteins, aptamers, cell penetrating peptides, matrix metalloprotease-cleavable peptides, integrins, protein transduction domains, epitopes, cell adhesion molecules, and other compounds known in the art (see, e.g., Steichen, S. et. al., European Journal of Pharmaceutical Sciences. 48(3):416-27 (2013); Dashpande, P., et al., Nanomedicine. 8(9):1509-28 (2013)).

Trigger release of NASC-CC/Cas encapsulated agents can be facilitated by the incorporation of distinct chemical moieties or sequence motifs into the NASC-CC/Cas composition or within the NASC-CC packaging agent. Attachment of biodegradable polymeric compositions (e.g., a modified PEG composition) to a NASC-CC/Cas or a NASC-CC packaging agent can allow for the breakdown of the NASC-CC/Cas or NASC-CC packaging agent upon cellular uptake. Engineered sensitive sites (i.e., proteolytic sensitive peptide sequences, pH sensitive copolymers, redox sensitive linkages, etc.) or combinations of engineered sensitive sites may be employed to facilitate release of NASC-CC encapsulated agents. Labile linkages between the NASC-CC and NASC-CC packaging agent, such as a pH sensitive linkages, can be utilized to encourage disassociation from the NASC-CC and the NASC-CC packaging agent in high pH environments (e.g., an endocytic vacuole). NASC-CC/Cas complexes can be further modified with organelle specific epitopes (i.e., a nuclear localization signal) for delivery of payload to specific organelles.

One of ordinary skill in the art, in view of the teachings of the specification, can use a variety of different NASC polynucleotide compositions to form a variety of nanostructures.

Any of the components of the nucleoprotein compositions comprising a NASC polynucleotide composition of the present invention or nucleic acid sequences encoding such components, as described above, can be incorporated into a kit, optionally including one or more reagents. In some embodiments, a kit includes a package with one or more containers holding the kit elements, as one or more separate compositions or, optionally, as admixture wherein the compatibility of the components will allow. In some embodiments, kits also comprise a buffer, a buffering agent, a salt, a sterile aqueous solution, and/or preservatives. Illustrative kits comprise one or more components of a NASC polynucleotide composition and optionally one or more cognate nucleic acid binding proteins, such as a Cpf1 and/or a Cas9 protein; and one or more nucleic acid sequences encoding one or more components of a NASC polynucleotide composition, and optionally one or more nucleic acid sequences encoding a Cpf1 and/or a Cas9 protein.

Furthermore, kits can further comprise instructions for using components of the nucleoprotein complexes comprising NASC polynucleotide compositions of the present invention or nucleic acid sequences encoding such components. Instructions included in kits of the invention can be affixed to packaging material or can be included as a package insert. Although the instructions are typically written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. Instructions can also include the address of an internet site that provides the instructions.

Another aspect of the invention relates to methods of making or manufacturing a NASC polynucleotide composition or a nucleic acid/protein composition comprising a NASC polynucleotide composition of the present invention. In one embodiment, the methods of making or manufacturing comprise chemically synthesizing polynucleotide components of a NASC polynucleotide composition. In some embodiments, a NASC polynucleotide composition comprises RNA bases and can be generated from DNA templates using in vitro transcription.

In some embodiments, NASC polynucleotide composition components can be modified by a moiety (e.g., a ligand moiety, a ligand binding moiety, an affinity tag, an exonuclease resistance moiety). Polynucleotide components can be connected to, for example, the 5' terminal sequence and/or 3' terminal sequence of a polynucleotide component.

A nucleic acid/protein composition comprising NASC polynucleotide composition can further comprise a detectable label, including a moiety that can provide a detectable signal. Examples of detectable labels include, but are not limited to, an enzyme, a radioisotope, a member of a specific binding pair, a fluorophore (FAM), a fluorescent protein (green fluorescent protein, red fluorescent protein, mCherry, tdTomato), an DNA or RNA aptamer together with a suitable fluorophore (enhanced GFP (EGFP), "Spinach"), a quantum dot, an antibody, and the like. A large number and variety of suitable detectable labels are well-known to one of ordinary skill in the art.

A nucleic acid/protein composition comprising a NASC polynucleotide composition or cells modified by use of a nucleic acid/protein composition comprising NASC polynucleotide composition, as described herein, can be used as a pharmaceutical composition formulated, for example, with a pharmaceutically acceptable excipient. Illustrative excipients include carriers, stabilizers, diluents, dispersing agents, suspending agents, thickening agents, and the like. The pharmaceutical composition can facilitate administration of a nucleic acid/protein composition comprising an engineered NASC polynucleotide composition to an organism. Pharmaceutical compositions can be administered in therapeutically effective amounts by various forms and routes including, for example, intravenous, subcutaneous, intramuscular, oral, aerosol, parenteral, ophthalmic, and pulmonary administration.

Numerous advantages may be obtained using the NASC polynucleotide compositions and nucleoprotein complexes of the present invention including, but not limited to, the following:

reduction in off-targeting binding using a nucleic acid/protein composition comprising nucleic acid binding proteins (e.g., Class 2 CRISPR-Cas proteins) and a NASC polynucleotide composition that targets binding to multiple target nucleic acid sequences using a single nucleoprotein complex relative to use of similarly targeted individual NATNA/nucleic acid binding protein complexes (e.g., a sgRNA/Cas9 protein complex);

tethering of a donor polynucleotide through use of a nucleic acid/protein composition comprising nucleic acid binding proteins (e.g., Class 2 CRISPR-Cas proteins) and a NASC polynucleotide composition to bring the donor polynucleotide into proximity of a cut in a double-stranded nucleic acid;

bringing two separate polynucleotides (e.g., two different chromosomes) or two regions of a single polynucleotide (e.g., two regions of a single chromosome) into proximity of each other using a nucleic acid/protein composition comprising nucleic acid binding proteins (e.g., Class 2 CRISPR-Cas proteins) and a NASC polynucleotide composition;

transcriptional modulation of a target gene by binding of a nucleic acid/protein composition comprising nucleic acid binding proteins (e.g., Class 2 CRISPR-Cas proteins) and a NASC polynucleotide composition to multiple regulatory sequences operably linked to the target gene;

transcriptional modulation of a target gene by binding of a nucleic acid/protein composition comprising nucleic acid binding proteins (e.g., Class 2 CRISPR-Cas proteins) and a NASC polynucleotide composition to bring two separate polynucleotides (e.g., trans-acting regulatory element) or two regions of a single polynucleotide (e.g., cis-acting regulatory element) into proximity of each other;

simultaneous targeting of multiple target nucleic acid sequences using a nucleic acid/protein composition comprising nucleic acid binding proteins (e.g., Class 2 CRISPR-Cas proteins) and a NASC polynucleotide composition, including embodiments wherein a donor polynucleotide is also tethered to the nucleic acid/protein composition;

forming biological nanostructures comprising a nucleic acid/protein composition comprising nucleic acid binding proteins (e.g., Class 2 CRISPR-Cas proteins) and a NASC polynucleotide composition, for example, for pharmaceutical formulation of small molecules;

building nanoscale architectures with nucleic acid/protein compositions comprising nucleic acid binding proteins (e.g., Class 2 CRISPR-Cas proteins) and NASC polynucleotide compositions that have predefined sizes and shapes; and designing nucleic acid/protein components, comprising nucleic acid/protein compositions comprising nucleic acid binding proteins (e.g., Class 2 CRISPR-Cas proteins) and NASC polynucleotide compositions, that self-assemble into predetermined complex architectures.

Various embodiments contemplated herein include, but are not limited to, one or more of the following. The embodiments are numbered for ease of reference.

Embodiments of the present invention include, but are not limited to, the following.

1. A complex of two or more engineered nucleic acid sequences forming a scaffold, comprising: a first engineered nucleic acid comprising—a first element 1 comprising a first double-stranded nucleic acid binding protein binding sequence having a first end and a second end—a second element 1 comprising a repeat nucleic acid sequence 1, wherein the repeat nucleic acid sequence 1 is proximal to the first end of the first double-stranded nucleic acid binding protein binding sequence—a third element 1 comprising a nucleic acid sequence 1;—and a second engineered nucleic acid comprising, a first element 2 comprising a second double-stranded nucleic acid binding protein binding sequence, having a first end and a second end—a second element 2 comprising a repeat nucleic acid sequence 1C, wherein the repeat nucleic acid sequence 1C is proximal to the first end of the first double-stranded nucleic acid binding protein binding sequence—and a third element 2 comprising a nucleic acid sequence 2; wherein the repeat nucleic acid sequence 1 is associated with the repeat nucleic acid sequence 1C through hydrogen bonding between the repeat nucleic acid sequence 1 and the repeat nucleic acid sequence 1C.

2. The complex of embodiment 1, wherein the first engineered nucleic acid comprises—the first element 1 further comprising—the first double-stranded nucleic acid binding protein binding sequence, wherein the first end is a 5' end and the second end is a 3' end—the second element 1 further comprising the repeat nucleic acid sequence 1 having a 5' end and a 3' end, wherein the 3' end of the repeat nucleic acid sequence 1 is located 5' of the 5' end of the first double-stranded nucleic acid binding protein binding sequence—and the third element 1 further comprising the nucleic acid sequence 1, having a 5' end and a 3' end, wherein the 5' end of the nucleic acid sequence 1 is located 3' of the 3' end of the first double-stranded nucleic acid binding protein binding sequence; and—the second engineered nucleic acid comprises, the first element 2 further comprising the second double-stranded nucleic acid binding protein binding sequence, wherein the first end is a 5' end and the second end is a 3' end—the second element 2 further comprising the repeat nucleic acid sequence 1C having a 5' end and a 3' end, wherein the 3' end of the repeat nucleic acid sequence 1C is located 5' of the 5' end of the 5' end of the second double-stranded nucleic acid binding protein binding sequence—and the third element 2 further comprising the nucleic acid sequence 2 has a 5' end and a 3' end, wherein the 5' end of the nucleic acid sequence 2 is located 3' of the 3' end of the second double-stranded nucleic acid binding protein binding sequence.

3. The complex of embodiment 1, wherein the first engineered nucleic acid comprises,—the first element 1 further comprising the first double-stranded nucleic acid binding protein binding sequence, wherein the first end is a 5' end and the second end is a 3' end—the second element 1 further comprising the repeat nucleic acid sequence 1, having a 5' end and a 3' end, wherein the 3' end of the repeat nucleic acid sequence 1 is located 5' of the 5' end of the first double-stranded nucleic acid binding protein binding sequence—and the third element 1 further comprising the nucleic acid sequence 1, having a 5' end and a 3' end, wherein the 3' end of the nucleic acid sequence 1 is located 5' of the 5' end of the repeat nucleic acid sequence 1; and the second engineered nucleic acid comprises—the first element 2 further comprising the second double-stranded nucleic acid binding protein binding sequence, wherein the first end is a 5' end and the second end is a 3' end—the second element 2 further comprising the repeat nucleic acid sequence 1C having a 5' end and a 3' end, wherein the 3' end of the repeat nucleic acid sequence 1C is located 5' of the 5' end of the 5' end of the second double-stranded nucleic acid binding protein binding sequence—and the third element 2 further comprising the nucleic acid sequence 2 has a 5' end and a 3' end, wherein the 3' end of the nucleic acid sequence 2 is located 5' of the 5' end of the repeat nucleic acid sequence 1C.

4. A complex of two or more engineered nucleic acid sequences forming a scaffold, comprising: a first engineered nucleic acid sequence comprising, a first element 1 comprising a first nucleic acid binding Class 2 CRISPR protein binding sequence, having a first end and a second end—a second element 1 comprising a repeat nucleic acid sequence 1, wherein the repeat nucleic acid sequence 1 is proximal to the first end of the first nucleic acid binding Class 2 CRISPR protein binding sequence—and a third element 1 comprising a nucleic acid sequence 1;—and a second engineered nucleic acid sequence comprising, a first element 2 comprising a second nucleic acid binding Class 2 CRISPR protein binding sequence, having a first end and a second end—a second element 2 comprising a repeat nucleic acid sequence 1C, wherein the repeat nucleic acid sequence 2 is proximal to the first end of the second nucleic acid binding Class 2 CRISPR protein binding sequence—and a third element 2 comprising a nucleic acid sequence 2; wherein the repeat nucleic acid sequence 1 is associated with the repeat nucleic acid sequence 1C through hydrogen bonding between the repeat nucleic acid sequence 1 and the repeat nucleic acid sequence 1C.

5. The complex of embodiment 4, wherein the first nucleic acid binding Class 2 CRISPR protein binding sequence is a Class 2 Type V CRISPR protein binding sequence, wherein the first end is a 5' end and the second end is a 3' end—the repeat nucleic acid sequence 1 has a 5' end and a 3' end, wherein the 3' end of the repeat nucleic acid sequence 1 is located 5' of the 5' end of the first nucleic acid binding Class 2 Type V CRISPR protein binding sequence—and the nucleic acid sequence 1 has a 5' end and a 3' end, wherein the 5' end of the nucleic acid sequence 1 is located 3' of the 3' end of the first nucleic acid binding Class 2 Type V CRISPR protein binding sequence;—and the second nucleic acid binding Class 2 CRISPR protein binding sequence is a Class 2 Type V CRISPR protein binding sequence, wherein the first end is a 5' end and the second end is a 3' end—the repeat nucleic acid sequence 2 has a 5' end and a 3' end, wherein the 3' end of the repeat nucleic acid sequence 2 is located 5' of the 5' end of the second nucleic acid binding Class 2 Type V CRISPR protein binding sequence—and the nucleic acid sequence 2 has a 5' end and a 3' end, wherein the 5' end of the nucleic acid sequence 2 is located 3' of the 3' end of the second nucleic acid binding Class 2 Type V CRISPR protein binding sequence.

6. The complex of embodiment 5, wherein the repeat nucleic acid sequence 1 further comprises a linker element nucleic acid sequence 1-1, having a 5' end and a 3' end—a repeat nucleic acid sequence 1a, having a 5' end and a 3' end—a linker element nucleic acid sequence 1-2, having a 5' end and a 3' end—a repeat nucleic acid sequence 1b, having a 5' end and a 3' end—and a linker element nucleic acid sequence 1-3, having a 5' end and a 3' end, arranged in the following 3' to 5' order: the linker element nucleic acid sequence 1-1, the repeat nucleic acid sequence 1a, the linker element nucleic acid sequence 1-2, the repeat nucleic acid sequence 1b, and the linker element nucleic acid sequence 1-3;—and the repeat nucleic acid sequence 2 further comprises a linker element nucleic acid sequence 2-1, having a 5' end and a 3' end—a repeat nucleic acid sequence 1bC, having a 5' end and a 3' end—a linker element nucleic acid sequence 2-2, having a 5' end and a 3' end—a repeat nucleic acid sequence 2a, having a 5' end and a 3' end—and a linker element nucleic acid sequence 2-3, having a 5' end and a 3' end, arranged in the following 3' to 5' order: the linker element nucleic acid sequence 2-1, the repeat nucleic acid sequence 1bC, the linker element nucleic acid sequence 2-2, the repeat nucleic acid sequence 2a, and the linker element nucleic acid sequence 2-3; wherein the repeat nucleic acid sequence 1 is associated with the repeat nucleic acid sequence 2 through hydrogen bonding between the repeat nucleic acid sequence 1b and the repeat nucleic acid sequence 1bC.

7. The complex of embodiment 6, further comprising a third engineered nucleic acid comprising, a first element 3 comprising a third nucleic acid binding Class 2 Type V CRISPR protein binding sequence, wherein the first end is a 5' end and the second end is a 3' end—and a second element 3 comprising a repeat nucleic acid sequence 3 having a 5' end and a 3' end, wherein the 3' end of the repeat nucleic acid sequence 3 is located 5' of the 5' end of the third nucleic acid binding Class 2 Type V CRISPR protein binding sequence, wherein the repeat nucleic acid binding sequence 3 further comprises a linker element nucleic acid sequence 3-1, having a 5' end and a 3' end—a repeat nucleic acid sequence 2aC, having a 5' end and a 3' end—a linker element nucleic acid sequence 3-2, having a 5' end and a 3' end—a repeat nucleic acid sequence 3a, having a 5' end and a 3' end—and a linker element nucleic acid sequence 3-3, having a 5' end and a 3' end, arranged in the following 3' to 5' order: the linker element nucleic acid sequence 3-1, the repeat nucleic acid sequence 2aC, the linker element nucleic acid sequence 3-2, the repeat nucleic acid sequence 3a, and the linker element nucleic acid sequence 3-3;—and a third element 3 comprising a nucleic acid sequence 3, having a 5' end and a 3' end, wherein the 5' end of the nucleic acid sequence 3 is located 3' of the 3' end of the first nucleic acid binding Class 2 Type V CRISPR protein binding sequence;—and a fourth engineered nucleic acid comprising, a first element 4 comprising a fourth nucleic acid binding Class 2 Type V CRISPR protein binding sequence, wherein the first end is a 5' end and the second end is a 3' end—a second element 4 comprising a repeat nucleic acid sequence 4 having a 5' end and a 3' end, wherein the 3' end of the repeat nucleic acid sequence 3 is located 5' of the 5' end of the fourth nucleic acid binding Class 2 Type V CRISPR protein binding sequence, wherein the repeat nucleic acid binding sequence 4 further comprises a linker element nucleic acid sequence 4-1, having a 5' end and a 3' end—a repeat nucleic acid sequence 3aC, having a 5' end and a 3' end—a linker element nucleic acid sequence 4-2, having a 5' end and a 3' end—a repeat nucleic acid sequence 1aC, having a 5' end and a 3' end—and a linker element nucleic acid sequence 4-3, having a 5' end and a 3' end, arranged in the following 3' to 5' order: the linker element nucleic acid sequence 4-1, the repeat nucleic acid sequence 3aC, the linker element nucleic acid sequence 4-2, the repeat nucleic acid sequence 1aC, and the linker element nucleic acid sequence 4-3;—and the third element 4 further comprising the nucleic acid sequence 4, having a 5' end and a 3' end, wherein the 5' end of the nucleic acid sequence 4 is located 3' of the 3' end of the first nucleic acid binding Class 2 Type V CRISPR protein binding sequence; wherein the repeat nucleic acid sequence 1 is associated with the repeat nucleic acid sequence 2 through hydrogen bonding between the repeat nucleic acid sequence 1b and the repeat nucleic acid sequence 1bC, the repeat nucleic acid sequence 1 is associated with the repeat nucleic acid sequence 4 through hydrogen bonding between the repeat nucleic acid sequence 1a and the repeat nucleic acid sequence 1aC, the repeat nucleic acid sequence 2 is associated with the repeat nucleic acid sequence 3 through hydrogen bonding between the repeat nucleic acid sequence 2a and the repeat nucleic acid sequence 2aC, and the repeat nucleic acid sequence 3 is associated with the repeat nucleic acid sequence 4 through hydrogen bonding between the repeat nucleic acid sequence 3a and the repeat nucleic acid sequence 3aC.

8. The complex of any one of embodiments 4 to 7, wherein the repeat nucleic acid sequence 1 and the repeat nucleic acid sequence 2 further comprise a double-stranded nucleic acid binding protein binding site 1 and the double-stranded nucleic acid binding protein binding site 1 is formed by hydrogen base-pair bonding between the repeat nucleic acid sequence 1 and the repeat nucleic acid sequence 2.

9. The complex of embodiment 8, wherein the double-stranded nucleic acid binding protein binding site 1 is a Csy4 protein binding site.

10. The complex of any one of embodiments 4 to 9, wherein the first engineered nucleic acid and the second engineered nucleic acid each comprises RNA, DNA, or a combination thereof.

11. The complex of embodiment 7, wherein the first engineered nucleic acid, the second engineered nucleic acid, the third engineered nucleic acid, and the fourth engineered nucleic acid each comprises RNA, DNA, or a combination thereof.

12. The complex of any one of embodiments 5 to 11, wherein the first nucleic acid binding Class 2 Type V CRISPR protein binding sequence and the second nucleic acid binding Class 2 Type V CRISPR protein binding sequence are each a Cpf1 protein binding sequence.

13. The complex of embodiment 7 or 11, wherein the first nucleic acid binding Class 2 Type V CRISPR protein binding sequence, the second nucleic acid binding Class 2 Type V CRISPR protein binding sequence, the third nucleic acid binding Class 2 Type 5 CRISPR protein binding sequence, and the fourth nucleic acid binding Class 2 Type V CRISPR protein binding sequence are each a Cpf1 protein binding sequence.

14. The complex of any one of embodiments 5, 6, 7, 8, 9, or 10, wherein (i) the nucleic acid sequence 1 further comprises a spacer nucleic acid sequence 1 and the nucleic acid sequence 2 further comprises a spacer nucleic acid sequence 2, and (ii) the spacer nucleic acid sequence 1 is complementary to a target nucleic acid sequence 1 and the spacer nucleic acid sequence 2 is complementary to a target nucleic acid sequence 2.

15. The complex of embodiment 14, wherein target nucleic acid sequence 1 and target nucleic acid sequence 2 are each a nucleic acid sequence selected from the group consisting of a single-stranded RNA, a single-stranded DNA, a double-stranded RNA, a double-stranded DNA, a single-stranded RNA/DNA hybrid, and a double-stranded RNA/DNA hybrid.

16. The complex of any one of embodiments 7, 11, or 13, wherein (i) the nucleic acid sequence 1 further comprises a spacer nucleic acid sequence 1, the nucleic acid sequence 2 further comprises a spacer nucleic acid sequence 2, the nucleic acid sequence 3 further comprises a spacer nucleic acid sequence 3, and the nucleic acid sequence 4 further comprises a spacer nucleic acid sequence 4, and (ii) the spacer nucleic acid sequence 1 is complementary to a target nucleic acid sequence 1, the spacer nucleic acid sequence 2 is complementary to a target nucleic acid sequence 2, the spacer nucleic acid sequence 3 is complementary to a target nucleic acid sequence 3, and the spacer nucleic acid sequence 4 is complementary to a target nucleic acid sequence 4.

17. The complex of embodiment 16, wherein the target nucleic acid sequence 1, the target nucleic acid sequence 2, the target nucleic acid 3, and the target nucleic acid 4 are each a nucleic acid sequence selected from the group consisting of a single-stranded RNA, a single-stranded DNA, a double-stranded RNA, a double-stranded DNA, a single-stranded RNA/DNA hybrid, and a double-stranded RNA/DNA hybrid.

18. A complex of the two or more engineered nucleic acid sequences forming the scaffold of any one of embodiments 1 to 17, the complex further comprising a first Class 2 Type V CRISPR protein bound to the first nucleic acid binding Class 2 Type V CRISPR protein binding sequence, and a second Class 2 Type V CRISPR protein bound to the second nucleic acid binding Class 2 Type V CRISPR protein binding sequence, wherein the first Class 2 Type V CRISPR protein and the second Class 2 Type V CRISPR protein are each selected from the group consisting of a Cpf1 protein and a catalytically inactive Cpf1 protein.

19. A complex of the two or more engineered nucleic acid sequences forming the scaffold of any one of embodiments 7, 11, 13, or 16, the complex further comprising a first Class 2 Type V CRISPR protein bound to the first nucleic acid binding Class 2 Type V CRISPR protein binding sequence, a second Class 2 Type V CRISPR protein bound to the second nucleic acid binding Class 2 Type V CRISPR protein binding sequence, a third Class 2 Type V CRISPR protein bound to the third nucleic acid binding Class 2 Type V CRISPR protein binding sequence, and a fourth Class 2 Type V CRISPR protein bound to the fourth nucleic acid binding Class 2 Type V CRISPR protein binding sequence, wherein the first Class 2 Type V CRISPR protein, the second Class 2 Type V CRISPR protein, the third Class 2 Type V CRISPR protein, and the fourth Class 2 Type V CRISPR protein are each selected from the group consisting of a Cpf1 protein and a catalytically inactive Cpf1 protein.

20. The complex of embodiment 4, wherein the first nucleic acid binding Class 2 CRISPR protein binding sequence is a Class 2 Type II CRISPR protein binding sequence, wherein the first end is a 5' end and the second end is a 3' end—the repeat nucleic acid sequence 1 has a 5' end and a 3' end, wherein the 3' end of the repeat nucleic acid sequence 1 is located 5' of the 5' end of the first nucleic acid binding Class 2 Type II CRISPR protein binding sequence—and the nucleic acid sequence 1 has a 5' end and a 3' end, wherein the 3' end of the nucleic acid sequence 1 is located 5' of the 5' end of the repeat nucleic acid sequence 1;—and the second nucleic acid binding Class 2 CRISPR protein binding sequence is a Class 2 Type II CRISPR protein binding sequence, wherein the first end is a 5' end and the second end is a 3' end—the repeat nucleic acid sequence 1C has a 5' end and a 3' end, wherein the 3' end of the repeat nucleic acid sequence 1C is located 5' of the 5' end of the second nucleic acid binding Class 2 Type II CRISPR protein binding sequence—and the nucleic acid sequence 2, having a 5' end and a 3' end, wherein the 3' end of the nucleic acid sequence 2 is located 5' of the 5' end of the repeat nucleic acid sequence 1C.

21. The complex of embodiment 20, wherein the repeat nucleic acid sequence 1 further comprises a linker element nucleic acid sequence 1-1, having a 5' end and a 3' end—a repeat nucleic acid sequence 1a, having a 5' end and a 3' end—a linker element nucleic acid sequence 1-2, having a 5' end and a 3' end—a repeat nucleic acid sequence 1b, having a 5' end and a 3' end—and a linker element nucleic acid sequence 1-3, having a 5' end and a 3' end, arranged in the following 3' to 5' order: the linker element nucleic acid sequence 1-1, the repeat nucleic acid sequence 1a, the linker element nucleic acid sequence 1-2, the repeat nucleic acid sequence 1b, and the linker element nucleic acid sequence 1-3;—and the repeat nucleic acid sequence 2 further comprises a linker element nucleic acid sequence 2-1, having a 5' end and a 3' end—a repeat nucleic acid sequence 1aC, having a 5' end and a 3' end—a linker element nucleic acid sequence 2-2, having a 5' end and a 3' end—a repeat nucleic acid sequence 1bC, having a 5' end and a 3' end—and a linker element nucleic acid sequence 2-3, having a 5' end and a 3' end, arranged in the following 3' to 5' order: the linker element nucleic acid sequence 2-3, the repeat nucleic acid sequence 1bC, the linker element nucleic acid sequence 2-2, the repeat nucleic acid sequence 1aC, and the linker element nucleic acid sequence 2-1; wherein the repeat nucleic acid sequence 1 is associated with the repeat nucleic acid sequence 2 through hydrogen bonding between the repeat nucleic acid sequence 1a and the repeat nucleic acid sequence 1aC and through hydrogen bonding between the repeat nucleic acid sequence 1b and the repeat nucleic acid sequence 1bC.

22. The complex of embodiment 21, wherein the repeat nucleic acid sequence 1a further comprises a repeat nucleic acid sequence 1a1, having a 5' end and a 3' end—a bulge nucleic acid sequence 1a1, having a 5' end and a 3' end—and a repeat nucleic acid sequence 1a2, having a 5' end and a 3' end, arranged in the following 3' to 5' order: the repeat nucleic acid sequence 1a1, the bulge nucleic acid sequence 1a1, and the repeat nucleic acid sequence 1a2;—and the repeat nucleic acid sequence 1b further comprises a repeat nucleic acid sequence 1b1, having a 5' end and a 3' end—a bulge nucleic acid sequence 1b1, having a 5' end and a 3' end—and a repeat nucleic acid sequence 1b2, having a 5' end and a 3' end, arranged in the following 3' to 5' order: the repeat nucleic acid sequence 1b1, the bulge nucleic acid sequence 1b1, and the repeat nucleic acid sequence 1b2; and the repeat nucleic acid sequence 1bC further comprises a repeat nucleic acid sequence 1b2C, having a 5' end and a 3' end—a bulge nucleic acid sequence 2b2, having a 5' end and a 3' end—and a repeat nucleic acid sequence 1b1C, having a 5' end and a 3' end, arranged in the following 3' to 5' order: the repeat nucleic acid sequence 1b2C, the bulge nucleic acid sequence 2b2, and the repeat nucleic acid sequence 1b1C—and the repeat nucleic acid sequence 1aC further comprises a repeat nucleic acid sequence 1a2C, having a 5' end and a 3' end—a bulge nucleic acid sequence 2a2, having a 5' end and a 3' end—and a repeat nucleic acid sequence 1a1C, having a 5' end and a 3' end, arranged in the following 3' to 5' order: the repeat nucleic acid sequence 1a2C, the bulge nucleic acid sequence 2a2, and the repeat nucleic acid sequence 1a1C; wherein the repeat nucleic acid sequence 1 is associated with the repeat nucleic acid sequence 2 through hydrogen bonding between the repeat nucleic acid sequence 1a1 and the repeat nucleic acid sequence 1a1C, the repeat nucleic acid sequence 1a2 and the repeat nucleic acid sequence 1a2C, the repeat nucleic acid sequence 1b1 and the repeat nucleic acid sequence 1b1C, the repeat nucleic acid sequence 1b2 and the repeat nucleic acid sequence 1b2C.

23. The complex of any one of embodiments 20, 21, or 22, wherein the repeat nucleic acid sequence 1 and the repeat nucleic acid sequence 2 comprise a double-stranded nucleic acid binding protein binding site 1 and the double-stranded nucleic acid binding protein binding site 1 is formed by hydrogen base-pair bonding between the repeat nucleic acid sequence 1 and the repeat nucleic acid sequence 2.

24. The complex of embodiment 23, wherein the double-stranded nucleic acid binding protein binding site 1 is a Csy4 protein binding site.

25. The complex of any one of embodiments 20 to 24, wherein the first engineered nucleic acid and the second engineered nucleic acid each comprises RNA, DNA, or a combination thereof.

26. The complex of any one of embodiments 20 to 25, wherein the first nucleic acid binding Class 2 Type II CRISPR protein binding sequence and the second nucleic acid binding Class 2 Type II CRISPR protein binding sequence are each a Cas9 protein binding sequence.

27. The complex of any one of embodiments 20 to 26, wherein (i) the nucleic acid sequence 1 further comprises a spacer nucleic acid sequence 1 and the nucleic acid sequence 2 further comprises a spacer nucleic acid sequence 2, and (ii) the spacer nucleic acid sequence 1 is complementary to a target nucleic acid sequence 1 and the spacer nucleic acid sequence 2 is complementary to a target nucleic acid sequence 2.

28. The complex of embodiment 27, wherein the target nucleic acid sequence 1 and the target nucleic acid sequence 2 are each a nucleic acid sequence selected from the group consisting of a single-stranded RNA, a single-stranded DNA, a double-stranded RNA, a double-stranded DNA, a single-stranded RNA/DNA hybrid, and a double-stranded RNA/DNA hybrid.

29. A complex of the two or more engineered nucleic acid sequences forming the scaffold of any one of embodiments 20 to 28, the complex further comprising a first Class 2 Type II CRISPR protein bound to the first nucleic acid binding Class 2 Type II CRISPR protein binding sequence, and a second Class 2 Type II CRISPR protein bound to the second nucleic acid binding Class 2 Type II CRISPR protein binding sequence, wherein the first Class 2 Type II CRISPR protein and the second Class 2 Type II CRISPR protein are each selected from the group consisting of a Cas9 protein and a catalytically inactive Cas9 protein.

30. A complex of three or more engineered nucleic acid sequences forming a scaffold, comprising: a first engineered nucleic acid comprising, a first CRISPR element 1 comprising—a first nucleic acid binding Class 2 Type II CRISPR protein binding sequence, having a 5' end and a 3' end—and a repeat nucleic acid sequence 1, having a 5' end and a 3' end, wherein the 3' end of the repeat nucleic acid sequence 1 is located 5' of the 5' end of the first nucleic acid binding Class 2 Type II CRISPR protein binding sequence, the repeat nucleic acid sequence 1 further comprising, a linker element nucleic acid sequence 1-1, having a 5' end and a 3' end—a repeat nucleic acid sequence 1a, having a 5' end and a 3' end—a linker element nucleic acid sequence 1-2, having a 5' end and a 3' end—a repeat nucleic acid sequence 1b, having a 5' end and a 3' end—and a linker element nucleic acid sequence 1-3, having a 5' end and a 3' end, arranged in the following 3' to 5' order: the linker element nucleic acid sequence 1-1, the repeat nucleic acid sequence 1a, the linker element nucleic acid sequence 1-2, the repeat nucleic acid sequence 1b, and the linker element nucleic acid sequence 1-3;—and a second CRISPR element 1 further comprising a nucleic acid sequence 1, having a 5' end and a 3' end, wherein (i) the 3' end of the nucleic acid sequence 1 is located 5' of the 5' end of the repeat nucleic acid sequence 1, and (ii) the nucleic acid sequence 1 comprises a spacer nucleic acid sequence 1;—a second engineered nucleic acid comprising,—a first CRISPR element 2 comprising—a second nucleic acid binding Class 2 Type II CRISPR protein binding sequence, having a 5' end and a 3' end—and a repeat nucleic acid sequence 2, having a 5' end and a 3' end, wherein the 3' end of the repeat nucleic acid sequence 2 is located 5' of the 5' end of the second nucleic acid binding Class 2 Type II CRISPR protein binding sequence, the repeat nucleic acid sequence 2 further comprising—a linker element nucleic acid sequence 2-3, having a 5' end and a 3' end—a repeat nucleic acid sequence 1bC, having a 5' end and a 3' end—a linker element nucleic acid sequence 2-4, having a 5' end and a 3' end—a repeat nucleic acid sequence 2a, having a 5' end and a 3' end—and a linker element nucleic acid sequence 2-5, having a 5' end and a 3' end, arranged in the following 3' to 5' order: the linker element nucleic acid sequence 2-3, the repeat nucleic acid sequence 1bC, the linker element nucleic acid sequence 2-4, the repeat nucleic acid sequence 2a, and the linker element nucleic acid sequence 2-5;—a second CRISPR element 2 comprising a nucleic acid sequence 2, having a 5' end and a 3' end, wherein (i) the 3' end of the nucleic acid sequence 1 is located 5' of the 5' end of the repeat nucleic acid sequence 2, and (ii) the nucleic acid sequence 2 comprises a spacer nucleic acid sequence 2;—and a third engineered nucleic acid comprising, a first CRISPR element 3 comprising a third nucleic acid binding Class 2 Type II CRISPR protein binding sequence, having a 5' end and a 3' end—and a repeat nucleic acid sequence 3, having a 5' end and a 3' end, wherein the 3' end of the repeat nucleic acid sequence 3 is located 5' of the 5' end of the third nucleic acid binding Class 2 Type II CRISPR protein binding sequence, the repeat nucleic acid sequence 3 further comprising a linker element nucleic acid sequence 3-1, having a 5' end and a 3' end—a repeat nucleic acid sequence 2aC, having a 5' end and a 3' end—a linker element nucleic acid sequence 3-2, having a 5' end and a 3' end—a repeat nucleic acid sequence 1aC-1, having a 5' end and a 3' end—and a linker element nucleic acid sequence 3-3, having a 5' end and a 3' end, arranged in the following 3' to 5' order: the linker element nucleic acid sequence 3-1, the repeat nucleic acid sequence 2aC, the linker element nucleic acid sequence 3-2, the repeat nucleic acid sequence 1aC-1, and the linker element nucleic acid sequence 3-3; a second CRISPR element 3 comprising a nucleic acid sequence 3, having a 5' end and a 3' end, wherein (i) the 3' end of the nucleic acid sequence 3 is located 5' of the 5' end of the repeat nucleic acid sequence 3, and (ii) the nucleic acid sequence 3 comprises a spacer nucleic acid sequence 3; wherein repeat nucleic acid sequence 1a is associated with the repeat nucleic acid sequence 1aC-1 through hydrogen bonding between the repeat nucleic acid sequence 1a and the repeat nucleic acid sequence 1aC-1, the repeat nucleic acid sequence 1b is associated with the repeat nucleic acid sequence 1bC through hydrogen bonding between the repeat nucleic acid sequence 1b and the repeat nucleic acid sequence 1bC, and the repeat nucleic acid sequence 2a is associated with the repeat nucleic acid sequence 2aC through hydrogen bonding between the repeat nucleic acid sequence 2a and the repeat nucleic acid sequence 2aC.

31. The complex of embodiment 30, wherein the repeat nucleic acid sequence 1 and the repeat nucleic acid sequence 2 comprise a double-stranded nucleic acid binding protein binding site 1 and the double-stranded nucleic acid binding protein binding site 1 is formed by hydrogen base-pair bonding between the repeat nucleic acid sequence 1 and the repeat nucleic acid sequence 2.

32. The complex of embodiment 31, wherein the double-stranded nucleic acid binding protein binding site 1 is a Csy4 protein binding site.

33. The complex of any one of embodiments 30, 31, or 32, wherein the first engineered nucleic acid, the second engineered nucleic acid, and the third engineered nucleic acid each comprises RNA, DNA, or a combination thereof.

34. The complex of any one of embodiments 30 to 33, wherein the first nucleic acid binding Class 2 Type II CRISPR protein binding sequence, the second nucleic acid binding Class 2 Type II CRISPR protein binding sequence, and the third nucleic acid binding Class 2 Type II CRISPR protein binding sequence are each a Cas9 protein binding sequence.

35. The complex of any one of embodiments 30 to 34, wherein (i) the nucleic acid sequence 1 further comprises a spacer nucleic acid sequence 1, the nucleic acid sequence 2 further comprises a spacer nucleic acid sequence 2, and the nucleic acid sequence 3 further comprises a spacer nucleic acid sequence 3, and (ii) the spacer nucleic acid sequence 1 is complementary to a target nucleic acid sequence 1, the spacer nucleic acid sequence 2 is complementary to a target nucleic acid sequence 2, and the spacer nucleic acid sequence 3 is complementary to a target nucleic acid sequence 3.

36. The complex of embodiment 35, wherein the target nucleic acid sequence 1, the target nucleic acid sequence 2, and the target nucleic acid sequence 3 are each a nucleic acid sequence selected from the group consisting of a single-stranded RNA, a single-stranded DNA, a double-stranded RNA, a double-stranded DNA, a single-stranded RNA/DNA hybrid, and a double-stranded RNA/DNA hybrid.

37. A complex of the three or more engineered nucleic acid sequences forming the scaffold of any one of embodiments 30 to 36, the complex further comprising a first Class 2 Type II CRISPR protein bound to the first nucleic acid binding Class 2 Type II CRISPR protein binding sequence, a second Class 2 Type II CRISPR protein bound to the second nucleic acid binding Class 2 Type II CRISPR protein binding sequence, and a third Class 2 Type II CRISPR protein bound to the third nucleic acid binding Class 2 Type II CRISPR protein binding sequence, wherein the first Class 2 Type II CRISPR protein, the second Class 2 Type II CRISPR protein, and the third Class 2 Type II CRISPR protein are each selected from the group consisting of a Cas9 protein and a catalytically inactive Cas9 protein.

38. A complex of two or more engineered nucleic acid sequences forming a scaffold, comprising: an engineered concatenated nucleic acid 1 having a 5' end and a 3' end comprising a first concatenate element 1 comprising a first nucleic acid binding Class 2 Type II CRISPR protein binding sequence, having a 5' end and a 3' end—a second concatenate element 1 comprising a repeat nucleic acid sequence A1 having a 5' end and a 3' end wherein the first nucleic acid binding Class 2 Type II CRISPR protein binding sequence is located 3' of the 3' end of the repeat nucleic acid sequence A1—a first concatenate element 2 comprising a second nucleic acid binding Class 2 Type II CRISPR protein binding sequence, having a 5' end and a 3' end—a second concatenate element 2 comprising a repeat nucleic acid sequence A2, having a 5' end and a 3' end, wherein the second nucleic acid binding Class 2 Type II CRISPR protein binding sequence is located 3' of the 3' end of the repeat nucleic acid sequence A2, wherein the 5' end of the first concatenate element 1 is covalently bound to the 3' end of the first concatenate element 2 to form the engineered concatenated nucleic acid 1;—a third concatenate element 1 having a 5' end and a 3' end comprising a repeat nucleic acid sequence A1C having a 5' end and a 3' end and a nucleic acid sequence 1 having a 5' end and a 3' end, wherein the nucleic acid sequence 1 is located 5' of the 5' end of the repeat nucleic acid sequence A C, wherein (i) the repeat nucleic acid sequence A1C is complementary to the repeat nucleic acid sequence A1, (ii) the repeat nucleic acid sequence A1C is associated with the repeat nucleic acid sequence A1 through hydrogen bonding between the repeat nucleic acid sequence A1C and the repeat nucleic acid sequence A1;—and a third concatenate element 2 having a 5' end and a 3' end comprising a repeat nucleic acid sequence A2C having a 5' end and a 3' end and a nucleic acid sequence 2 having a 5' end and a 3' end, wherein the nucleic acid sequence 2 is located 5' of the 5' end of the repeat nucleic acid sequence A2C, wherein (i) the repeat nucleic acid sequence A2C is complementary to the repeat nucleic acid sequence A2, (ii) the repeat nucleic acid sequence A2C is associated to the repeat nucleic acid sequence A2, and (iii) the repeat nucleic acid sequence A2C is associated with the repeat nucleic acid sequence A2 through hydrogen bonding between the repeat nucleic acid sequence A2C and the repeat nucleic acid sequence A2.

39. The complex of embodiment 38, wherein the repeat nucleic acid sequence A1 further comprises a linker element nucleic acid sequence A1-1 having a 5' end and a 3' end, the 3' end of the linker element nucleic acid sequence A1-1 located 5' of the 5' end of the first nucleic acid binding Class 2 Type II CRISPR protein binding sequence, the linker element nucleic acid sequence A1-1 comprising, a repeat nucleic acid sequence A1-1 having a 5' end and a 3' end, and a bulge nucleic acid sequence A1-1, having a 5' end and a 3' end, the 3' end of the bulge nucleic acid sequence A1-1 adjacent the 5' end of the repeat nucleic acid sequence A1-1—and a linker element nucleic acid sequence A1-2, having a 5' end and a 3' end, comprising, a repeat nucleic acid sequence A1-2, having a 5' end and a 3' end, the 3' end of the linker element nucleic acid sequence A1-2 located 5' of the 5' end of the linker element nucleic acid A 1-1;—the repeat nucleic acid sequence A2 further comprises a linker element nucleic acid sequence A2-1 having a 5' end and a 3' end, the 3' end of the linker element nucleic acid sequence A2-1 located 5' of the 5' end of the second nucleic acid binding Class 2 Type II CRISPR protein binding sequence, the linker element nucleic acid sequence A2-1 comprising, a repeat nucleic acid sequence A2-1 having a 5' end and a 3' end, and a bulge nucleic acid sequence A2-1, having a 5' end and a 3' end, the 3' end of the bulge nucleic acid sequence A2-1 adjacent the 5' end of the repeat nucleic acid sequence A2-1—and a linker element nucleic acid sequence A2-2, having a 5' end and a 3' end, comprising, a repeat nucleic acid sequence A2-2, having a 5' end and a 3' end, the 3' end of the linker element nucleic acid sequence A2-2 located 5' of the 5' end of the linker element nucleic acid A2-1;—the third concatenate element 1 wherein the repeat nucleic acid sequence A1C further comprises a linker element nucleic acid sequence A1-1C comprising a repeat nucleic acid sequence A1-1C having a 5' end and a 3' end, the 5' end of the repeat nucleic acid sequence A1-1C located 3' of the 3' end of the nucleic acid sequence 1, and a bulge nucleic acid sequence A1-1C, having a 5' end and a 3' end, the 5' end of the bulge nucleic acid sequence A1-1C located 3' of the 3' end of the repeat nucleic acid sequence A1-1C, wherein (i) the repeat nucleic acid sequence A1-1C is complementary to the repeat nucleic acid sequence A1-1, and (ii) the repeat nucleic acid sequence A1-1C is associated with the repeat nucleic acid sequence A1-1 through hydrogen bonding between the repeat nucleic acid sequence A1-1C and the repeat nucleic acid sequence A1-1—and a linker element nucleic acid sequence A1-2C having a 5' end and a 3' end, comprising a repeat nucleic acid sequence A1-2C, having a 5' end and a 3' end, the 5' end of the linker element nucleic acid sequence A1-2C located 3' of the 3' end of the linker element nucleic acid sequence A1-1C, wherein (i) the repeat nucleic acid sequence A1-2C is complementary to the repeat nucleic acid sequence A1-2, and (ii) the repeat nucleic acid sequence A1-2C is associated with the repeat nucleic acid sequence A1-2 through hydrogen bonding between the repeat nucleic acid sequence A1-2C and the repeat nucleic acid sequence A1-2;—and the repeat nucleic acid sequence A2C further comprises a linker element nucleic acid sequence A2-1C comprising a repeat nucleic acid sequence A2-1C having a 5' end and a 3' end, the 5' end of the repeat nucleic acid sequence A2-1C located 3' of the 3' end of the nucleic acid sequence 2, and a bulge nucleic acid sequence A2-1C, having a 5' end and a 3' end, the 5' end of the bulge nucleic acid sequence A2-1C located 3' of the 3' end of the repeat nucleic acid sequence A2-1C, wherein (i) the repeat nucleic acid sequence A2-1C is complementary to the repeat nucleic acid sequence A2-1, and (ii) the repeat nucleic acid sequence A2-1C is associated with the repeat nucleic acid sequence A2-1 through hydrogen bonding between the repeat nucleic acid sequence A2-1C and the repeat nucleic acid sequence A2-1—and a linker element nucleic acid sequence A2-2C having a 5' end and a 3' end, comprising a repeat nucleic acid sequence A2-2C, having a 5' end and a 3' end, the 5' end of the linker element nucleic acid sequence A2-2C located 3' of the 3' end of the linker element nucleic acid sequence A2-1C, wherein (i) the repeat nucleic acid sequence A2-2C is complementary to the repeat nucleic acid sequence A2-2, and (ii) the repeat nucleic acid sequence A2-2C is associated with the repeat nucleic acid sequence A2-2 through hydrogen bonding between the repeat nucleic acid sequence A2-2C and the repeat nucleic acid sequence A2-2.

40. The complex of embodiment 38 or 39, wherein the repeat nucleic acid sequence A1 and the repeat nucleic acid sequence A1C further comprise a double-stranded nucleic acid binding protein binding site 1 and the double-stranded nucleic acid binding protein binding site 1 is formed by hydrogen base-pair bonding between the repeat nucleic acid sequence A1 and the repeat nucleic acid sequence A1C.

41. The complex of any one of embodiments 38 to 40, wherein the repeat nucleic acid sequence A2 and the repeat nucleic acid sequence A2C further comprise a double-stranded nucleic acid binding protein binding site 2 and the double-stranded nucleic acid binding protein binding site 2 is formed by hydrogen base-pair bonding between the repeat nucleic acid sequence A2 and the repeat nucleic acid sequence A2C.

42. The complex of embodiment 40 or 41, wherein the double-stranded nucleic acid binding protein binding site 1 is a Csy4 protein binding site.

43. The complex of any one of 38 to 42, wherein the engineered concatenated nucleic acid 1, the third concatenate element 1, and the third concatenate element 2 each comprises RNA, DNA, or a combination thereof.

44. The complex of any one of 38 to 43, wherein the first nucleic acid binding Class 2 Type II CRISPR protein binding sequence and the second nucleic acid binding Class 2 Type II CRISPR protein binding sequence are each a Cas9 protein binding sequence.

45. The complex of any one of 38 to 44, wherein (i) the nucleic acid sequence 1 further comprises a spacer nucleic acid sequence 1 and the nucleic acid sequence 2 further comprises a spacer nucleic acid sequence 2, and (ii) the spacer nucleic acid sequence 1 is complementary to a target nucleic acid sequence 1 and the spacer nucleic acid sequence 2 is complementary to a target nucleic acid sequence 2.

46. The complex of embodiment 45, wherein the target nucleic acid sequence 1 and the target nucleic acid sequence 2 are each a nucleic acid sequence selected from the group consisting of a single-stranded RNA, a single-stranded DNA, a double-stranded RNA, a double-stranded DNA, a single-stranded RNA/DNA hybrid, and a double-stranded RNA/DNA hybrid.

47. A complex of the two or more engineered nucleic acid sequences forming the scaffold of any one of embodiments 38 to 46 the complex further comprising a first Class 2 Type II CRISPR protein bound to the first nucleic acid binding Class 2 Type II CRISPR protein binding sequence and a second Class 2 Type II CRISPR protein bound to the second nucleic acid binding Class 2 Type II CRISPR protein binding sequence, wherein the first Class 2 Type II CRISPR protein and the second Class 2 Type II CRISPR protein are each selected from the group consisting of a Cas9 protein and a catalytically inactive Cas9 protein.

48. A complex of two or more engineered nucleic acid sequences forming a scaffold, comprising: an engineered concatenated split-nexus nucleic acid 1, having a 5' end and a 3' end, comprising a first split-nexus element 1, having a 5' end and a 3' end, comprising a first nucleic acid binding Class 2 Type II CRISPR protein binding sequence and a split-nexus stem element nucleic acid sequence 1-1 having a 5' end and a 3' end wherein the first nucleic acid binding Class 2 Type II CRISPR protein binding sequence is located 3' to the 3' end of the split-nexus stem element nucleic acid sequence 1-1—and a first split-nexus element 2 having a 5' end and a 3' end, comprising a second nucleic acid binding Class 2 Type II CRISPR protein binding sequence and a split-nexus stem element nucleic acid sequence 2-1 having a 5' end and a 3' end wherein the second nucleic acid binding Class 2 Type II CRISPR protein binding sequence is located 3' to the 3' end of the split-nexus stem element nucleic acid sequence 2-1,—and an auxiliary polynucleotide 1-1 having a 5' end and a 3' end, wherein the 5' end of the first split-nexus element 1 is covalently bound to the 3' end of the auxiliary polynucleotide 1-1, and the 5' end of the auxiliary polynucleotide 1-1 is covalently bound to the 3' end of the first split-nexus element 2 to form the concatenated split-nexus element;—a second split-nexus element 1, having a 5' end and a 3' end, comprising a nucleic acid sequence 1 having a 5' end and a 3' end and a first stem element nucleic acid sequence 1-1 having a 5' end and a 3' end, wherein the 3' end of the nucleic acid sequence 1 is covalently bound to the 5' end of the first stem element nucleic acid sequence 1-1—a loop element nucleic acid sequence 1 having a 5' end and a 3' end, wherein the 3' end of the first stem element nucleic acid sequence 1-1 is covalently bound to the 5' end of the loop element nucleic acid sequence 1—a first stem element nucleic acid sequence 1-2 having a 5' end and a 3' end, wherein the 3' end of the loop element nucleic acid sequence 1 is covalently bound to the 5' end of the first stem element nucleic acid sequence 1-2—a connective nucleic acid sequence 1 having a 5' end and a 3' end, wherein the 3' end of the first stem element nucleic acid sequence 1-2 is covalently bound to the 5' end of the connective nucleic acid sequence 1—and a split-nexus stem element nucleic acid sequence 1-2, wherein the 3' end of the connective nucleic acid sequence 1 is covalently bound to the 5' end of the split-nexus stem element nucleic acid sequence 1-2, wherein (i) the first stem element nucleic acid sequence 1-1 and the first stem element nucleic acid sequence 1-2 form a first stem element 1 by hydrogen base-pair bonding between the first stem element nucleic acid sequence 1-1 and the first stem element nucleic acid sequence 1-2, and (ii) the split-nexus stem element nucleic acid sequence 1-1 and the split-nexus stem element nucleic acid sequence 1-2 form a split-nexus stem element 1 by hydrogen base-pair bonding between the split-nexus stem element nucleic acid sequence 1-1 and the split-nexus stem element nucleic acid sequence 1-2;—and a second split-nexus element 2, having a 5' end and a 3' end, comprising a nucleic acid sequence 2 having a 5' end and a 3' end and a first stem element nucleic acid sequence 2-1 having a 5' end and a 3' end, wherein the 3' end of the nucleic acid sequence 2 is covalently bound to the 5' end of the first stem element nucleic acid sequence 2-1—a loop element nucleic acid sequence 2 having a 5' end and a 3' end, wherein the 3' end of the first stem element nucleic acid sequence 2-1 is covalently bound to the 5' end of the loop element nucleic acid sequence 2—a first stem element nucleic acid sequence 2-2 having a 5' end and a 3' end, wherein the 3' end of the loop element nucleic acid sequence 2 is covalently bound to the 5' end of the first stem element nucleic acid sequence 2-2—a connective nucleic acid sequence 2 having a 5' end and a 3' end, wherein the 3' end of the first stem element nucleic acid sequence 2-2 is covalently bound to the 5' end of the connective nucleic acid sequence 2—and a split-nexus stem element nucleic acid sequence 2-2, wherein the 3' end of the connective nucleic acid sequence 1 is covalently bound to the 5' end of the split-nexus stem element nucleic acid sequence 2-2, wherein (i) the first stem element nucleic acid sequence 2-1 and the first stem element nucleic acid sequence 2-2 form a first stem element 2 by hydrogen base-pair bonding between the first stem element nucleic acid sequence 2-1 and the first stem element nucleic acid sequence 2-2, and (ii) the split-nexus stem element nucleic acid sequence 2-1 and the split-nexus stem element nucleic acid sequence 2-2 form a split-nexus stem element 2 by hydrogen base-pair bonding between the split-nexus stem element nucleic acid sequence 2-1 and the split-nexus stem element nucleic acid sequence 2-2.

49. The complex of embodiment 48, wherein the first stem element 1 further comprises in a 5' to 3' direction a lower stem element nucleic acid sequence 1-1, a bulge element nucleic acid sequence 1-1, an upper stem element nucleic acid sequence 1-1, the loop element nucleic acid sequence 1, an upper stem element nucleic acid sequence 1-2, a bulge element nucleic acid sequence 1-2, and a lower stem element nucleic acid sequence 1-2, wherein the upper stem element nucleic acid sequence 1-1 and the upper stem element nucleic acid sequence 1-2 form an upper stem element 1 by hydrogen base-pair bonding between the upper stem element nucleotide sequence 1-1 and the upper stem element nucleotide sequence 1-2, and the lower stem element nucleic acid sequence 1-1 and the lower stem element nucleic acid sequence 1-2 form a lower stem element 1 by hydrogen base-pair bonding between the lower stem element nucleic acid sequence 1-1 and the lower stem element nucleotide sequence 1-2.

50. The complex of embodiment 48 or 49, wherein the first stem element 2 further comprises in a 5' to 3' direction a lower stem element nucleic acid sequence 2-1, a bulge element nucleic acid sequence 2-1, an upper stem element nucleic acid sequence 2-1, the loop element nucleic acid sequence 2, an upper stem element nucleic acid sequence 2-2, a bulge element nucleic acid sequence 2-2, and a lower stem element nucleic acid sequence 2-2, wherein the upper stem element nucleic acid sequence 2-1 and the upper stem element nucleic acid sequence 2-2 form an upper stem element 2 by hydrogen base-pair bonding between the upper stem element nucleotide sequence 2-1 and the upper stem element nucleotide sequence 2-2, and the lower stem element nucleic acid sequence 2-1 and the lower stem element nucleic acid sequence 2-2 form a lower stem element 2 by hydrogen base-pair bonding between the lower stem element nucleic acid sequence 2-1 and the lower stem element nucleotide sequence 2-2.

51. The complex of any one of embodiments 48 to 50, wherein the second split-nexus element 1 further comprises an auxiliary polynucleotide 1-2, having a 5' and a 3' end, wherein 5' end of the auxiliary polynucleotide 1-2 is 3' of the 3' end of the split-nexus stem element nucleic acid sequence 1-2, wherein the auxiliary polynucleotide 1-2 is associated with the auxiliary polynucleotide 1-1 through hydrogen base-pair bonding.

52. The complex of embodiment 51, wherein the auxiliary polynucleotide 1-1 and the auxiliary polynucleotide 1-2 further comprise a double-stranded nucleic acid binding protein binding site 1 and the double-stranded nucleic acid binding protein binding site 1 is formed by hydrogen base-pair bonding between the auxiliary polynucleotide 1-1 and the auxiliary polynucleotide 1-2.

53. The complex of embodiment 52, wherein the double-stranded nucleic acid binding protein binding site 1 is a Csy4 protein binding site 1.

54. The complex of any one of embodiments 48 to 53, wherein the second split-nexus element 2 further comprises an auxiliary polynucleotide 2-2, having a 5' and a 3' end, wherein 5' end of the auxiliary polynucleotide 2-2 is 3' of the 3' end of the split-nexus stem element nucleic acid sequence 2-2—and the first split-nexus element 2 further comprises an auxiliary polynucleotide 2-1 having a 5' end and a 3' end, wherein (i) the 5' end of the first split-nexus element 2 is covalently bound to the 3' end of the auxiliary polynucleotide 2-1, and (ii) the auxiliary polynucleotide 2-2 is associated with the auxiliary polynucleotide 2-1 through hydrogen base-pair bonding.

55. The complex of embodiment 54, wherein the auxiliary polynucleotide 2-1 and the auxiliary polynucleotide 2-2 further comprise a double-stranded nucleic acid binding protein binding site 2 and the double-stranded nucleic acid binding protein binding site 2 is formed by hydrogen base-pair bonding between the auxiliary polynucleotide 2-1 and the auxiliary polynucleotide 2-2.

56. The complex of embodiment 55, wherein the double-stranded nucleic acid binding protein binding site 2 is a Csy4 protein binding site 2.

57. The complex of any one of 48 to 56, wherein the engineered concatenated split-nexus nucleic acid 1, the third concatenate element 1, and the third concatenate element 2 each comprises RNA, DNA, or a combination thereof.

58. The complex of any one of 48 to 57, wherein the first nucleic acid binding Class 2 Type II CRISPR protein binding sequence and the second nucleic acid binding Class 2 Type II CRISPR protein binding sequence are each a Cas9 protein binding sequence.

59. The complex of any one of 48 to 58, wherein (i) the nucleic acid sequence 1 further comprises a spacer nucleic acid sequence 1 and the nucleic acid sequence 2 further comprises a spacer nucleic acid sequence 2, and (ii) the spacer nucleic acid sequence 1 is complementary to a target nucleic acid sequence 1 and the spacer nucleic acid sequence 2 is complementary to a target nucleic acid sequence 2.

60. The complex of embodiment 59, wherein the target nucleic acid sequence 1 and the target nucleic acid sequence 2 are each a nucleic acid sequence selected from the group consisting of a single-stranded RNA, a single-stranded DNA, a double-stranded RNA, a double-stranded DNA, a single-stranded RNA/DNA hybrid, and a double-stranded RNA/DNA hybrid.

61. A complex of the two or more engineered nucleic acid sequences forming the scaffold of any one of embodiments 48 to 60, the complex further comprising a first Class 2 Type II CRISPR protein bound to the first nucleic acid binding Class 2 Type II CRISPR protein binding sequence and a second Class 2 Type II CRISPR protein bound to the second nucleic acid binding Class 2 Type II CRISPR protein binding sequence, wherein the first Class 2 Type II CRISPR protein and the second Class 2 Type II CRISPR protein are each selected from the group consisting of a Cas9 protein and a catalytically inactive Cas9 protein.

62. An engineered nucleic acid scaffold, comprising; a first engineered nucleic acid comprising—a first element 1 comprising a first nucleic acid binding Class 2 Type II CRISPR protein binding sequence, having a 5' end and a 3' end—and a second element 1 comprising a repeat nucleic acid sequence 1 having a 5' end and a 3' end, wherein the 3' end of the repeat nucleic acid sequence 1 is located 5' of the 5' end of the first nucleic acid binding Class 2 Type II CRISPR protein binding sequence, the repeat nucleic acid sequence 1 further comprising a linker element nucleic acid sequence 1-1, having a 5' end and a 3' end—a repeat nucleic acid sequence 1a, having a 5' end and a 3' end—a linker element nucleic acid sequence 1-2, having a 5' end and a 3' end—a repeat nucleic acid sequence 1b, having a 5' end and a 3' end—and a linker element nucleic acid sequence 1-3, having a 5' end and a 3' end, arranged in the following 3' to 5' order: the linker element nucleic acid sequence 1-1, the repeat nucleic acid sequence 1a, the linker element nucleic acid sequence 1-2, the repeat nucleic acid sequence 1b, and the linker element nucleic acid sequence 1-3; wherein no nucleic acid sequence within the repeat nucleic acid sequence 1 associates with any nucleic acid sequence within the repeat nucleic acid sequence 1 to form a stem element through hydrogen bonding capable of binding to a Class 2 Type II CRISPR-Cas protein.

63. The engineered nucleic acid scaffold of embodiment 62, further comprising a third element 1 comprising a nucleic acid sequence 1, having a 5' end and a 3' end, wherein (i) the 3' end of the nucleic acid sequence 1 is covalently attached to the 5' end of the repeat nucleic acid sequence 1, and (ii) the nucleic acid sequence 1 comprises a spacer nucleic acid sequence 1.

64. The engineered nucleic acid scaffold of embodiment 62 or 63, further comprising: a second engineered nucleic acid comprising—a first element 2 comprising a second nucleic acid binding Class 2 Type II CRISPR protein binding sequence, having a 5' end and a 3' end—and a second element 2 comprising the repeat nucleic acid sequence 1C has a 5' end and a 3' end, wherein the 3' end of the repeat nucleic acid sequence 1C is located 5' of the 5' end of the second nucleic acid binding Class 2 Type II CRISPR protein binding sequence, the repeat nucleic acid sequence 2 further comprising, a linker element nucleic acid sequence 2-1, having a 5' end and a 3' end—a repeat nucleic acid sequence 1bC, having a 5' end and a 3' end—a linker element nucleic acid sequence 2-2, having a 5' end and a 3' end—a repeat nucleic acid sequence 1aC, having a 5' end and a 3' end—and a linker element nucleic acid sequence 2-3, having a 5' end and a 3' end, arranged in the following 3' to 5' order: the linker element nucleic acid sequence 2-3, the repeat nucleic acid sequence 1bC, the linker element nucleic acid sequence 2-2, the repeat nucleic acid sequence 1aC, and the linker element nucleic acid sequence 2-1; wherein the repeat nucleic acid sequence 1 is associated with the repeat nucleic acid sequence 2 through hydrogen bonding between the repeat nucleic acid sequence 1a and the repeat nucleic acid sequence 1aC and through hydrogen bonding between the repeat nucleic acid sequence 1b and the repeat nucleic acid sequence 1bC.

65. The engineered nucleic acid scaffold of embodiment 64, further comprising, a third element 2 comprises a nucleic acid sequence 2, having a 5' end and a 3' end, wherein (i) the 3' end of the nucleic acid sequence 2 is covalently attached to the 5' end of the repeat nucleic acid sequence 1C, and (ii) the nucleic acid sequence 2 comprises a spacer nucleic acid sequence 2.

Although preferred embodiments of the present invention have been shown and described herein, it will be obvious to those skilled in the art that such embodiments are provided by way of example only. From the above description and the following Examples, one skilled in the art can ascertain essential characteristics of this invention and, without departing from the spirit and scope thereof, can make changes, substitutions, variations, and modifications of the invention to adapt it to various usages and conditions. Such changes, substitutions, variations, and modifications are also intended to fall within the scope of the present disclosure.

EXPERIMENTAL

Aspects of the present invention are illustrated in the following Examples. Efforts have been made to ensure accuracy with respect to numbers used (e.g., amounts, concentrations, percent changes, and the like) but some experimental errors and deviations should be accounted for. Unless indicated otherwise, temperature is in degrees Centigrade and pressure is at or near atmospheric. It should be understood that these Examples are given by way of illustration only and are not intended to limit the scope of what the inventors regard as various aspects of the present invention.

Example 1

In Silico Design of NASC Polynucleotide Components

This Example provides a description of the design of NASC polynucleotide components for a number of embodiments of the NASCs described herein.

Table 9 sets forth a correlation between NASC polynucleotide components and structures illustrated in the figures. The column "Assoc. Cas protein" lists the Cas proteins with which the NASC polynucleotide component can be used. Unless otherwise indicated, the Cas9 protein is a *S. pyogenes* Cas9 protein (*S. pyogenes* Cas9 protein, SEQ ID NO. 100 or *S. pyogenes* dCas9 protein (SEQ ID NO. 101)). The Cpf1 protein is an *Acidaminococcus* sp. Cpf1 protein (dCpf SEQ ID NO. 105) unless otherwise indicated.

Sequences that hybridize between polynucleotide components are underlined. Nucleic acid target binding sequences are indicated by a series of twenty Ns, wherein N is any nucleotide. A nucleic acid target binding sequence can be engineered by one of ordinary skill in the art.

TABLE 9

Examples of NASC Polynucleotide Component Sequences

| FIG. | FIG. indicator | NASC component generic designation | Assoc. Cas protein | Sequence | SEQ ID NO. |
|---|---|---|---|---|---|
| 4A | 1-1, 1-2, 1-3 | NASC-PC1 | Cpf1 | CUCCGGCGAUGUCACAC CGAACUGAUAAUUUCUA CUCUUGUAGAUNNNNNN NNNNNNNNNNNNNN | SEQ ID NO. 64 |

TABLE 9-continued

Examples of NASC Polynucleotide Component Sequences

| FIG. | FIG. indicator | NASC component generic designation | Assoc. Cas protein | Sequence | SEQ ID NO. |
|---|---|---|---|---|---|
| 4A | 2-3, 2-2, 2-1 | NASC-PC2 | Cpf1 | UCGGUGUGACAUCGCCG GAGUUGAUAAAUUUCUA CUCUUGUAGAUNNNNNN NNNNNNNNNNNNNNN | SEQ ID NO. 65 |
| 4B | 1-1 | NASC-PC1-1 | Cpf1 | CUCCGGCGAUGUCACAC CGAACUGAUAAUUUCUA C | SEQ ID NO. 66 |
| 4B | 1-3 | NASC-PC1-2 | Cpf1 | GUAGAUNNNNNNNNNNN NNNNNNNNNN | SEQ ID NO. 67 |
| 4B | 2-1 | NASC-PC2-1 | Cpf1 | UCGGUGUGACAUCGCCG GAGUUGAUAAAUUUGU AG | SEQ ID NO. 68 |
| 4B | 2-3 | NASC-PC2-2 | Cpf1 | CUACAUNNNNNNNNNNN NNNNNNNNN | SEQ ID NO. 69 |
| 4C | 1-1, 1-3, 1-2 | NASC-PC1 | Cpf1 | AAUUUCUACUCUUGUAG AUNNNNNNNNNNNNNN NNNNNNACUGAUCUCCG GCGAUGUCACACCGA | SEQ ID NO. 70 |
| 4C | 2-2, 2-3, 2-2 | NASC-PC2 | Cpf1 | AAUUUCUACUCUUGUAG AUNNNNNNNNNNNNNN NNNNNNUUGAUAUCGGU GUGACAUCGCCGGAG | SEQ ID NO. 71 |
| 4M | 1-1,1-2, 1-3,1-4 | NASC-PC1 | Cpf1 | CUCCGGCGAUGUCACAC CGAACUGAUAAUUUCUA CUCUUGUAGAUNNNNNN NNNNNNNNNNNNNNUU GAUAGUCUAAGGCAGCU AGGGUCU | SEQ ID NO. 72 |
| 4M | 2-1, 2-2, 2-3 | NASC-PC2 | Cpf1 | UCGGUGUGACAUCGCCG GAGUUGAUAAAUUUCUA CUCUUGUAGAUNNNNNN NNNNNNNNNNNNNNN | SEQ ID NO. 73 |
| 4M | 3-2, 3-3, 3-1 | NASC-PC3 | Cpf1 | AAUUUCUACUCUUGUAG AUNNNNNNNNNNNNNNN NNNNNUACCAAAGACCC UAGCUGCCUUAGAC | SEQ ID NO. 74 |
| 5D | 507-500 I | NASC-PC1 | Cpf1 | CUCCGGCGAUGUCACAC CGAACUGAUGUCUAAGG CAGCUAGGGUCUUUGAU AAAUUUCUACUCUUGUA GAUNNNNNNNNNNNNNN NNNNNN | SEQ ID NO. 75 |
| 5D | 508-515 II | NASC-PC2 | Cpf1 | UGCGAACCACUGUGAGC CAGUACCAAUCGGUGUG ACAUCGCCGGAGUUGAU AAAUUUCUACUCUUGUA GAUNNNNNNNNNNNNNN NNNNNN | SEQ ID NO. 76 |
| 5F | VIII 507-503 | NASC- PC1-1 | Cpf1 | CUCCGGCGAUGUCACAC CGAACUGAUGUCUAAGG CAGCUAGGGUCUUUGAU AAAUUCUAC | SEQ ID NO. 77 |
| 5F | VIII 502-500 | NASC- PC1-2 | Cpf1 | GUAGAUNNNNNNNNNNN NNNNNNNNNN | SEQ ID NO. 78 |
| 5F | V 508-512 | NASC- PC2-1 | Cpf1 | UGCGAACCACUGUGAGC CAGUACCAAUCGGUGUG ACAUCGCCGGAGUUGAU AAAUUUGUAG | SEQ ID NO. 79 |

TABLE 9-continued

Examples of NASC Polynucleotide Component Sequences

| FIG. | FIG. indicator | NASC component generic designation | Assoc. Cas protein | Sequence | SEQ ID NO. |
|---|---|---|---|---|---|
| 5F | V 513-515 | NASC-PC2-2 | Cpf1 | CUACAUNNNNNNNNNNN NNNNNNNN | SEQ ID NO. 80 |
| 6D | 611-601 | NASC-PC1 | Cas9 | NNNNNNNNNNNNNNNNN NNNGUUUUAGUCCCUAA UUAAAUUUCUUGAAAUU GGUAUAUAAGGAGGGAC UACAACAAAGAGUUUGC GGGACUCUGCGGGGUUA CAAUCCCUAAAACCGC UUUUAAAAUUCAAAUAA AUUUUGCUUU | SEQ ID NO. 81 |
| 6D | 612-622 | NASC-PC2 | Cas9 | NNNNNNNNNNNNNNNNN NNNGUUGUAGUCCCUCC UUAUAUACCAAGAAAAA GAAAUUUAAUUAGGGAC UAAAACAAAGAGUUUGC GGGACUCUGCGGGGUUA CAAUCCCUAAAACCGC UUUUAAAAUUCAAAUAA AUUUUGCUUU | SEQ ID NO. 82 |
| 6G | 611-601 | NASC-PC1 | Cas9 | NNNNNNNNNNNNNNNNN NNNGUCUCAGAGCUAUG CAGUCCUGGACAACUGC CGAACCUCAUGAGAAUC CAAGUAUGUGUAAGGCU AGUCCGUUAUCAACUUG AAAAAGUGGCACCGAGU CGGUGCUU | SEQ ID NO. 83 |
| 6G | 622-612 | NASC-PC2 | Cas9 | NNNNNNNNNNNNNNNNN NNNNGCACAUGAGGAUU CUCAUGAGGGACGGCAG AAGAACAGGACUGCAUA GCAAGUUGAGAUAAGGC UAGUCCGUUAUCAACUU GAAAAAGUGGCACCGAG UCGGUGCUU | SEQ ID NO. 84 |
| 6I | IV | NASC-PC1 | Cas9 | NNNNNNNNNNNNNNNNN NNNGUUUUAGAGCUAUG CUGUUUUGGAAAGGUCA UGUCCUUCAAAGUUGUA AUAAGGCUAGUCCGUUA UCAACUUGAAAAAGUGG CACCGAGUCGGUGCUU | SEQ ID NO. 85 |
| 6I | V | NASC-PC2 | Cas9 | NNNNNNNNNNNNNNNNN NNNGUAAUAGAAUCGUG CUGAAAAGGAAACAAAA CAGCAUAGCAAGUUAAA AUAAGGCUAGUCCGUUA UCAACUUGAAAAAGUGG CACCGAGUCGGUGCUU | SEQ ID NO. 86 |
| 6I | VI | NASC-PC3 | Cas9 | NNNNNNNNNNNNNNNNN NNNGUUACAGAUGAAGG ACAUGACCGAAACUUUU CAGCACGAUAAGUUAUU AUAAGGCUAGUCCGUUA UCAACUUGAAAAAGUGG CACCGAGUCGGUGCUU | SEQ ID NO. 87 |
| 7B | 725-722 | NASC-PC1 | Cas9 | NNNNNNNNNNNNNNNNN NNNGUUUUAGUCCCUAA UUAAAUUUCUU | SEQ ID NO. 88 |
| 7B | 721-718 | NASC-PC2 | Cas9 | NNNNNNNNNNNNNNNNN NNNGUUGUAGUCCCUCC UUAUAUACCAA | SEQ ID NO. 89 |

TABLE 9-continued

Examples of NASC Polynucleotide Component Sequences

| FIG. | FIG. indicator | NASC component generic designation | Assoc. Cas protein | Sequence | SEQ ID NO. |
|---|---|---|---|---|---|
| 7B | 717-700 | NASC-PC-NTS | Cas9 | AAGAAAUUUAAUUAGGG ACUAAAACAAAGAGUUU GCGGGACUCUGCGGGGU UACAAUCCCCUAAAACC GCUUUUAAAAUUCAAAU AAAUUUUGCUUUAGUUG AUAAAUUUGGUAUAUAA GGAGGGACUACAACAAA GAGUUUGCGGGACUCUG CGGGGUUACAAUCCCCU AAAACCGCUUUUAAAAU UCAAAUAAAUUUUGCUU U | SEQ ID NO. 90 |
| 8L | I 809-817 | NASC-PC1 | Cas9 | NNNNNNNNNNNNNNNNN NNNGUUUUAGAGCTATG CTGTGAAAACAGCATAG CAAGUUAAAAUAAGGCU ACUGCCG | SEQ ID NO. 91 |
| 8L | II 828-836 | NASC-PC2 | Cas9 | NNNNNNNNNNNNNNNNN NNNGUUUUAGAGCTATG CTGTGAAAACAGCATAG CAAGUUAAAAUAAGGCU AGUCACG | SEQ ID NO. 92 |
| 8L | 835-800 | NASC-PC-NTS | Cas9 | CGGCAGUCCGUUAUCAA CUUGAAAAAGUGGCACC GAGUCGGUGCUUAGUUG AUAAAUCGUGACGUCCG UUAUCAACUUGAAAAAG UGGCACCGAGUCGGUGC UUU | SEQ ID NO. 93 |
| 9A | II + I | NASC-PC1-2TS | Cas9 Cpf1 | NNNNNNNNNNNNNNNNN NNNGUUUUAGAGCUAUG CUGUGAAAACAGCAUAG CAAGUUAAAAUAAGGCU AGUCCGUUAUCAACUUG AAAAAGUGGCACCGAGU CGGUGCUUACUGAUAAU UUCUACUCUUGUAGAUN NNNNNNNNNNNNNNNNN NN | SEQ ID NO. 94 |
| 6J | VII | NASC-PC1-2TS | Cas9 Cpf1 | NNNNNNNNNNNNNNNNN NNNGUUUUAGAGCUAUG CUGUUACCAAUUGAUAG UAGAUNNNNNNNNNNNN NNNNNNNN | SEQ ID NO. 97 |
| 6J | VIII | NASC-PC-NTS | Cpf1 Cas9 | AAUUUCUACUUGAUAAC AGCAUAGCAAGUUAAAA UAAGGCUAUCCGUUAUC AACUUGAAAAAGUGGCA CCGAGUCGGUGCUUU | SEQ ID NO. 98 |
| 6K | X | NASC-PC1 | Cas9 | NNNNNNNNNNNNNNNNN NNNGUUUUUGUACUCUC AAGAUUCAAAUAACAGC AUAGCAAGUUAAAAUAA GGCUAUCCGUUAUCAAC UUGAAAAAGUGGCACCG AGUCGGUGCUUU | SEQ ID NO. 95 |

TABLE 9-continued

Examples of NASC Polynucleotide Component Sequences

| FIG. | FIG. indicator | NASC component generic designation | Assoc. Cas protein | Sequence | SEQ ID NO. |
|---|---|---|---|---|---|
| 6K | IX | NASC-PC2 | Cas9* | NNNNNNNNNNNNNNNNNN NNNGUUUUAGAGCUAUG CUGUUACGUAAAUCUUG CAGAAGCUACAAAGAUA AGGCUUCAUGCCGAAAU CAACACCCUGUCAUUUU AUGGCAGGGUGUUU | SEQ ID NO. 96 |

*S. thermophilus CRISPR-I Cas9 protein, SEQ ID NO. 108 or S. thermophilus CRISPR-I dCas9 protein, SEQ ID NO. 109

Following the guidance of the present specification, one or ordinary skill in the art can design NASC polynucleotide components (e.g., based on other NASC polynucleotide components described herein) for different cognate Cas proteins (e.g., C. jejuni Cas9 protein (SEQ ID NO. 103), C. jejuni dCas9 protein (SEQ ID NO. 56), S. aureus Cas9 (SEQ ID NO. 99), S. aureus dCas9 (SEQ ID NO. 102), Lachnospiraceae bacterium Cpf1 protein (SEQ ID NO. 106), Lachnospiraceae bacterium dCpf1 protein (SEQ ID NO. 107) or Acidaminococcus sp. Cpf1 (SEQ ID NO. 104).

Example 2

Production of sgRNAs and NASC Polynucleotide Components

This Example describes production of sgRNAs and NASC polynucleotide components NASC-PC1 (Table 9, generic target sequence SEQ ID NO. 83) and NASC-PC2 (Table 9, generic target sequence SEQ ID NO. 84), as illustrated in FIG. 6G. The sgRNAs and NASC polynucleotide components described in this Example were used in Cas cleavage assays (Example 5).

NASC-PC1 and NASC-PC2 comprised different first stem element nucleic acid sequences (illustrated in FIG. 6E, 608-609 and 619-620) to limit formation of secondary structures within each NASC-PC that may interfere with the formation of stable secondary structure between the NASC-PC1 first stem element nucleic acid sequences and NASC-PC2 first stem element nucleic acid sequences complementary to the first stem element nucleic acid sequence.

Two sgRNA backbones were used (sgRNA-1 and sgRNA-2), each comprising different upper stem and lower stem nucleic acid sequences (illustrated in FIG. 2C, 221-222/227-228 and 223-224/225-226, respectively); the bulge sequences were the same.

Four nucleic acid target-binding sequences, each 20 nucleotides in length, were selected. One of the four nucleic acid target binding sequences was incorporated at the 5' end of a sgRNA-1 and a sgRNA-2 backbone, and the 5' end of a NASC-PC1 and a NASC-PC2. The four double-stranded DNA target sequences were as follows: Target 1 (AAVST1) corresponded to a human AAVS-1 target sequence. Target 2 (VT2), Target 3 (VT3) and Target 4 (VT4) were DNA target sequences present in the vector sequence (SEQ ID NO. 20).

RNA components were produced by in vitro transcription using a T7 Quick High Yield RNA Synthesis Kit (New England Biolabs, Ipswich, Mass.) from a double-stranded DNA template incorporating a T7 promoter at the 5' end of the DNA sequences.

A double-stranded DNA template for each sgRNA, NASC-PC1, and NASC-PC2 was assembled by PCR using 3' overlapping oligonucleotide primers containing DNA sequences corresponding to each sgRNA, NASC-PC1, and NASC-PC2. The oligonucleotide primers are presented in Table 10.

TABLE 10

Overlapping Primers for Generation of sgRNA, NASC-PC1, and NASC-PC2 Encoding Templates

| Construct designation | Target | Oligonucleotide |
|---|---|---|
| sgRNA-1-AAVST1 | target-1 | SEQ ID NO. 1, 3, 11, 12, 2 |
| sgRNA-1-VT2 | target-2 | SEQ ID NO. 1, 4, 11, 12, 2 |
| sgRNA-1-VT3 | target-3 | SEQ ID NO. 1, 5, 11, 12, 2 |
| sgRNA-1-VT4 | target-4 | SEQ ID NO. 1, 6, 11, 12, 2 |
| sgRNA-2-AAVST1 | target-1 | SEQ ID NO. 1, 7, 13, 14, 2 |
| sgRNA-2-VT2 | target-2 | SEQ ID NO. 1, 8, 13, 14, 2 |
| sgRNA-2-VT3 | target-3 | SEQ ID NO. 1, 9, 13, 14, 2 |
| sgRNA-2-VT4 | target-4 | SEQ ID NO. 1, 10, 13, 14, 2 |
| NASC-PC1-AAVST1 | target-1 | SEQ ID NO. 1, 3, 15, 16, 2 |
| NASC-PC1-VT2 | target-2 | SEQ ID NO. 1, 4, 15, 16, 2 |
| NASC-PC1-VT3 | target-3 | SEQ ID NO. 1, 5, 15, 16, 2 |
| NASC-PC1-VT4 | target-4 | SEQ ID NO. 1, 6, 15, 16, 2 |
| NASC-PC2-AAVST1 | target-1 | SEQ ID NO. 1, 7, 17, 18, 2 |
| NASC-PC2-VT2 | target-2 | SEQ ID NO. 1, 8, 17, 18, 2 |
| NASC-PC2-VT3 | target-3 | SEQ ID NO. 1, 9, 17, 18, 2 |
| NASC-PC2-VT4 | target-4 | SEQ ID NO. 1, 10, 17, 18, 2 |

The DNA primers were present at a concentration of 2 nM each. One DNA primer corresponded to the T7 promoter (SEQ ID NO. 1) and the other to the 3' end of the RNA sequence (SEQ ID NO. 2) and were used at a concentration of 640 nM to drive the amplification reaction. PCR reactions were performed using Q5 Hot Start High-Fidelity 2× Master Mix (New England Biolabs, Ipswich, Mass.) following the manufacturer's instructions. PCR assembly reactions were carried out using the following thermal cycling conditions: 98° C. for 2 minutes; 2 cycles of 20 seconds at 98° C., 20 seconds at 52.5° C., 20 seconds at 72° C.; followed by 32 cycles of 20 seconds at 98° C., 20 seconds at 57° C., 20 seconds at 72° C.; and a final extension at 72° C. for 2 minutes. DNA product quality was evaluated after the PCR reaction by agarose gel electrophoresis (1.5%, SYBR® Safe, Life Technologies, Grand Island, N.Y.).

Between 0.25-0.5 μg of the DNA template for each sgRNA, NASC-PC1, and NASC-PC2 was used as a template for transcription using T7 High Yield RNA Synthesis Kit (New England Biolabs, Ipswich, Mass.) for approximately 16 hours at 37° C. Transcription reactions were treated with DNase I (New England Biolabs, Ipswich, Mass.) and purified using GeneJet RNA Cleanup and Concentration Kit (Life Technologies, Grand Island, N.Y.). RNA yield was quantified using the Nanodrop™ 2000 System (Thermo Scientific, Wilmington, Del.). The quality of the transcribed RNA was checked by agarose gel electrophoresis (2%, SYBR® Safe; Life Technologies, Grand Island, N.Y.). The sgRNA and NASC polynucleotide component sequences are shown in Table 11.

TABLE 11 sgRNA, NASC-PC1, and NASC-PC2 Sequences

| Name | Sequence* | SEQ ID NO. |
|---|---|---|
| sgRNA-1-AAVST1 | GGGGCCACUAGGGACAGGAUGUCUCAGAGCUAUGCAGUCCUGGACAACUGCCGAACAGGACUGCAUAGCAAGUUGAGAUAAGGCUAGUCCGUUAUCAACUUGAAAAAGUGGCACCGAGUCGGUGCUU | SEQ ID NO. 25 |
| sgRNA-1-VT2 | GUAGGCUAUAGUGUAGAUCUGUCUCAGAGCUAUGCAGUCCUGGACAACUGCCGAACAGGACUGCAUAGCAAGUUGAGAUAAGGCUAGUCCGUUAUCAACUUGAAAAAGUGGCACCGAGUCGGUGCUU | SEQ ID NO. 26 |
| sgRNA-1-VT3 | GGAAAAAGUGGAAGCGGCGAGUCUCAGAGCUAUGCAGUCCUGGACAACUGCCGAACAGGACUGCAUAGCAAGUUGAGAUAAGGCUAGUCCGUUAUCAACUUGAAAAAGUGGCACCGAGUCGGUGCUU | SEQ ID NO. 27 |
| sgRNA-1-VT4 | GGCGAUAAGUCGUGUCUUACGUCUCAGAGCUAUGCAGUCCUGGACAACUGCCGAACAGGACUGCAUAGCAAGUUGAGAUAAGGCUAGUCCGUUAUCAACUUGAAAAAGUGGCACCGAGUCGGUGCUU | SEQ ID NO. 28 |
| sgRNA-2-AAVST1 | GGGGCCACUAGGGACAGGAUGCACAUGAGGAUUCUCAUGAGGGACGGCAGAAGAACCUCAUGAAAUCCAAGUAUGUGUAAGGCUAGUCCGUUAUCAACUUGAAAAAGUGGCACCGAGUCGGUGCUU | SEQ ID NO. 29 |
| sgRNA-2-VT2 | GUAGGCUAUAGUGUAGAUCUGCACAUGAGGAUUCUCAUGAGGGACGGCAGAAGAACCUCAUGAAAUCCAAGUAUGUGUAAGGCUAGUCCGUUAUCAACUUGAAAAAGUGGCACCGAGUCGGUGCUU | SEQ ID NO. 30 |
| sgRNA-2-VT3 | GGAAAAAGUGGAAGCGGCGAGCACAUGAGGAUUCUCAUGAGGGACGGCAGAAGAACCUCAUGAGAAUCCAAGUAUGUGUAAGGCUAGUCCGUUAUCAACUUGAAAAAGUGGCACCGAGUCGGUGCUU | SEQ ID NO. 31 |
| sgRNA-2-VT4 | GGCGAUAAGUCGUGUCUUACGCACAUGAGGAUUCUCAUGAGGGACGGCAGAAGAACCUCAUGAGAAUCCAAGUAUGUGUAAGGCUAGUCCGUUAUCAACUUGAAAAAGUGGCACCGAGUCGGUGCUU | SEQ ID NO. 32 |
| NASC-PC1-AAVST1 | GGGGCCACUAGGGACAGGAU<u>GUCUCAG</u><u>AGCUA</u><u>UGCAGUCCUGGACAACUGCCGAAC</u><u>CUCAUGAG</u><u>AAUCCAAGUAUGUGUAAGGCUAGUCCGUUAUC</u>AACUUGAAAAAGUGGCACCGAGUCGGUGCUU | SEQ ID NO. 33 |
| NASC-PC1-VT2 | GUAGGCUAUAGUGUAGAUC<u>UGUCUCAGAGCUA</u><u>UGCAGUCCUGGACAACUGCCGAACCUCAUGAG</u><u>AAUCCAAGUAUGUGUAAGGCUAGUCCGUUAUC</u>AACUUGAAAAAGUGGCACCGAGUCGGUGCUU | SEQ ID NO. 34 |
| NASC-PC1-VT3 | GGAAAAAGUGGAAGCGGCGA<u>GUCUCAGAGCUA</u><u>UGCAGUCCUGGACAACUGCCGAACCUCAUGAG</u><u>AAUCCAAGUAUGUGUAAGGCUAGUCCGUUAUC</u>AACUUGAAAAAGUGGCACCGAGUCGGUGCUU | SEQ ID NO. 35 |
| NASC-PC1-VT4 | GGCGAUAAGUCGUGUCUUAC<u>GUCUCAGAGCUA</u><u>UGCAGUCCUGGACAACUGCCGAACCUCAUGAG</u><u>AAUCCAAGUAUGUGUAAGGCUAGUCCGUUAUC</u>AACUUGAAAAAGUGGCACCGAGUCGGUGCUU | SEQ ID NO. 36 |
| NASC-PC2-AAVST1 | GGGGCCACUAGGGACAGGAU<u>GCACAUGAGGAU</u><u>UCUCAUGAGGGACGGCAGAAGAAC</u><u>AGGACUGC</u><u>AUAGCAAGUUGAGAU</u>AAGGCUAGUCCGUUAUCAACUUGAAAAAGUGGCACCGAGUCGGUGCUU | SEQ ID NO. 37 |
| NASC-PC2-VT2 | GUAGGCUAUAGUGUAGAUCU<u>GCACAUGAGGAU</u><u>UCUCAUGAGGGAC</u>GGCAGAAGAAC<u>AGGACUGC</u><u>AUAGCAAGUUGAGAUAAGGCUAGUCCGUUAUC</u>AACUUGAAAAAGUGGCACCGAGUCGGUGCUU | SEQ ID NO. 38 |
| NASC-PC2-VT3 | GGAAAAAGUGGAAGCGGCGA<u>GCACAUGAGGAU</u><u>UCUCAUGAGGGAC</u>GGCAGAAGAAC<u>AGGACUGC</u><u>AUAGCAAGUUGAGAU</u>AAGGCUAGUCCGUUAUCAACUUGAAAAAGUGGCACCGAGUCGGUGCUU | SEQ ID NO. 39 |
| NASC-PC2-VT4 | GGCGAUAAGUCGUGUCUUAC<u>GCACAUGAGGAU</u><u>UCUCAUGAGGGACGGCAGAAGAAC</u><u>AGGACUGC</u><u>AUAGCAAGUUGAGAU</u>AAGGCUAGUCCGUUAUCAACUUGAAAAAGUGGCACCGAGUCGGUGCUU | SEQ ID NO. 40 |

*NASC-PC hybridizing regions are underlined

This method for production of sgRNA and NASC polynucleotide components can be applied to the production of other the sgRNA and NASC polynucleotide components by one of ordinary skill in the art in view of the teachings of the specification.

Example 3

Production of Double-Stranded DNA Target Sequences for Use in Cleavage Assays by Cloning of Double-Stranded DNA Target Sequences into Plasmids Double-stranded DNA target sequences for use in the in vitro Cas protein cleavage assays were produced though the ligation of a double-stranded nucleic acid target sequence (e.g., the AAVS-1 target sequence) into a cloning vector backbone. Each vector was transformation into a suitable strain of *E. coli* for production of double-stranded DNA target sequences.

A 25 nucleotide single-stranded DNA target sequence corresponding to the human Adeno-Associated Virus Integration Site 1 (AAVS-1) was appended in silico with a randomized nucleic acid sequence of 47 nucleotides at the 5' end and a randomized nucleic acid sequence of 53 nucleotides at the 3' end. Forward and reverse oligonucleotide primers compatible with the Electra™ Vector System (DNA2.0, Newark, Calif.) were incorporated at the 5' end and the 3' end of the DNA target sequence, producing a 237 bp single-stranded DNA sequence. A nucleic acid sequence of 237 bp single-stranded DNA ("DNA cloning fragment"), as well as nucleic acid sequences of forward and reverse amplification oligonucleotide primers, were provided to a commercial manufacturer for synthesis. These single-stranded DNA sequences are shown in Table 12.

TABLE 12

Single-stranded DNA Sequences

| Description | Sequence* | SEQ ID NO. |
|---|---|---|
| DNA cloning Fragment | TACACGTACTTAGTCGCTGAAGCTCTTCTATGCAAGCAGAAGACGGCATACGAGATCGAGTAATGTGACTGGAGTTCAGACGTGTGCTCTTCCGATCTGCTACTGGGGCCACTAGGGACAGGATNGGTGCTAGCTCAGATCGGA | SEQ ID NO. 19 |

TABLE 12-continued

Single-stranded DNA Sequences

| Description | Sequence* | SEQ ID NO. |
|---|---|---|
| | AGAGCGTCGTGTAGGGAAAGAGTG TAGGCTATAGTGTAGATCTCGGTG GTCGCCGTATCATTGGTAGAAGAG CCGTCAATCGAGTTCGTACCT | |
| Forward primer | TACACGTACTTAGTCGCTGAAGCT CTTCTATGCAAGCAGAAGACGGCA TACGAGAT | SEQ ID NO. 21 |
| Reverse primer | AGGTACGAACTCGATTGACGGCTC TTCTACCAATGATACGGCGACCAC CGAGATCT | SEQ ID NO. 22 |

*AAVS-1 DNA target sequence comprising a PAM is underlined

The single-stranded DNA cloning fragment was amplified via PCR to generate double-stranded DNA for use with the Electra™ Vector System (DNA2.0, Newark, Calif.). The PCR reaction mixture was as follows: 0.5 unit KAPA HiFi Hot Start DNA Polymerase (Kapa Biosystems, Wilmington, Mass.), 1× reaction buffer, 0.3 mM dNTPs, 200 nM forward primer (SEQ ID NO. 21), 200 nM reverse primer (SEQ ID NO. 22), and 80 nM of the DNA cloning fragment (SEQ ID NO. 19) in a total volume of 25 µL. The DNA cloning fragment was amplified using the following conditions: 95° C. for 4 minutes, 30 cycles of 20 seconds at 98° C., 20 seconds at 60° C., and 30 seconds at 72° C., followed by a final extension at 72° C. for 5 minutes. PCR products were purified using Spin Smart™ PCR purification tubes (Denville Scientific, South Plainfield, N.J.) and quantified using a Nanodrop™ 2000 UV-Vis spectrophotometer (Thermo Scientific, Wilmington, Del.).

The double-stranded DNA cloning fragment was cloned into the commercially available "pD441-SR: T5-sRBS-ORF, Ecoli-Elec D" vector (an Electra™ bacterial DNA vector (DNA2.0, Newark, Calif.)) using the manufacturer's cloning protocol. The following cloning reaction mixture was prepared: 20 ng of the PCR-amplified cloning fragment, 20 ng of the bacterial DNA vector, 2 µl of Electra™ buffer mix (DNA2.0, Newark, Calif.), and 1 µl of Electra™ enzyme mix (DNA2.0, Newark, Calif.) in a final volume of 20 µL. The cloning reaction mixture was then briefly vortexed, subjected to centrifugation using benchtop centrifuge, and incubated at room temperature for 20 minutes.

After incubation, 1 µL of One Shot® Mach1™ T1R (Thermo Scientific, Wilmington, Del.) chemically competent *E. coli* cells were mixed with 2 µL of the cloning reaction mixture to form a transformation mixture that was incubated in ice for 30 minutes. The transformation mixture was heat-shocked for 30 seconds at 42° C., and incubated in ice for 2 minutes. 250 µL of room temperature S.O.C. medium (Thermo Scientific, Wilmington, Del.) was added to the transformation mixture, and the mixture was incubated at 37° C. for 1 hour with shaking. After this incubation, 50 µL of the cell mixture was spread onto an LB agar plate with 50 µg/mL kanamycin, and the plate was incubated overnight at 37° C. for bacterial colony formation.

Five bacterial colonies were picked and transferred to separate 15 mL culture tubes containing 5 mL of LB supplemented with 50 µg/mL kanamycin culture medium and the tubes were incubated for 8 hours with shaking. Cells were pelleted by centrifugation at 4000 RPM for 15 minutes, culture medium was aspirated, and the cells were re-suspended in 200 µL of LB culture medium without antibiotics. DNA vectors were extracted from the bacteria of each of the five bacterial colonies using QIAprep Spin Miniprep Kit (Qiagen, Venlo, Netherlands) following the manufacturer's instructions. DNA vector yields were quantified using a Nanodrop™ 2000 UV-Vis spectrophotometer (Thermo Scientific, Wilmington, Del.). 250 ng of each DNA vector was Sanger sequenced to verify incorporation of the DNA cloning fragment corresponding to SEQ ID NO. 19. The full DNA vector sequence, including AAVS-1 target sequence, is provided as SEQ ID NO. 20.

A bacterial clone identified as containing a DNA vector comprising the DNA cloning fragment was cultured in 100 mL of LB supplemented with 50 µg/mL kanamycin culture medium and grown overnight at 37° C. with shaking. Cells were pelleted by centrifugation at 4000 RPM for 15 minutes, culture medium was aspirated, and the DNA vector was purified using a QIAprep Spin Maxiprep Kit (Qiagen, Venlo, Netherlands) following the manufacturer's instructions. DNA vector yields were quantified using a Nanodrop™ 2000 UV-Vis spectrophotometer (Thermo Scientific, Wilmington, Del.).

The DNA vector was prepared to be used in Cas cleavage assay by linearization of the circular vector with an AscI Type II restriction endonuclease. To linearize the circular DNA vector, the following reaction mixture was assembled: 1 unit of AscI restriction endonuclease (New England Biolabs, Ipswich, Mass.) per 1 µg of circular DNA vector, and 1× CutSmart® buffer (New England Biolabs, Ipswich, Mass.) in a final volume of 50 µL. The reaction mixture was incubated for 1 hour at 37° C., and the reaction stopped by incubation at 80° C. for 20 minutes. Linear DNA vector was purified using the QIAquick PCR Purification Kit (Qiagen, Venlo, Netherlands) following the manufacturer's instructions. Linear DNA vector yields were quantified using a Nanodrop™ 2000 UV-Vis spectrophotometer (Thermo Scientific, Wilmington, Del.).

Other suitable cloning methods and DNA vectors can be used for the incorporation of double-stranded DNA target sequences following essentially the method described in this Example. If linearization of the DNA vector is undesirable or unnecessary, a circular DNA vector can be used in Cas cleavage assays.

Example 4

Production of Double-Stranded DNA Target Sequences for Use in Cleavage Assays Using PCR Double-stranded DNA target sequences for use in in vitro Cas protein cleavage assays can be produced using PCR amplification of selected nucleic acid target sequences from genomic human DNA.

Genomic human DNA comprising the Adeno-Associated Virus Integration Site 1 (AAVS-1) can be prepared by phenol-chloroform extraction from human cell line K562 (American Type Culture Collection (ATCC), Manassas, Va.). PCR reactions can be carried out with Q5 Hot Start High-Fidelity 2× Master Mix (New England Biolabs, Ipswich, Mass.) following the manufacturer's instructions. 20 ng/µL gDNA in a final volume of 25 µl can be used to amplify the selected nucleic acid target sequence under the following conditions: 98° C. for 2 minutes, 35 cycles of 20 seconds at 98° C., 20 seconds at 60° C., 20 seconds at 72° C., and a final extension at 72° C. for 2 minutes. PCR products can be purified using Spin Smart™ PCR purification tubes (Denville Scientific, South Plainfield, N.J.) and can be quantified using a Nanodrop™ 2000 UV-Vis spectrophotometer (Thermo Scientific, Wilmington, Del.).

Examples of forward and reverse primers that can be used for amplification of the AAVS-1 DNA target sequences from gDNA are presented in Table 13.

TABLE 13

AAVS-1 DNA Target Sequence Oligonucleotide Primers

| SEQ ID NO. | Sequence |
|---|---|
| SEQ ID NO. 23 | CCCCGTTCTCCTGTGGATTC |
| SEQ ID NO. 24 | ATCCTCTCTGGCTCCATCGT |

The AAVS-1 DNA target sequence can be amplified using SEQ ID NO. 23 and SEQ ID NO. 24 to produce a 495 bp double-stranded AAVS-1 DNA target sequence.

Other suitable double-stranded DNA target sequences can be obtained using essentially the same method by choosing suitable oligonucleotide primers. gDNA from the any organism (e.g., plant, bacteria, yeast, algae, and the like) can be used instead of DNA derived from human cells. Furthermore, DNA target sequences can be amplified via PCR from polynucleotides other than gDNA (e.g., vectors and gel isolated DNA fragments).

Example 5

Cas Cleavage Assays

This Example illustrates the use of a NASC polynucleotide compositions and a Cas9 protein in an in vitro assay to evaluate cleavage percentages of nucleic acid target sequences by the NASC polynucleotide compositions.

NASC-PC1 and NASC-PC2 comprised different first stem element nucleic acid sequences to limit formation of secondary structures within each NASC-PC that may interfere with the formation of stable secondary structure through hydrogen bond formation between the NASC-PC1 first stem element nucleic acid sequences and NASC-PC2 first stem element nucleic acid sequences complementary to the NASC-PC1 first stem element nucleic acid sequence.

The generic components of the NASC polynucleotide composition used in this Example were NASC-PC1 (Table 9, generic target sequence SEQ ID NO. 83) and NASC-PC2 (Table 9, generic target sequence SEQ ID NO. 84). The general structure of this NASC-P1/NASC-P2 pair is illustrated in FIG. 6G.

Ribonucleoprotein complexes of sgRNA/Cas9 protein and NASC-PC1/NASC-PC2/Cas9 protein were used in in vitro Cas9 cleavage assays to evaluate percent cleavage of each complex relative to the corresponding double-stranded DNA target sequences on a DNA vector.

The ribonucleoprotein complexes of sgRNA/Cas9 protein and NASC-PC1/NASC-PC2/Cas9 used the sgRNA and NASC-PC1/NASC-P2 constructs set forth in Example 2 Table 11. Target 1 (AAVST1) corresponded to a human AAVS-1 target sequence. Target 2 (VT2), Target 3 (VT3) and Target 4 (VT4) were DNA target sequences present in the vector sequence (SEQ ID NO. 20). In a cleavage reaction with only a single sgRNA or single NASC polynucleotide component, the linearized vector was used. In a cleavage reaction with two sgRNAs or NASC-PC1/NASC-PC2 components, the circular vector was used. Cleavage of the linear plasmid with a sgRNA yielded two DNA fragments, cleavage of the circular plasmid with two sgRNA or NASC-PC1/NASC-PC2 components yielded two DNA target fragments. The size of the double-stranded DNA target sequences and the sizes of the predicted cleavage fragments are presented in Table 14.

TABLE 14

Target and Cleavage Fragment Sizes

| Target | DNA target vector | Fragment 1 (bp) | Fragment 2 (bp) |
|---|---|---|---|
| AAVST1 | Linear | 1706 | 2469 |
| VT2 | Linear | 1769 | 2406 |
| VT3 | Linear | 3214 | 961 |
| VT4 | Linear | 350 | 3825 |
| AAVST1/VT3 | Circular | 1509 | 2666 |
| AAVST1/VT4 | Circular | 1357 | 2818 |
| VT2/VT3 | Circular | 1446 | 2729 |
| VT2/VT4 | Circular | 1420 | 2755 |

The sgRNA and NASC-PC1/NASC-PC2 components were diluted to a suitable working concentration. sgRNA and NASC-PC components were aliquoted into separate tubes to a final concentration of 50 nM. Pairs of sgRNAs and NASC-PC1/NASC-PC2 components were aliquoted into separate tubes to a final concentration of 50 nM for each component. All RNAs were incubated for 2 minutes at 95° C., removed from thermocycler, and allowed to equilibrate to room temperature. The combinations of the sgRNA and NASC-PC1/NASC-PC2 components that were used in cleavage reactions are presented in Table 15.

TABLE 15 sgRNA and NASC-PC1/NASC-PC2 Reaction Mixture Components

| Reaction | RNA-1 type | SEQ ID NO. | RNA-2 type | SEQ ID NO. |
|---|---|---|---|---|
| 1 | sgRNA-1-AAVST1 | SEQ ID NO. 25 | — | — |
| 2 | sgRNA-1-VT2 | SEQ ID NO. 26 | — | — |
| 3 | sgRNA-1-VT3 | SEQ ID NO. 27 | — | — |
| 4 | sgRNA-1-VT4 | SEQ ID NO. 28 | — | — |
| 5 | sgRNA-2-AAVST1 | SEQ ID NO. 29 | — | — |
| 6 | sgRNA-2-VT2 | SEQ ID NO. 30 | — | — |
| 7 | sgRNA-2-VT3 | SEQ ID NO. 31 | — | — |
| 8 | sgRNA-2-VT4 | SEQ ID NO. 32 | — | — |
| 9 | NASC-PC1-AAVST1 | SEQ ID NO. 33 | — | — |
| 10 | NASC-PC1-VT2 | SEQ ID NO. 34 | — | — |
| 11 | NASC-PC1-VT3 | SEQ ID NO. 35 | — | — |
| 12 | NASC-PC1-VT4 | SEQ ID NO. 36 | — | — |
| 13 | NASC-PC2-AAVST1 | SEQ ID NO. 37 | — | — |
| 14 | NASC-PC2-VT2 | SEQ ID NO. 38 | — | — |
| 15 | NASC-PC2-VT3 | SEQ ID NO. 39 | — | — |
| 16 | NASC-PC2-VST4 | SEQ ID NO. 40 | — | — |

TABLE 15-continued sgRNA and NASC-PC1/NASC-PC2 Reaction Mixture Components

| Reaction | RNA-1 type | SEQ ID NO. | RNA-2 type | SEQ ID NO. |
|---|---|---|---|---|
| 17 | sgRNA-1-AAVST1 | SEQ ID NO. 25 | sgRNA-2-VT3 | SEQ ID NO. 31 |
| 18 | NASC-PC1-AAVST1 | SEQ ID NO. 33 | NASC-PC2-VT3 | SEQ ID NO. 39 |
| 19 | sgRNA-1-AAVST1 | SEQ ID NO. 25 | sgRNA-2-VT4 | SEQ ID NO. 32 |
| 20 | NASC-PC1-AAVST1 | SEQ ID NO. 33 | NASC-PC2-VT4 | SEQ ID NO. 40 |
| 21 | sgRNA-1-VT2 | SEQ ID NO. 26 | sgRNA-2-VT3 | SEQ ID NO. 31 |
| 22 | NASC-PC1-VT2 | SEQ ID NO. 34 | NASC-PC2-VT3 | SEQ ID NO. 39 |
| 23 | sgRNA-1-VT2 | SEQ ID NO. 26 | sgRNA-2-VT4 | SEQ ID NO. 32 |
| 24 | NASC-PC1-VT2 | SEQ ID NO. 34 | NASC-PC2-VT4 | SEQ ID NO. 40 |

Each sgRNA reaction mixture component(s) and NASC-PC1/NASC-PC2 reaction mixture component(s) was added to a Cas9 reaction mix. S. pyogenes Cas9 protein was recombinantly expressed in E. coli and purified for use in the in vitro biochemical cleavage assay. The Cas9 reaction mixture comprised Cas9 protein diluted to a final concentration of 200 nM in reaction buffer (20 mM HEPES, 100 mM KCl, 5 mM $MgCl_2$, and 5% glycerol at pH 7.4). Each Cas9 reaction mixture was incubated at 37° C. for 10 minutes. Cleavage in each Cas9 reaction mixture was initiated by addition of the DNA target vector to a final concentration of 5 nM. Each Cas9 reaction mixture was mixed, centrifuged briefly, and incubated for 15 minutes at 37° C. The cleavage reaction was terminated by the addition of Proteinase K (Denville Scientific, South Plainfield, N.J.) at a final concentration of 0.2 µg/µL and 0.44 mg/µL RNase A Solution (SigmaAldrich, St. Louis, Mo.) to each Cas9 reaction mixture.

Each Cas9 reaction mixture was then incubated for 25 minutes at 37° C. and 25 minutes at 55° C. Each Cas9 reaction mixture was evaluated for cleavage activity using the Fragment Analyzer™ (Advanced Analytical Technologies, Ames, Iowa) System and the DNF-474-05000 High Sensitivity NGS Reagent Kit (Advanced Analytical Technologies, Ames, Iowa). The data from the Fragment Analyzer™ System provided the concentration of each cleavage fragment and of the DNA target vector that remained after cleavage for each Cas9 reaction mixture. For each Cas9 reaction mixture, percent cleavage was calculated by dividing the sum of the cleavage fragments by the sum of both the cleavage fragments and the DNA target vector that remained after cleavage.

Table 16 presents the cleavage data for each of the ribonucleoprotein complexes of sgRNA/Cas9 protein and NASC-PC1/NASC-PC2/Cas9.

TABLE 16

Biochemical Cleavage of DNA Target Sequences with sgRNA/Cas9 Protein Complexes and NASC-PC1/NASC-PC2/Cas9 Protein Complexes

| Reaction | SEQ ID NO. | RNA-1 type | SEQ ID NO. | RNA-2 type | Percent cleavage |
|---|---|---|---|---|---|
| 1 | SEQ ID NO. 25 | sgRNA-1-AAVST1 | — | — | 100% |
| 2 | SEQ ID NO. 29 | sgRNA-1-VT2 | — | — | 95% |
| 3 | SEQ ID NO. 26 | sgRNA-1-VT3 | — | — | 92% |
| 4 | SEQ ID NO. 30 | sgRNA-1-VT4 | — | — | 94% |
| 5 | SEQ ID NO. 27 | sgRNA-2-AAVST1 | — | — | 100% |
| 6 | SEQ ID NO. 31 | sgRNA-2-VT2 | — | — | 100% |
| 7 | SEQ ID NO. 28 | sgRNA-2-VT3 | — | — | 96% |
| 8 | SEQ ID NO. 32 | sgRNA-2-VT4 | — | — | 95% |
| 9 | SEQ ID NO. 33 | NASC-PC1-AAVST1 | — | — | LOD* |
| 10 | SEQ ID NO. 37 | NASC-PC1-VT2 | — | — | LOD |
| 11 | SEQ ID NO. 34 | NASC-PC1-VT3 | — | — | LOD |
| 12 | SEQ ID NO. 38 | NASC-PC1-VT4 | — | — | LOD |
| 13 | SEQ ID NO. 35 | NASC-PC2-AAVST1 | — | — | LOD |
| 14 | SEQ ID NO. 39 | NASC-PC2-VT2 | — | — | LOD |
| 15 | SEQ ID NO. 36 | NASC-PC2-VT3 | — | — | LOD |
| 16 | SEQ ID NO. 40 | NASC-PC2-VT4 | — | — | LOD |
| 17 | SEQ ID NO. 25 | sgRNA-1-AAVST1 | SEQ ID NO. 31 | sgRNA-2-VT3 | 88% |
| 18 | SEQ ID NO. 33 | NASC-PC1-AAVST1 | SEQ ID NO. 39 | NASC-PC2-VT3 | 89% |
| 19 | SEQ ID NO. 25 | sgRNA-1-AAVST1 | SEQ ID NO. 32 | sgRNA-2-VT4 | 91% |
| 20 | SEQ ID NO. 33 | NASC-PC1-AAVST1 | SEQ ID NO. 40 | NASC-PC2-VT4 | 92% |
| 21 | SEQ ID NO. 26 | sgRNA-1-VT2 | SEQ ID NO. 31 | sgRNA-2-VT3 | 81% |
| 22 | SEQ ID NO. 34 | NASC-PC1-VT2 | SEQ ID NO. 39 | NASC-PC2-VT3 | 86% |
| 23 | SEQ ID NO. 26 | sgRNA-1-VT2 | SEQ ID NO. 32 | sgRNA-2-VT4 | 94% |
| 24 | SEQ ID NO. 34 | NASC-PC1-VT2 | SEQ ID NO. 40 | NASC-PC2-VT4 | 96% |

*LOD indicates cleavage values below the limit of detection

The data presented in Table 16 demonstrates that each NASC-PC1/NASC-PC2/Cas9 protein complex of Reactions 18, 20, 22, and 24 (Table 16) facilitated Cas protein mediated site-specific cleavage of the two DNA target sequences corresponding to the two nucleic acid target binding sequences of the NASC-PC1/NASC-PC2/Cas9 protein complex. Furthermore, the percent of site-specific cleavage by each NASC-PC1/NASC-PC2/Cas9 protein complex was essentially equivalent to site-specific cleavage of the same two DNA target sequences by two sgRNA/Cas9 protein complexes, wherein one sgRNA/Cas9 protein complex targeted cleavage at a first DNA target sequence and a second sgRNA/Cas9 protein complex targeted cleavage at a second DNA target sequence (compare percent cleavage of reactions 17 with 18; 19 with 20; 21 with 22; and 23 with 24). The data presented in Table 16 also demonstrates each NASC-PC1 was required to be paired with a complementary NASC-PC2 in order to target site-specific cleavage by the associated Cas9 proteins (see Table 16, Reactions 9-16); that is, an individual polynucleotide component of a NASC polynucleotide composition was incapable of supporting Cas protein mediated site-specific cleavage.

Following the guidance of the present specification and Examples, the biochemical cleavage assay described in this Example can be practiced by one of ordinary skill in the art with other NASC polynucleotide compositions and cognate Cas proteins (e.g., Cas9 proteins and Cpf1 proteins).

Example 6

Deep Sequencing Analysis for Detection of Target Sequence Modifications in Eukaryotic Cells This Example illustrates the use of deep sequencing analysis to evaluate and compare the percent cleavage in cells using NASC polynucleotide composition/Cas protein complexes relative to selected double-stranded DNA target sequences.

A. Genome Target Sequence Selection

Two target nucleic acid sequences can be selected from exonic regions in the human genome (e.g., X-Ray Repair Cross Complementing 5 (XRCC5) gene sequence). Nucleic acid sequences twenty nucleotides in length that are 5' adjacent to PAM sequences (e.g., a *S. pyogenes* Cas9 PAM 5'—NGG) can be selected, for example, the XRCC5 target DNA sequences presented in Table 17.

TABLE 17

XRCC5 Target DNA Sequences

| Target name | Target sequence | hg38 chromosomal coordinate | SEQ ID NO. |
|---|---|---|---|
| XRCC5T1 | GGTGGACAAG CGGCAGATAG | chr2: 216109346- 216109365 | SEQ ID NO. 41 |
| XRCC5T3 | GCACCATGTT GCCGGTCCTC | chr2: 216109421- 216109440 | SEQ ID NO. 42 |

B. Construction of NASC Polynucleotide Compositions

A NASC polynucleotide composition comprising NASC-PC1 and NASC-PC2 can be used. Nucleic acid target binding sequences corresponding to XRCC5T1 can be incorporated at the 5' end of NASC-PC1, and nucleic acid target binding sequences corresponding to XRCC5T3 can be incorporated at the 5' end of NASC-PC2. As positive controls, a nucleic acid target binding sequence corresponding to XRCC5T1 can be incorporated at the 5' end of a sgRNA, and a nucleic acid target binding sequences corresponding to XRCC5T3 can be incorporated at the 5' end of a sgRNA. NASC-PC1, NASC-PC2, and sgRNAs can be produced as described in Example 2. Examples of sequences for NASC-PC1, NASC-PC2, and sgRNAs are given in Table 18.

TABLE 18 sgRNA and NASC Polynucleotide Component Sequences

| Component designation | RNA Type | RNA sequence* | SEQ ID NO. |
|---|---|---|---|
| sgRNA-XRCC5-T1 | sgRNA | GGUGGACAAGCGGCAGAUAGGUUU UAGAGCUAUGCUGUUUUGGAAACA AAACAGCAUAGCAAGUUAAAUAA GGCUAGUCCGUUAUCAACUUGAAA AAGUGGCACCGAGUCGGUGCUU | SEQ ID NO. 43 |
| sgRNA-XRCC5-T3 | sgRNA | GCACCAUGUUGCCGGUCCUCGUUU UAGAGCUAUGCUGUUUUGGAAACA AAACAGCAUAGCAAGUUAAAUAA GGCUAGUCCGUUAUCAACUUGAAA AAGUGGCACCGAGUCGGUGCUU | SEQ ID NO. 44 |
| NASC-PC1-XRCC5-T1 | NASC₁ | GGUGGACAAGCGGCAGAUAG<u>GUUU</u> <u>UAGAGCUAUGCUGUUUUGGAAACU</u> UUUCAGCACGAUAAGUUAUUAUAA GGCUAGUCCGUUAUCAACUUGAAA AAGUGGCACCGAGUCGGUGCUU | SEQ ID NO. 45 |
| NASC-PC2-XRCC5-T3 | NASC₁C | GCACCAUGUUGCCGGUCCUC<u>GUAA</u> <u>UAGAAUCGUGCUGAAAAGGAAACA</u> AAACAGCAUAGCAAGUUAAAUAA GGCUAGUCCGUUAUCAACUUGAAA AAGUGGCACCGAGUCGGUGCUU | SEQ ID NO. 46 |

*NASC-PC hybridizing regions are underlined

C. Formation of NASC/Cas9 Protein Nucleoprotein Complexes

*S. pyogenes* Cas9 can be C-terminally tagged with two nuclear localization sequences (NLS) and can be recombinantly expressed in *E. coli*, and purified using chromatographic methods. Ribonucleoprotein complexes can be formed at a concentration of 80 pmol Cas9 protein:120 pmol NASC-PC1:120 pmols NASC-PC2. Control sgRNA components can be individually assembled into ribonucleoprotein complexes with Cas9 protein in a similar manner. Prior to assembly with the Cas9 protein, NASC-PC1, NASC-PC2, and the sgRNAs can be diluted to the desired concentration (120 pmol) in a final volume of 2 μL, incubated for 2 minutes at 95° C., removed from the thermocycler, and allowed to equilibrate to room temperature. The Cas9 protein can be diluted to an appropriate concentration in binding buffer (20 mM HEPES, 100 mM KCl, 5 mM $MgCl_2$, and 5% glycerol at pH 7.4) to a final volume of 3 μL and can be mixed with the 2 μL of each NASC-PC1, NASC-PC2, and the sgRNAs followed by incubation at 37° C. for 30 minutes.

D. Cell Transfections Using the NASC/Cas9 Ribonucleoprotein Complexes

Ribonucleoprotein complexes can be transfected into HEK293 cells (ATCC, Manassas Va.), using the Nucleofector® 96-well Shuttle System (Lonza, Allendale, N.J.) following the manufacturer's protocol. Ribonucleoprotein complexes can be dispensed in a 5 μL final volume into individual wells of a 96-well plate, wherein the wells contain the HEK293 cells in culture medium. The cell culture medium can be removed from the wells of the plate and the cells can be detached with TrypLE™ enzyme (Thermo Scientific, Wilmington, Del.). Suspended HEK293 cells can be pelleted by centrifugation for 3 minutes at 200×g, TrypLE reagents can be aspirated, and cells can be washed with calcium and magnesium-free phosphate buffered saline (PBS). Cells can be pelleted by centrifugation for 3 minutes at 200×g the PBS aspirated and the cell pellet can be re-suspended in 10 mL of calcium and magnesium-free PBS.

The cells can be counted using the Countess® II Automated Cell Counter (Life Technologies, Grand Island, N.Y.). 2.2×10⁷ cells can be transferred to a 1.5 ml microfuge tube and pelleted. The PBS can be aspirated and the cells can be re-suspended in Nucleofector™ SF solution (Lonza, Allendale, N.J.) to a density of 1×10$^7$ cells/mL. 20 µL of the cell suspension can be added to each individual well containing 5 µL of ribonucleoprotein complexes, and the entire volume from each well can be transferred to a well of a 96-well Nucleocuvette™ Plate (Lonza, Allendale, N.J.). The plate can be loaded onto the Nucleofector™ 96-well Shuttle™ (Lonza, Allendale, N.J.) and cells can be nucleofected using the 96-CM-130 Nucleofector™ program (Lonza, Allendale, N.J.). Post-nucleofection, 70 µL Dulbecco's Modified Eagle Medium (DMEM; Thermo Scientific, Wilmington, Del.) supplemented with 10% Fetal Bovine Serum (FBS; Thermo Scientific, Wilmington, Del.), penicillin, and streptomycin (Life Technologies, Grand Island, N.Y.) can be added to each well and then 50 µL of the cell suspension can be transferred to a 96-well cell culture plate containing 150 µL pre-warmed DMEM complete culture medium. The plate can be then transferred to a tissue culture incubator and maintained at 37° C. in 5% CO$_2$ for 48 hours.

E. Double-stranded DNA Target Sequence Generation for Deep Sequencing gDNA can be isolated from the HEK293 cells 48 hours after transfection of the ribonucleoprotein complexes using 50 µL QuickExtract DNA Extraction solution (Epicentre, Madison, Wis.) per well, followed by incubation at 37° C. for 10 minutes, 65° C. for 6 minutes and 95° C. for 3 minutes to stop the reaction. The isolated gDNA can be diluted with 50 µL sterile water and samples can be stored at −80° C.

Using the isolated gDNA, a first PCR can be performed using Q5 Hot Start High-Fidelity 2× Master Mix (New England Biolabs, Ipswich, Mass.) at 1× concentration, primers at 0.5 µM each, 3.75 µL of gDNA in a final volume of 10 µL and amplified 98° C. for 1 minute, 35 cycles of 10 seconds at 98° C., 20 seconds at 60° C., 30 seconds at 72° C., and a final extension at 72° C. for 2 minutes. Primers can be designed to amplify either the XRCC5_T1 region (e.g., SEQ ID NO. 47 and SEQ ID NO. 48) or XRCC5_T3 (SEQ ID NO. 49 and SEQ ID NO. 50). gDNA prepped from the NASC-PC1/NASC-PC2/Cas9 nucleofected samples and the sgRNA/Ca9 nucleofected samples can be amplified with both primer pairs, separately, to assess editing of each target site by the ribonucleoproteins. Each PCR reaction can be diluted 1:100 in water.

A "barcoding" PCR can be set up using unique index primers for each sample to facilitate multiplex sequencing. Examples of such primer pairs are shown in Table 19.

TABLE 19

Barcoding Primers

| ID | Sample | Primer |
| --- | --- | --- |
| BARCODING PRIMER set-1 | XRCC5_T1-sgRNA | SEQ ID NO. 51, 52 |
| BARCODING PRIMER set-2 | XRCC5_T3-sgRNA | SEQ ID NO. 51, 53 |
| BARCODING PRIMER set-3 | XRCC5-T1 NASC-PC1 | SEQ ID NO. 51, 54 |
| BARCODING PRIMER set-4 | XRCC5-T13 NASC-PC1 | SEQ ID NO. 51, 55 |

The barcoding PCR can be performed using Q5 Hot Start High-Fidelity 2× Master Mix (New England Biolabs, Ipswich, Mass.) at 1× concentration, primers at 0.5 µM each (Table 19), 1 µL of 1:100 diluted first PCR, in a final volume of 10 µL, and can be amplified 98° C. for 1 minutes, 12 cycles of 10 seconds at 98° C., 20 seconds at 60° C., 30 seconds at 72° C., and a final extension at 72° C. for 2 minutes.

F. SPRIselect Clean-Up

All the barcoding PCR reactions can be pooled and transferred into a single microfuge ("amplicon library") tube for SPRIselect bead-based cleanup (Beckman Coulter, Pasadena, Calif.) of amplicons for sequencing.

To each tube, 0.9× volumes of SPRIselect beads can be added, mixed, and incubated at room temperature for 10 minutes. The microfuge tube can be placed on magnetic tube stand (Beckman Coulter, Pasadena, Calif.) until the solution clears. Supernatant can be removed and discarded, and the residual beads can be washed with 1 volume of 85% ethanol, and incubated at room temperature for 30 seconds. After incubation, ethanol can be aspirated and beads can be air dried at room temperature for 10 minutes. Each microfuge tube can be removed from the magnetic stand and 0.25× volumes of Qiagen EB buffer (Qiagen, Venlo, Netherlands) can be added to the beads, mixed vigorously, and incubated for 2 minutes at room temperature. Each microfuge tube can be returned to the magnet, incubated until the solution had cleared, and then the supernatant containing the purified amplicons can be dispensed into a clean microfuge tube. The purified amplicon library can be quantified using the Nanodrop™ 2000 System (Thermo Scientific, Wilmington, Del.) and library quality can be analyzed using the Fragment Analyzer™ System (Advanced Analytical Technologies, Ames, Iowa) and the DNF-910 Double-stranded DNA Reagent Kit (Advanced Analytical Technologies, Ames, Iowa).

G. Deep Sequencing Set-up

The pooled amplicon library can be normalized to a 4 nM concentration as calculated from quantified values and the average size of the amplicons. The amplicon library can be analyzed on MiSeq Sequencer (Illumina, San Diego, Calif.) with MiSeq Reagent Kit v2 (Illumina, San Diego, Calif.) for 300 cycles with two 151-cycle paired-end runs plus two eight-cycle index reads.

H. Deep Sequencing Data Analysis

The identities of products in the sequencing data can be determined based on the index barcode sequences adapted onto the amplicons in the barcoding PCR. A computational script can be used to process the MiSeq data that executes, for example, the following tasks:

Reads can be aligned to the human genome (build GRCh38/38) using Bowtie (bowtie-bio.sourceforge.net/index.shtml) software.

Aligned reads can be compared to the expected wild-type locus region (e.g., XRCC5_T1 or XRCC5_T3).

Locus sequence and reads not aligning to any part of the target locus can be discarded.

Reads matching wild-type target locus sequences can be tallied.

Reads with indels (insertion or deletion of bases) can be categorized by indel type and tallied.

Total indel reads can be divided by the sum of wild-type reads and indel reads to give percent-mutated reads.

Through the identification of indel sequences at the regions targeted by the NASC-PC1/NASC-PC2/Cas9 protein ribonucleoprotein complexes and the sgRNA/Cas9 protein ribonucleoprotein complexes, sequence-specific targeting of in a human cell line can be determined. Editing in NASC-PC1/NASC-PC2 samples can be compared to the editing efficiencies of sgRNA controls.

Following the guidance of the present specification and Examples, the in cell editing of a genomic sequence can be practiced by one of ordinary skill in the art with other Cas proteins and their cognate the NASC polynucleotide compositions.

Example 7

Identification and Screening of crRNAs

In this Example, a method is described through which crRNAs of species having a Class 2 CRISPR system can be identified. The method presented here is adapted from Chylinski, K., et al., RNA Biology 10(5):726-737 (2013). Not all of the following steps are required for screening nor must the order of the steps be as presented.

A. Identify a Species Containing a Class 2 CRISPR Locus

Using the Basic Local Alignment Search Tool (BLAST, blast.ncbi.nlm.nih.gov/Blast.cgi), a search of the genomes of various species can be conducted to identify Class 2 CRISPR Cas nucleases, (e.g., Cas9 protein, Cpf1 protein, Cas9-like proteins, Cpf1-like proteins, etc.). Class 2 CRISPR systems exhibit a high diversity in sequence across species, however Class 2 CRISPR nuclease orthologs have conserved domains, for example, an HNH endonuclease domain and/or a RuvC/RNase H domain. Primary BLAST results can be filtered for identified domains, incomplete or truncated sequences can be discarded, and species having Class 2 CRISPR nuclease orthologs can be identified.

If a Class 2 CRISPR nuclease ortholog can be identified in a species, sequences adjacent to the Cas protein ortholog coding sequence (e.g., a Cas9 protein or a Cpf1 protein) can be probed for other Cas proteins and an associated repeat-spacer array to identify all sequences belonging to the CRISPR-Cas locus. This may be done by alignment to other known Class 2 CRISPR loci.

Once the sequence of the Class 2 CRISPR locus for the nuclease ortholog can be identified for the species, in silico predictive screening can be used to extract the crRNA sequence. The crRNA sequence is contained within CRISPR repeat array and can be identified by its hallmark repeating sequences interspaced by foreign spacer sequences.

B. Preparation of RNA-Seq Library

The putative CRISPR array containing the individual crRNA identified in silico can be further validated using RNA sequencing (RNA-seq).

Cells from species identified as comprising putative crRNA can be procured from a commercial repository (e.g., ATCC, Manassas, Va.; German Collection of Microorganisms and Cell Cultures GmbH (DSMZ), Braunschweig, Germany).

Cells can be grown to mid-log phase and total RNA prepped using Trizol reagent (SigmaAldrich, St. Louis, Mo.) and treated with DNaseI (Fermentas, Vilnius, Lithuania).

10 µg of the total RNA can be treated with Ribo-Zero rRNA Removal Kit (Illumina, San Diego, Calif.) and the remaining RNA purified using RNA Clean and Concentrators (Zymo Research, Irvine, Calif.).

A library can be then prepared using a TruSeq Small RNA Library Preparation Kit (Illumina, San Diego, Calif.) following the manufacturer's instructions. This results in cDNAs having adapter sequences.

The resulting cDNA library can be sequenced using MiSeq Sequencer (Illumina, San Diego, Calif.).

C. Processing of Sequencing Data

Sequencing reads of the cDNA library can be processed, for example, using the following method.

Adapter sequences can be removed using cutadapt 1.1 (pypi.python.org/pypi/cutadapt/1.1) and about 15 nt can be trimmed from the 3' end of the read to improve read quality.

Reads can be aligned to the genome of the respective species (i.e., from which the putative crRNA was identified) using Bowtie 2 (http://bowtie-bio.sourceforge.net/bowtie2/index.shtml).

The Sequence Alignment/Map (SAM) file, generated by Bowtie 2, can be converted into a Binary Alignment/Map (BAM) file using SAMTools (samtools.sourceforge.net/) for subsequent sequencing analysis steps.

Read coverage mapping to the CRISPR locus or loci, can be calculated from the BAM file using BedTools (bedtools.readthedocs.org/en/latest/).

The BED file, generated in the previous step, can be loaded into Integrative Genomics Viewer (IGV; www.broadinstitute.org/igv/) to visualize the sequencing read pileup. Read pile-ups can be used to identify the 5' and 3' ends of the transcribed putative crRNA sequence.

The RNA-seq data can be used to validate that a putative crRNA element sequence is actively transcribed in vivo. Confirmed hits from comparison of the in silico and RNA-seq screens can be validated for functional ability to support Class 2 CRISPR nuclease cleavage of a double-stranded DNA target nucleic acid sequences using the methods outline herein (e.g., Examples 2, 3, and 5). It is known in the art that Class 2 Type V CRISPR systems only requires a crRNA to facilitate Cpf1 nuclease cleavage of a double-stranded DNA target sequence, whereas Class 2 Type II CRISPR systems require a crRNA and a cognate tracrRNA to facilitate Cas9 nuclease cleavage of a double-stranded DNA target sequence.

Following the guidance of the present specification and Examples, the identification of crRNA sequences associated with Cas9 proteins can be practiced by one of ordinary skill in the art.

Example 8

Identification and Screening of tracrRNAs

This Example illustrates a method by which tracrRNAs of species having, for example, a Class 2 Type II CRISPR-Cas9 system can be identified. This is adapted from Chylinski, K., et al., RNA Biology 10(5):726-737 (2013). Not all of the following steps are required for screening nor must the order of the steps be as presented.

A. Identify a Species Containing a CRISPR-Cas9 Type-II System

Using the Basic Local Alignment Search Tool (BLAST, blast.ncbi.nlm.nih.gov/Blast.cgi), a search of the genomes of various species can be conducted to identify a Cas9 protein. Class 2 Type II CRISPR-Cas9 systems exhibit a high diversity in sequence across species, however Cas9 orthologs exhibit conserved domain architectures of a central HNH endonuclease domain and a split RuvC/RNase domain. Primary BLAST results can be filtered for identified domains; incomplete or truncated sequences can be discarded and Cas9 orthologs can be identified.

If a Cas9 ortholog can be identified in a species, sequences adjacent to the Cas9 ortholog-coding sequence can be probed for other Cas proteins and a Cas-associated repeat-spacer array to identify all sequences belonging to the CRISPR-Cas9 locus. This may be done by alignment to other known Class 2 Type II CRISPR-Cas9 loci, with the knowledge that closely related species exhibit similar CRISPR-Cas9 locus architecture (e.g., Cas protein composition, size, orientation, location of array, location of tracrRNA, etc.). The tracrRNA element is typically contained within the Class 2 Type II CRISPR-Cas9 locus and can be readily identified by its sequence complementarity to the repeat elements in the repeat-spacer array. The tracr sequences complementary to the repeat elements are called the tracr anti-repeat sequences.

Once the sequence of the CRISPR-Cas9 locus corresponding to the Cas9 ortholog is identified for a species, in silico predictive screening can be used to extract the tracr anti-repeat sequence to identify the Cas-associated tracrRNA. Putative anti-repeats can be screened, for example, as follows.

If the repeat sequence is from a known species, the repeat sequence can be identified in and retrieved from the CRISPRdb database (crispr.u-psud.fr/crispr/). If the repeat sequence is not from a known species, the repeat sequence can be predicted employing CRISPRfinder software (crispr.u-psud.fr/Server/) using the Class 2 Type II CRISPR-Cas9 locus for the species as described above.

The identified repeat sequence for the species can be used to probe the CRISPR-Cas9 locus for the anti-repeat sequence (e.g., using the BLASTp algorithm or the like). The search is typically restricted to intergenic regions of the CRISPR-Cas9 locus.

An identified tracr anti-repeat region can be validated for complementarity to the identified repeat sequence.

A putative anti-repeat region can be probed in the regions 5' and 3' of the putative anti-repeat region for the presence of a Rho-independent transcriptional terminator (TransTerm HP, transterm.cbcb.umd.edu/).

By combining the identified sequence comprising the anti-repeat element and the Rho-independent transcriptional terminator the sequence can be determined to be the putative tracrRNA of the given species.

B. Preparation of RNA-Seq Library

The in silico identified, putative tracrRNA can be further validated using RNA sequencing (RNA-seq).

Cells from species comprising the putative tracrRNA can be procured from a commercial repository (e.g., ATCC, Manassas Va.; DSMZ, Braunschweig, Germany).

Cells can be grown to mid-log phase and total RNA prepared using Trizol reagent (SigmaAldrich, St. Louis, Mo.) and treated with DNaseI (Fermentas, Vilnius, Lithuania).

10 µg of the total RNA can be treated using a Ribo-Zero rRNA Removal Kit (Illumina, San Diego, Calif.) and the remaining RNA purified using RNA Clean and Concentrators (Zymo Research, Irvine, Calif.).

A library can be prepared using a TruSeq Small RNA Library Preparation Kit (Illumina, San Diego, Calif.) following the manufacturer's instructions. This results in cDNAs having adapter sequences.

The resulting cDNA library can be sequenced using a MiSeq Sequencer (Illumina, San Diego, Calif.).

C. Processing of Sequencing Data

Sequencing reads of the cDNA library can be processed, for example, using the following method.

Adapter sequences can be removed using cutadapt 1.1 (pypi.python.org/pypi/cutadapt/1.1) and about 15 nt can be trimmed from the 3'end of the read to improve read quality.

Reads can be aligned to the genome of the respective species (i.e., from which the putative crRNA was identified) using Bowtie 2 (http://bowtie-bio.sourceforge.net/bowtie2/index.shtml).

The Sequence Alignment/Map (SAM) file generated by Bowtie 2 can be converted into a Binary Alignment/Map (BAM) file using SAMTools (http://samtools.sourceforge.net/) for subsequent sequencing analysis steps.

Read coverage mapping to the CRISPR locus or loci can be calculated from the BAM file using BedTools (bedtools.readthedocs.org/en/latest/).

The BED file, generated in the previous step, can be loaded into Integrative Genomics Viewer (IGV; www.broadinstitute.org/igv/) to visualize the sequencing read pileup. Read pile-ups can be used to identify the 5' and 3' ends of the transcribed putative tracrRNA sequence.

The RNA-seq data can be used to validate that a putative tracrRNA element sequence is actively transcribed in vivo. Confirmed hits from the comparison of the in silico and RNA-seq screens can be validated for functional ability of the identified tracrRNA sequence and its cognate crRNA to support Cas9-mediated cleavage of a double-stranded DNA target sequence using methods outline herein (e.g., Examples 2, 3, and 5).

Following the guidance of the present specification and Examples, the identification of tracrRNA sequences related to Cas9 proteins can be accomplished by one of ordinary skill in the art.

Example 9

T7E1 Assay for Detection of Target Sequence Modifications in Eukaryotic Cells

This Example illustrates the use of T7E1 assays to evaluate and compare the percent cleavage in vivo of NASC/Cas9 protein complexes (e.g., NASC-PC1/NASC-PC2/Cas9 protein complexes) relative to selected double-stranded DNA target sequences.

A. Cell Transfections Using Cas Polynucleotide Components

NASC-PC1 and NASC-PC2 can be transfected into HEK293 cells constitutively expressing *S. pyogenes* Cas9 (HEK293-Cas9), using the Nucleofector® 96-well Shuttle System (Lonza, Allendale, N.J.) and the following protocol. NASC-PC1 and NASC-PC2 can be individually diluted to appropriate concentration (e.g., 120 pmol), mixed together, incubated for 2 minutes at 95° C., removed from the thermocycler, allowed to equilibrate to room temperature, and dispensed in a 5 µL final volume in a 96-well plate. Culture medium can be aspirated from HEK293-Cas9 cells, the cells can be washed once with calcium and magnesium-free PBS, and can be trypsinized by the addition of TrypLE (Life Technologies, Grand Island, N.Y.) followed by incubation at 37° C. for 3-5 minutes. Trypsinized cells can be gently pipetted up and down to form a single-cell suspension and added to DMEM complete culture medium composed of DMEM culture medium (Life Technologies, Grand Island, N.Y.) containing 10% Fetal Bovine Serum (FBS; Thermo Scientific, Wilmington, Del.) and supplemented with penicillin and streptomycin (Life Technologies, Grand Island, N.Y.).

The cells can be pelleted by centrifugation for 3 minutes at 200×g, the culture medium can be aspirated, and cells can be re-suspended in PBS. The cells can be counted using the Countess® II Automated Cell Counter (Life Technologies, Grand Island, N.Y.). $2.2 \times 10^7$ cells can be transferred to a 1.5 ml microfuge tube and pelleted. The PBS can be aspirated and the cells can be re-suspended in Nucleofector™ SF (Lonza, Allendale, N.J.) solution to a density of $1 \times 10^7$ cells/mL. 20 µL of the cell suspension can be added to individual wells containing 5 µL of NASC-PC1/NASC-PC2 and the entire volume can be transferred to the wells of a 96-well Nucleocuvette™ Plate (Lonza, Allendale, N.J.). The plate can be loaded onto the Nucleofector™ 96-well Shuttle™ (Lonza, Allendale, N.J.) and cells can be nucleofected using the 96-CM-130 Nucleofector™ program (Lonza, Allendale, N.J.). Post-nucleofection, 70 µL DMEM complete culture medium can be added to each well, and 50 µL of the cell suspension can be transferred to a collagen coated 96-well cell culture plate containing 150 µL prewarmed DMEM complete culture medium. The plate can be transferred to a tissue culture incubator and maintained at 37° C. in 5% $CO_2$ for 48 hours.

B. Double-stranded DNA Target Sequence Generation for T7E1 Assay gDNA can be isolated from HEK293-Cas9 cells 48 hours after transfection with NASC-PC1/NASC-PC2 using 50 µL QuickExtract DNA Extraction solution (Epicentre, Madison, Wis.) per well followed by incubation at 37° C. for 10 minutes, 65° C. for 6 minutes and 95° C. for 3 minutes to stop the reaction. gDNA can be diluted with 150 µL water and samples can be stored at −80° C.

DNA for T7E1 can be generated by PCR amplification of double-stranded DNA target sequences (e.g., XRCC5_T1 and XRCC5_T3) from isolated gDNA. PCR reactions can be set up using 8 µL gDNA as template with KAPA HiFi Hot Start polymerase and contain 0.5 U of polymerase, 1× reaction buffer, 0.4 mM dNTPs and 300 nM forward and reverse primers directed to one of the double-stranded DNA target sequences (e.g., SEQ ID NO. 47/SEQ ID NO. 48 and SEQ ID NO. 49/SEQ ID NO. 50) in a total volume of 25 µL. The DNA target sequences can be amplified using the following conditions; 95° C. for 5 minutes, 4 cycles of 20 seconds at 98° C., 20 seconds at 70° C., minus 2° C./cycle, 30 seconds at 72° C., followed by 30 cycles of 15 seconds at 98° C., 20 seconds at 62° C., 20 seconds at 72° C., and a final extension at 72° C. for 1 minute.

C. T7E1 Assay

PCR-amplified double-stranded DNA target sequences for T7E1 assays can be denatured at 95° C. for 10 minutes and then allowed to re-anneal by cooling to 25° C. at −0.5° C./second in a thermal cycler. The re-annealed DNA can be incubated with 0.5 µL T7 Endonuclease I in 1× NEBuffer 2 buffer (New England Biolabs, Ipswich, Mass.) in a total volume of 15 µL for 25 minutes at 37° C. T7E1 reactions can be analyzed using the Fragment Analyzer™ System (Advanced Analytical Technologies, Ames, Iowa) and the DNF-910 Double-stranded DNA Reagent Kit (Advanced Analytical Technologies, Ames, Iowa). The Fragment Analyzer™ System provides the concentration of each cleavage fragment and of the double-stranded DNA target sequence that remains after cleavage.

Cleavage percentages of the double-stranded DNA target sequences can be calculated from the concentration of each cleavage fragment and the double-stranded DNA target sequence that remains after cleavage has taken place, using the following formula:

$$\% \text{ cleavage} \approx \left(1 - \sqrt{\left(1 - \frac{(frag1 + frag2)}{(frag1 + frag2 + \text{parent})}\right)}\right) \quad \text{EQUATION 1}$$

In Equation 1, frag1 and frag2 concentrations correspond to the concentration of Cas9 cleavage fragments of the double-stranded DNA target sequence and parent corresponds to the double-stranded DNA target sequence that remains after cleavage has taken place.

The T7E1 assay for detection of target sequence modifications in eukaryotic cells provides data to demonstrate that the NASC polynucleotide compositions described herein facilitate Cas9-mediated site-specific in vivo cleavage of multiple double-stranded DNA target sequences. sgRNA, crRNA, and/or crRNA/tracrRNA polynucleotides having the same DNA target binding sequence as the NASC polynucleotide composition can also be included in the assay to compare the Cas-mediated site-specific cleavage percentages between the constructs.

Following the guidance of the present specification and Examples, the T7E1 assay described in this Example can be practiced by one of ordinary skill in the art with other Cas proteins and their cognate NASC polynucleotide compositions.

Example 10

Probing for Sites Tolerant of Modification in Class 2 Type V Cpf1 Guide RNA Backbones This Example describes the generation and testing of various modifications of Class 2 Type V guide crRNAs and their suitability for use in constructing NASC polynucleotide components. The method described below is adapted from Briner, A., et al., Molecular Cell 56(2):333-339 (2014). Not all of the following steps are required for screening nor must the order of the steps be as presented.

In this Example, modifications can be introduced into the crRNA backbone, and the modified crRNA tested with a cognate Cpf1 nuclease to facilitate identification of regions or positions in the Cpf1-crRNA backbone wherein linkages for NASC polynucleotide components can be engineered.

A crRNA from a Class 2 Type V CRISPR system (e.g., *Acidaminococcus* sp. Cpf1) can be selected for engineering. The crRNA sequence can be modified in silico to introduce one or more base substitutions, deletions, or insertions into nucleic acid sequences in regions selected from one or more of the following regions: nucleic acid sequences 5' of the pseudo-knot, Cpf1-stem RNA sequence 1, the pseudo-knot loop (loop element nucleic acid sequence), Cpf1-stem RNA sequence 1C, or the spacer element.

The crRNA sequence can be modified in silico to introduce one or more break in the phosphodiester backbone in one or more regions selected from the following: nucleic acid sequences 5' of the pseudo-knot, Cpf1-stem RNA sequence 1, the pseudo-knot loop (loop element nucleic acid sequence), Cpf1-stem RNA sequence 1C, or the spacer element.

Base modification can also be used to introduce mismatches in the hydrogen base-pair interactions of any of the crRNA regions, or base-pair mutation introducing an alternative hydrogen base-pair interaction through substitution of two bases, wherein the alternative hydrogen base-pair interaction differs from the original hydrogen base-pair interaction (e.g., the original hydrogen base-pair interaction is Watson-Crick base pairing and the substitution of the two bases form a reverse Hoogsteen base pairing). Substitution of bases can also be used to introduce hydrogen base-pair interaction within the crRNA backbone (e.g., within the pseudo-knot loop sequence).

Regions of the crRNA can be independently engineered to introduce secondary structure elements into the crRNA backbone. Such secondary structure elements include, but are not limited to, the following: stem-loop elements, stem elements, pseudo-knots, and ribozymes. Furthermore, the crRNA guide RNA backbone can be modified to delete portions of the crRNA backbone either through deletion at the 5' end, 3' end or internal to the crRNA. Alternative backbone structures can also be introduced.

In silico designed crRNA sequences can be provided to a commercial manufacturer for synthesis.

Modified crRNAs can be evaluated for their ability to support cleavage of a double-stranded DNA target sequence mediated by the cognate Cpf1 protein to the crRNA that gave rise to the modified crRNA. Amplification of double-stranded DNA target sequences and the biochemical cleavage assay can be carried out in a manner similar to those described in Example 4 and Example 5, respectively. Modified crRNA that are capable of mediating cleavage of a DNA target sequence with their cognate Cpf1 proteins can be validated for activity in cells using the method described in Example 6.

Following the guidance of the present specification and Examples, the modification of a Cpf1 crRNA (e.g., introduction or deletion of various sequences, and/or introduction or deletion of secondary structural modifications) can be used to probe for locations for insertion or linkages to facilitate making NASC polynucleotide compositions. This Example can be practiced by one of ordinary skill in the art with other Type V CRISPR Cpf1 proteins and other Type V CRISPR crRNA in view of the teachings of the present specification.

Example 11

Probing for Sites Tolerant of Modification in Class 2 Type II Cas9 Guide RNA Backbones This Example describes the generation and testing of various modifications of Class 2 Type II guide RNA(s) and their suitability for use in constructing NASC polynucleotide compositions.

In this Example, modifications can be introduced into the RNA backbone of Class 2 Type II CRISPR guide RNA(s) (e.g., dual-guide RNAs or single-guide RNAs) to identify locations for engineering or attachment of various nucleic acid sequences. The method described below is adapted from Briner, A., et al., Molecular Cell 56(2):333-339 (2014). Not all of the following steps are required for screening nor must the order of the steps be as presented.

A Class 2 Type II CRISPR sgRNA, crRNA, tracrRNA, or crRNA and tracrRNA (collectively referred to a "Cas9 guide RNA") can be selected for engineering.

The Cas9 guide RNA sequence can be modified in silico to introduce one or more base substitutions, deletions, or insertions into regions selected from one or more of the following: a nucleic acid target binding sequence, a lower stem nucleic acid sequence, a bulge nucleic acid sequence, an upper stem nucleic acid sequence, a first stem-loop element nucleic acid sequence, a nexus nucleic acid sequence, a linking nucleic acid sequence, and/or 3' hairpins. The Cas9 guide RNA sequence can be modified in silico to introduce one or more breaks in the phosphodiester backbone in one or more regions selected from the following: a nucleic acid target binding sequence, a lower stem nucleic acid sequence, a bulge nucleic acid sequence, an upper stem nucleic acid sequence, a first stem-loop element nucleic acid sequence, a nexus nucleic acid sequence, a linking nucleic acid sequence, and 3' hairpins.

Base modification can be used to introduce mismatches in the hydrogen base-pair interactions of any of the Cas9 guide RNA regions. Base-pair mutation can be used to introduce an alternative hydrogen base-pair interaction through substitution of two bases, wherein the alternative hydrogen base-pair interaction differs from the original hydrogen base-pair interaction (e.g., the original hydrogen base-pair interaction is Watson-Crick base pairing and the substitution of the two bases form a reverse Hoogsteen base pairing). Substitution of bases can also be used to introduce hydrogen base-pair interaction within the Cas9 guide RNA backbone (e.g., within the bulge sequence).

Regions of the Cas9 guide RNA can be independently engineered to introduce secondary structure elements into the Cas9 guide RNA backbone. Such secondary structure elements include, but are not limited to, the following: stem-loop elements, stem elements, pseudo-knots, and ribozymes. Furthermore, the Cas9 guide RNA backbone can be modified to delete portions of the Cas9 guide RNA backbone through deletion at the 5' end, 3' end, and/or or internal to the Cas9 guide RNA. Alternative backbone structures can also be introduced.

In silico designed Class 2 Type II CRISPR Cas9 guide RNA sequences can be provided to a commercial manufacturer for synthesis.

Modified Class 2 Type II CRISPR Cas9 guide RNAs can be evaluated for ability to support cleavage of a double-stranded DNA target sequence mediated by the cognate Cas9 protein to the Cas9 guide RNA that gave rise to the modified Cas9 guide RNA. Amplification of a double-stranded DNA target sequences and the biochemical cleavage assay can be carried out in a manner similar to those described in Example 4 and Example 5, respectively. Modified Cas9 guide RNAs capable of mediating cleavage of a DNA target sequence with their cognate Cas9 proteins can be validated for activity in cells using the method described in Example 6.

Following the guidance of the present specification and Examples, the modification of a Cas9 guide RNA(s) (e.g., introduction or deletion of various sequences, and/or introduction or deletion of secondary structural modifications) can be used to probe for locations for insertion or linkages to facilitate making NASC polynucleotide compositions. This Example can be practiced by one of ordinary skill in the art with other Type II CRISPR Cas9 proteins and other Type II CRISPR Cas9 guide RNA in view of the teachings of the present specification.

Example 12

Screening of NASC Polynucleotide Compositions Comprising DNA Target Binding Sequences This Example illustrates the use of NASC polynucleotide compositions of the present invention to modify DNA target sequences present in human gDNA and measure the level of cleavage activity at those sites.

Target sites (DNA target sequences) can be first selected from gDNA. Individual components of NASC polynucleotide compositions can be designed to target the selected sequences. Assays (e.g., as described in Example 5) can be performed to determine the level of DNA target sequence cleavage.

Not all of the following steps are required for every screening nor must the order of the steps be as presented, and the screening can be coupled to other experiments, or form part of a larger experiment.

A. Selecting DNA Target Regions (DNA Target Sequences) from gDNA

PAM sequences (i.e., NGG, TTN, etc.) for a Cas protein (e.g., *S. pyogenes* Cas9 or *Acidaminococcus* sp. Cpf1) can be identified within the selected genomic region.

One or more Cas9 DNA target sequences (20 nucleotides in length) that are 5' adjacent to a PAM sequence can be identified and selected or one or more Cpf1 DNA target sequences (20-24 nucleotide in length) that are 3' adjacent to a PAM sequence can be identified and selected.

Criteria for selection of nucleic acid target sequences can include, but are not limited to, the following: homology to other regions in the genome, percent G-C content, melting temperature, presences of homopolymer within the spacer, distance between the two sequences, and other criteria known to one skilled in the art.

If a Type II CRISPR NASC polynucleotide composition is desired to be used, the DNA target binding sequence can be incorporated at the 5' end. If a Type V CRISPR NASC polynucleotide composition is desired to be used, the DNA target binding sequence can be incorporated at the 3' end. A commercial manufacturer typically synthesizes NASC polynucleotide compositions based on provided sequences. Alternatively, the NASC polynucleotide compositions can be produced as described in Example 2 by in vitro transcription.

NASC polynucleotide compositions as described herein can be used with cognate Class 2 Type II CRISPR nuclease (e.g., a Cas9 nuclease), a Class 2 Type V CRISPR nuclease (e.g., a Cpf1 nuclease), or both a cognate Class 2 Type II CRISPR nuclease and a Class 2 Type V CRISPR nuclease to form NASC/Cas protein complexes.

B. Determination of Cleavage Percentages and Specificity

In vitro cleavage percentages and specificity (e.g., the amount of off-target binding) related to NASC polynucleotide compositions can be determined, for example, using the cleavage assays described in Example 5 and can be compared as follows:

(1) If only a single pair of DNA target sequences can be identified or selected for a NASC, the cleavage percentage and specificity for each of the DNA target sequences can be determined. If so desired, cleavage percentage and/or specificity can be altered in further experiments using methods including, but not limited to, modifying the NASC; or introducing effector proteins/effector protein-binding sequences to modify the NASC, a NASC polynucleotide component, or the Cas protein; or introducing ligand/ligand binding moieties to modify the NASC polynucleotide or the Cas protein.

(2) If multiple pairs of DNA target sequences can be identified or selected for a NASC, the percentage cleavage data and site-specificity data obtained from the cleavage assays can be compared between different DNAs comprising the target binding sequence to identify the DNA target sequences having the desired cleavage percentage and specificity. Cleavage percentage data and specificity data provide criteria on which to base choices for a variety of applications. For example, in some situations the activity of the NASC polynucleotide composition may be the most important factor. In other situations, the specificity of the cleavage site may be relatively more important than the cleavage percentage. If so desired, cleavage percentage and/or specificity can be altered in further experiments using methods including, but not limited to, modifying the NASC; or introducing effector proteins/effector protein-binding sequences to modify the NASC, a NASC polynucleotide component, or the Cas protein; or introducing ligand/ligand binding moieties to modify the NASC polynucleotide component or the Cas protein.

Alternatively, or in addition to the in vitro analysis, in cell cleavage percentages and specificities associated with NASC polynucleotide compositions can be obtained using, for example, the method described in Example 6, can be compared as follows:

(1) If only a single pair of DNA target sequences can be identified or selected for a NASC, the cleavage percentage and specificity for each of the DNA target sequences can be determined. If so desired, cleavage percentage and/or specificity can be altered in further experiments using methods including, but not limited to, modifying the NASC; or introducing effector proteins/effector protein-binding sequences to modify the NASC, a NASC polynucleotide component, or the Cas protein; or introducing ligand/ligand binding moieties to modify the NASC polynucleotide component or the Cas protein.

(2) If multiple pairs of DNA target sequences can be identified or selected for a NASC, the percentage cleavage data and site-specificity data obtained from the cleavage assays can be compared between different DNAs comprising the target binding sequence to identify the DNA target sequences having the desired cleavage percentage and specificity. Cleavage percentage data and specificity data provide criteria on which to base choices for a variety of applications. For example, in some situations the activity of the NASC polynucleotide composition may be the most important factor. In other situations, the specificity of the cleavage site may be relatively more important than the cleavage percentage. If so desired, cleavage percentage and/or specificity can be altered in further experiments using methods including, but not limited to, modifying the NASC; or introducing effector proteins/effector protein-binding sequences to modify the NASC, a NASC polynucleotide component, or the Cas protein; or introducing ligand/ligand binding moieties to modify the NASC polynucleotide component or the Cas protein.

Following the guidance of the present specification and Examples, the screening described in this Example can be practiced by one of ordinary skill in the art with other NASC polynucleotide compositions for use with cognate Class 2 Type II CRISPR Cas9 proteins, cognate Class 2 Type V CRISPR Cpf1 proteins, or both cognate Class 2 Type II CRISPR Cas9 proteins and cognate Class 2 Type V CRISPR Cpf1 proteins.

Example 13

Engineering of Ribonucleoprotein Closed-Cage Complexes Comprising NASC Polynucleotide Compositions This Example illustrates the use of NASC polynucleotide compositions of the present invention for formation of NASC-CC closed-cage complexes for packaging of small molecules.

A NASC-CC can be engineered, for example, using a first NASC polynucleotide composition and a second NASC polynucleotide composition, each having the general structure shown in FIG. 6H (FIG. 6H, I, NASC-PC1; FIG. 6H, II, NASC-PC2; and FIG. 6H, III, NASC-PC-3). The first NASC polynucleotide composition and the second NASC polynucleotide composition can be used in combination with three double-stranded DNA sequences. Each double-stranded DNA sequence ("a double-stranded DNA brace sequence") can comprise two unique DNA target sequences, wherein the first DNA target sequence is complementary to a first nucleic acid binding sequence of the first NASC polynucleotide composition, and the second DNA target sequence is complementary to a second nucleic acid binding sequence of the second NASC polynucleotide composition.

NASC-CC and associated Cas proteins can be used to create closed-cage complexes suitable for the packaging of molecules. The size of the cage can be varied by changing the design of the NASC-CC components or by binding different length DNA target sequences.

A. Design of NASC-CC Components

A first NASC polynucleotide composition (referred to in this Example as a "NASC-triplex1") can be engineered comprising a NASC-PC1, a NASC-PC2, and a NASC-PC3, which are similar in structure to those depicted in FIG. 6A (referred to in this Example as a "NASC-PC1-triplex1," a "NASC-PC2-triplex1," and a "NASC-PC3-triplex1"). A first 20-nucleotide DNA target sequence can be added to the 5' end (see, e.g., FIG. 6A, 610-611) of each of NASC-PC1-triplex1, NASC-PC2-triplex1, and NASC-PC3-triplex1. The DNA target sequence typically will be selected to have no or limited homology to native DNA sequences in an organism into which the NASC-CC are to be introduced (e.g., human gDNA or plant gDNA).

A second NASC polynucleotide composition (referred to in this Example as "NASC-triplex2") can be engineered comprising a NASC-PC1-triplex2, a NASC-PC2-triplex2, and a NASC-PC3-triplex2, which are similar in structure to those depicted in FIG. 6A. A second 20-nucleotide DNA target sequence can be added to the 5' end (see, e.g., FIG. 6A, 610-611) of each of NASC-PC1-triplex2, NASC-PC2-triplex2, and NASC-PC3-triplex2. The DNA target sequence typically will be selected to have no or limited homology to native DNA sequences in an organism into which the NASC-CC are to be introduced (e.g., human gDNA or plant gDNA). Furthermore, the 20-nucleotide DNA target sequences should be distinct from (i.e., not complementary to) the DNA target sequences engineered in the NASC-triplex 1.

Illustrative components of NASC-triplex1 and NASC-triplex2 are presented in Table 20. In the table, the "Target sequence" column indicates the 20 bp DNA target sequence that is complementary to the nucleic acid target binding sequence in the corresponding NASC polynucleotide component.

TABLE 20

NASC-triplex1 and NASC-triplex2 Components

| NASC-triplex | NASC component | Target sequence | Sequence* | SEQ ID NO. |
|---|---|---|---|---|
| NASC-triplex1 | NASC-PC1-triplex1 | 1 | AUCUUGUUGACACGAGGAAUGU UUUAGUCCCUAAUUAAAUUUCU UGAAAUUGGUAUAUAAGGAGGG ACUACAACAAAGAGUUUGCGGG ACUCUGCGGGGUUACAAUCCCC UAAAACCGCUUUUAAAAUUCAA AUAAAUUUUGCUUU | SEQ ID NO. 57 |
| NASC-triplex1 | NASC-PC2-triplex1 | 1 | AUCUUGUUGACACGAGGAAUGU UGUAGUCCCUCCUUAUAUACCA AGAAAAAGAAAUUUAAAACUGA ACUCCAACAAAGAGUUUGCGGG ACUCUGCGGGGUUACAAUCCCC UAAAACCGCUUUUAAAAUUCAA AUAAAUUUUGCUUU | SEQ ID NO. 58 |
| NASC-triplex1 | NASC-PC3-triplex1 | 1 | AUCUUGUUGACACGAGGAAUGU UGGAGUUCAGUUUUAAAUUUCU UGAAAAAGAAAUUUAAUUAGGG ACUAAAACAAAGAGUUUGCGGG ACUCUGCGGGGUUACAAUCCCC UAAAACCGCUUUUAAAAUUCAA AUAAAUUUUGCUUU | SEQ ID NO. 59 |
| NASC-triplex2 | NASC-PC1-triplex2 | 2 | CGAUAUAAUACAGCAAGGUGGU UUUAGACCCCUCUUCCAUUUCG CGAAAGCGUUUUGAGAGAGUGA ACUACAACAAAGAGUUUGCGGG ACUCUGCGGGGUUACAAUCCCC UAAAACCGCUUUUAAAAUUCAA AUAAAUUUUGCUUU | SEQ ID NO. 60 |
| NASC-triplex2 | NASC-PC2-triplex2 | 2 | CGAUAUAAUACAGCAAGGUGGU UGUAGUUCACUCUCUCAAAACG CGAAAAAGAAAUUUAAUAAGGA ACUACAACAAAGAGUUUGCGGG ACUCUGCGGGGUUACAAUCCCC UAAAACCGCUUUUAAAAUUCAA AUAAAUUUUGCUUU | SEQ ID NO. 61 |

TABLE 20-continued

NASC-triplex1 and NASC-triplex2 Components

| NASC-triplex | NASC component | Target sequence | Sequence* | SEQ ID NO. |
|---|---|---|---|---|
| NASC-triplex2 | NASC-PC3-triplex2 | 2 | CGAUAUAAUACAGCAAGGUG<u>GU<br>UGUAGUUCCUUAUUAAAUUUCU</u><br>UGAAAGCGAAAUGGAAGAGGGG<br>UCUAAAACAAAGAGUUUGCGGG<br>ACUCUGCGGGGUUACAAUCCCC<br>UAAAACCGCUUUUAAAAUUCAA<br>AUAAAUUUUGCUUU | SEQ ID NO. 62 |

*NASC-triplex hybridizing regions are underlined

A double-stranded DNA brace sequence can be engineered to incorporate, in the 5' to 3' direction, a 20 nucleotide random sequence at the 5' end, target sequence 1, the *C. jejuni* PAM sequence 5'-NNNACA-3' (where "N" is any nucleotide), 50 nucleotides of random sequence, the reverse compliment of the *C. jejuni* PAM sequence, the reverse compliment of target sequence 2, and a randomize 20-nucleotide sequence at the 3' end. The double-stranded DNA brace sequence will be targetable by *C. jejuni* dCas9 proteins when bound to both the NASC-PC1-triplex1 and the NASC-PC1-TRP2 and will bring the two NASCs within proximity of one another. The sequence of the double-stranded DNA brace sequence can be provided to a commercial manufacturer for synthesis of the double-stranded DNA. Alternatively, the sequence of the double-stranded DNA brace sequence can be constructed using single-stranded DNA oligonucleotides, similar to the construction of double-stranded DNA template presented in Example 2.

An illustrative sequence for a double-stranded DNA brace sequence is shown in Table 21.

TABLE 21

Double-stranded DNA Brace Sequence

| Sequence* | SEQ ID NO. |
|---|---|
| CGTCGCTATGATTTGCCTATATCTTGTTGACACGAGGA<br>ATGTAAACAACGAGTTCCGCTATTGGGATGGAGTTTAA<br>CTGTCGCAACTCTCATCGCAATGTCAGTCACCTTGCTG<br>TATTATATCGCGCATGATAAAGTACGCCAT | SEQ ID NO. 63 |

*Target and PAM sequences are bolded

B. Engineering and Production of *C. jejuni* dCas9 protein

A *C. jejuni* (e.g., *C. jejuni* NCTC 1168; SEQ ID NO. 103) Cas9 amino acid sequence can be mutated from an aspartic acid at amino acid position 8 to an alanine (D8A) and a histidine at position 559 to alanine (D8A/H559A) to generate a nuclease-inactive form of the *C. jejuni* Cas9 protein (*C. jejuni* dCas9 protein; SEQ ID NO. 56). *C. jejuni* dCas9 protein will remain capable of binding to a NASC-triplex1. Three *C. jejuni* dCas9 proteins are capable of binding to the NASC-triplex1 and directing the NASC-triplex1 to bind the target sequences complementary to the nucleic acid target binding sequences therein. The *C. jejuni* dCas9 protein can be C-terminally tagged with two nuclear localization sequences (NLS) and can be recombinantly expressed in *E. coli*, and purified using chromatographic methods.

C. Formation of NASC-CCs

NASC-triplex1 can be formed by mixing NASC-PC1-triplex1, NASC-PC2-triplex1, and NASC-PC3-triplex1 (Table 20) in equal molar concentration, incubating for 2 minutes at 95° C., annealing by cooling to 25° C. at −0.5° C./second in a thermal cycler, and then allowing the mixture to equilibrate to room temperature. NASC-triplex2 can be formed by mixing NASC-PC1-triplex2, NASC-PC2-triplex2, and NASC-PC3-triplex2 (Table 20) in equal molar concentration, incubating for 2 minutes at 95° C., annealing by cooling to 25° C. at −0.5° C./second in a thermal cycler, and then allowing the mixture to equilibrate to room temperature.

Ribonucleoprotein closed-cage complexes can be formed by mixing NASC-triplex1 in the presence of an excess concentration of the *C. jejuni* dCas9 protein in a binding buffer (20 mM HEPES, 100 mM KCl, 5 mM MgCl$_2$, and 5% glycerol at pH 7.4) and incubating at 37° C. for 20 minutes. The double-stranded DNA brace sequence can be added at a limiting concentration to the mixture comprising the NASC-triplex1/dCas9 protein complex, and incubated for 37° C. for 20 minutes. NASC-triplex2 can be added to the mixture of NASC-triplex1/dCas9 protein/double-stranded DNA brace sequences at an equivalent concentration of NASC-triplex1. The mixture can be incubated for 1 hour at 37° C. NASC-triplex1/dCas9 protein/double-stranded DNA brace sequences/NASC-triplex2/dCas9 protein closed-cage complexes can be frozen at −80° C. for long-term storage.

FIG. 6L illustrates an example of an underlying nucleic acid scaffold structure (NASC-CC), with Cas proteins omitted for clarity. NASC-triplex1 and NASC-triplex2 are the structures in this figure that correspond to the structure shown in FIG. 6G. The dashed lines in this figure give an indication of the kinds of connections created by the double-stranded DNA brace sequences between NASC-triplex1 and NASC-triplex2. FIG. 6M illustrates the NASC-CC in complex with the dCas9 protein proteins. The dCas9 protein proteins are represented in this figure by the grey circles.

Following the guidance of the present specification and Example, the formulation of other NASC-CC ribonucleoprotein closed-cage complexes (e.g., comprising various combinations of the NASC compositions described herein) can be practiced by one of ordinary skill in the art with other NASC compositions and cognate Cas proteins.

Example 14

Structural Analysis of NASC Ribonucleoprotein Closed-Cage Complexes

The following Example describes characterization of NASC-CC/dCas protein closed-cage complexes to verify proper assembly and assess the size and volume of assembled NASC-CC/dCas protein complexes. The method described below is adapted from Andersen, F., et al., Nucleic Acids Research 36(4): 1113-1119 (2008) and Lapinaite, A., et al., Nature 502(7472):519-523 (2013). Not all of the following steps are required for screening nor must the order of the steps be as presented.

A. Electrophoretic Mobility Shift Assay of NASC-CC/dCas Protein Complexes

NASC-CC/dCas protein complexes can be formulated as described in Example 13, modified so that a radiolabeled double-stranded DNA brace sequence can be used. The double-stranded DNA brace sequence can be radiolabeled by preparing the following reaction mixture: double-stranded DNA brace sequences in the presence of T4 polynucleotide kinase (New England Biolabs, Ipswich, Mass.), γ-($^{32}$P) ATP (Promega, Madison, Wis.), and IX T4 polynucleotide kinase reaction buffer. The reaction mixture can be incubated and then heat inactivated at 65° C. for 20 minutes. Radiolabeled DNA can be purified using an Illustrated MicroSpin G-25 column (GE Healthcare, Pittsburgh, Pa.).

Alternatively, one or more of the NASC-CC components can be radiolabeled in a similar manner.

Radiolabeled NASC-CC/dCas9 protein complexes can be aliquoted into a 10 μL volume, and resolved at 4° C. by electrophoresis in a 8% native polyacrylamide gel containing 1× Tris/Borate/EDTA buffer (90 mM Tris, 90 mM boric acid, 2 mM EDTA at pH 8.3) and 5 mM MgCl$_2$. The gel can be subsequently dried and imaged using the PMI™ system (Bio-Rad Laboratories, Hercules, Calif.). Individual polynucleotide components of the NASC-CC (e.g., NASC-PC1-triplex1, NASC-PC2-triplex1, NASC-PC3-triplex1, NASC-PC1-triplex2, NASC-PC2-triplex2, NASC-PC3-triplex2, double-stranded DNA brace sequences, and/or individual components complexed with dCas9 protein) can be used as controls for comparison to identify the electrophoretic mobility shift of the completely formed NASC-CC/dCas9 protein complexes.

B. Small Angle X-ray Scattering of NASC-CC/dCas9 Protein Complexes

NASC-CC/dCas9 protein complexes, described in Example 13, can be dialyzed at 4° C. in a buffer of 20 mM HEPES, 100 mM KCl, 5 mM MgCl$_2$, and 5% glycerol at pH 7.4. The dialyzed preparation of NASC-CC/dCas9 protein complexes can be dispensed into the wells of a 96-well plate using a concentration series from 1 mg/mL to 5 mg/mL in a final volume of 40 μL.

Small angle X-ray scattering (SAXS) measurements can be collected at a service provider, such as The Advanced Light Source (Berkeley, Calif.), using a Structurally Integrated BiologY for Life Sciences (SIBYLS) beamline with a Mar165CCD detector. Data can be collected in multiple frames with exposure time ranges of 0.5 second to 10 seconds and detector distances of 1.5 meters to 5 meters. Optimal collection conditions can be evaluated for minimal radiation damage to sample as well as optimal signal to noise ratios. Similarly, beamline kiloelectron-volts (keV) energy can be tuned from a range of 7 keV to 15 keV. Buffer-only control can be used as background and subtracted from measurements.

Data processing and analysis can be performed using standard beamline software and PRIMUS (Konarev, P., et al., Journal of Applied Crystallography 36:1277-1282 (2003)). Data modeling can be performed using SAXS analysis programs, such as an open source software suite (e.g., ATSAS 2.7.2, Petoukhov, M., et al., Journal of Applied Crystallography 45:342-350 (2012)). Atomic coordinates of Cas9 protein and single-guide RNA in different nucleotide bound states (e.g., sgRNA only, sgRNA plus target strand, sgRNA plus target and non-target strand), as well as structures (e.g., nucleases, proteins, double-stranded DNA and RNA) are available from the Protein Database (PDB, www.rcsb.org/pdb/home/home.do) or Electron Microscopy Data Bank (EMDB, www.ebi.ac.uk/pdbe/emdb/). These atomic coordinates can be used to calculate the internal volume, pore size, and closed-cage sizes of the NASC-CC/dCas9 protein complexes by modeling, combined with SAXS data.

NASC-CC/dCas9 protein complexes can be modified to increase or decrease the internal volume, pore size, or closed-cage sizes as needed for the packaging and delivery of biomolecules, proteins, or other payloads. Such modifications can include, but are not limited to, lengthening or shortening of the first stem element nucleic acid sequence (FIG. 6A, 608-609; FIG. 6H, 623-624/658-657, 626-625/627-628, 652-651/655-646), and/or the double-stranded DNA brace sequence (Table 21).

Following the guidance of the present specification and Examples, analysis of the structural features of NASC-CC/Cas protein complexes, including internal volumes, pore sizes, and closed-cage sizes, can be practiced by one of ordinary skill in the art.

As is apparent to one of skill in the art, various modification and variations of the above embodiments can be made without departing from the spirit and scope of this invention. Such modifications and variations are within the scope of this invention.

The invention claimed is:

1. A method of bringing a donor polynucleotide into proximity of a double-strand break (DSB) in DNA in a cell, comprising:
introducing the DSB in the DNA,
contacting a nucleic acid/protein composition with the DNA, the nucleic acid/protein composition comprising a composition of engineered Class 2 Type II CRISPR-nucleic acid sequences forming a scaffold ("NASC"), the Class 2 Type II CRISPR-NASC composition comprising
a first engineered nucleic acid component ("NASC-PC1") comprising, in a 5' to 3' direction,
a spacer element 1 comprising a nucleic acid target binding sequence 1, wherein a nucleic acid target sequence 1 is in proximity to the DSB,
a repeat element 1 comprising a repeat nucleic acid sequence 1, and
a nucleic acid binding protein binding element 1 comprising a double-stranded nucleic acid binding protein binding sequence 1,
wherein the spacer element 1 is covalently connected with the repeat element 1, and the repeat element 1 is covalently connected with the nucleic acid binding protein binding element 1; and
a second engineered nucleic acid component ("NASC-PC2") comprising, in a 5' to 3' direction,
a spacer element 2 comprising a nucleic acid target binding sequence 2,
a repeat element 2 comprising a repeat nucleic acid sequence 2, and
a nucleic acid binding protein binding element 2 comprising a double-stranded nucleic acid binding protein binding sequence 2,
wherein the spacer element 2 is covalently connected with the repeat element 2, and the repeat element 2 is covalently connected with the nucleic acid binding protein binding element 2;
wherein there is a connection between the repeat nucleic acid sequence 1 and the repeat nucleic acid sequence 2 through hydrogen-bonded base pairs, and
the connection forms the Class 2 Type II CRISPR-NASC composition,
a first catalytically inactive Class 2 Type II CRISPR-Cas9 protein associated with the Class 2 Type II CRISPR-NASC composition and a second catalytically inactive Class 2 Type II CRISPR-Cas9 protein associated with the Class 2 Type II CRISPR-NASC composition; and
a donor polynucleotide comprising a nucleic acid target sequence 2, wherein there is a connection between the nucleic acid target sequence 2 and the nucleic acid target binding sequence 2 through hydrogen-bonded base pairs;
wherein the contacting facilitates the binding of the nucleic acid/protein composition to the nucleic acid target sequence 1, and bringing the donor polynucleotide into proximity of the double-strand break (DSB).

2. The method of claim 1, wherein the first Class 2 Type II CRISPR-Cas9 protein and the second Class 2 Type II CRISPR-Cas9 protein are the same Class 2 Type II CRISPR-Cas9 protein.

3. The method of claim 1, wherein
the spacer element 1 further comprises a linker element nucleic acid sequence 3' of the nucleic acid target binding sequence 1 and 5' of the repeat element 1; and
the spacer element 2 further comprises a linker element nucleic acid sequence 3' of the nucleic acid target binding sequence 1 and 5' of the repeat element 1.

4. The method of claim 1, wherein
the repeat element 1 further comprises, in a 5' to 3' direction, a repeat nucleic acid sequence 1b, a linker element nucleic acid sequence 1-2, and a repeat nucleic acid sequence 1a; and
the repeat element 2 further comprises, in a 5' to 3' direction, a repeat nucleic acid sequence 1aC, a linker element nucleic acid sequence 2-2, a repeat nucleic acid sequence 1bC;
wherein the repeat nucleic acid sequence 1b and the repeat nucleic acid sequence 1bC are connected through hydrogen-bonded base pairs, and the repeat nucleic acid sequence 1a and the repeat nucleic acid sequence 1aC are connected through hydrogen-bonded base pairs.

5. The method of claim 4, wherein
the repeat nucleic acid sequence 1b further comprises, in a 5' to 3' direction,
a repeat nucleic acid sequence 1b2,
a bulge nucleic acid sequence 1b1, and
a repeat nucleic acid sequence 1b1;
the repeat nucleic acid sequence 1a further comprises, in a 5' to 3' direction,
a repeat nucleic acid sequence 1a2,
a bulge nucleic acid sequence 1a1, and
a repeat nucleic acid sequence 1a1;

the repeat nucleic acid sequence 1aC further comprises, in a 5' to 3' direction,
  a repeat nucleic acid sequence 1a1C,
  a bulge nucleic acid sequence 2a2, and
  a repeat nucleic acid sequence 1a2C; and
the repeat nucleic acid sequence 1bC further comprises, in a 5' to 3' direction,
  a repeat nucleic acid sequence 1b1C,
  a bulge nucleic acid sequence 2b2, and
  a repeat nucleic acid sequence 1b2C;
wherein the repeat nucleic acid sequence 1a1 and the repeat nucleic acid sequence 1a1C are connected through hydrogen-bonded base pairs, the repeat nucleic acid sequence 1a2 and the repeat nucleic acid sequence 1a2C are connected through hydrogen-bonded base pairs, the repeat nucleic acid sequence 1b1 and the repeat nucleic acid sequence 1b1C are connected through hydrogen-bonded base pairs, and the repeat nucleic acid sequence 1b2 and the repeat nucleic acid sequence 1b2C are connected through hydrogen-bonded base pairs.

6. The method of claim 5, wherein
the linker element nucleic acid sequence 1-2 further comprises, in a 5' to 3' direction,
  a linker element nucleic acid sequence 1-2-2,
  a repeat nucleic acid sequence 1-2a, and
  a linker element nucleic acid sequence 1-2-1;
the linker element nucleic acid sequence 2-2 further comprises, in a 5' to 3' direction,
  a linker element nucleic acid sequence 2-2-1,
  a repeat nucleic acid sequence 1-2aC, and
  a linker element nucleic acid sequence 2-2-2;
wherein the repeat nucleic acid sequence 1-2a and the repeat nucleic acid sequence 1-2aC are connected through hydrogen-bonded base pairs and form a double-stranded nucleic acid region 1-2.

7. The method of claim 6, wherein
the double-stranded nucleic acid region 1-2 further comprises an effector protein binding site;
the repeat nucleic acid sequence 1-2a further comprises an effector protein binding site nucleic acid sequence 1-2a; and
the repeat nucleic acid sequence 1-2aC further comprises an effector protein binding site nucleic acid sequence 1-2aC;
wherein the effector binding site is formed by hydrogen base-pair bonding between the effector protein binding site nucleic acid sequence 1-2a and the effector protein binding site nucleic acid sequence 1-2aC.

8. The method of claim 7, wherein the effector protein binding site is a Csy4 protein binding site.

9. The method of claim 1, wherein
the repeat nucleic acid sequence 1 further comprises an affinity tag 1; and
the repeat nucleic acid sequence 2 further comprises an affinity tag 2;
wherein the affinity tag 1 is connected with affinity tag 2.

10. The method of claim 1, wherein the NASC-PC1 comprises RNA, DNA, or RNA and DNA.

11. The method of claim 1, wherein the NASC-PC2 comprises RNA, DNA, or RNA and DNA.

12. The method of claim 1, wherein the first catalytically inactive Class 2 Type II CRISPR-Cas9 protein is the same as the second catalytically inactive Class 2 Type II CRISPR-Cas9 protein, and the first catalytically inactive Class 2 Type II CRISPR-Cas9 protein and the second catalytically inactive Class 2 Type II CRISPR-Cas9 protein are each selected from the group consisting of a *Streptococcus pyogenes* Cas9 protein, a *Streptococcus thermophilus* Cas9 protein, a *Staphylococcus aureus* Cas9 protein, and a *Campylobacter jejuni* Cas9 protein.

13. The nucleic acid/protein composition of claim 1, wherein the first catalytically inactive Class 2 Type II CRISPR-Cas9 protein is different from the second catalytically inactive Class 2 Type II CRISPR-Cas9 protein, and the first catalytically inactive Class 2 Type II CRISPR-Cas9 protein and the second catalytically inactive Class 2 Type II CRISPR-Cas9 protein are each selected from the group consisting of a *Streptococcus pyogenes* Cas9 protein, a *Streptococcus thermophilus* Cas9 protein, a *Staphylococcus aureus* Cas9 protein, and a *Campylobacter jejuni* Cas9 protein.

14. The method of claim 1, wherein introducing the DSB in the DNA comprises contacting a nucleoprotein complex comprising a catalytically active Class 2 Type II CRISPR-Cas9/guide with the DNA.

15. The method of claim 14, wherein the guide is a single-guide RNA (sgRNA).

16. The method of claim 14, wherein the guide is a dual guide RNA.

17. The method of claim 14, wherein the catalytically active Cas9 protein is selected from the group consisting of a *Streptococcus pyogenes* Cas9 protein, a *Streptococcus thermophilus* Cas9 protein, a *Staphylococcus aureus* Cas9 protein, a *Neisseria meningitidis* Cas9 protein, and an orthologous Cas9 protein.

18. The method of claim 17, wherein the catalytically active Cas9 protein is a *Streptococcus pyogenes* Cas9 protein.

19. The method of claim 1, wherein the cell is a eukaryotic cell.

20. The method of claim 1, wherein the cell is selected from the group consisting of a bacterial cell, a yeast cell, a mammalian cell, and a plant cell.

* * * * *

UNITED STATES PATENT AND TRADEMARK OFFICE
CERTIFICATE OF CORRECTION

PATENT NO. : 10,100,333 B2
APPLICATION NO. : 15/971863
DATED : October 16, 2018
INVENTOR(S) : Paul Daniel Donohoue and Andrew Paul May Page 1 of 1

It is certified that error appears in the above-identified patent and that said Letters Patent is hereby corrected as shown below:

In the Specification

In Column 9, Line 6, delete "split-*nexus*", and insert -- split-nexus --, therefor.

In Column 112, Line 48, delete "Type-II", and insert -- Type II --, therefor.

In Column 125, Line 21, delete "Radiolabeled", and insert -- Radio-labeled --, therefor.

In the Claims

In Column 238, Line 27, Claim 1, delete "double-strand break (DSB).", and insert -- DSB. --, therefor.

In Column 238, Line 47, Claim 4, delete "2-2, a repeat", and insert -- 2-2, and a repeat --, therefor.

In Column 240, Line 20, Claim 13, delete "nucleic acid/protein composition", and insert -- method --, therefor.

In Column 240, Line 34, Claim 14, delete "Cas9/guide", and insert -- Cas9 protein/guide --, therefor.

Signed and Sealed this
Eleventh Day of December, 2018

Andrei Iancu
*Director of the United States Patent and Trademark Office*